(12) United States Patent
Yu et al.

(10) Patent No.: US 11,761,045 B2
(45) Date of Patent: Sep. 19, 2023

(54) SPLICE VARIANTS ASSOCIATED WITH NEOMORPHIC SF3B1 MUTANTS

(71) Applicant: Eisai R&D Management Co., Ltd., Tokyo (JP)

(72) Inventors: Lihua Yu, Acton, MA (US); Kian Huat Lim, Burlington, MA (US); Jacob D. Feala, Franklin, MA (US); Silvia Buonamici, Boston, MA (US); Yoshiharu Mizui, Boston, MA (US); Peter G. Smith, Arlington, MA (US); Ping Zhu, Boxborough, MA (US); Eunice Sun Park, Arlington, MA (US); Michael W. Seiler, Watertown, MA (US); Marco Peter Fekkes, Waltham, MA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 17/098,940

(22) Filed: Nov. 16, 2020

(65) Prior Publication Data

US 2021/0130909 A1     May 6, 2021

Related U.S. Application Data

(63) Continuation of application No. 15/755,225, filed as application No. PCT/US2016/049490 on Aug. 30, 2016, now Pat. No. 10,889,866.

(60) Provisional application No. 62/212,876, filed on Sep. 1, 2015.

(51) Int. Cl.

| *C12Q 1/6886* | (2018.01) |
|---|---|
| *A61P 35/00* | (2006.01) |
| *A61K 31/4545* | (2006.01) |
| *A61K 31/495* | (2006.01) |
| *A61K 31/55* | (2006.01) |
| *C12Q 1/02* | (2006.01) |
| *C12Q 1/6806* | (2018.01) |
| *C12Q 1/6841* | (2018.01) |

(52) U.S. Cl.
CPC ........ *C12Q 1/6886* (2013.01); *A61K 31/4545* (2013.01); *A61K 31/495* (2013.01); *A61K 31/55* (2013.01); *A61P 35/00* (2018.01); *C12Q 1/025* (2013.01); *C12Q 1/6806* (2013.01); *C12Q 1/6841* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| 7,550,503 | B2 | 6/2009 | Kotake et al. |
|---|---|---|---|
| 7,816,401 | B2 | 10/2010 | Kanada et al. |
| 7,884,128 | B2 | 2/2011 | Kanada et al. |
| 7,919,237 | B2 | 4/2011 | Dimitrov et al. |
| 8,519,115 | B2 | 8/2013 | Dahl |
| 9,481,669 | B2 | 11/2016 | Keaney et al. |
| 2007/0015271 | A1 | 1/2007 | Rosen et al. |
| 2010/0021918 | A1 | 1/2010 | Yoshihara et al. |
| 2014/0364439 | A1 | 12/2014 | Wu et al. |

FOREIGN PATENT DOCUMENTS

| JP | 2013184887 A2 | 9/2013 |
|---|---|---|
| WO | WO 01/36684 A2 | 5/2001 |
| WO | WO 01/36684 A3 | 5/2001 |
| WO | WO 01/60890 A2 | 8/2001 |
| WO | WO 01/75067 A2 | 10/2001 |
| WO | WO 2003/099813 A1 | 12/2003 |
| WO | WO 2004/011459 A1 | 2/2004 |
| WO | WO 2004/011661 A1 | 2/2004 |
| WO | WO 2004/050890 A1 | 6/2004 |
| WO | WO 2005/052152 A1 | 6/2005 |
| WO | WO 2006/009276 A1 | 1/2006 |
| WO | WO 2008/126918 A1 | 10/2008 |
| WO | WO 2013/070521 A1 | 5/2013 |
| WO | WO 2014/165753 A1 | 10/2014 |
| WO | WO 2017/040526 A2 | 3/2017 |
| WO | WO 2017/040526 A3 | 3/2017 |

OTHER PUBLICATIONS

Mupo et al Leukemia. 2017. 31: 720-727 (Year: 2017).*
Maguire et al J Pathology, Nov. 26, 2014. 235:571-580 and Supporting Information, 5 pages and Table S9, 25 pages total (Year: 2014).*
Conte et al Br J Haematology. 2015. 171: 478-479 and Supporting Material, 35 pages total. (Year: 2015).*
Dolatshad et al Leukemia. Nov. 2014. 29: 1092-1103 (Year: 2014).*
International Patent Application No. PCT/US2021/057839, filed Nov. 3, 2021, by Eisai R&D Management Co., Ltd.: International Search Report and Written Opinion, dated Feb. 2, 2022.
Seiler et al., (2018) "H3B-8800, an orally available small-molecule splicing modulator, induces lethality in spliceosome-mutant cancers", Nat Med, 24(4):497-504.
Shiozawa et al., (2018) "Aberrant splicing and defective mRNA production induced by somatic spliceosome mutations in myelodysplasia", Nat Commun., 9(1):3649 (16 pages).
Steensma et al., (2019) "Results of a Clinical Trial of H3B-8800, a Splicing Modulator, in Patients with Myelodysplastic Syndromes (MDS), Acute Myeloid Leukemia (AML) or Chronic Myelomonocytic Leukemia (CMML)", Blood 134(1):673 (5 pages).

(Continued)

*Primary Examiner* — Carla J Myers
(74) *Attorney, Agent, or Firm* — Finnegan, Henderson, Farabow, Garrett & Dunner LLP

(57) ABSTRACT

Splice variants associated with neomorphic SF3B1 mutations are described herein. This application also relates to methods of detecting the described splice variants, and uses for diagnosing cancer, evaluating modulators of SF3B1, and methods of treating cancer associated with mutations in SF3B1.

25 Claims, 24 Drawing Sheets

Specification includes a Sequence Listing.

(56) References Cited

OTHER PUBLICATIONS

Steensma et al., (2021) "Phase I First-in-Human Dose Escalation Study of the oral SF3B1 modulator H3B-8800 in myeloid neoplasm", Nature, 35:3542-3550.

Bonnal et al., (2012) "The spliceosome as a target of novel antitumour drugs", Nat. Rev. Drug Discov., 11:847-859.

Buonamici et al., (2014) "SF3B1 Mutations induce common and lineage specific aberrant messenger RNA splicing in malignancies including chronic lymphocytic leukemia and confer sensitivity to spliceosome inhibition", Haematologica, Suppl. 1; 99:227.

Buonamici et al., (2014) "Cancer-Associated Mutations in SF3B1 Exhibit Neomorphic Splicing Activity and Block Erythroid Differentiation", Blood, 124(21):4615.

Convertini et al., (2014) "Sudemycin E influences alternative splicing and changes chromatin modifications", Nucleic Acids Research, 42(8):4947-4961.

Cummings et al., (2017) "Improving genetic diagnosis in Mendelian disease with transcriptome sequencing", Science Translational Medicine, 9:1-11.

Darman et al., (2015) "Cancer-Associated SF3B1 Hotspot Mutations Induce Cryptic 30 Splice Site Selection through Use of a Different Branch Point", Cell Reports, 13(5):1033-1045.

Database Geneseq (2002) "DNA encoding novel human diagnostic protein #543", Database accession No. AAS64739.

Database EMBL (2005) "*Homo sapiens* cDNA clone SKMUS2007303, 5' end, mRNA sequence", Database accession No. DA898882.

Database EMBL (2007) "*Homo sapiens* cDNA, clone LYMPB2001721, 5' end, mRNA sequence", Database accession No. DC428363.

Database EMBL (2009), "*Homo sapiens* cDNA FLJ59337 complete cds, highly similar to DCC-interacting protein 13 beta", Database accession No. AK297100.

Eskens et al., (2013) "Phase I pharmacokinetic and pharmacodynamic study of the first-in-class spliceosome inhibitor E7107 in patients with advanced solid tumors", Clin. Cancer Res., 19:6296-6304.

Furney et al., (2013) "SF3B1 Mutations Are Associated with Alternative Splicing in Uveal Melanoma", Cancer Discovery, 3(10):1122-1129.

Gentien et al., (2014) "A common alternative splicing signature is associated with SF3B1 mutations in malignancies from different cell lineages", Leukemia, 28(6):1355-1357.

International Patent Application No. PCT/US2016/049490, filed Aug. 30, 2016, by Eisai R&D Management Co., Ltd.: International Search Report and Written Opinion, dated Mar. 14, 2017.

Jayasinghe et al., (2018) "Systematic Analysis of Splice-Site-Creating Mutations in Cancer", Cell Reports, 23:270-281.

Johnson et al., (2003) "Genome-wide survey of human alternative pre-mRNA splicing with exon junction microarrays", Science 302:2141-2144.

Kanada et al., (2007) "Total Synthesis of the Potent Antitumor Macrolides Pladienolide Band D", Angew. Chem. Int. Ed., 46:4350-4355.

Kimura et al., (2006) "Diversification of transcriptional modulation: large-scale identification and characterization of putative alternative promoters of human genes", Genome Research, 16(1):55-65.

Kotake et al., (2007) "Splicing factor SF3b as a target of the antitumor natural product pladienolide", Nature Chemical Biology, 3:570-575.

Kulkami et al., (2011) "Digital Multiplexed Gene Expression Analysis Using the NanoString nCounter System" Current Protocols in Molecular Biology, 94:25.

Li et al., (2009) "The Sequence Alignment/Map format and SAMtools", Bioinformatics, 25(16):2078-2079.

Maguire et al., (2014) "575 SF3B1 mutations are associated with alternative splicing in ER-positive breast cancer", European Journal of Cancer, 50:186.

McCullough et al., (2005) "High throughput alternative splicing quantification by primer extension and matrix-assisted laser desorption/ionization time-of-flight mass spectrometry", Nucleic Acids Research, 33(11):e99.

Milani et al., (2006) "Detection of alternatively spliced transcripts in leukemia cell lines by minisequencing on microarrays", Clin. Chem., 52:202-211.

Modrek et al., (2001) "Genome-wide detection of alternative splicing in expressed sequences of human genes", Nucleic Acids Research, 29:2850-2859.

Pellizzoni et al., (1998) "Novel function for SMN, the spinal muscular atrophy disease gene product, in pre-mRNA splicing", Cell, 95:615-624.

Prigodich et al., (2012) "Multiplexed Nanoflares: mRNA Detection in Live Cells", Anal. Chem., 84(4):2062-2066.

Ren et al., (2012) "RNA-Seq analysis of prostate cancer in the Chinese population identifies recurrent gene fusions, cancer-associated long noncoding RNAs and aberrant alternative splicings", Cell. Res., 22:806-821.

Sakai et al., (2004) "Pladienolides, New Substances from Culture of Streptomyces platensis Mer-11107. I. Taxonomy, Fermentation, Isolation and Screening", The Journal of Antibiotics, 57(3):173-179.

Seferos et al., (2007) "Nano-flares: Probes for Transfection and mRNA Detection in Living Cells", J. Am. Chem. Soc., 129(50):15477-15479.

"Tissue-Specific Transcriptome Used to Enhance Exome-, Genome-Based Dystrophy Diagnoses" (2017) genomeweb, 2 pages.

Van Dijk et al., (2014) "Ten years of next generation sequencing technology", Trends Genet, 30(9):418-426.

Wan et al., (2013) "Review Article SF3B1 mutations in chronic lymphocytic leukemia", Blood, 121(23):4627-4634.

Wan et al., (2013) "SF3B1 Mutation Alters the Selection of 3' RNA Splice Sites in Chronic Lymphocytic Leukemia", Blood, 122(21):117.

Wang et al., (2011) "SF3B1 and Other Novel Cancer Genes in Chronic Lymphocytic Leukemia", N.E. Journal of Medicine, 365(26):2497-2506.

Wang et al., (2012) "RNAscope: a novel in situ RNA analysis platform for formalin-fixed, paraffin-embedded tissues", J. Mol. Diagn., 14(1):22-29.

Yokoi et al., (2011) "Biological validation that SF3b is a target of the antitumor macrolide pladienolide", FEBS J., 278:4870-4880.

Yoshida et al., (2011) "Frequent pathway mutations of splicing machinery in myelodysplasia", Nature, 478:64-69.

Extended European Search Report dated Oct. 19, 2021, received in EP Application No. 21174658.1 (10 pgs.).

\* cited by examiner

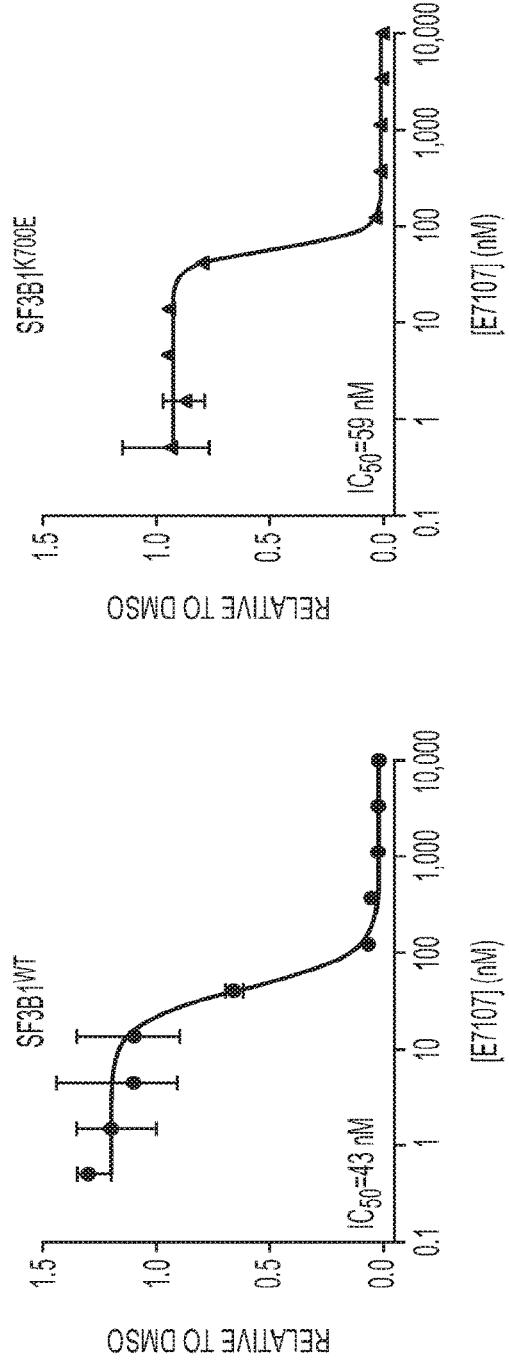
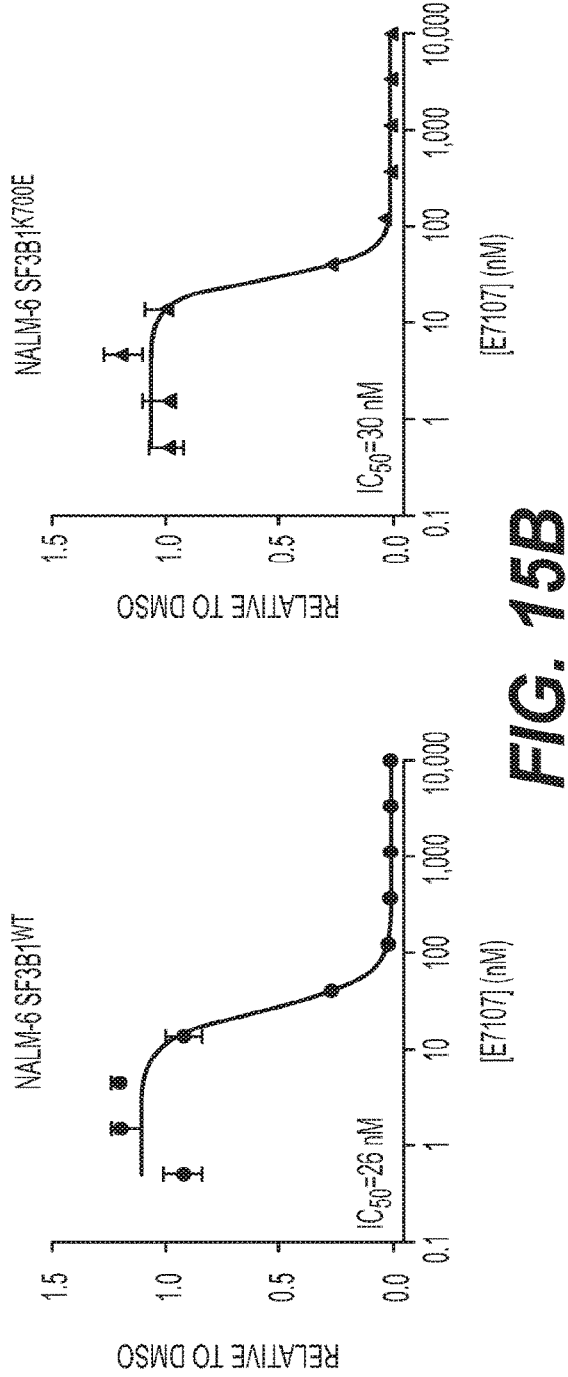
FIG. 15A
FIG. 15B

```
SEQUENCE LISTING

<160> NUMBER OF SEQ ID NOS: 1200

<210> SEQ ID NO 1
<211> LENGTH: 40
<212> TYPE: DNA
<213> ORGANISM: Homo sapiens

<400> SEQUENCE: 1
agcaagtaga agtctataaa atttaccccc agatacagct                    40

<210> SEQ ID NO 2
<211> LENGTH: 40
<212> TYPE: DNA
<213> ORGANISM: Homo sapiens

<400> SEQUENCE: 2
agcaagtaga agtctataaa atacagctgg ctgaaataac                    40

<210> SEQ ID NO 3
<211> LENGTH: 40
<212> TYPE: DNA
<213> ORGANISM: Homo sapiens

<400> SEQUENCE: 3
cgggccgcat catccgggag agcactgtgt tccagctgcc                    40

<210> SEQ ID NO 4
<211> LENGTH: 40
<212> TYPE: DNA
<213> ORGANISM: Homo sapiens

<400> SEQUENCE: 4
cgggccgcat catccgggag ctgcccggtg tccaccctga                    40

<210> SEQ ID NO 5
<211> LENGTH: 40
<212> TYPE: DNA
<213> ORGANISM: Homo sapiens

<400> SEQUENCE: 5
ctggagccgg cgggaaggag tgtgctggtt cctctcccca                    40

<210> SEQ ID NO 6
<211> LENGTH: 40
<212> TYPE: DNA
<213> ORGANISM: Homo sapiens
```

```
<400> SEQUENCE: 6
ctggagccgg cgggaaggag gcaagctgca gcagttcgag                              40

<210> SEQ ID NO 7
<211> LENGTH: 40
<212> TYPE: DNA
<213> ORGANISM: Homo sapiens

<400> SEQUENCE: 7 ggccctttg tcctcactag catttctgtt ctgacaggtt                               40

<210> SEQ ID NO 8
<211> LENGTH: 40
<212> TYPE: DNA
<213> ORGANISM: Homo sapiens

<400> SEQUENCE: 8 ggccctttg tcctcactag gttcttggca tggagctgag                               40

<210> SEQ ID NO 9
<211> LENGTH: 40
<212> TYPE: DNA
<213> ORGANISM: Homo sapiens

<400> SEQUENCE: 9
tgggaggagc atgtcaacag agtttccctt ataggactgg                              40

<210> SEQ ID NO 10
<211> LENGTH: 40
<212> TYPE: DNA
<213> ORGANISM: Homo sapiens

<400> SEQUENCE: 10
tgggaggagc atgtcaacag gactggctgg acaatggccc                              40

<210> SEQ ID NO 11
<211> LENGTH: 40
<212> TYPE: DNA
<213> ORGANISM: Homo sapiens

<400> SEQUENCE: 11
gatggtggat gaacccacag ttttttttt tcaggtatat                               40

<210> SEQ ID NO 12
<211> LENGTH: 40
<212> TYPE: DNA
<213> ORGANISM: Homo sapiens

<400> SEQUENCE: 12
gatggtggat gaacccacag gtatatgtcc tcattttcct                              40

<210> SEQ ID NO 13
<211> LENGTH: 40
<212> TYPE: DNA
<213> ORGANISM: Homo sapiens

<400> SEQUENCE: 13
tacctctggt tcctgtgcag tcttcgcccc tcttttctta                              40

<210> SEQ ID NO 14
<211> LENGTH: 40
<212> TYPE: DNA
```

```
<213> ORGANISM: Homo sapiens

<400> SEQUENCE: 14
tacctctggt tcctgtgcag ttctgtggca cttgccctgg            40

<210> SEQ ID NO 15
<211> LENGTH: 40
<212> TYPE: DNA
<213> ORGANISM: Homo sapiens

<400> SEQUENCE: 15
ttggaccgga aaagactttg agtctctttt tgcagatgat            40

<210> SEQ ID NO 16
<211> LENGTH: 40
<212> TYPE: DNA
<213> ORGANISM: Homo sapiens

<400> SEQUENCE: 16
ttggaccgga aaagactttg atgatggatg ccaaccagcg            40

<210> SEQ ID NO 17
<211> LENGTH: 40
<212> TYPE: DNA
<213> ORGANISM: Homo sapiens

<400> SEQUENCE: 17
acccaagcct tgaggtttca tttcccccctc ccaggatttc           40

<210> SEQ ID NO 18
<211> LENGTH: 40
<212> TYPE: DNA
<213> ORGANISM: Homo sapiens

<400> SEQUENCE: 18
acccaagcct tgaggtttca gcctgggcag catggccgta            40

<210> SEQ ID NO 19
<211> LENGTH: 40
<212> TYPE: DNA
<213> ORGANISM: Homo sapiens

<400> SEQUENCE: 19
agcattgcta gaagcagcag cttttgcaga tcctgaggta            40

<210> SEQ ID NO 20
<211> LENGTH: 40
<212> TYPE: DNA
<213> ORGANISM: Homo sapiens

<400> SEQUENCE: 20
agcattgcta gaagcagcag gaattggcaa attgtcaact            40

<210> SEQ ID NO 21
<211> LENGTH: 40
<212> TYPE: DNA
<213> ORGANISM: Homo sapiens

<400> SEQUENCE: 21
caagtatatg actgaagaag atcctgaatt ccagcaaaac            40

<210> SEQ ID NO 22
<211> LENGTH: 40
```

<212> TYPE: DNA
<213> ORGANISM: Homo sapiens

<400> SEQUENCE: 22
caagtatatg actgaagaag gtgagccttt ttctcaagag        40

<210> SEQ ID NO 23
<211> LENGTH: 40
<212> TYPE: DNA
<213> ORGANISM: Homo sapiens

<400> SEQUENCE: 23
tgcagtttgg tcagtctgtg ccttcctcac ccctctcctc        40

<210> SEQ ID NO 24
<211> LENGTH: 40
<212> TYPE: DNA
<213> ORGANISM: Homo sapiens

<400> SEQUENCE: 24
tgcagtttgg tcagtctgtg ggctctgtgg tatatgactg        40

<210> SEQ ID NO 25
<211> LENGTH: 40
<212> TYPE: DNA
<213> ORGANISM: Homo sapiens

<400> SEQUENCE: 25
tctttggaaa atctaatcaa ttttctgcct ataggggaag        40

<210> SEQ ID NO 26
<211> LENGTH: 40
<212> TYPE: DNA
<213> ORGANISM: Homo sapiens

<400> SEQUENCE: 26
tctttggaaa atctaatcaa gggaaggaag atctatgaac        40

<210> SEQ ID NO 27
<211> LENGTH: 40
<212> TYPE: DNA
<213> ORGANISM: Homo sapiens

<400> SEQUENCE: 27
gtatcaaagt gtggactgag atttgtcttc ctttaggatt        40

<210> SEQ ID NO 28
<211> LENGTH: 40
<212> TYPE: DNA
<213> ORGANISM: Homo sapiens

<400> SEQUENCE: 28
gtatcaaagt gtggactgag gattccattg caaagccaca        40

<210> SEQ ID NO 29
<211> LENGTH: 40
<212> TYPE: DNA
<213> ORGANISM: Homo sapiens

<400> SEQUENCE: 29
agaactgcac ctacacacag ccctgttcac aggtgcagac        40

<210> SEQ ID NO 30

```
<211> LENGTH: 40
<212> TYPE: DNA
<213> ORGANISM: Homo sapiens

<400> SEQUENCE: 30
agaactgcac ctacacacag gtgcagaccc gcagctctga                              40

<210> SEQ ID NO 31
<211> LENGTH: 40
<212> TYPE: DNA
<213> ORGANISM: Homo sapiens

<400> SEQUENCE: 31
ggagcagtgc agttgtgaaa tcattacttc tagatgatgc                              40

<210> SEQ ID NO 32
<211> LENGTH: 40
<212> TYPE: DNA
<213> ORGANISM: Homo sapiens

<400> SEQUENCE: 32
ggagcagtgc agttgtgaaa gttttgattc atggattcac                              40

<210> SEQ ID NO 33
<211> LENGTH: 40
<212> TYPE: DNA
<213> ORGANISM: Homo sapiens

<400> SEQUENCE: 33
ctatttcact ctcccccgaa cctatccagg ttcctcctcc                              40

<210> SEQ ID NO 34
<211> LENGTH: 40
<212> TYPE: DNA
<213> ORGANISM: Homo sapiens

<400> SEQUENCE: 34
ctatttcact ctcccccgaa atgagcccat ccagccaatt                              40

<210> SEQ ID NO 35
<211> LENGTH: 40
<212> TYPE: DNA
<213> ORGANISM: Homo sapiens

<400> SEQUENCE: 35
tttgcaggga atgggctaca tccccttggt tctctgttac                              40

<210> SEQ ID NO 36
<211> LENGTH: 40
<212> TYPE: DNA
<213> ORGANISM: Homo sapiens

<400> SEQUENCE: 36
tttgcaggga atgggctaca taccatctgc cagcatgact                              40

<210> SEQ ID NO 37
<211> LENGTH: 40
<212> TYPE: DNA
<213> ORGANISM: Homo sapiens

<400> SEQUENCE: 37
tgaccacgga gtacctgggg ccctttttc tctttccttc                               40
```

```
<210> SEQ ID NO 38
<211> LENGTH: 40
<212> TYPE: DNA
<213> ORGANISM: Homo sapiens

<400> SEQUENCE: 38
tgaccacgga gtacctgggg atcatgacca acacggggaa                             40

<210> SEQ ID NO 39
<211> LENGTH: 40
<212> TYPE: DNA
<213> ORGANISM: Homo sapiens

<400> SEQUENCE: 39
agacctacca gaaggctatg tgtttattaa ttttacagaa                             40

<210> SEQ ID NO 40
<211> LENGTH: 40
<212> TYPE: DNA
<213> ORGANISM: Homo sapiens

<400> SEQUENCE: 40
agacctacca gaaggctatg aacagaggac aacgcaacaa                             40

<210> SEQ ID NO 41
<211> LENGTH: 40
<212> TYPE: DNA
<213> ORGANISM: Homo sapiens

<400> SEQUENCE: 41
atttggactc gctagcaatg atgtctgttt atttttagag                             40

<210> SEQ ID NO 42
<211> LENGTH: 40
<212> TYPE: DNA
<213> ORGANISM: Homo sapiens

<400> SEQUENCE: 42
atttggactc gctagcaatg agcatgacct ctcaatggca                             40

<210> SEQ ID NO 43
<211> LENGTH: 40
<212> TYPE: DNA
<213> ORGANISM: Homo sapiens

<400> SEQUENCE: 43
catgtggaat cccaatgccg gccctgtcc tcctccccca                              40

<210> SEQ ID NO 44
<211> LENGTH: 40
<212> TYPE: DNA
<213> ORGANISM: Homo sapiens

<400> SEQUENCE: 44
catgtggaat cccaatgccg ggcagccagg gccaaatcca                             40

<210> SEQ ID NO 45
<211> LENGTH: 40
<212> TYPE: DNA
<213> ORGANISM: Homo sapiens

<400> SEQUENCE: 45
ctgggaggtg gcattcaaag ccccacctttt tgtctcccca                            40
```

<210> SEQ ID NO 46
<211> LENGTH: 40
<212> TYPE: DNA
<213> ORGANISM: Homo sapiens

<400> SEQUENCE: 46
ctgggaggtg gcattcaaag gctcttcaga ggtgttcctg          40

<210> SEQ ID NO 47
<211> LENGTH: 40
<212> TYPE: DNA
<213> ORGANISM: Homo sapiens

<400> SEQUENCE: 47
ggatgaccgg gatgcctcag tcactttaca gctgcatcgt          40

<210> SEQ ID NO 48
<211> LENGTH: 40
<212> TYPE: DNA
<213> ORGANISM: Homo sapiens

<400> SEQUENCE: 48
ggatgaccgg gatgcctcag atggggagga tgagaagccc          40

<210> SEQ ID NO 49
<211> LENGTH: 40
<212> TYPE: DNA
<213> ORGANISM: Homo sapiens

<400> SEQUENCE: 49
acatgaaggt ggacggagag gctcccctcc caccccaggt          40

<210> SEQ ID NO 50
<211> LENGTH: 40
<212> TYPE: DNA
<213> ORGANISM: Homo sapiens

<400> SEQUENCE: 50
acatgaaggt ggacggagag gtactgagga caaatcagtt          40

<210> SEQ ID NO 51
<211> LENGTH: 40
<212> TYPE: DNA
<213> ORGANISM: Homo sapiens

<400> SEQUENCE: 51
agagaagtcg tttcattcaa gtcagctaag acacaagcag          40

<210> SEQ ID NO 52
<211> LENGTH: 40
<212> TYPE: DNA
<213> ORGANISM: Homo sapiens

<400> SEQUENCE: 52
agagaagtcg tttcattcaa gttggtgtaa tcagctgggg          40

<210> SEQ ID NO 53
<211> LENGTH: 40
<212> TYPE: DNA
<213> ORGANISM: Homo sapiens

<400> SEQUENCE: 53
tcactcaaac agtaaacgag ttttatcatt tacaggtatg          40

<210> SEQ ID NO 54
<211> LENGTH: 40
<212> TYPE: DNA
<213> ORGANISM: Homo sapiens

<400> SEQUENCE: 54
tcactcaaac agtaaacgag gtatgtgacg cattcccaga        40

<210> SEQ ID NO 55
<211> LENGTH: 40
<212> TYPE: DNA
<213> ORGANISM: Homo sapiens

<400> SEQUENCE: 55
cgatctccca aaaggagaag tctgaccagt cttttctaca        40

<210> SEQ ID NO 56
<211> LENGTH: 40
<212> TYPE: DNA
<213> ORGANISM: Homo sapiens

<400> SEQUENCE: 56
cgatctccca aaaggagaag cccctcccct cgccgagaaa        40

<210> SEQ ID NO 57
<211> LENGTH: 40
<212> TYPE: DNA
<213> ORGANISM: Homo sapiens

<400> SEQUENCE: 57
ttattttaca caatccaaag ccagttgcag ggtctgatga        40

<210> SEQ ID NO 58
<211> LENGTH: 40
<212> TYPE: DNA
<213> ORGANISM: Homo sapiens

<400> SEQUENCE: 58
ttattttaca caatccaaag cttatggtgc attaccagcc        40

<210> SEQ ID NO 59
<211> LENGTH: 40
<212> TYPE: DNA
<213> ORGANISM: Homo sapiens

<400> SEQUENCE: 59
tgcctgtgga catcaccaag cctcgtcctc cccaggtgcc        40

<210> SEQ ID NO 60
<211> LENGTH: 40
<212> TYPE: DNA
<213> ORGANISM: Homo sapiens

<400> SEQUENCE: 60
tgcctgtgga catcaccaag gtgccgcctg cccctgtcaa        40

<210> SEQ ID NO 61
<211> LENGTH: 40
<212> TYPE: DNA
<213> ORGANISM: Homo sapiens

<400> SEQUENCE: 61
agttagaatc caaaccagag tgttgtcttt tctcccccca                    40

<210> SEQ ID NO 62
<211> LENGTH: 40
<212> TYPE: DNA
<213> ORGANISM: Homo sapiens

<400> SEQUENCE: 62
agttagaatc caaaccagag ctcctggtac agtttgttca                    40

<210> SEQ ID NO 63
<211> LENGTH: 40
<212> TYPE: DNA
<213> ORGANISM: Homo sapiens

<400> SEQUENCE: 63
atatgctgga atggttcctt gtcacaatgc acgacacccg                    40

<210> SEQ ID NO 64
<211> LENGTH: 40
<212> TYPE: DNA
<213> ORGANISM: Homo sapiens

<400> SEQUENCE: 64
atatgctgga atggttcctt accgaccgct cgggagctcg                    40

<210> SEQ ID NO 65
<211> LENGTH: 40
<212> TYPE: DNA
<213> ORGANISM: Homo sapiens

<400> SEQUENCE: 65
atcagaaatt cgtacaacag gtttcttta aagctcctgg                     40

<210> SEQ ID NO 66
<211> LENGTH: 40
<212> TYPE: DNA
<213> ORGANISM: Homo sapiens

<400> SEQUENCE: 66
atcagaaatt cgtacaacag ctcctggagc tttttgatag                    40

<210> SEQ ID NO 67
<211> LENGTH: 40
<212> TYPE: DNA
<213> ORGANISM: Homo sapiens

<400> SEQUENCE: 67
aaatgaagaa actcctaaag cctctctctt tctttgttta                    40

<210> SEQ ID NO 68
<211> LENGTH: 40
<212> TYPE: DNA
<213> ORGANISM: Homo sapiens

<400> SEQUENCE: 68
aaatgaagaa actcctaaag ataaagtcct gtttatgacc                    40

<210> SEQ ID NO 69
<211> LENGTH: 40
<212> TYPE: DNA
<213> ORGANISM: Homo sapiens

<400> SEQUENCE: 69
cataaaattc taacagctaa ttctctttcc tctgtcttca         40

<210> SEQ ID NO 70
<211> LENGTH: 40
<212> TYPE: DNA
<213> ORGANISM: Homo sapiens

<400> SEQUENCE: 70
cataaaattc taacagctaa gcaagcactg agcgaggtga         40

<210> SEQ ID NO 71
<211> LENGTH: 40
<212> TYPE: DNA
<213> ORGANISM: Homo sapiens

<400> SEQUENCE: 71
gcctgccttt gatgccctgg attttgcccg aacaggtcag         40

<210> SEQ ID NO 72
<211> LENGTH: 40
<212> TYPE: DNA
<213> ORGANISM: Homo sapiens

<400> SEQUENCE: 72
gcctgccttt gatgccctgg gtcagttgac tggcggctat         40

<210> SEQ ID NO 73
<211> LENGTH: 40
<212> TYPE: DNA
<213> ORGANISM: Homo sapiens

<400> SEQUENCE: 73
ccaagctggt gtgcgcacag gcctctcttc ccgcccaggc         40

<210> SEQ ID NO 74
<211> LENGTH: 40
<212> TYPE: DNA
<213> ORGANISM: Homo sapiens

<400> SEQUENCE: 74
ccaagctggt gtgcgcacag gcatcatcgg gaagaagcac         40

<210> SEQ ID NO 75
<211> LENGTH: 40
<212> TYPE: DNA
<213> ORGANISM: Homo sapiens

<400> SEQUENCE: 75
ctcctttggg tttgggccag gccccaggtc ccaccacagc         40

<210> SEQ ID NO 76
<211> LENGTH: 40
<212> TYPE: DNA
<213> ORGANISM: Homo sapiens

<400> SEQUENCE: 76
ctcctttggg tttgggccag tgacctggct tgtcctcagc         40

<210> SEQ ID NO 77
<211> LENGTH: 40
<212> TYPE: DNA
<213> ORGANISM: Homo sapiens

<400> SEQUENCE: 77
aatattgctt taccaaacag ggacccctte cccttcccca                              40

<210> SEQ ID NO 78
<211> LENGTH: 40
<212> TYPE: DNA
<213> ORGANISM: Homo sapiens

<400> SEQUENCE: 78
aatattgctt taccaaacag gtcacggagg agtaaagtat                              40

<210> SEQ ID NO 79
<211> LENGTH: 40
<212> TYPE: DNA
<213> ORGANISM: Homo sapiens

<400> SEQUENCE: 79
cagttataaa ctctagagtg agtttatttt ccttttacaa                              40

<210> SEQ ID NO 80
<211> LENGTH: 40
<212> TYPE: DNA
<213> ORGANISM: Homo sapiens

<400> SEQUENCE: 80
cagttataaa ctctagagtg cttactgcag tgcatggtat                              40

<210> SEQ ID NO 81
<211> LENGTH: 40
<212> TYPE: DNA
<213> ORGANISM: Homo sapiens

<400> SEQUENCE: 81
gcctgccccg gaaactcaag atgttcagcg atgcaggtag                              40

<210> SEQ ID NO 82
<211> LENGTH: 40
<212> TYPE: DNA
<213> ORGANISM: Homo sapiens

<400> SEQUENCE: 82
gcctgccccg gaaactcaag atggcggtgg gacccccga                               40

<210> SEQ ID NO 83
<211> LENGTH: 40
<212> TYPE: DNA
<213> ORGANISM: Homo sapiens

<400> SEQUENCE: 83
ttcaggaggt ggagcaccag ataatttttt tcctcacaca                              40

<210> SEQ ID NO 84
<211> LENGTH: 40
<212> TYPE: DNA
<213> ORGANISM: Homo sapiens

<400> SEQUENCE: 84
ttcaggaggt ggagcaccag ttgcggtctt gtagtaagag                              40

<210> SEQ ID NO 85
<211> LENGTH: 40
<212> TYPE: DNA
<213> ORGANISM: Homo sapiens

<400> SEQUENCE: 85
ggatccttca cccgtgtctg tctttgcaga caggttctgt                    40

<210> SEQ ID NO 86
<211> LENGTH: 40
<212> TYPE: DNA
<213> ORGANISM: Homo sapiens

<400> SEQUENCE: 86
ggatccttca cccgtgtctg gacccgtgca tctcttccga                    40

<210> SEQ ID NO 87
<211> LENGTH: 40
<212> TYPE: DNA
<213> ORGANISM: Homo sapiens

<400> SEQUENCE: 87
atttggatcc tgtgttcctc ttttttttctg ttaaagatac                    40

<210> SEQ ID NO 88
<211> LENGTH: 40
<212> TYPE: DNA
<213> ORGANISM: Homo sapiens

<400> SEQUENCE: 88
atttggatcc tgtgttcctc atacaactag accaaaacga                    40

<210> SEQ ID NO 89
<211> LENGTH: 40
<212> TYPE: DNA
<213> ORGANISM: Homo sapiens

<400> SEQUENCE: 89
agatgtcagg tgggagaaag cctttgattg tcttttcagc                    40

<210> SEQ ID NO 90
<211> LENGTH: 40
<212> TYPE: DNA
<213> ORGANISM: Homo sapiens

<400> SEQUENCE: 90
agatgtcagg tgggagaaag ctgttggaga cacagttgca                    40

<210> SEQ ID NO 91
<211> LENGTH: 40
<212> TYPE: DNA
<213> ORGANISM: Homo sapiens

<400> SEQUENCE: 91
agaaagagca taaattggaa atattggaca tgggcgtatc                    40

<210> SEQ ID NO 92
<211> LENGTH: 40
<212> TYPE: DNA
<213> ORGANISM: Homo sapiens

<400> SEQUENCE: 92
agaaagagca taaattggaa gagtacaagc gcaagctagc                    40

<210> SEQ ID NO 93
<211> LENGTH: 40
<212> TYPE: DNA

<213> ORGANISM: Homo sapiens

<400> SEQUENCE: 93
tcagccctct gaactacaaa ggtgtttgtt cacagagatc 40

<210> SEQ ID NO 94
<211> LENGTH: 40
<212> TYPE: DNA
<213> ORGANISM: Homo sapiens

<400> SEQUENCE: 94
tcagccctct gaactacaaa acagaagagc ctgcaagtga 40

<210> SEQ ID NO 95
<211> LENGTH: 40
<212> TYPE: DNA
<213> ORGANISM: Homo sapiens

<400> SEQUENCE: 95
ccggggcctt cgtgagaccg cttgttttct gcaggtgcag 40

<210> SEQ ID NO 96
<211> LENGTH: 40
<212> TYPE: DNA
<213> ORGANISM: Homo sapiens

<400> SEQUENCE: 96
ccggggcctt cgtgagaccg gtgcaggcct ggggtagtct 40

<210> SEQ ID NO 97
<211> LENGTH: 40
<212> TYPE: DNA
<213> ORGANISM: Homo sapiens

<400> SEQUENCE: 97
caagtccatc tctaattcag ggtctgactt gcagccaact 40

<210> SEQ ID NO 98
<211> LENGTH: 40
<212> TYPE: DNA
<213> ORGANISM: Homo sapiens

<400> SEQUENCE: 98
caagtccatc tctaattcag gcaaggccag gccccagccc 40

<210> SEQ ID NO 99
<211> LENGTH: 40
<212> TYPE: DNA
<213> ORGANISM: Homo sapiens

<400> SEQUENCE: 99
caagatagat attatagcag gtggcttttg ttttacagaa 40

<210> SEQ ID NO 100
<211> LENGTH: 40
<212> TYPE: DNA
<213> ORGANISM: Homo sapiens

<400> SEQUENCE: 100
caagatagat attatagcag aacttcgata tgacctgcca 40

<210> SEQ ID NO 101
<211> LENGTH: 40

<212> TYPE: DNA
<213> ORGANISM: Homo sapiens

<400> SEQUENCE: 101
gaaaccaact aaaggcaaag cccatttttcc ttctttcgca                              40

<210> SEQ ID NO 102
<211> LENGTH: 40
<212> TYPE: DNA
<213> ORGANISM: Homo sapiens

<400> SEQUENCE: 102
gaaaccaact aaaggcaaag gtaaaaaaca tgaagcagat                               40

<210> SEQ ID NO 103
<211> LENGTH: 40
<212> TYPE: DNA
<213> ORGANISM: Homo sapiens

<400> SEQUENCE: 103
ggggacagtg aaatttggtg gcaagaatga ggtgacactg                               40

<210> SEQ ID NO 104
<211> LENGTH: 40
<212> TYPE: DNA
<213> ORGANISM: Homo sapiens

<400> SEQUENCE: 104
ggggacagtg aaatttggtg ggcagctgct ttcctttgac                               40

<210> SEQ ID NO 105
<211> LENGTH: 40
<212> TYPE: DNA
<213> ORGANISM: Homo sapiens

<400> SEQUENCE: 105
ctcagagcca ggctgtagag atgttttcta cctttccaca                               40

<210> SEQ ID NO 106
<211> LENGTH: 40
<212> TYPE: DNA
<213> ORGANISM: Homo sapiens

<400> SEQUENCE: 106
ctcagagcca ggctgtagag tccgctctat caagctgaag                               40

<210> SEQ ID NO 107
<211> LENGTH: 40
<212> TYPE: DNA
<213> ORGANISM: Homo sapiens

<400> SEQUENCE: 107
gaggagccac actctgacag atacctggct gagagctggc                               40

<210> SEQ ID NO 108
<211> LENGTH: 40
<212> TYPE: DNA
<213> ORGANISM: Homo sapiens

<400> SEQUENCE: 108
gaggagccac actctgacag tgagggtgcg gggtcaggcg                               40

<210> SEQ ID NO 109

```
<211> LENGTH: 40
<212> TYPE: DNA
<213> ORGANISM: Homo sapiens

<400> SEQUENCE: 109
actcgcgcct cttccatctg ttttgtcgca gccggaatac                    40

<210> SEQ ID NO 110
<211> LENGTH: 40
<212> TYPE: DNA
<213> ORGANISM: Homo sapiens

<400> SEQUENCE: 110
actcgcgcct cttccatctg ccggaataca cctggcgtct                    40

<210> SEQ ID NO 111
<211> LENGTH: 40
<212> TYPE: DNA
<213> ORGANISM: Homo sapiens

<400> SEQUENCE: 111
acttccttag tggtttccag gttgccaggg cactgcagct                    40

<210> SEQ ID NO 112
<211> LENGTH: 40
<212> TYPE: DNA
<213> ORGANISM: Homo sapiens

<400> SEQUENCE: 112
acttccttag tggtttccag gtggtggtgc tcaccaacac                    40

<210> SEQ ID NO 113
<211> LENGTH: 40
<212> TYPE: DNA
<213> ORGANISM: Homo sapiens

<400> SEQUENCE: 113
gtcttgagaa ttggaagcag gtggtggtgc tcaccaacac                    40

<210> SEQ ID NO 114
<211> LENGTH: 40
<212> TYPE: DNA
<213> ORGANISM: Homo sapiens

<400> SEQUENCE: 114
tccagagccc acagtcccag ctgcacctta cctgctcccc                    40

<210> SEQ ID NO 115
<211> LENGTH: 40
<212> TYPE: DNA
<213> ORGANISM: Homo sapiens

<400> SEQUENCE: 115
tccagagccc acagtcccag gggtccatga tgccgagctg                    40

<210> SEQ ID NO 116
<211> LENGTH: 40
<212> TYPE: DNA
<213> ORGANISM: Homo sapiens

<400> SEQUENCE: 116
ccaagttttg tgaaagaaag tgtatgtttt gttcacgaca                    40
```

```
<210> SEQ ID NO 117
<211> LENGTH: 40
<212> TYPE: DNA
<213> ORGANISM: Homo sapiens

<400> SEQUENCE: 117
ccaagttttg tgaaagaaag aacatcagat accaaaccta                40

<210> SEQ ID NO 118
<211> LENGTH: 40
<212> TYPE: DNA
<213> ORGANISM: Homo sapiens

<400> SEQUENCE: 118
tcttcacaga acacactcaa gtgcttgtag gtcttggtgc                40

<210> SEQ ID NO 119
<211> LENGTH: 40
<212> TYPE: DNA
<213> ORGANISM: Homo sapiens

<400> SEQUENCE: 119
tcttcacaga acacactcaa ccccctgcct gggatgcgcc                40

<210> SEQ ID NO 120
<211> LENGTH: 40
<212> TYPE: DNA
<213> ORGANISM: Homo sapiens

<400> SEQUENCE: 120
gagaagctca cgattaccag gcacctcatt gtgaacatgc                40

<210> SEQ ID NO 121
<211> LENGTH: 40
<212> TYPE: DNA
<213> ORGANISM: Homo sapiens

<400> SEQUENCE: 121
tcttggagga gccagtacag gcacctcatt gtgaacatgc                40

<210> SEQ ID NO 122
<211> LENGTH: 40
<212> TYPE: DNA
<213> ORGANISM: Homo sapiens

<400> SEQUENCE: 122 gtgggggggcc attgctgcat tttgtatttt ccaggtacag               40

<210> SEQ ID NO 123
<211> LENGTH: 40
<212> TYPE: DNA
<213> ORGANISM: Homo sapiens

<400> SEQUENCE: 123 gtgggggggcc attgctgcat gtacagtctt tgcccgctgc               40

<210> SEQ ID NO 124
<211> LENGTH: 40
<212> TYPE: DNA
<213> ORGANISM: Homo sapiens

<400> SEQUENCE: 124
tactgaaatg tgatgaacat atccaggtaa tcgagagacc                40
```

<210> SEQ ID NO 125
<211> LENGTH: 40
<212> TYPE: DNA
<213> ORGANISM: Homo sapiens

<400> SEQUENCE: 125
tactgaaatg tgatgaacat atccagaagc ttggaagctg                              40

<210> SEQ ID NO 126
<211> LENGTH: 40
<212> TYPE: DNA
<213> ORGANISM: Homo sapiens

<400> SEQUENCE: 126
gaatctctta tcattgatgg ttcctgttca gattgtgatg                              40

<210> SEQ ID NO 127
<211> LENGTH: 40
<212> TYPE: DNA
<213> ORGANISM: Homo sapiens

<400> SEQUENCE: 127
gaatctctta tcattgatgg tttatttatg gagattctta                              40

<210> SEQ ID NO 128
<211> LENGTH: 40
<212> TYPE: DNA
<213> ORGANISM: Homo sapiens

<400> SEQUENCE: 128
ctccatgctc agctctctgg tttctttcag ggcctgccat                              40

<210> SEQ ID NO 129
<211> LENGTH: 40
<212> TYPE: DNA
<213> ORGANISM: Homo sapiens

<400> SEQUENCE: 129
ctccatgctc agctctctgg ggaaggtgaa gaaggagctg                              40

<210> SEQ ID NO 130
<211> LENGTH: 40
<212> TYPE: DNA
<213> ORGANISM: Homo sapiens

<400> SEQUENCE: 130
cttggagctg acgccgacgg ggaactgaca agatcacatt                              40

<210> SEQ ID NO 131
<211> LENGTH: 40
<212> TYPE: DNA
<213> ORGANISM: Homo sapiens

<400> SEQUENCE: 131
cttggagctg acgccgacgg tttattgcag ggaactgaca                              40

<210> SEQ ID NO 132
<211> LENGTH: 40
<212> TYPE: DNA
<213> ORGANISM: Homo sapiens

<400> SEQUENCE: 132
tccagcctgg gcgacagaag tcttgtctca agaagaaaac                              40

<210> SEQ ID NO 133
<211> LENGTH: 40
<212> TYPE: DNA
<213> ORGANISM: Homo sapiens

<400> SEQUENCE: 133
ctatcaaaag aggatatgtt tcttgtctca agaagaaaac               40

<210> SEQ ID NO 134
<211> LENGTH: 40
<212> TYPE: DNA
<213> ORGANISM: Homo sapiens

<400> SEQUENCE: 134
tgcggagcaa gagtggacat cgtttgtttc ccatttctcc               40

<210> SEQ ID NO 135
<211> LENGTH: 40
<212> TYPE: DNA
<213> ORGANISM: Homo sapiens

<400> SEQUENCE: 135
tgcggagcaa gagtggacat aaactttaca ttttcctgtt               40

<210> SEQ ID NO 136
<211> LENGTH: 40
<212> TYPE: DNA
<213> ORGANISM: Homo sapiens

<400> SEQUENCE: 136
agtccagccc cagcatggca cctctcccca ctcctaggtc               40

<210> SEQ ID NO 137
<211> LENGTH: 40
<212> TYPE: DNA
<213> ORGANISM: Homo sapiens

<400> SEQUENCE: 137
agtccagccc cagcatggca gtcctgtaca tccaggcctt               40

<210> SEQ ID NO 138
<211> LENGTH: 40
<212> TYPE: DNA
<213> ORGANISM: Homo sapiens

<400> SEQUENCE: 138
caagcaggtc caaagagaga ttttggtaaa cagagctcca               40

<210> SEQ ID NO 139
<211> LENGTH: 40
<212> TYPE: DNA
<213> ORGANISM: Homo sapiens

<400> SEQUENCE: 139
caagcaggtc caaagagaga agctccaaga gtcaggatcg               40

<210> SEQ ID NO 140
<211> LENGTH: 40
<212> TYPE: DNA
<213> ORGANISM: Homo sapiens

<400> SEQUENCE: 140
ctctctccaa cctgcattct catctcgccc acagttggat                   40

<210> SEQ ID NO 141
<211> LENGTH: 40
<212> TYPE: DNA
<213> ORGANISM: Homo sapiens

<400> SEQUENCE: 141
ctctctccaa cctgcattct ttggatcgat caacccggga                   40

<210> SEQ ID NO 142
<211> LENGTH: 40
<212> TYPE: DNA
<213> ORGANISM: Homo sapiens

<400> SEQUENCE: 142
caccacgccg aggccacgag acattgatgg aagcagaaac                   40

<210> SEQ ID NO 143
<211> LENGTH: 40
<212> TYPE: DNA
<213> ORGANISM: Homo sapiens

<400> SEQUENCE: 143
caccacgccg aggccacgag tatttcatag acattgatgg                   40

<210> SEQ ID NO 144
<211> LENGTH: 40
<212> TYPE: DNA
<213> ORGANISM: Homo sapiens

<400> SEQUENCE: 144
gcctcactga gcaaccaaga gtagtgactt gtcaggagga                   40

<210> SEQ ID NO 145
<211> LENGTH: 40
<212> TYPE: DNA
<213> ORGANISM: Homo sapiens

<400> SEQUENCE: 145
gcctcactga gcaaccaaga gtgtcagttg tacccgaggc                   40

<210> SEQ ID NO 146
<211> LENGTH: 40
<212> TYPE: DNA
<213> ORGANISM: Homo sapiens

<400> SEQUENCE: 146
gggagatgga taccgacttg ctcaatttca gtgatcaacg                   40

<210> SEQ ID NO 147
<211> LENGTH: 40
<212> TYPE: DNA
<213> ORGANISM: Homo sapiens

<400> SEQUENCE: 147
gggagatgga taccgacttg tgatcaacga tgggaagctg                   40

<210> SEQ ID NO 148
<211> LENGTH: 40
<212> TYPE: DNA
<213> ORGANISM: Homo sapiens

<400> SEQUENCE: 148
aggatgtggc tggcacagaa gtgtcatcag gtccctgcag    40

<210> SEQ ID NO 149
<211> LENGTH: 40
<212> TYPE: DNA
<213> ORGANISM: Homo sapiens

<400> SEQUENCE: 149
aggatgtggc tggcacagaa atgagtcagt ctgacagtgg    40

<210> SEQ ID NO 150
<211> LENGTH: 40
<212> TYPE: DNA
<213> ORGANISM: Homo sapiens

<400> SEQUENCE: 150
ttctccagga ccttgccaga ccttttctat agggaatcaa    40

<210> SEQ ID NO 151
<211> LENGTH: 40
<212> TYPE: DNA
<213> ORGANISM: Homo sapiens

<400> SEQUENCE: 151
ttctccagga ccttgccaga ggaatcaaag actccatctg    40

<210> SEQ ID NO 152
<211> LENGTH: 40
<212> TYPE: DNA
<213> ORGANISM: Homo sapiens

<400> SEQUENCE: 152
agctgaaatt tccagtaaag gggggtttta ttcttctttt    40

<210> SEQ ID NO 153
<211> LENGTH: 40
<212> TYPE: DNA
<213> ORGANISM: Homo sapiens

<400> SEQUENCE: 153
agctgaaatt tccagtaaag cctggagatt tgaaaagag    40

<210> SEQ ID NO 154
<211> LENGTH: 40
<212> TYPE: DNA
<213> ORGANISM: Homo sapiens

<400> SEQUENCE: 154
gatgtcactg tgactatcaa gggccgtctt tcttctaggt    40

<210> SEQ ID NO 155
<211> LENGTH: 40
<212> TYPE: DNA
<213> ORGANISM: Homo sapiens

<400> SEQUENCE: 155
gatgtcactg tgactatcaa gtcttccatc gacagtgaac    40

<210> SEQ ID NO 156
<211> LENGTH: 40
<212> TYPE: DNA
<213> ORGANISM: Homo sapiens

<400> SEQUENCE: 156
tatccattcc tgagttacag tataaacttc cttctcatgc                                40

<210> SEQ ID NO 157
<211> LENGTH: 40
<212> TYPE: DNA
<213> ORGANISM: Homo sapiens

<400> SEQUENCE: 157
tatccattcc tgagttacag tgtcttaata ttgaaaatga                                40

<210> SEQ ID NO 158
<211> LENGTH: 40
<212> TYPE: DNA
<213> ORGANISM: Homo sapiens

<400> SEQUENCE: 158
tacaagagct gggtggagag ggtcccaaca ggtattatcg                                40

<210> SEQ ID NO 159
<211> LENGTH: 40
<212> TYPE: DNA
<213> ORGANISM: Homo sapiens

<400> SEQUENCE: 159
tacaagagct gggtggagag gtattatcga gacattgcaa                                40

<210> SEQ ID NO 160
<211> LENGTH: 40
<212> TYPE: DNA
<213> ORGANISM: Homo sapiens

<400> SEQUENCE: 160
agccatttat tgtcccgtg ggaaccaatc tgccctttg                                  40

<210> SEQ ID NO 161
<211> LENGTH: 40
<212> TYPE: DNA
<213> ORGANISM: Homo sapiens

<400> SEQUENCE: 161
agccatttat tgtcccgtg ggttttttc cagggaacca                                  40

<210> SEQ ID NO 162
<211> LENGTH: 40
<212> TYPE: DNA
<213> ORGANISM: Homo sapiens

<400> SEQUENCE: 162
agttacaacg aacacctcag tgactctttt acaggaggca                                40

<210> SEQ ID NO 163
<211> LENGTH: 40
<212> TYPE: DNA
<213> ORGANISM: Homo sapiens

<400> SEQUENCE: 163
agttacaacg aacacctcag gaggcaataa cagatggctt                                40

<210> SEQ ID NO 164
<211> LENGTH: 40
<212> TYPE: DNA
<213> ORGANISM: Homo sapiens

<400> SEQUENCE: 164
tcacacagga taatttgaaa gtgtcagttg tacccgaggc                                40

<210> SEQ ID NO 165
<211> LENGTH: 40
<212> TYPE: DNA
<213> ORGANISM: Homo sapiens

<400> SEQUENCE: 165
cggcgcgggc aacctggcgg cccccatttc aggtctgaag                                40

<210> SEQ ID NO 166
<211> LENGTH: 40
<212> TYPE: DNA
<213> ORGANISM: Homo sapiens

<400> SEQUENCE: 166
cggcgcgggc aacctggcgg gtctgaaggg gcgtctcgat                                40

<210> SEQ ID NO 167
<211> LENGTH: 40
<212> TYPE: DNA
<213> ORGANISM: Homo sapiens

<400> SEQUENCE: 167
ccaccgccat cgacgtgcag tacctctttt taccaccagg                                40

<210> SEQ ID NO 168
<211> LENGTH: 40
<212> TYPE: DNA
<213> ORGANISM: Homo sapiens

<400> SEQUENCE: 168
ccaccgccat cgacgtgcag gtggggctcc tgtacgaaga                                40

<210> SEQ ID NO 169
<211> LENGTH: 40
<212> TYPE: DNA
<213> ORGANISM: Homo sapiens

<400> SEQUENCE: 169
ctatgggctc actcctctgg tcctcctgtt gcagttcgtc                                40

<210> SEQ ID NO 170
<211> LENGTH: 40
<212> TYPE: DNA
<213> ORGANISM: Homo sapiens

<400> SEQUENCE: 170
ctatgggctc actcctctgg ttcgtcgcct gcagcttcga                                40

<210> SEQ ID NO 171
<211> LENGTH: 40
<212> TYPE: DNA
<213> ORGANISM: Homo sapiens

<400> SEQUENCE: 171
tatctctggg aaaaaacaca tttctttttt tgcaggggac                                40

<210> SEQ ID NO 172
<211> LENGTH: 40
<212> TYPE: DNA

<213> ORGANISM: Homo sapiens

<400> SEQUENCE: 172
tatctctggg aaaaaacaca gggacctgat ggggtgcagc                    40

<210> SEQ ID NO 173
<211> LENGTH: 40
<212> TYPE: DNA
<213> ORGANISM: Homo sapiens

<400> SEQUENCE: 173
tcatccagag cccagagcag ggatgtctg accagatgca                     40

<210> SEQ ID NO 174
<211> LENGTH: 40
<212> TYPE: DNA
<213> ORGANISM: Homo sapiens

<400> SEQUENCE: 174
tcatccagag cccagagcag atgcaagtgc tgctggacca                    40

<210> SEQ ID NO 175
<211> LENGTH: 40
<212> TYPE: DNA
<213> ORGANISM: Homo sapiens

<400> SEQUENCE: 175
ccaaggactg cactgtgaag gcccccgccc cgcgacctgg                    40

<210> SEQ ID NO 176
<211> LENGTH: 40
<212> TYPE: DNA
<213> ORGANISM: Homo sapiens

<400> SEQUENCE: 176
ccaaggactg cactgtgaag atctggagca acgacctgac                    40

<210> SEQ ID NO 177
<211> LENGTH: 40
<212> TYPE: DNA
<213> ORGANISM: Homo sapiens

<400> SEQUENCE: 177
cccgagctca gagagtaaat tctccttaca gacactgaaa                    40

<210> SEQ ID NO 178
<211> LENGTH: 40
<212> TYPE: DNA
<213> ORGANISM: Homo sapiens

<400> SEQUENCE: 178
cccgagctca gagagtaaat atgagatcgc ctctgtccca                    40

<210> SEQ ID NO 179
<211> LENGTH: 40
<212> TYPE: DNA
<213> ORGANISM: Homo sapiens

<400> SEQUENCE: 179
gtgcttggag ccctgtgcag actttccgca gggtgtgcgc                    40

<210> SEQ ID NO 180
<211> LENGTH: 40

<212> TYPE: DNA
<213> ORGANISM: Homo sapiens

<400> SEQUENCE: 180
gtgcttggag ccctgtgcag cctggtgaca gactttccgc                          40

<210> SEQ ID NO 181
<211> LENGTH: 40
<212> TYPE: DNA
<213> ORGANISM: Homo sapiens

<400> SEQUENCE: 181
gctggacacg ctgaccaagg catcacttag gagctgctac                          40

<210> SEQ ID NO 182
<211> LENGTH: 40
<212> TYPE: DNA
<213> ORGANISM: Homo sapiens

<400> SEQUENCE: 182
gctggacacg ctgaccaagg tgttggtagc cttatatgaa                          40

<210> SEQ ID NO 183
<211> LENGTH: 40
<212> TYPE: DNA
<213> ORGANISM: Homo sapiens

<400> SEQUENCE: 183
cccctgagat gaagaaagag ctccctgttg acagctgcct                          40

<210> SEQ ID NO 184
<211> LENGTH: 40
<212> TYPE: DNA
<213> ORGANISM: Homo sapiens

<400> SEQUENCE: 184
cccctgagat gaagaaagag ctcctgagca gcctgactga                          40

<210> SEQ ID NO 185
<211> LENGTH: 40
<212> TYPE: DNA
<213> ORGANISM: Homo sapiens

<400> SEQUENCE: 185
ctgaactttg ggcctgaatg atgtgtttgg accccgaata                          40

<210> SEQ ID NO 186
<211> LENGTH: 40
<212> TYPE: DNA
<213> ORGANISM: Homo sapiens

<400> SEQUENCE: 186
ctgaactttg ggcctgaatg gctccgagct ctgtccagtg                          40

<210> SEQ ID NO 187
<211> LENGTH: 40
<212> TYPE: DNA
<213> ORGANISM: Homo sapiens

<400> SEQUENCE: 187
agatcgcctg gctcagtcag tttttctctc tagacatggc                          40

<210> SEQ ID NO 188

```
<211> LENGTH: 40
<212> TYPE: DNA
<213> ORGANISM: Homo sapiens

<400> SEQUENCE: 188
agatcgcctg gctcagtcag acatggccaa acgtgtagcc                         40

<210> SEQ ID NO 189
<211> LENGTH: 40
<212> TYPE: DNA
<213> ORGANISM: Homo sapiens

<400> SEQUENCE: 189
ggaggtggac ctgagtgaac aatttctccc ctcttttag                          40

<210> SEQ ID NO 190
<211> LENGTH: 40
<212> TYPE: DNA
<213> ORGANISM: Homo sapiens

<400> SEQUENCE: 190
ggaggtggac ctgagtgaac cacccaactg gtcagctaac                         40

<210> SEQ ID NO 191
<211> LENGTH: 40
<212> TYPE: DNA
<213> ORGANISM: Homo sapiens

<400> SEQUENCE: 191
tacagatggt aaaatgcaag tttgattttt catatccagg                         40

<210> SEQ ID NO 192
<211> LENGTH: 40
<212> TYPE: DNA
<213> ORGANISM: Homo sapiens

<400> SEQUENCE: 192
tacagatggt aaaatgcaag gaattgccac aagcagtctg                         40

<210> SEQ ID NO 193
<211> LENGTH: 40
<212> TYPE: DNA
<213> ORGANISM: Homo sapiens

<400> SEQUENCE: 193
ccctgctcat cacctacggg tctgtcccag gctctctggg                         40

<210> SEQ ID NO 194
<211> LENGTH: 40
<212> TYPE: DNA
<213> ORGANISM: Homo sapiens

<400> SEQUENCE: 194
ccctgctcat cacctacggg ccctatgcca tcaatgggaa                         40

<210> SEQ ID NO 195
<211> LENGTH: 40
<212> TYPE: DNA
<213> ORGANISM: Homo sapiens

<400> SEQUENCE: 195
ggctcccatt ctggttaaag agtgttctca tttccaatag                         40
```

```
<210> SEQ ID NO 196
<211> LENGTH: 40
<212> TYPE: DNA
<213> ORGANISM: Homo sapiens

<400> SEQUENCE: 196
ggctcccatt ctggttaaag gccagtctgc catccatcca                              40

<210> SEQ ID NO 197
<211> LENGTH: 40
<212> TYPE: DNA
<213> ORGANISM: Homo sapiens

<400> SEQUENCE: 197
ctgcacttat aaatattcag tgttccacct tgcagacccg                              40

<210> SEQ ID NO 198
<211> LENGTH: 40
<212> TYPE: DNA
<213> ORGANISM: Homo sapiens

<400> SEQUENCE: 198
ctgcacttat aaatattcag acccgagggg aagctgcagc                              40

<210> SEQ ID NO 199
<211> LENGTH: 40
<212> TYPE: DNA
<213> ORGANISM: Homo sapiens

<400> SEQUENCE: 199
cgctggcacc atgaacccag tatttccagg accaagtgag                              40

<210> SEQ ID NO 200
<211> LENGTH: 40
<212> TYPE: DNA
<213> ORGANISM: Homo sapiens

<400> SEQUENCE: 200
cgctggcacc atgaacccag agagcagtat ctttattgag                              40

<210> SEQ ID NO 201
<211> LENGTH: 40
<212> TYPE: DNA
<213> ORGANISM: Homo sapiens

<400> SEQUENCE: 201
ccctagtctg attcctttag gttggtgtaa tcagctgggg                              40

<210> SEQ ID NO 202
<211> LENGTH: 40
<212> TYPE: DNA
<213> ORGANISM: Homo sapiens

<400> SEQUENCE: 202
ttccccatca acatcaaaag ttttgttgtc tgcagttcca                              40

<210> SEQ ID NO 203
<211> LENGTH: 40
<212> TYPE: DNA
<213> ORGANISM: Homo sapiens

<400> SEQUENCE: 203
ttccccatca acatcaaaag ttccaatggt ggcagtaaga                              40
```

<210> SEQ ID NO 204
<211> LENGTH: 40
<212> TYPE: DNA
<213> ORGANISM: Homo sapiens

<400> SEQUENCE: 204
ccagctgcat tgcaagttcg gactgtgagt ccctgcaggc                                40

<210> SEQ ID NO 205
<211> LENGTH: 40
<212> TYPE: DNA
<213> ORGANISM: Homo sapiens

<400> SEQUENCE: 205
ccagctgcat tgcaagttcg gggtgcggaa gactcacaac                                40

<210> SEQ ID NO 206
<211> LENGTH: 40
<212> TYPE: DNA
<213> ORGANISM: Homo sapiens

<400> SEQUENCE: 206
ggccagcccc cttctccacg gccttgccca ctaggtaacc                                40

<210> SEQ ID NO 207
<211> LENGTH: 40
<212> TYPE: DNA
<213> ORGANISM: Homo sapiens

<400> SEQUENCE: 207
ggccagcccc cttctccacg gtaaccatgt gcgaccgaaa                                40

<210> SEQ ID NO 208
<211> LENGTH: 40
<212> TYPE: DNA
<213> ORGANISM: Homo sapiens

<400> SEQUENCE: 208
cgctctccgc cttccagaag gggtctcctt atgccaggga                                40

<210> SEQ ID NO 209
<211> LENGTH: 40
<212> TYPE: DNA
<213> ORGANISM: Homo sapiens

<400> SEQUENCE: 209
agggagacgt tccctgcctg gggtctcctt atgccaggga                                40

<210> SEQ ID NO 210
<211> LENGTH: 40
<212> TYPE: DNA
<213> ORGANISM: Homo sapiens

<400> SEQUENCE: 210
ttggaagcga atcccccaag tcctttgttc ttttgcagtg                                40

<210> SEQ ID NO 211
<211> LENGTH: 40
<212> TYPE: DNA
<213> ORGANISM: Homo sapiens

<400> SEQUENCE: 211
ttggaagcga atcccccaag tgatgtatat ctctcatcaa                                40

<210> SEQ ID NO 212
<211> LENGTH: 40
<212> TYPE: DNA
<213> ORGANISM: Homo sapiens

<400> SEQUENCE: 212
ctacggcggt gccctcctca cccccttttc atcccccgcc                               40

<210> SEQ ID NO 213
<211> LENGTH: 40
<212> TYPE: DNA
<213> ORGANISM: Homo sapiens

<400> SEQUENCE: 213
ctacggcggt gccctcctca gcatctccct gatcatgtgg                               40

<210> SEQ ID NO 214
<211> LENGTH: 40
<212> TYPE: DNA
<213> ORGANISM: Homo sapiens

<400> SEQUENCE: 214
cctggtcgca gttcaacaag atgaggaatc tgatgctcag                               40

<210> SEQ ID NO 215
<211> LENGTH: 40
<212> TYPE: DNA
<213> ORGANISM: Homo sapiens

<400> SEQUENCE: 215
cctggtcgca gttcaacaag gagatcctgc tgggccgtgg                               40

<210> SEQ ID NO 216
<211> LENGTH: 40
<212> TYPE: DNA
<213> ORGANISM: Homo sapiens

<400> SEQUENCE: 216
caccaagcag aggcttccag tctgtctgcc ctttctgtag                               40

<210> SEQ ID NO 217
<211> LENGTH: 40
<212> TYPE: DNA
<213> ORGANISM: Homo sapiens

<400> SEQUENCE: 217
caccaagcag aggcttccag gccagaagcc ttttaaaagg                               40

<210> SEQ ID NO 218
<211> LENGTH: 40
<212> TYPE: DNA
<213> ORGANISM: Homo sapiens

<400> SEQUENCE: 218
gggactcccc caaagacaag cttttctttc agtaaatgta                               40

<210> SEQ ID NO 219
<211> LENGTH: 40
<212> TYPE: DNA
<213> ORGANISM: Homo sapiens

<400> SEQUENCE: 219
gggactcccc caaagacaag gtcccatttt cagtgcccaa                            40

<210> SEQ ID NO 220
<211> LENGTH: 40
<212> TYPE: DNA
<213> ORGANISM: Homo sapiens

<400> SEQUENCE: 220
gcactgctgt tcaacctcgg cttctcccttt cctctcaccc                           40

<210> SEQ ID NO 221
<211> LENGTH: 40
<212> TYPE: DNA
<213> ORGANISM: Homo sapiens

<400> SEQUENCE: 221
gcactgctgt tcaacctcgg gggcaagtat agcgcatttg                            40

<210> SEQ ID NO 222
<211> LENGTH: 40
<212> TYPE: DNA
<213> ORGANISM: Homo sapiens

<400> SEQUENCE: 222
acgagaccat tgccttcaag gagccctctc tgtccccgc                             40

<210> SEQ ID NO 223
<211> LENGTH: 40
<212> TYPE: DNA
<213> ORGANISM: Homo sapiens

<400> SEQUENCE: 223
acgagaccat tgccttcaag gtgccgagca gagagatcga                            40

<210> SEQ ID NO 224
<211> LENGTH: 40
<212> TYPE: DNA
<213> ORGANISM: Homo sapiens

<400> SEQUENCE: 224
aagatgtccc tgtgaggatt gtgtgtttgt ttccacaggc                            40

<210> SEQ ID NO 225
<211> LENGTH: 40
<212> TYPE: DNA
<213> ORGANISM: Homo sapiens

<400> SEQUENCE: 225
aagatgtccc tgtgaggatt gcactgggtg caagttcctg                            40

<210> SEQ ID NO 226
<211> LENGTH: 40
<212> TYPE: DNA
<213> ORGANISM: Homo sapiens

<400> SEQUENCE: 226
agagaagtcg tttcattcaa tctgattcct ttaggtcagc                            40

<210> SEQ ID NO 227
<211> LENGTH: 40
<212> TYPE: DNA
<213> ORGANISM: Homo sapiens

<400> SEQUENCE: 227
agcccagcag ttccgaaatg tctcccttct ccagcgcccc      40

<210> SEQ ID NO 228
<211> LENGTH: 40
<212> TYPE: DNA
<213> ORGANISM: Homo sapiens

<400> SEQUENCE: 228
agcccagcag ttccgaaatg cgcccccatt cctggaggac      40

<210> SEQ ID NO 229
<211> LENGTH: 40
<212> TYPE: DNA
<213> ORGANISM: Homo sapiens

<400> SEQUENCE: 229
ccctcccccg gctcctgtcg gcctgggcag catggccgta      40

<210> SEQ ID NO 230
<211> LENGTH: 40
<212> TYPE: DNA
<213> ORGANISM: Homo sapiens

<400> SEQUENCE: 230
tgattccaag caaaaaccag ccttcccta ggtcttcaga       40

<210> SEQ ID NO 231
<211> LENGTH: 40
<212> TYPE: DNA
<213> ORGANISM: Homo sapiens

<400> SEQUENCE: 231
tgattccaag caaaaaccag gctccatcta ctctttgaag      40

<210> SEQ ID NO 232
<211> LENGTH: 40
<212> TYPE: DNA
<213> ORGANISM: Homo sapiens

<400> SEQUENCE: 232
caagtccatc tctaattcag ccaactctca aggcaaggcc      40

<210> SEQ ID NO 233
<211> LENGTH: 40
<212> TYPE: DNA
<213> ORGANISM: Homo sapiens

<400> SEQUENCE: 233
ctatcaaaag aggatatgtt cattttagga ggccaaggca      40

<210> SEQ ID NO 234
<211> LENGTH: 40
<212> TYPE: DNA
<213> ORGANISM: Homo sapiens

<400> SEQUENCE: 234
gtcttccaat ggcccctcag ccttttctct aggaaatgat      40

<210> SEQ ID NO 235
<211> LENGTH: 40
<212> TYPE: DNA
<213> ORGANISM: Homo sapiens

```
<400> SEQUENCE: 235
gtcttccaat ggcccctcag gaaatgatac acctgaagaa                           40

<210> SEQ ID NO 236
<211> LENGTH: 40
<212> TYPE: DNA
<213> ORGANISM: Homo sapiens

<400> SEQUENCE: 236
gcacctcccc gggacgcctg cccttgtctg gaaagaagtt                           40

<210> SEQ ID NO 237
<211> LENGTH: 40
<212> TYPE: DNA
<213> ORGANISM: Homo sapiens

<400> SEQUENCE: 237
gcacctcccc gggacgcctg tcaccggact ttgctgagga                           40

<210> SEQ ID NO 238
<211> LENGTH: 40
<212> TYPE: DNA
<213> ORGANISM: Homo sapiens

<400> SEQUENCE: 238
tggaccccag accacaccgg aagaaatgag ccagaagtga                           40

<210> SEQ ID NO 239
<211> LENGTH: 40
<212> TYPE: DNA
<213> ORGANISM: Homo sapiens

<400> SEQUENCE: 239
gtcccggaac cacatgcacg aagaaatgag ccagaagtga                           40

<210> SEQ ID NO 240
<211> LENGTH: 40
<212> TYPE: DNA
<213> ORGANISM: Homo sapiens

<400> SEQUENCE: 240
tctgtgttcc catcgcacag gaatcctacg ccaacgtgaa                           40

<210> SEQ ID NO 241
<211> LENGTH: 40
<212> TYPE: DNA
<213> ORGANISM: Homo sapiens

<400> SEQUENCE: 241
tgtatgacgt cactgaccag gaatcctacg ccaacgtgaa                           40

<210> SEQ ID NO 242
<211> LENGTH: 40
<212> TYPE: DNA
<213> ORGANISM: Homo sapiens

<400> SEQUENCE: 242
ggaatatgat cccacccctcg tacttctcaa agaggatggc                          40

<210> SEQ ID NO 243
<211> LENGTH: 40
<212> TYPE: DNA
<213> ORGANISM: Homo sapiens
```

```
<400> SEQUENCE: 243
ggaatatgat cccaccctcg aatcaaccta ccgacaccaa                              40

<210> SEQ ID NO 244
<211> LENGTH: 40
<212> TYPE: DNA
<213> ORGANISM: Homo sapiens

<400> SEQUENCE: 244
gaactggcac cgacagacag tgtcccctcc ctccccagat                              40

<210> SEQ ID NO 245
<211> LENGTH: 40
<212> TYPE: DNA
<213> ORGANISM: Homo sapiens

<400> SEQUENCE: 245
gaactggcac cgacagacag atcctgtttc tggaccttgg                              40

<210> SEQ ID NO 246
<211> LENGTH: 40
<212> TYPE: DNA
<213> ORGANISM: Homo sapiens

<400> SEQUENCE: 246
tgatgaagac ctttccccag atctcttagg tgaagacatg                              40

<210> SEQ ID NO 247
<211> LENGTH: 40
<212> TYPE: DNA
<213> ORGANISM: Homo sapiens

<400> SEQUENCE: 247
tgatgaagac ctttccccag gccccgagca ttcctctgat                              40

<210> SEQ ID NO 248
<211> LENGTH: 40
<212> TYPE: DNA
<213> ORGANISM: Homo sapiens

<400> SEQUENCE: 248
ccaggccgac atggagagca gccccaccca caggcaagga                              40

<210> SEQ ID NO 249
<211> LENGTH: 40
<212> TYPE: DNA
<213> ORGANISM: Homo sapiens

<400> SEQUENCE: 249
ccaggccgac atggagagca gcaaggagcc cggcctgttt                              40

<210> SEQ ID NO 250
<211> LENGTH: 40
<212> TYPE: DNA
<213> ORGANISM: Homo sapiens

<400> SEQUENCE: 250
acatgaaggt ggacggagag ttctctgtga ccagacatga                              40

<210> SEQ ID NO 251
<211> LENGTH: 40
<212> TYPE: DNA
```

<213> ORGANISM: Homo sapiens

<400> SEQUENCE: 251
ttcgtccata tgtgcataag cttcttctct tttctctttt                            40

<210> SEQ ID NO 252
<211> LENGTH: 40
<212> TYPE: DNA
<213> ORGANISM: Homo sapiens

<400> SEQUENCE: 252
ttcgtccata tgtgcataag atcctcgtgg tcattgaacc                            40

<210> SEQ ID NO 253
<211> LENGTH: 40
<212> TYPE: DNA
<213> ORGANISM: Homo sapiens

<400> SEQUENCE: 253
agggatggcc agtggtagtg ggtctccaac tgaattcctt                            40

<210> SEQ ID NO 254
<211> LENGTH: 40
<212> TYPE: DNA
<213> ORGANISM: Homo sapiens

<400> SEQUENCE: 254
agaagggagc gatactacag ggtctccaac tgaattcctt                            40

<210> SEQ ID NO 255
<211> LENGTH: 40
<212> TYPE: DNA
<213> ORGANISM: Homo sapiens

<400> SEQUENCE: 255
ccaatgtggt tcaaaacaca ttatctcatc tgcagggtaa                            40

<210> SEQ ID NO 256
<211> LENGTH: 40
<212> TYPE: DNA
<213> ORGANISM: Homo sapiens

<400> SEQUENCE: 256
ccaatgtggt tcaaaacaca ggtaaaagtg tcttaactgg                            40

<210> SEQ ID NO 257
<211> LENGTH: 40
<212> TYPE: DNA
<213> ORGANISM: Homo sapiens

<400> SEQUENCE: 257
ccattgatgc aaacgcagca atggagtttc gctcctgttg                            40

<210> SEQ ID NO 258
<211> LENGTH: 40
<212> TYPE: DNA
<213> ORGANISM: Homo sapiens

<400> SEQUENCE: 258
ccattgatgc aaacgcagca gaacttgcca catcagactc                            40

<210> SEQ ID NO 259
<211> LENGTH: 40

```
<212> TYPE: DNA
<213> ORGANISM: Homo sapiens

<400> SEQUENCE: 259
gctgcatctg gaggtcctgg gaagcagaat ctggtaatat        40

<210> SEQ ID NO 260
<211> LENGTH: 40
<212> TYPE: DNA
<213> ORGANISM: Homo sapiens

<400> SEQUENCE: 260
cagtgttagt gaatgactat gaagcagaat ctggtaatat        40

<210> SEQ ID NO 261
<211> LENGTH: 40
<212> TYPE: DNA
<213> ORGANISM: Homo sapiens

<400> SEQUENCE: 261
acaaggacac agaaaacaag ccttcccaca caggccctgc        40

<210> SEQ ID NO 262
<211> LENGTH: 40
<212> TYPE: DNA
<213> ORGANISM: Homo sapiens

<400> SEQUENCE: 262
acaaggacac agaaaacaag ctggagcacc gctgcacctc        40

<210> SEQ ID NO 263
<211> LENGTH: 40
<212> TYPE: DNA
<213> ORGANISM: Homo sapiens

<400> SEQUENCE: 263
agctcggacc aagcgctcag ttttaaaatt gctatagctt        40

<210> SEQ ID NO 264
<211> LENGTH: 40
<212> TYPE: DNA
<213> ORGANISM: Homo sapiens

<400> SEQUENCE: 264
agctcggacc aagcgctcag cttagcctgc gacgcttatg        40

<210> SEQ ID NO 265
<211> LENGTH: 40
<212> TYPE: DNA
<213> ORGANISM: Homo sapiens

<400> SEQUENCE: 265 aggggctct ttatataatg tttgtgcctt tctttcgcag        40

<210> SEQ ID NO 266
<211> LENGTH: 40
<212> TYPE: DNA
<213> ORGANISM: Homo sapiens

<400> SEQUENCE: 266 aggggctct ttatataatg tgctgcatgg tgctgaacca        40

<210> SEQ ID NO 267
```

```
<211> LENGTH: 40
<212> TYPE: DNA
<213> ORGANISM: Homo sapiens

<400> SEQUENCE: 267
gcccccaact gagaagctgg gctggagtgc tgtggcacaa                              40

<210> SEQ ID NO 268
<211> LENGTH: 40
<212> TYPE: DNA
<213> ORGANISM: Homo sapiens

<400> SEQUENCE: 268
gcccccaact gagaagctgg tgcccttggt gtggtggaag                              40

<210> SEQ ID NO 269
<211> LENGTH: 40
<212> TYPE: DNA
<213> ORGANISM: Homo sapiens

<400> SEQUENCE: 269
gaacgagatc tcatcccact aactacaaag agctggagct                              40

<210> SEQ ID NO 270
<211> LENGTH: 40
<212> TYPE: DNA
<213> ORGANISM: Homo sapiens

<400> SEQUENCE: 270
agtatcagaa ggacaaaaag aactacaaag agctggagct                              40

<210> SEQ ID NO 271
<211> LENGTH: 40
<212> TYPE: DNA
<213> ORGANISM: Homo sapiens

<400> SEQUENCE: 271
tgaaggtcca gggcatggag cctgtctcct ggcagtgtct                              40

<210> SEQ ID NO 272
<211> LENGTH: 40
<212> TYPE: DNA
<213> ORGANISM: Homo sapiens

<400> SEQUENCE: 272
tgaaggtcca gggcatggag tgtctctatg gctgctacgt                              40

<210> SEQ ID NO 273
<211> LENGTH: 40
<212> TYPE: DNA
<213> ORGANISM: Homo sapiens

<400> SEQUENCE: 273
ggcggccgcg ccggctccag gaaatggcaa ctgctgacag                              40

<210> SEQ ID NO 274
<211> LENGTH: 40
<212> TYPE: DNA
<213> ORGANISM: Homo sapiens

<400> SEQUENCE: 274
ggcggccgcg ccggctccag ggccatgaag cccccaggag                              40
```

```
<210> SEQ ID NO 275
<211> LENGTH: 40
<212> TYPE: DNA
<213> ORGANISM: Homo sapiens

<400> SEQUENCE: 275
ccttccagct acatcgaaac gcatgaggat gttgtatttc                    40

<210> SEQ ID NO 276
<211> LENGTH: 40
<212> TYPE: DNA
<213> ORGANISM: Homo sapiens

<400> SEQUENCE: 276
ccttccagct acatcgaaac tttacctaaa gcagtaaaaa                    40

<210> SEQ ID NO 277
<211> LENGTH: 40
<212> TYPE: DNA
<213> ORGANISM: Homo sapiens

<400> SEQUENCE: 277
cttttctctt cttttatag gttgaacaaa tcctggcaga                     40

<210> SEQ ID NO 278
<211> LENGTH: 40
<212> TYPE: DNA
<213> ORGANISM: Homo sapiens

<400> SEQUENCE: 278
gatgtgatga actatcttcg gttgaacaaa tcctggcaga                    40

<210> SEQ ID NO 279
<211> LENGTH: 40
<212> TYPE: DNA
<213> ORGANISM: Homo sapiens

<400> SEQUENCE: 279
gcactgggca ttcagaaaag tctctcttcc tcacccctgc                    40

<210> SEQ ID NO 280
<211> LENGTH: 40
<212> TYPE: DNA
<213> ORGANISM: Homo sapiens

<400> SEQUENCE: 280
gcactgggca ttcagaaaag gttctccccg gaggtgctgg                    40

<210> SEQ ID NO 281
<211> LENGTH: 40
<212> TYPE: DNA
<213> ORGANISM: Homo sapiens

<400> SEQUENCE: 281
ctgtcacagg ggagtttacg tcttgcatgt ctctcttaca                    40

<210> SEQ ID NO 282
<211> LENGTH: 40
<212> TYPE: DNA
<213> ORGANISM: Homo sapiens

<400> SEQUENCE: 282
ctgtcacagg ggagtttacg ggaatgccag agcagtgggc                    40
```

```
<210> SEQ ID NO 283
<211> LENGTH: 40
<212> TYPE: DNA
<213> ORGANISM: Homo sapiens

<400> SEQUENCE: 283
gggtgcaaaa gatcctgcag ccattccagg ttgctgaggt                    40

<210> SEQ ID NO 284
<211> LENGTH: 40
<212> TYPE: DNA
<213> ORGANISM: Homo sapiens

<400> SEQUENCE: 284
gggtgcaaaa gatcctgcag gactacaaat ccctccagga                    40

<210> SEQ ID NO 285
<211> LENGTH: 40
<212> TYPE: DNA
<213> ORGANISM: Homo sapiens

<400> SEQUENCE: 285
ggcaccccaa aagatggcag atcagtctct ccctgttctc                    40

<210> SEQ ID NO 286
<211> LENGTH: 40
<212> TYPE: DNA
<213> ORGANISM: Homo sapiens

<400> SEQUENCE: 286
ggcaccccaa aagatggcag gtgcgagccc gaccaaggat                    40

<210> SEQ ID NO 287
<211> LENGTH: 40
<212> TYPE: DNA
<213> ORGANISM: Homo sapiens

<400> SEQUENCE: 287
gcatctcagc ccaagagaag tttctttgca ggttatattc                    40

<210> SEQ ID NO 288
<211> LENGTH: 40
<212> TYPE: DNA
<213> ORGANISM: Homo sapiens

<400> SEQUENCE: 288
gcatctcagc ccaagagaag gttatattcc cagaggatgt                    40

<210> SEQ ID NO 289
<211> LENGTH: 40
<212> TYPE: DNA
<213> ORGANISM: Homo sapiens

<400> SEQUENCE: 289
cttgccttcc catcctcctg caaacacctg ccacctttct                    40

<210> SEQ ID NO 290
<211> LENGTH: 40
<212> TYPE: DNA
<213> ORGANISM: Homo sapiens

<400> SEQUENCE: 290
cttgccttcc catcctcctg aacttccagg tcctgagtca                    40
```

```
<210> SEQ ID NO 291
<211> LENGTH: 40
<212> TYPE: DNA
<213> ORGANISM: Homo sapiens

<400> SEQUENCE: 291
ctacacagag ctgcagcaag gtgtgcaccc agctgcaggt                           40

<210> SEQ ID NO 292
<211> LENGTH: 40
<212> TYPE: DNA
<213> ORGANISM: Homo sapiens

<400> SEQUENCE: 292
ctacacagag ctgcagcaag ctctgtccca aatgggctac                           40

<210> SEQ ID NO 293
<211> LENGTH: 40
<212> TYPE: DNA
<213> ORGANISM: Homo sapiens

<400> SEQUENCE: 293
acctgttacc actttcaaaa tttctgtgct aaacagtgtt                           40

<210> SEQ ID NO 294
<211> LENGTH: 40
<212> TYPE: DNA
<213> ORGANISM: Homo sapiens

<400> SEQUENCE: 294
acctgttacc actttcaaaa atctacagac agtcaatgtg                           40

<210> SEQ ID NO 295
<211> LENGTH: 40
<212> TYPE: DNA
<213> ORGANISM: Homo sapiens

<400> SEQUENCE: 295
agacaaggga ttggtggaaa cattttattt tacagaattg                           40

<210> SEQ ID NO 296
<211> LENGTH: 40
<212> TYPE: DNA
<213> ORGANISM: Homo sapiens

<400> SEQUENCE: 296
agacaaggga ttggtggaaa aattgacagc gtatgccatg                           40

<210> SEQ ID NO 297
<211> LENGTH: 40
<212> TYPE: DNA
<213> ORGANISM: Homo sapiens

<400> SEQUENCE: 297
caacgagaac aagctatcag ttacttttac cccacagggc                           40

<210> SEQ ID NO 298
<211> LENGTH: 40
<212> TYPE: DNA
<213> ORGANISM: Homo sapiens

<400> SEQUENCE: 298
```

```
caacgagaac aagctatcag ggctgctaag gaagcaaaaa                             40

<210> SEQ ID NO 299
<211> LENGTH: 40
<212> TYPE: DNA
<213> ORGANISM: Homo sapiens

<400> SEQUENCE: 299
tctatatccc ctctaagacg cacttctttc ccctctgtag                             40

<210> SEQ ID NO 300
<211> LENGTH: 40
<212> TYPE: DNA
<213> ORGANISM: Homo sapiens

<400> SEQUENCE: 300
tctatatccc ctctaagacg gacctgggtg cagccgcagg                             40

<210> SEQ ID NO 301
<211> LENGTH: 40
<212> TYPE: DNA
<213> ORGANISM: Homo sapiens

<400> SEQUENCE: 301
tggagccagt tactgggcag gtgtgttttt gtgacagtca                             40

<210> SEQ ID NO 302
<211> LENGTH: 40
<212> TYPE: DNA
<213> ORGANISM: Homo sapiens

<400> SEQUENCE: 302
tggagccagt tactgggcag gtgtctgtac tggtgatgtg                             40

<210> SEQ ID NO 303
<211> LENGTH: 40
<212> TYPE: DNA
<213> ORGANISM: Homo sapiens

<400> SEQUENCE: 303
aaaagaaact gaggaatcag tatcacaggc agaagctctg                             40

<210> SEQ ID NO 304
<211> LENGTH: 40
<212> TYPE: DNA
<213> ORGANISM: Homo sapiens

<400> SEQUENCE: 304
aaaagaaact gaggaatcag ccttagtatc acaggcagaa                             40

<210> SEQ ID NO 305
<211> LENGTH: 40
<212> TYPE: DNA
<213> ORGANISM: Homo sapiens

<400> SEQUENCE: 305
cagcactagg ttataaagag gagtctagta aaagccctaa                             40

<210> SEQ ID NO 306
<211> LENGTH: 40
<212> TYPE: DNA
<213> ORGANISM: Homo sapiens

<400> SEQUENCE: 306
```
cagcactagg ttataaagag aggatgtctt atatcttaaa        40

<210> SEQ ID NO 307
<211> LENGTH: 40
<212> TYPE: DNA
<213> ORGANISM: Homo sapiens

<400> SEQUENCE: 307 gccccgttt tcctgcccag cccttgtcct cagtgcaccc        40

<210> SEQ ID NO 308
<211> LENGTH: 40
<212> TYPE: DNA
<213> ORGANISM: Homo sapiens

<400> SEQUENCE: 308 gccccgttt tcctgcccag tacctgaagc tgcgggagcg        40

<210> SEQ ID NO 309
<211> LENGTH: 40
<212> TYPE: DNA
<213> ORGANISM: Homo sapiens

<400> SEQUENCE: 309
gccgccgccg ccgccgccag gctctgatgc tggtgtctgg        40

<210> SEQ ID NO 310
<211> LENGTH: 40
<212> TYPE: DNA
<213> ORGANISM: Homo sapiens

<400> SEQUENCE: 310
caccttatga agtatagcag gctctgatgc tggtgtctgg        40

<210> SEQ ID NO 311
<211> LENGTH: 40
<212> TYPE: DNA
<213> ORGANISM: Homo sapiens

<400> SEQUENCE: 311
agtggcagtg gctgtaccag cccacaggaa acaacccgta        40

<210> SEQ ID NO 312
<211> LENGTH: 40
<212> TYPE: DNA
<213> ORGANISM: Homo sapiens

<400> SEQUENCE: 312
agtggcagtg gctgtaccag ctcttggtgg agggctccac        40

<210> SEQ ID NO 313
<211> LENGTH: 40
<212> TYPE: DNA
<213> ORGANISM: Homo sapiens

<400> SEQUENCE: 313
gagattctga agataaggag ttctcttgta ggatgccact        40

<210> SEQ ID NO 314
<211> LENGTH: 40
<212> TYPE: DNA
<213> ORGANISM: Homo sapiens

```
<400> SEQUENCE: 314
gagattctga agataaggag gtaaaacctg tttagaaatt                           40

<210> SEQ ID NO 315
<211> LENGTH: 40
<212> TYPE: DNA
<213> ORGANISM: Homo sapiens

<400> SEQUENCE: 315
ccaagagaca gcacattcag ctcctgagca gcctgactga                           40

<210> SEQ ID NO 316
<211> LENGTH: 40
<212> TYPE: DNA
<213> ORGANISM: Homo sapiens

<400> SEQUENCE: 316
tcagagcagt cgggacacag gacacctgac tgatagtgaa                           40

<210> SEQ ID NO 317
<211> LENGTH: 40
<212> TYPE: DNA
<213> ORGANISM: Homo sapiens

<400> SEQUENCE: 317
ctacgacagt gaagattcag gacacctgac tgatagtgaa                           40

<210> SEQ ID NO 318
<211> LENGTH: 40
<212> TYPE: DNA
<213> ORGANISM: Homo sapiens

<400> SEQUENCE: 318
ctgttgtgtc cgttttgaag agcccttttgc tcctccctca                          40

<210> SEQ ID NO 319
<211> LENGTH: 40
<212> TYPE: DNA
<213> ORGANISM: Homo sapiens

<400> SEQUENCE: 319
ctgttgtgtc cgttttgaag aatgaacgga gaccagaatt                           40

<210> SEQ ID NO 320
<211> LENGTH: 40
<212> TYPE: DNA
<213> ORGANISM: Homo sapiens

<400> SEQUENCE: 320
ccggccctac aggctggcgg ataaacccac tgccctacag                           40

<210> SEQ ID NO 321
<211> LENGTH: 40
<212> TYPE: DNA
<213> ORGANISM: Homo sapiens

<400> SEQUENCE: 321
ccctccgcct cctgatgcag ataaacccac tgccctacag                           40

<210> SEQ ID NO 322
<211> LENGTH: 40
<212> TYPE: DNA
<213> ORGANISM: Homo sapiens
```

```
<400> SEQUENCE: 322
gagattctga agataaggag gatgccactg gaaatgttga                            40

<210> SEQ ID NO 323
<211> LENGTH: 40
<212> TYPE: DNA
<213> ORGANISM: Homo sapiens

<400> SEQUENCE: 323
tgaaaagtcc agaggaagag gttgtggcag cactgcctga                            40

<210> SEQ ID NO 324
<211> LENGTH: 40
<212> TYPE: DNA
<213> ORGANISM: Homo sapiens

<400> SEQUENCE: 324
tcctggagga gctacgcagg gttgtggcag cactgcctga                            40

<210> SEQ ID NO 325
<211> LENGTH: 40
<212> TYPE: DNA
<213> ORGANISM: Homo sapiens

<400> SEQUENCE: 325
gtcatggcag aagacctcca tccaagacat ctctggcatc                            40

<210> SEQ ID NO 326
<211> LENGTH: 40
<212> TYPE: DNA
<213> ORGANISM: Homo sapiens

<400> SEQUENCE: 326
ctatagctac tggatatggg tccaagacat ctctggcatc                            40

<210> SEQ ID NO 327
<211> LENGTH: 40
<212> TYPE: DNA
<213> ORGANISM: Homo sapiens

<400> SEQUENCE: 327
ccggagcccc ttcaaaaaag acttttcgtg ttttacagtc                            40

<210> SEQ ID NO 328
<211> LENGTH: 40
<212> TYPE: DNA
<213> ORGANISM: Homo sapiens

<400> SEQUENCE: 328
ccggagcccc ttcaaaaaag tctgttgcca gaatcggcca                            40

<210> SEQ ID NO 329
<211> LENGTH: 40
<212> TYPE: DNA
<213> ORGANISM: Homo sapiens

<400> SEQUENCE: 329
ccacagatac tattaggagg ccataccacc ctgaacgcgc                            40

<210> SEQ ID NO 330
<211> LENGTH: 40
<212> TYPE: DNA
```

<210> SEQ ID NO 330
<211> LENGTH: 40
<212> TYPE: DNA
<213> ORGANISM: Homo sapiens

<400> SEQUENCE: 330
ccacagatac tattaggagg gaatttatca tggcatccag          40

<210> SEQ ID NO 331
<211> LENGTH: 40
<212> TYPE: DNA
<213> ORGANISM: Homo sapiens

<400> SEQUENCE: 331
tgttcaagtt cccaaagcag gagatcctgc tgggccgtgg          40

<210> SEQ ID NO 332
<211> LENGTH: 40
<212> TYPE: DNA
<213> ORGANISM: Homo sapiens

<400> SEQUENCE: 332
actcccagct caatgcaatg gttccatacc atctggtact          40

<210> SEQ ID NO 333
<211> LENGTH: 40
<212> TYPE: DNA
<213> ORGANISM: Homo sapiens

<400> SEQUENCE: 333
actcccagct caatgcaatg gctcatcaga ttcaagagat          40

<210> SEQ ID NO 334
<211> LENGTH: 40
<212> TYPE: DNA
<213> ORGANISM: Homo sapiens

<400> SEQUENCE: 334
atcactgtga cttccctgag gtctctgctc ctcagctgct          40

<210> SEQ ID NO 335
<211> LENGTH: 40
<212> TYPE: DNA
<213> ORGANISM: Homo sapiens

<400> SEQUENCE: 335
atcactgtga cttccctgag ctgctgtccc ccagcaacgt          40

<210> SEQ ID NO 336
<211> LENGTH: 40
<212> TYPE: DNA
<213> ORGANISM: Homo sapiens

<400> SEQUENCE: 336
atcctctcaa tcaaaataag tttgtgtgca cttttctgct          40

<210> SEQ ID NO 337
<211> LENGTH: 40
<212> TYPE: DNA
<213> ORGANISM: Homo sapiens

<400> SEQUENCE: 337
atcctctcaa tcaaaataag ggtaaaccag acttgaatac          40

<210> SEQ ID NO 338
<211> LENGTH: 40

```
<212> TYPE: DNA
<213> ORGANISM: Homo sapiens

<400> SEQUENCE: 338
ctattccttt attgaatttg ttttcttcat cattctagat                              40

<210> SEQ ID NO 339
<211> LENGTH: 40
<212> TYPE: DNA
<213> ORGANISM: Homo sapiens

<400> SEQUENCE: 339
ctattccttt attgaatttg atactttcat tcagaaaacc                              40

<210> SEQ ID NO 340
<211> LENGTH: 40
<212> TYPE: DNA
<213> ORGANISM: Homo sapiens

<400> SEQUENCE: 340
agtcatacct ggagcagcag tttgtttctt ttctagaaaa                              40

<210> SEQ ID NO 341
<211> LENGTH: 40
<212> TYPE: DNA
<213> ORGANISM: Homo sapiens

<400> SEQUENCE: 341
agtcatacct ggagcagcag aaaaaattga agaactgtc                               40

<210> SEQ ID NO 342
<211> LENGTH: 40
<212> TYPE: DNA
<213> ORGANISM: Homo sapiens

<400> SEQUENCE: 342
gcaaccagtt tgggcatcag ctgcccttct ctcctgtagg                              40

<210> SEQ ID NO 343
<211> LENGTH: 40
<212> TYPE: DNA
<213> ORGANISM: Homo sapiens

<400> SEQUENCE: 343
gcaaccagtt tgggcatcag gagaacgcca agaacgaaga                              40

<210> SEQ ID NO 344
<211> LENGTH: 40
<212> TYPE: DNA
<213> ORGANISM: Homo sapiens

<400> SEQUENCE: 344
ccatggtcaa aaaatggcag caccaacagg tccgccaaat                              40

<210> SEQ ID NO 345
<211> LENGTH: 40
<212> TYPE: DNA
<213> ORGANISM: Homo sapiens

<400> SEQUENCE: 345
ccatggtcaa aaaatggcag acaatgattg aagctcacgt                              40

<210> SEQ ID NO 346
```

```
<211> LENGTH: 40
<212> TYPE: DNA
<213> ORGANISM: Homo sapiens

<400> SEQUENCE: 346
gcctgatgcc cgaatttcag gccatgaagt acttgtcata                           40

<210> SEQ ID NO 347
<211> LENGTH: 40
<212> TYPE: DNA
<213> ORGANISM: Homo sapiens

<400> SEQUENCE: 347
gcctgatgcc cgaatttcag tttggcactt acagcgaatc                           40

<210> SEQ ID NO 348
<211> LENGTH: 40
<212> TYPE: DNA
<213> ORGANISM: Homo sapiens

<400> SEQUENCE: 348
agattgaagc taaaattaag ttttctgtct tacccattcc                           40

<210> SEQ ID NO 349
<211> LENGTH: 40
<212> TYPE: DNA
<213> ORGANISM: Homo sapiens

<400> SEQUENCE: 349
agattgaagc taaaattaag gagctgacaa gtacttgtag                           40

<210> SEQ ID NO 350
<211> LENGTH: 40
<212> TYPE: DNA
<213> ORGANISM: Homo sapiens

<400> SEQUENCE: 350
agcacaagct atgtatcaag cataactttc ttctacagga                           40

<210> SEQ ID NO 351
<211> LENGTH: 40
<212> TYPE: DNA
<213> ORGANISM: Homo sapiens

<400> SEQUENCE: 351
agcacaagct atgtatcaag gattctggag tgaagcagat                           40

<210> SEQ ID NO 352
<211> LENGTH: 40
<212> TYPE: DNA
<213> ORGANISM: Homo sapiens

<400> SEQUENCE: 352
agatgtaaaa gtgtcactgt tttggttttc agttacagct                           40

<210> SEQ ID NO 353
<211> LENGTH: 40
<212> TYPE: DNA
<213> ORGANISM: Homo sapiens

<400> SEQUENCE: 353
agatgtaaaa gtgtcactgt ttacagctttt cttcctggct                          40
```

<210> SEQ ID NO 354
<211> LENGTH: 40
<212> TYPE: DNA
<213> ORGANISM: Homo sapiens

<400> SEQUENCE: 354
ctgcagcctc cgcctcccag gaacttgcca catcagactc        40

<210> SEQ ID NO 355
<211> LENGTH: 40
<212> TYPE: DNA
<213> ORGANISM: Homo sapiens

<400> SEQUENCE: 355
aggatgatgc agcatccaac tggtcttttt gtgttctgtg        40

<210> SEQ ID NO 356
<211> LENGTH: 40
<212> TYPE: DNA
<213> ORGANISM: Homo sapiens

<400> SEQUENCE: 356
aggatgatgc agcatccaac gcgggcacat gaacgccccc        40

<210> SEQ ID NO 357
<211> LENGTH: 40
<212> TYPE: DNA
<213> ORGANISM: Homo sapiens

<400> SEQUENCE: 357
tggtgaaatg gaccccaaag tctttctctt tcaagtacct        40

<210> SEQ ID NO 358
<211> LENGTH: 40
<212> TYPE: DNA
<213> ORGANISM: Homo sapiens

<400> SEQUENCE: 358
tggtgaaatg gaccccaaag tacctgctat tgaggagaac        40

<210> SEQ ID NO 359
<211> LENGTH: 40
<212> TYPE: DNA
<213> ORGANISM: Homo sapiens

<400> SEQUENCE: 359
agcttaaaga actgtattcg tttgactgca accctggagt        40

<210> SEQ ID NO 360
<211> LENGTH: 40
<212> TYPE: DNA
<213> ORGANISM: Homo sapiens

<400> SEQUENCE: 360
gatcaaggca accgggaaag tttgactgca accctggagt        40

<210> SEQ ID NO 361
<211> LENGTH: 40
<212> TYPE: DNA
<213> ORGANISM: Homo sapiens

<400> SEQUENCE: 361
aacacaccaa ctttgtggag gtcctggcaa tctccgttgc        40

```
<210> SEQ ID NO 362
<211> LENGTH: 40
<212> TYPE: DNA
<213> ORGANISM: Homo sapiens

<400> SEQUENCE: 362
aacacaccaa ctttgtggag ttccggaact ttaagatcat                40

<210> SEQ ID NO 363
<211> LENGTH: 40
<212> TYPE: DNA
<213> ORGANISM: Homo sapiens

<400> SEQUENCE: 363
gcgggtctgc agcctacgca aactgaagca ggcccagacc                40

<210> SEQ ID NO 364
<211> LENGTH: 40
<212> TYPE: DNA
<213> ORGANISM: Homo sapiens

<400> SEQUENCE: 364
gttccaggtc ctcctggcag aactgaagca ggcccagacc                40

<210> SEQ ID NO 365
<211> LENGTH: 40
<212> TYPE: DNA
<213> ORGANISM: Homo sapiens

<400> SEQUENCE: 365
cccgctgccc cagctcaaag atcagtgcta acatcttccg                40

<210> SEQ ID NO 366
<211> LENGTH: 40
<212> TYPE: DNA
<213> ORGANISM: Homo sapiens

<400> SEQUENCE: 366
attctgatat agtaaaaatg atcagtgcta acatcttccg                40

<210> SEQ ID NO 367
<211> LENGTH: 40
<212> TYPE: DNA
<213> ORGANISM: Homo sapiens

<400> SEQUENCE: 367
atgagtttcc caccgatggg gaggaagacc gcaggaagga                40

<210> SEQ ID NO 368
<211> LENGTH: 40
<212> TYPE: DNA
<213> ORGANISM: Homo sapiens

<400> SEQUENCE: 368
atgagtttcc caccgatggg gagatgtcag cgcaggagga                40

<210> SEQ ID NO 369
<211> LENGTH: 40
<212> TYPE: DNA
<213> ORGANISM: Homo sapiens

<400> SEQUENCE: 369
agtttattta acatttgatg agcctacctt gtacaatgct                40
```

<210> SEQ ID NO 370
<211> LENGTH: 40
<212> TYPE: DNA
<213> ORGANISM: Homo sapiens

<400> SEQUENCE: 370
agtttattta acatttgatg aacttcgaga aaccaagacc               40

<210> SEQ ID NO 371
<211> LENGTH: 40
<212> TYPE: DNA
<213> ORGANISM: Homo sapiens

<400> SEQUENCE: 371
ccacctagca gccaccagag accagaggtg gcacaggcag               40

<210> SEQ ID NO 372
<211> LENGTH: 40
<212> TYPE: DNA
<213> ORGANISM: Homo sapiens

<400> SEQUENCE: 372
ccacctagca gccaccagag gttacaaggg gagagtggcc               40

<210> SEQ ID NO 373
<211> LENGTH: 40
<212> TYPE: DNA
<213> ORGANISM: Homo sapiens

<400> SEQUENCE: 373
tccaggatcc tgaggcatgg ccatatcagc gggaacaaga               40

<210> SEQ ID NO 374
<211> LENGTH: 40
<212> TYPE: DNA
<213> ORGANISM: Homo sapiens

<400> SEQUENCE: 374
ggcagcggag gggcgacaaa ccatatcagc gggaacaaga               40

<210> SEQ ID NO 375
<211> LENGTH: 40
<212> TYPE: DNA
<213> ORGANISM: Homo sapiens

<400> SEQUENCE: 375
ggcaacttcg ttaatatgag ctttctactc aacaggtcta               40

<210> SEQ ID NO 376
<211> LENGTH: 40
<212> TYPE: DNA
<213> ORGANISM: Homo sapiens

<400> SEQUENCE: 376
ggcaacttcg ttaatatgag gtctatccag gaaaatggtg               40

<210> SEQ ID NO 377
<211> LENGTH: 40
<212> TYPE: DNA
<213> ORGANISM: Homo sapiens

<400> SEQUENCE: 377

```
ggagcctggg catctcgttg ccctgcccgt ctccctccca                              40

<210> SEQ ID NO 378
<211> LENGTH: 40
<212> TYPE: DNA
<213> ORGANISM: Homo sapiens

<400> SEQUENCE: 378
ggagcctggg catctcgttg gtggagctgg caacaggaca                              40

<210> SEQ ID NO 379
<211> LENGTH: 40
<212> TYPE: DNA
<213> ORGANISM: Homo sapiens

<400> SEQUENCE: 379
ctggtgtgct tgggagccag ggttatcatg aagattaaat                              40

<210> SEQ ID NO 380
<211> LENGTH: 40
<212> TYPE: DNA
<213> ORGANISM: Homo sapiens

<400> SEQUENCE: 380
ctggtgtgct tgggagccag agatcacctc ctacaccact                              40

<210> SEQ ID NO 381
<211> LENGTH: 40
<212> TYPE: DNA
<213> ORGANISM: Homo sapiens

<400> SEQUENCE: 381
attggaggag cttctggaaa gatgccctct tcgcttccca                              40

<210> SEQ ID NO 382
<211> LENGTH: 40
<212> TYPE: DNA
<213> ORGANISM: Homo sapiens

<400> SEQUENCE: 382
attggaggag cttctggaaa gtgctcttga tgatttcgat                              40

<210> SEQ ID NO 383
<211> LENGTH: 40
<212> TYPE: DNA
<213> ORGANISM: Homo sapiens

<400> SEQUENCE: 383
aatgacgtgc tgcaccactg ggccctgacg cgcggaaagt                              40

<210> SEQ ID NO 384
<211> LENGTH: 40
<212> TYPE: DNA
<213> ORGANISM: Homo sapiens

<400> SEQUENCE: 384
aatgacgtgc tgcaccactg ccagcgcaag caggcccggg                              40

<210> SEQ ID NO 385
<211> LENGTH: 40
<212> TYPE: DNA
<213> ORGANISM: Homo sapiens

<400> SEQUENCE: 385
```

```
gcctggggtg gagagggcag ccccccagct accacaagaa                          40

<210> SEQ ID NO 386
<211> LENGTH: 40
<212> TYPE: DNA
<213> ORGANISM: Homo sapiens

<400> SEQUENCE: 386
gcctggggtg gagagggcag tctgggatgt ggcattggct                          40

<210> SEQ ID NO 387
<211> LENGTH: 40
<212> TYPE: DNA
<213> ORGANISM: Homo sapiens

<400> SEQUENCE: 387
ggaaatggga caggaggcag aggatcacag gctttaaaat                          40

<210> SEQ ID NO 388
<211> LENGTH: 40
<212> TYPE: DNA
<213> ORGANISM: Homo sapiens

<400> SEQUENCE: 388
ggaaatggga caggaggcag cttttctctc aacagaggat                          40

<210> SEQ ID NO 389
<211> LENGTH: 40
<212> TYPE: DNA
<213> ORGANISM: Homo sapiens

<400> SEQUENCE: 389
agaccgactg ccagtaatag gagattgtga agacctttga                          40

<210> SEQ ID NO 390
<211> LENGTH: 40
<212> TYPE: DNA
<213> ORGANISM: Homo sapiens

<400> SEQUENCE: 390
agaccgactg ccagtaatag agcctgttag tattaatgaa                          40

<210> SEQ ID NO 391
<211> LENGTH: 40
<212> TYPE: DNA
<213> ORGANISM: Homo sapiens

<400> SEQUENCE: 391
tcatgctagc cgaggcccag tggcggccag aggagtccga                          40

<210> SEQ ID NO 392
<211> LENGTH: 40
<212> TYPE: DNA
<213> ORGANISM: Homo sapiens

<400> SEQUENCE: 392
tcatgctagc cgaggcccag gaaaccacta tcagcggcct                          40

<210> SEQ ID NO 393
<211> LENGTH: 40
<212> TYPE: DNA
<213> ORGANISM: Homo sapiens
```

<400> SEQUENCE: 393
gaaggcagct gagcaaacag ttctctccct tgcagctgcc                         40

<210> SEQ ID NO 394
<211> LENGTH: 40
<212> TYPE: DNA
<213> ORGANISM: Homo sapiens

<400> SEQUENCE: 394
gaaggcagct gagcaaacag ctgcccggga acaggcaaag                         40

<210> SEQ ID NO 395
<211> LENGTH: 40
<212> TYPE: DNA
<213> ORGANISM: Homo sapiens

<400> SEQUENCE: 395
gccaacagcc aattctacag gtacaacaaa taacactgtg                         40

<210> SEQ ID NO 396
<211> LENGTH: 40
<212> TYPE: DNA
<213> ORGANISM: Homo sapiens

<400> SEQUENCE: 396
gccaacagcc aattctacag ctaaacccac agttcagccc                         40

<210> SEQ ID NO 397
<211> LENGTH: 40
<212> TYPE: DNA
<213> ORGANISM: Homo sapiens

<400> SEQUENCE: 397
cccatcaact gcacccactc ccctctgacg tccatcatct                         40

<210> SEQ ID NO 398
<211> LENGTH: 40
<212> TYPE: DNA
<213> ORGANISM: Homo sapiens

<400> SEQUENCE: 398
cccatcaact gcacccactc ctgtgtggac ctggatgaca                         40

<210> SEQ ID NO 399
<211> LENGTH: 40
<212> TYPE: DNA
<213> ORGANISM: Homo sapiens

<400> SEQUENCE: 399
gcggaaagaa ttgcatgaag agcgacaaca acacaaccag                         40

<210> SEQ ID NO 400
<211> LENGTH: 40
<212> TYPE: DNA
<213> ORGANISM: Homo sapiens

<400> SEQUENCE: 400
gcggaaagaa ttgcatgaag tttgccatct cttggagcaa                         40

<210> SEQ ID NO 401
<211> LENGTH: 40
<212> TYPE: DNA
<213> ORGANISM: Homo sapiens

```
<400> SEQUENCE: 401
tgtgggaatt acaattcaag cttatcacac agactttcag                              40

<210> SEQ ID NO 402
<211> LENGTH: 40
<212> TYPE: DNA
<213> ORGANISM: Homo sapiens

<400> SEQUENCE: 402
aagaagggat ggcagagaag cttatcacac agactttcag                              40

<210> SEQ ID NO 403
<211> LENGTH: 40
<212> TYPE: DNA
<213> ORGANISM: Homo sapiens

<400> SEQUENCE: 403
cttcctcaag tcgcccaaag ctcccccgtt tcttctcccc                              40

<210> SEQ ID NO 404
<211> LENGTH: 40
<212> TYPE: DNA
<213> ORGANISM: Homo sapiens

<400> SEQUENCE: 404
cttcctcaag tcgcccaaag acaacgtgga cgaccccacg                              40

<210> SEQ ID NO 405
<211> LENGTH: 40
<212> TYPE: DNA
<213> ORGANISM: Homo sapiens

<400> SEQUENCE: 405
tcttcgctgg tggcaaactg tatcgtgaag agcgcttccg                              40

<210> SEQ ID NO 406
<211> LENGTH: 40
<212> TYPE: DNA
<213> ORGANISM: Homo sapiens

<400> SEQUENCE: 406
tcttcgctgg tggcaaactg cgggtgcatc tcgacatcca                              40

<210> SEQ ID NO 407
<211> LENGTH: 40
<212> TYPE: DNA
<213> ORGANISM: Homo sapiens

<400> SEQUENCE: 407
gcaagaagta caaagtggag tatgtgcttt gttgtgacag                              40

<210> SEQ ID NO 408
<211> LENGTH: 40
<212> TYPE: DNA
<213> ORGANISM: Homo sapiens

<400> SEQUENCE: 408
gcaagaagta caaagtggag tatcctatca tgtacagcac                              40

<210> SEQ ID NO 409
<211> LENGTH: 40
<212> TYPE: DNA
```

<213> ORGANISM: Homo sapiens

<400> SEQUENCE: 409
tgtaggagca atgactgttg cattctttt ctttaggtat 40

<210> SEQ ID NO 410
<211> LENGTH: 40
<212> TYPE: DNA
<213> ORGANISM: Homo sapiens

<400> SEQUENCE: 410
tgtaggagca atgactgttg gtatgggcta ttccatgtat 40

<210> SEQ ID NO 411
<211> LENGTH: 40
<212> TYPE: DNA
<213> ORGANISM: Homo sapiens

<400> SEQUENCE: 411
ccttcctgga tcccctaag gtggtattaa agataatcaa 40

<210> SEQ ID NO 412
<211> LENGTH: 40
<212> TYPE: DNA
<213> ORGANISM: Homo sapiens

<400> SEQUENCE: 412
aagtgcagat agatggcctt gtggtattaa agataatcaa 40

<210> SEQ ID NO 413
<211> LENGTH: 40
<212> TYPE: DNA
<213> ORGANISM: Homo sapiens

<400> SEQUENCE: 413
caggtctaac tcgcttccag gccccagcag atgaacctga 40

<210> SEQ ID NO 414
<211> LENGTH: 40
<212> TYPE: DNA
<213> ORGANISM: Homo sapiens

<400> SEQUENCE: 414
caggtctaac tcgcttccag gctgaagctt cagaaaagga 40

<210> SEQ ID NO 415
<211> LENGTH: 40
<212> TYPE: DNA
<213> ORGANISM: Homo sapiens

<400> SEQUENCE: 415
cctccccata cctgagctcg atggcggtgg gaccccccga 40

<210> SEQ ID NO 416
<211> LENGTH: 40
<212> TYPE: DNA
<213> ORGANISM: Homo sapiens

<400> SEQUENCE: 416
gcaaaaggat ataccaggag catttatttc aggggtcctc 40

<210> SEQ ID NO 417
<211> LENGTH: 40

```
<212> TYPE: DNA
<213> ORGANISM: Homo sapiens

<400> SEQUENCE: 417
gcaaaaggat ataccaggag gggtcctcaa gattcgagat                40

<210> SEQ ID NO 418
<211> LENGTH: 40
<212> TYPE: DNA
<213> ORGANISM: Homo sapiens

<400> SEQUENCE: 418
cactccaatt tatagattct gattcttcat catggtgtga                40

<210> SEQ ID NO 419
<211> LENGTH: 40
<212> TYPE: DNA
<213> ORGANISM: Homo sapiens

<400> SEQUENCE: 419
cactccaatt tatagattct ttcttaaaca cttccagtaa                40

<210> SEQ ID NO 420
<211> LENGTH: 40
<212> TYPE: DNA
<213> ORGANISM: Homo sapiens

<400> SEQUENCE: 420
tgagagtctt cagttactag tttgtctttc ctagatccag                40

<210> SEQ ID NO 421
<211> LENGTH: 40
<212> TYPE: DNA
<213> ORGANISM: Homo sapiens

<400> SEQUENCE: 421
tgagagtctt cagttactag aggcggattt ccctgactga                40

<210> SEQ ID NO 422
<211> LENGTH: 40
<212> TYPE: DNA
<213> ORGANISM: Homo sapiens

<400> SEQUENCE: 422
ttaacagcat tttgttttgc gattcctgcc agctcccagg                40

<210> SEQ ID NO 423
<211> LENGTH: 40
<212> TYPE: DNA
<213> ORGANISM: Homo sapiens

<400> SEQUENCE: 423
cccagtcatt caacaggaag gattcctgcc agctcccagg                40

<210> SEQ ID NO 424
<211> LENGTH: 40
<212> TYPE: DNA
<213> ORGANISM: Homo sapiens

<400> SEQUENCE: 424
gatgaatgct gacatggatg atctctctgc aagagtagat                40

<210> SEQ ID NO 425
```

```
<211> LENGTH: 40
<212> TYPE: DNA
<213> ORGANISM: Homo sapiens

<400> SEQUENCE: 425
gatgaatgct gacatggatg cagttgatgc tgaaaatcaa                    40

<210> SEQ ID NO 426
<211> LENGTH: 40
<212> TYPE: DNA
<213> ORGANISM: Homo sapiens

<400> SEQUENCE: 426
gtcaatgctt ccatgtccag ctttctgtct tctaggttcc                    40

<210> SEQ ID NO 427
<211> LENGTH: 40
<212> TYPE: DNA
<213> ORGANISM: Homo sapiens

<400> SEQUENCE: 427
gtcaatgctt ccatgtccag gttccctccc catatggtcc                    40

<210> SEQ ID NO 428
<211> LENGTH: 40
<212> TYPE: DNA
<213> ORGANISM: Homo sapiens

<400> SEQUENCE: 428
tatggcaagg aggtcgacct tctctttccc agctgggcct                    40

<210> SEQ ID NO 429
<211> LENGTH: 40
<212> TYPE: DNA
<213> ORGANISM: Homo sapiens

<400> SEQUENCE: 429
tatggcaagg aggtcgacct ctgggcctgt ggggtgatct                    40

<210> SEQ ID NO 430
<211> LENGTH: 40
<212> TYPE: DNA
<213> ORGANISM: Homo sapiens

<400> SEQUENCE: 430
tggttttacc tcggatagag acatttgtta tcgctgtggt                    40

<210> SEQ ID NO 431
<211> LENGTH: 40
<212> TYPE: DNA
<213> ORGANISM: Homo sapiens

<400> SEQUENCE: 431
tggttttacc tcggatagag gtttccagtt tgtttcctcg                    40

<210> SEQ ID NO 432
<211> LENGTH: 40
<212> TYPE: DNA
<213> ORGANISM: Homo sapiens

<400> SEQUENCE: 432
gaatccgtat ctgggaacag agccctttgc tcctccctca                    40
```

```
<210> SEQ ID NO 433
<211> LENGTH: 40
<212> TYPE: DNA
<213> ORGANISM: Homo sapiens

<400> SEQUENCE: 433
gaatccgtat ctgggaacag aatgaacgga gaccagaatt                    40

<210> SEQ ID NO 434
<211> LENGTH: 40
<212> TYPE: DNA
<213> ORGANISM: Homo sapiens

<400> SEQUENCE: 434
tccaggagtt ccaggttccg tgtttcactt caagcccact                    40

<210> SEQ ID NO 435
<211> LENGTH: 40
<212> TYPE: DNA
<213> ORGANISM: Homo sapiens

<400> SEQUENCE: 435
tttgactagg gtccaaccag tgtttcactt caagcccact                    40

<210> SEQ ID NO 436
<211> LENGTH: 40
<212> TYPE: DNA
<213> ORGANISM: Homo sapiens

<400> SEQUENCE: 436
gggcctgatg aatgacatcg cttcctcggc agtcatggga                    40

<210> SEQ ID NO 437
<211> LENGTH: 40
<212> TYPE: DNA
<213> ORGANISM: Homo sapiens

<400> SEQUENCE: 437
gggcctgatg aatgacatcg cagccttccc tgcacccacc                    40

<210> SEQ ID NO 438
<211> LENGTH: 40
<212> TYPE: DNA
<213> ORGANISM: Homo sapiens

<400> SEQUENCE: 438
agccccagga tgcctcgcag ctctcggaag aactggttgt                    40

<210> SEQ ID NO 439
<211> LENGTH: 40
<212> TYPE: DNA
<213> ORGANISM: Homo sapiens

<400> SEQUENCE: 439
agccccagga tgcctcgcag acgtgccttc tgccatgatt                    40

<210> SEQ ID NO 440
<211> LENGTH: 40
<212> TYPE: DNA
<213> ORGANISM: Homo sapiens

<400> SEQUENCE: 440
acttgcctgt gaatttcgag tctttccctc tgaaacaggt                    40
```

<210> SEQ ID NO 441
<211> LENGTH: 40
<212> TYPE: DNA
<213> ORGANISM: Homo sapiens

<400> SEQUENCE: 441
acttgcctgt gaatttcgag gtggcccggg agagtggccc                    40

<210> SEQ ID NO 442
<211> LENGTH: 40
<212> TYPE: DNA
<213> ORGANISM: Homo sapiens

<400> SEQUENCE: 442
tacccgggac aaccccaagg ccgcccaccc cacccccat                     40

<210> SEQ ID NO 443
<211> LENGTH: 40
<212> TYPE: DNA
<213> ORGANISM: Homo sapiens

<400> SEQUENCE: 443
tacccgggac aaccccaagg ggctctgtga cctctgcccc                    40

<210> SEQ ID NO 444
<211> LENGTH: 40
<212> TYPE: DNA
<213> ORGANISM: Homo sapiens

<400> SEQUENCE: 444
catagtggaa gtgatagatc ttcttttcca cattacagtg                    40

<210> SEQ ID NO 445
<211> LENGTH: 40
<212> TYPE: DNA
<213> ORGANISM: Homo sapiens

<400> SEQUENCE: 445
catagtggaa gtgatagatc tggcctgaag cacgaggaca                    40

<210> SEQ ID NO 446
<211> LENGTH: 40
<212> TYPE: DNA
<213> ORGANISM: Homo sapiens

<400> SEQUENCE: 446
gctgtacctt caggaacagg cccttctcc caggtttcca                     40

<210> SEQ ID NO 447
<211> LENGTH: 40
<212> TYPE: DNA
<213> ORGANISM: Homo sapiens

<400> SEQUENCE: 447
gctgtacctt caggaacagg gtttccatgc tgagctcctg                    40

<210> SEQ ID NO 448
<211> LENGTH: 40
<212> TYPE: DNA
<213> ORGANISM: Homo sapiens

<400> SEQUENCE: 448
taaagcgact cattgagcag gaggtggtat aacagacaga                    40

<210> SEQ ID NO 449
<211> LENGTH: 40
<212> TYPE: DNA
<213> ORGANISM: Homo sapiens

<400> SEQUENCE: 449
taaagcgact cattgagcag gcaaaaggca ggattgtggt                                40

<210> SEQ ID NO 450
<211> LENGTH: 40
<212> TYPE: DNA
<213> ORGANISM: Homo sapiens

<400> SEQUENCE: 450
tgggaatctg gccagagaag tctttctgtc ttgttttgaa                                40

<210> SEQ ID NO 451
<211> LENGTH: 40
<212> TYPE: DNA
<213> ORGANISM: Homo sapiens

<400> SEQUENCE: 451
tgggaatctg gccagagaag gtgcttgaca tcctccagca                                40

<210> SEQ ID NO 452
<211> LENGTH: 40
<212> TYPE: DNA
<213> ORGANISM: Homo sapiens

<400> SEQUENCE: 452
agaaaacatc gaattcagag cttgataatg gaactataca                                40

<210> SEQ ID NO 453
<211> LENGTH: 40
<212> TYPE: DNA
<213> ORGANISM: Homo sapiens

<400> SEQUENCE: 453
agaaaacatc gaattcagag agttccagaa gacagcgaac                                40

<210> SEQ ID NO 454
<211> LENGTH: 40
<212> TYPE: DNA
<213> ORGANISM: Homo sapiens

<400> SEQUENCE: 454
cgtccgccag tcgtcccgag gcatgaagaa ctcttgactg                                40

<210> SEQ ID NO 455
<211> LENGTH: 40
<212> TYPE: DNA
<213> ORGANISM: Homo sapiens

<400> SEQUENCE: 455
agccgggcgt tgggggaaag gcatgaagaa ctcttgactg                                40

<210> SEQ ID NO 456
<211> LENGTH: 40
<212> TYPE: DNA
<213> ORGANISM: Homo sapiens

<400> SEQUENCE: 456
actaatcttc agcatgccat tcggcgtggc acaagcctaa                                40

<210> SEQ ID NO 457
<211> LENGTH: 40
<212> TYPE: DNA
<213> ORGANISM: Homo sapiens

<400> SEQUENCE: 457
caaacacctc ttgattataa tcggcgtggc acaagcctaa                                40

<210> SEQ ID NO 458
<211> LENGTH: 40
<212> TYPE: DNA
<213> ORGANISM: Homo sapiens

<400> SEQUENCE: 458
caccacaaaa tcacagacag cttgcttgcc ttttgtttta                                40

<210> SEQ ID NO 459
<211> LENGTH: 40
<212> TYPE: DNA
<213> ORGANISM: Homo sapiens

<400> SEQUENCE: 459
caccacaaaa tcacagacag cagctgcagt atctcggaag                                40

<210> SEQ ID NO 460
<211> LENGTH: 40
<212> TYPE: DNA
<213> ORGANISM: Homo sapiens

<400> SEQUENCE: 460
ctcctactac acaatctaag atttcagaaa tggccaaaga                                40

<210> SEQ ID NO 461
<211> LENGTH: 40
<212> TYPE: DNA
<213> ORGANISM: Homo sapiens

<400> SEQUENCE: 461
agagctcaaa gaagtgttta atttcagaaa tggccaaaga                                40

<210> SEQ ID NO 462
<211> LENGTH: 40
<212> TYPE: DNA
<213> ORGANISM: Homo sapiens

<400> SEQUENCE: 462
atttccagag gatttacact tttgcttgac agggtcagtg                                40

<210> SEQ ID NO 463
<211> LENGTH: 40
<212> TYPE: DNA
<213> ORGANISM: Homo sapiens

<400> SEQUENCE: 463
atttccagag gatttacact ggtcagtgct gcttgcccat                                40

<210> SEQ ID NO 464
<211> LENGTH: 40
<212> TYPE: DNA
<213> ORGANISM: Homo sapiens

<400> SEQUENCE: 464

```
gagtcggcgc cgagaacatg tttcctgtgg gccgcatcca                              40
```

<210> SEQ ID NO 465
<211> LENGTH: 40
<212> TYPE: DNA
<213> ORGANISM: Homo sapiens

<400> SEQUENCE: 465

```
cacagagagc tgggctacag tttcctgtgg gccgcatcca                              40
```

<210> SEQ ID NO 466
<211> LENGTH: 40
<212> TYPE: DNA
<213> ORGANISM: Homo sapiens

<400> SEQUENCE: 466

```
tgacgttctc tgtgctccag tggtttctcc cacaggttcc                              40
```

<210> SEQ ID NO 467
<211> LENGTH: 40
<212> TYPE: DNA
<213> ORGANISM: Homo sapiens

<400> SEQUENCE: 467

```
tgacgttctc tgtgctccag gttcccggcc cccaagtcgc                              40
```

<210> SEQ ID NO 468
<211> LENGTH: 40
<212> TYPE: DNA
<213> ORGANISM: Homo sapiens

<400> SEQUENCE: 468

```
caaacacctc ttgattataa cacgcaggta acatggatgt                              40
```

<210> SEQ ID NO 469
<211> LENGTH: 40
<212> TYPE: DNA
<213> ORGANISM: Homo sapiens

<400> SEQUENCE: 469

```
tactccagct tcagcaacag cacctacaga agcggctcaa                              40
```

<210> SEQ ID NO 470
<211> LENGTH: 40
<212> TYPE: DNA
<213> ORGANISM: Homo sapiens

<400> SEQUENCE: 470

```
tactccagct tcagcaacag caggtgatac cctgtcggtc                              40
```

<210> SEQ ID NO 471
<211> LENGTH: 40
<212> TYPE: DNA
<213> ORGANISM: Homo sapiens

<400> SEQUENCE: 471

```
tctcagctga cgaatgcaag gcaccaacgg agagacagct                              40
```

<210> SEQ ID NO 472
<211> LENGTH: 40
<212> TYPE: DNA
<213> ORGANISM: Homo sapiens

<400> SEQUENCE: 472
ggcatgcaac caggcaccag gcaccaacgg agagacagct    40

<210> SEQ ID NO 473
<211> LENGTH: 40
<212> TYPE: DNA
<213> ORGANISM: Homo sapiens

<400> SEQUENCE: 473
tcaaatcatt tacctccaag cagccagctc ctgtcaccat    40

<210> SEQ ID NO 474
<211> LENGTH: 40
<212> TYPE: DNA
<213> ORGANISM: Homo sapiens

<400> SEQUENCE: 474
tcaaatcatt tacctccaag aggactcctg atggatttga    40

<210> SEQ ID NO 475
<211> LENGTH: 40
<212> TYPE: DNA
<213> ORGANISM: Homo sapiens

<400> SEQUENCE: 475
agcaaaaagg ggtgtctcag aatctccggc ctgtgaaact    40

<210> SEQ ID NO 476
<211> LENGTH: 40
<212> TYPE: DNA
<213> ORGANISM: Homo sapiens

<400> SEQUENCE: 476
agcaaaaagg ggtgtctcag gccactcttc acctccacca    40

<210> SEQ ID NO 477
<211> LENGTH: 40
<212> TYPE: DNA
<213> ORGANISM: Homo sapiens

<400> SEQUENCE: 477
tgttgcctcc gcggccgcag gacagcaggt gccaggcttc    40

<210> SEQ ID NO 478
<211> LENGTH: 40
<212> TYPE: DNA
<213> ORGANISM: Homo sapiens

<400> SEQUENCE: 478
tggtcatggc caaaccctgg gacagcaggt gccaggcttc    40

<210> SEQ ID NO 479
<211> LENGTH: 40
<212> TYPE: DNA
<213> ORGANISM: Homo sapiens

<400> SEQUENCE: 479
tgcctaaggc ggatttgaat ctctttctct cccttcagaa    40

<210> SEQ ID NO 480
<211> LENGTH: 40
<212> TYPE: DNA
<213> ORGANISM: Homo sapiens

<400> SEQUENCE: 480
tgcctaaggc ggatttgaat aatcttatct tggctttgga        40

<210> SEQ ID NO 481
<211> LENGTH: 40
<212> TYPE: DNA
<213> ORGANISM: Homo sapiens

<400> SEQUENCE: 481
tggtcatggc caaaccctgg gctccaccct catccagctg        40

<210> SEQ ID NO 482
<211> LENGTH: 40
<212> TYPE: DNA
<213> ORGANISM: Homo sapiens

<400> SEQUENCE: 482
tgcagattcc aaagaaacg aaagcagaag atgaggatat         40

<210> SEQ ID NO 483
<211> LENGTH: 40
<212> TYPE: DNA
<213> ORGANISM: Homo sapiens

<400> SEQUENCE: 483
ccttccaccc aagggaactg aaagcagaag atgaggatat        40

<210> SEQ ID NO 484
<211> LENGTH: 40
<212> TYPE: DNA
<213> ORGANISM: Homo sapiens

<400> SEQUENCE: 484
aggagggccc cctgccgctg gcaacaactc ccagccctgc        40

<210> SEQ ID NO 485
<211> LENGTH: 40
<212> TYPE: DNA
<213> ORGANISM: Homo sapiens

<400> SEQUENCE: 485
aggagggccc cctgccgctg ctgacccctt tggcccgctt        40

<210> SEQ ID NO 486
<211> LENGTH: 40
<212> TYPE: DNA
<213> ORGANISM: Homo sapiens

<400> SEQUENCE: 486
aacaactgcc cagctttgag tggcaataat attgaactgg        40

<210> SEQ ID NO 487
<211> LENGTH: 40
<212> TYPE: DNA
<213> ORGANISM: Homo sapiens

<400> SEQUENCE: 487
aacaactgcc cagctttgag gaaatctgaa atagagtact        40

<210> SEQ ID NO 488
<211> LENGTH: 40
<212> TYPE: DNA

```
<213> ORGANISM: Homo sapiens

<400> SEQUENCE: 488
gttgtgccca tgacctccag gttaggatta attgagtggc                          40

<210> SEQ ID NO 489
<211> LENGTH: 40
<212> TYPE: DNA
<213> ORGANISM: Homo sapiens

<400> SEQUENCE: 489
gttgtgccca tgacctccag tgatcccagg gcaccgccgt                          40

<210> SEQ ID NO 490
<211> LENGTH: 40
<212> TYPE: DNA
<213> ORGANISM: Homo sapiens

<400> SEQUENCE: 490
gttaatgggt ttaatggaga gggcggcgaa gaggacccgc                          40

<210> SEQ ID NO 491
<211> LENGTH: 40
<212> TYPE: DNA
<213> ORGANISM: Homo sapiens

<400> SEQUENCE: 491
gttaatgggt ttaatggaga tgagaaggca accaaagtgc                          40

<210> SEQ ID NO 492
<211> LENGTH: 40
<212> TYPE: DNA
<213> ORGANISM: Homo sapiens

<400> SEQUENCE: 492
gcaaggagca acagcgatgg tgagaaggca accaaagtgc                          40

<210> SEQ ID NO 493
<211> LENGTH: 40
<212> TYPE: DNA
<213> ORGANISM: Homo sapiens

<400> SEQUENCE: 493
agtttgagat gaagcgaatg gatcctggct tcctggacaa                          40

<210> SEQ ID NO 494
<211> LENGTH: 40
<212> TYPE: DNA
<213> ORGANISM: Homo sapiens

<400> SEQUENCE: 494
agtttgagat gaagcgaatg ctcccccctac cagggggtcgc                        40

<210> SEQ ID NO 495
<211> LENGTH: 40
<212> TYPE: DNA
<213> ORGANISM: Homo sapiens

<400> SEQUENCE: 495
agaaaccttg aacgacaaag tggaatttttt atactgtgac                         40

<210> SEQ ID NO 496
<211> LENGTH: 40
```

<212> TYPE: DNA
<213> ORGANISM: Homo sapiens

<400> SEQUENCE: 496
agaaaccttg aacgacaaag agacgtgagt cttgctgtgt        40

<210> SEQ ID NO 497
<211> LENGTH: 40
<212> TYPE: DNA
<213> ORGANISM: Homo sapiens

<400> SEQUENCE: 497
accccttggg catcgatcct gcccttctcct cagcacaaga        40

<210> SEQ ID NO 498
<211> LENGTH: 40
<212> TYPE: DNA
<213> ORGANISM: Homo sapiens

<400> SEQUENCE: 498
accccttggg catcgatcct atttggagcc tggctgccaa        40

<210> SEQ ID NO 499
<211> LENGTH: 40
<212> TYPE: DNA
<213> ORGANISM: Homo sapiens

<400> SEQUENCE: 499
taaagtgttg gctttactta aatttatctt tacagatact        40

<210> SEQ ID NO 500
<211> LENGTH: 40
<212> TYPE: DNA
<213> ORGANISM: Homo sapiens

<400> SEQUENCE: 500
taaagtgttg gctttactta atactgcaaa caatttagtt        40

<210> SEQ ID NO 501
<211> LENGTH: 40
<212> TYPE: DNA
<213> ORGANISM: Homo sapiens

<400> SEQUENCE: 501
acctcgtcag aaacaaccag agttcccccg tttctagagg        40

<210> SEQ ID NO 502
<211> LENGTH: 40
<212> TYPE: DNA
<213> ORGANISM: Homo sapiens

<400> SEQUENCE: 502
acctcgtcag aaacaaccag aggttggacc agcctcaatg        40

<210> SEQ ID NO 503
<211> LENGTH: 40
<212> TYPE: DNA
<213> ORGANISM: Homo sapiens

<400> SEQUENCE: 503
aaagatttca gaagaaatac tatttctctt tcaggtatac        40

<210> SEQ ID NO 504

```
<211> LENGTH: 40
<212> TYPE: DNA
<213> ORGANISM: Homo sapiens

<400> SEQUENCE: 504
aaagatttca gaagaaatac gtataccaac tgcagcctta                        40

<210> SEQ ID NO 505
<211> LENGTH: 40
<212> TYPE: DNA
<213> ORGANISM: Homo sapiens

<400> SEQUENCE: 505
ccaaaagagg ggataatgag ggaaggtgaa gaaggagctg                        40

<210> SEQ ID NO 506
<211> LENGTH: 40
<212> TYPE: DNA
<213> ORGANISM: Homo sapiens

<400> SEQUENCE: 506
tcatcttgaa aaatgaaaat tcctatttta cagctgagga                        40

<210> SEQ ID NO 507
<211> LENGTH: 40
<212> TYPE: DNA
<213> ORGANISM: Homo sapiens

<400> SEQUENCE: 507
tcatcttgaa aaatgaaaat gtggataggc atgtagacct                        40

<210> SEQ ID NO 508
<211> LENGTH: 40
<212> TYPE: DNA
<213> ORGANISM: Homo sapiens

<400> SEQUENCE: 508
accctgtcta ccagcctgtg ttttctgcca cctacaggat                        40

<210> SEQ ID NO 509
<211> LENGTH: 40
<212> TYPE: DNA
<213> ORGANISM: Homo sapiens

<400> SEQUENCE: 509
accctgtcta ccagcctgtg gatagaccat gaagctgaag                        40

<210> SEQ ID NO 510
<211> LENGTH: 40
<212> TYPE: DNA
<213> ORGANISM: Homo sapiens

<400> SEQUENCE: 510
tgacacagcc ctgcaggcag ggtccgtgca ggacctttcc                        40

<210> SEQ ID NO 511
<211> LENGTH: 40
<212> TYPE: DNA
<213> ORGANISM: Homo sapiens

<400> SEQUENCE: 511
tgacacagcc ctgcaggcag aaggatcccg caaacgtgga                        40
```

```
<210> SEQ ID NO 512
<211> LENGTH: 40
<212> TYPE: DNA
<213> ORGANISM: Homo sapiens

<400> SEQUENCE: 512
gcggggcgag ggcagctccg cgtttctctg aattctcccc                40

<210> SEQ ID NO 513
<211> LENGTH: 40
<212> TYPE: DNA
<213> ORGANISM: Homo sapiens

<400> SEQUENCE: 513
gcggggcgag ggcagctccg ggaaggaacg tcccagggat                40

<210> SEQ ID NO 514
<211> LENGTH: 40
<212> TYPE: DNA
<213> ORGANISM: Homo sapiens

<400> SEQUENCE: 514
ccacctcacc atcacccagg gcagcccctc cacagggccc                40

<210> SEQ ID NO 515
<211> LENGTH: 40
<212> TYPE: DNA
<213> ORGANISM: Homo sapiens

<400> SEQUENCE: 515
ccacctcacc atcacccagg ccctcaggca gcccctccac                40

<210> SEQ ID NO 516
<211> LENGTH: 40
<212> TYPE: DNA
<213> ORGANISM: Homo sapiens

<400> SEQUENCE: 516
gccaacctag agcccccctg ctctctgcct cttacagatg                40

<210> SEQ ID NO 517
<211> LENGTH: 40
<212> TYPE: DNA
<213> ORGANISM: Homo sapiens

<400> SEQUENCE: 517
gccaacctag agcccccctg atgactggca tagcctgggc                40

<210> SEQ ID NO 518
<211> LENGTH: 40
<212> TYPE: DNA
<213> ORGANISM: Homo sapiens

<400> SEQUENCE: 518
aaccggggga gcgaggcacg tttctttccc cacctttcta                40

<210> SEQ ID NO 519
<211> LENGTH: 40
<212> TYPE: DNA
<213> ORGANISM: Homo sapiens

<400> SEQUENCE: 519
aaccggggga gcgaggcacg gagtgtacct cacagccttc                40
```

<210> SEQ ID NO 520
<211> LENGTH: 40
<212> TYPE: DNA
<213> ORGANISM: Homo sapiens

<400> SEQUENCE: 520
cacacagact gcgttcgatg agtgtcttcc ccctgcctta                                40

<210> SEQ ID NO 521
<211> LENGTH: 40
<212> TYPE: DNA
<213> ORGANISM: Homo sapiens

<400> SEQUENCE: 521
cacacagact gcgttcgatg ccttgctgtt caccctgatg                                40

<210> SEQ ID NO 522
<211> LENGTH: 40
<212> TYPE: DNA
<213> ORGANISM: Homo sapiens

<400> SEQUENCE: 522
gtttttacct ctgcctcctg atctctcatc ctaggttttc                                40

<210> SEQ ID NO 523
<211> LENGTH: 40
<212> TYPE: DNA
<213> ORGANISM: Homo sapiens

<400> SEQUENCE: 523
gtttttacct ctgcctcctg gttttcatac tctgcacacc                                40

<210> SEQ ID NO 524
<211> LENGTH: 40
<212> TYPE: DNA
<213> ORGANISM: Homo sapiens

<400> SEQUENCE: 524
cactgctggg agagtggaag ttgcttccac agattcctga                                40

<210> SEQ ID NO 525
<211> LENGTH: 40
<212> TYPE: DNA
<213> ORGANISM: Homo sapiens

<400> SEQUENCE: 525
cactgctggg agagtggaag attcctgaga gctgccggcc                                40

<210> SEQ ID NO 526
<211> LENGTH: 40
<212> TYPE: DNA
<213> ORGANISM: Homo sapiens

<400> SEQUENCE: 526
gattttggag aggcaaccaa ctttgttttt cacagattcc                                40

<210> SEQ ID NO 527
<211> LENGTH: 40
<212> TYPE: DNA
<213> ORGANISM: Homo sapiens

<400> SEQUENCE: 527
gattttggag aggcaaccaa attccctgga ctttgtcacc                                40

<210> SEQ ID NO 528
<211> LENGTH: 40
<212> TYPE: DNA
<213> ORGANISM: Homo sapiens

<400> SEQUENCE: 528
tgcagaactg gataaagaag tgtatttttt tgtctcaatt          40

<210> SEQ ID NO 529
<211> LENGTH: 40
<212> TYPE: DNA
<213> ORGANISM: Homo sapiens

<400> SEQUENCE: 529
tgcagaactg gataaagaag gtgcttctaa agtaaagaaa          40

<210> SEQ ID NO 530
<211> LENGTH: 40
<212> TYPE: DNA
<213> ORGANISM: Homo sapiens

<400> SEQUENCE: 530
actcttatgc agtccccatg aggttatgct tatgtttctc          40

<210> SEQ ID NO 531
<211> LENGTH: 40
<212> TYPE: DNA
<213> ORGANISM: Homo sapiens

<400> SEQUENCE: 531
actcttatgc agtccccatg aggagatcct agtctcacca          40

<210> SEQ ID NO 532
<211> LENGTH: 40
<212> TYPE: DNA
<213> ORGANISM: Homo sapiens

<400> SEQUENCE: 532
agtgttttac catggatgtt gtcattccag ggctcctcag          40

<210> SEQ ID NO 533
<211> LENGTH: 40
<212> TYPE: DNA
<213> ORGANISM: Homo sapiens

<400> SEQUENCE: 533
agtgttttac catggatgtt ggctcctcag tggctgtgac          40

<210> SEQ ID NO 534
<211> LENGTH: 40
<212> TYPE: DNA
<213> ORGANISM: Homo sapiens

<400> SEQUENCE: 534
tttatgatgc tgctttaaag ttttgttaat gtttttcttt          40

<210> SEQ ID NO 535
<211> LENGTH: 40
<212> TYPE: DNA
<213> ORGANISM: Homo sapiens

<400> SEQUENCE: 535
tttatgatgc tgctttaaag ctcattaatg aaattgaaga                              40

<210> SEQ ID NO 536
<211> LENGTH: 40
<212> TYPE: DNA
<213> ORGANISM: Homo sapiens

<400> SEQUENCE: 536
atctaaaaac agaagagcag gtccttttt aggtgcaaaa                               40

<210> SEQ ID NO 537
<211> LENGTH: 40
<212> TYPE: DNA
<213> ORGANISM: Homo sapiens

<400> SEQUENCE: 537
atctaaaaac agaagagcag gtgcaaaaac ttcaagctat                              40

<210> SEQ ID NO 538
<211> LENGTH: 40
<212> TYPE: DNA
<213> ORGANISM: Homo sapiens

<400> SEQUENCE: 538
ggattgcagc caacacaaag tttctcttca taggaatgtc                              40

<210> SEQ ID NO 539
<211> LENGTH: 40
<212> TYPE: DNA
<213> ORGANISM: Homo sapiens

<400> SEQUENCE: 539
ggattgcagc caacacaaag gaatgtccca aatgccatgt                              40

<210> SEQ ID NO 540
<211> LENGTH: 40
<212> TYPE: DNA
<213> ORGANISM: Homo sapiens

<400> SEQUENCE: 540
ggtttcgagt ttgaatagtg ttttgcttgt ttgtttgttt                              40

<210> SEQ ID NO 541
<211> LENGTH: 40
<212> TYPE: DNA
<213> ORGANISM: Homo sapiens

<400> SEQUENCE: 541
ggtttcgagt ttgaatagtg gtcagattga agttatcatg                              40

<210> SEQ ID NO 542
<211> LENGTH: 40
<212> TYPE: DNA
<213> ORGANISM: Homo sapiens

<400> SEQUENCE: 542
cgcaagtact tcctgcccca tccagcagca cacagtggga                              40

<210> SEQ ID NO 543
<211> LENGTH: 40
<212> TYPE: DNA
<213> ORGANISM: Homo sapiens

<400> SEQUENCE: 543

```
cgcaagtact tcctgcccca ggtagtggtg actgtgaacc                                40
```

<210> SEQ ID NO 544
<211> LENGTH: 40
<212> TYPE: DNA
<213> ORGANISM: Homo sapiens

<400> SEQUENCE: 544

```
ttcataacaa accagtaaat cacattcagg aattcaccaa                                40
```

<210> SEQ ID NO 545
<211> LENGTH: 40
<212> TYPE: DNA
<213> ORGANISM: Homo sapiens

<400> SEQUENCE: 545

```
tcatcaatgc cccgaccttg cacattcagg aattcaccaa                                40
```

<210> SEQ ID NO 546
<211> LENGTH: 40
<212> TYPE: DNA
<213> ORGANISM: Homo sapiens

<400> SEQUENCE: 546

```
aaatttaaca ttactcatag tttttgctgt tttacagagt                                40
```

<210> SEQ ID NO 547
<211> LENGTH: 40
<212> TYPE: DNA
<213> ORGANISM: Homo sapiens

<400> SEQUENCE: 547

```
aaatttaaca ttactcatag agtaagccat atcaaagact                                40
```

<210> SEQ ID NO 548
<211> LENGTH: 40
<212> TYPE: DNA
<213> ORGANISM: Homo sapiens

<400> SEQUENCE: 548

```
caccgggagc tgcagggccg cccettgtcc atcccaggca                                40
```

<210> SEQ ID NO 549
<211> LENGTH: 40
<212> TYPE: DNA
<213> ORGANISM: Homo sapiens

<400> SEQUENCE: 549

```
caccgggagc tgcagggccg gcacgagcag ctgcaggccc                                40
```

<210> SEQ ID NO 550
<211> LENGTH: 40
<212> TYPE: DNA
<213> ORGANISM: Homo sapiens

<400> SEQUENCE: 550

```
attggacaca gagatgggat atcgtgacgt ctgcatccac                                40
```

<210> SEQ ID NO 551
<211> LENGTH: 40
<212> TYPE: DNA
<213> ORGANISM: Homo sapiens

<400> SEQUENCE: 551
ctgtctctag gctaagcaga atcgtgacgt ctgcatccac          40

<210> SEQ ID NO 552
<211> LENGTH: 40
<212> TYPE: DNA
<213> ORGANISM: Homo sapiens

<400> SEQUENCE: 552
gggacctcac caagcgcccg cccctcatca acctgcagat          40

<210> SEQ ID NO 553
<211> LENGTH: 40
<212> TYPE: DNA
<213> ORGANISM: Homo sapiens

<400> SEQUENCE: 553
gggacctcac caagcgcccg atctgcaggc aggccctgaa          40

<210> SEQ ID NO 554
<211> LENGTH: 40
<212> TYPE: DNA
<213> ORGANISM: Homo sapiens

<400> SEQUENCE: 554
gagtgtgaat catctgtgaa tttcacatca ctcatttaac          40

<210> SEQ ID NO 555
<211> LENGTH: 40
<212> TYPE: DNA
<213> ORGANISM: Homo sapiens

<400> SEQUENCE: 555
gagtgtgaat catctgtgaa ccagctgaaa gaaacattgg          40

<210> SEQ ID NO 556
<211> LENGTH: 40
<212> TYPE: DNA
<213> ORGANISM: Homo sapiens

<400> SEQUENCE: 556
tcatcaatgc cccgaccttg gttcatgaac acattgaggt          40

<210> SEQ ID NO 557
<211> LENGTH: 40
<212> TYPE: DNA
<213> ORGANISM: Homo sapiens

<400> SEQUENCE: 557
gcatttctga gaaggctcgg gtcctctccc gcaggggctg          40

<210> SEQ ID NO 558
<211> LENGTH: 40
<212> TYPE: DNA
<213> ORGANISM: Homo sapiens

<400> SEQUENCE: 558
gcatttctga gaaggctcgg gggctggctt tgacctacag          40

<210> SEQ ID NO 559
<211> LENGTH: 40
<212> TYPE: DNA
<213> ORGANISM: Homo sapiens

```
<400> SEQUENCE: 559
gccagtccag agccctcaag ttcttcttct cagctcttgt                    40

<210> SEQ ID NO 560
<211> LENGTH: 40
<212> TYPE: DNA
<213> ORGANISM: Homo sapiens

<400> SEQUENCE: 560
gccagtccag agccctcaag ctcttgtggc catggagaag                    40

<210> SEQ ID NO 561
<211> LENGTH: 40
<212> TYPE: DNA
<213> ORGANISM: Homo sapiens

<400> SEQUENCE: 561
tggccgaggc gctgaccaag accttactca ggggatcctc                    40

<210> SEQ ID NO 562
<211> LENGTH: 40
<212> TYPE: DNA
<213> ORGANISM: Homo sapiens

<400> SEQUENCE: 562
tggccgaggc gctgaccaag gctgagggca gaggaggcct                    40

<210> SEQ ID NO 563
<211> LENGTH: 40
<212> TYPE: DNA
<213> ORGANISM: Homo sapiens

<400> SEQUENCE: 563
tctacttggt gggcttcttg catttatttt gttttaggat                    40

<210> SEQ ID NO 564
<211> LENGTH: 40
<212> TYPE: DNA
<213> ORGANISM: Homo sapiens

<400> SEQUENCE: 564
tctacttggt gggcttcttg gatttgtttg gtgtcagcat                    40

<210> SEQ ID NO 565
<211> LENGTH: 40
<212> TYPE: DNA
<213> ORGANISM: Homo sapiens

<400> SEQUENCE: 565
gctcctgctc agtatatccg tttttatctg ctttcttcag                    40

<210> SEQ ID NO 566
<211> LENGTH: 40
<212> TYPE: DNA
<213> ORGANISM: Homo sapiens

<400> SEQUENCE: 566
gctcctgctc agtatatccg atacacacca tctcagcaag                    40

<210> SEQ ID NO 567
<211> LENGTH: 40
<212> TYPE: DNA
```

```
<213> ORGANISM: Homo sapiens

<400> SEQUENCE: 567
gaaatagggc acagatccag tttttctttta attttagact                    40

<210> SEQ ID NO 568
<211> LENGTH: 40
<212> TYPE: DNA
<213> ORGANISM: Homo sapiens

<400> SEQUENCE: 568
gaaatagggc acagatccag actgtgatag atgccaacat                     40

<210> SEQ ID NO 569
<211> LENGTH: 40
<212> TYPE: DNA
<213> ORGANISM: Homo sapiens

<400> SEQUENCE: 569
gcaacctgtg ttttacaaag gttttatttt ttagatggtg                     40

<210> SEQ ID NO 570
<211> LENGTH: 40
<212> TYPE: DNA
<213> ORGANISM: Homo sapiens

<400> SEQUENCE: 570
gcaacctgtg ttttacaaag atggtgtcct acagcagcca                     40

<210> SEQ ID NO 571
<211> LENGTH: 40
<212> TYPE: DNA
<213> ORGANISM: Homo sapiens

<400> SEQUENCE: 571 ccccctgaagt actagcaaag catgttaata ttttataggt                    40

<210> SEQ ID NO 572
<211> LENGTH: 40
<212> TYPE: DNA
<213> ORGANISM: Homo sapiens

<400> SEQUENCE: 572 ccccctgaagt actagcaaag gtacaggcaa ttaaacttct                    40

<210> SEQ ID NO 573
<211> LENGTH: 40
<212> TYPE: DNA
<213> ORGANISM: Homo sapiens

<400> SEQUENCE: 573
gttcctcact ttgaatgagg tgttttttgat tctgcaggtg                    40

<210> SEQ ID NO 574
<211> LENGTH: 40
<212> TYPE: DNA
<213> ORGANISM: Homo sapiens

<400> SEQUENCE: 574
gttcctcact ttgaatgagg gtgcatggta ctcagtaggt                     40

<210> SEQ ID NO 575
<211> LENGTH: 40
```

```
<212> TYPE: DNA
<213> ORGANISM: Homo sapiens

<400> SEQUENCE: 575
tcttggaagg cagagaaaag atatttctag agcatttggg                             40

<210> SEQ ID NO 576
<211> LENGTH: 40
<212> TYPE: DNA
<213> ORGANISM: Homo sapiens

<400> SEQUENCE: 576
tcttggaagg cagagaaaag tctacctcga gacctatggc                             40

<210> SEQ ID NO 577
<211> LENGTH: 40
<212> TYPE: DNA
<213> ORGANISM: Homo sapiens

<400> SEQUENCE: 577
aacccggaga gaaaagggag tttgttttta ggtcagagtc                             40

<210> SEQ ID NO 578
<211> LENGTH: 40
<212> TYPE: DNA
<213> ORGANISM: Homo sapiens

<400> SEQUENCE: 578
aacccggaga gaaaagggag caactgatgt tgccatgcag                             40

<210> SEQ ID NO 579
<211> LENGTH: 40
<212> TYPE: DNA
<213> ORGANISM: Homo sapiens

<400> SEQUENCE: 579
aatcttcccc aagatgtatg ttctatgttc cagcagagat                             40

<210> SEQ ID NO 580
<211> LENGTH: 40
<212> TYPE: DNA
<213> ORGANISM: Homo sapiens

<400> SEQUENCE: 580
aatcttcccc aagatgtatg gttatatcaa tcagtgaaaa                             40

<210> SEQ ID NO 581
<211> LENGTH: 40
<212> TYPE: DNA
<213> ORGANISM: Homo sapiens

<400> SEQUENCE: 581
ctctcttgtc agacaagcag ttgtctcttc caggtaatgg                             40

<210> SEQ ID NO 582
<211> LENGTH: 40
<212> TYPE: DNA
<213> ORGANISM: Homo sapiens

<400> SEQUENCE: 582
ctctcttgtc agacaagcag gtaatggaga ctatacagtg                             40

<210> SEQ ID NO 583
```

```
<211> LENGTH: 40
<212> TYPE: DNA
<213> ORGANISM: Homo sapiens

<400> SEQUENCE: 583
gcagagctgt ggcttaccag tccctccttg ttccagatgt          40

<210> SEQ ID NO 584
<211> LENGTH: 40
<212> TYPE: DNA
<213> ORGANISM: Homo sapiens

<400> SEQUENCE: 584
gcagagctgt ggcttaccag atgtggcaaa atctggcaaa          40

<210> SEQ ID NO 585
<211> LENGTH: 40
<212> TYPE: DNA
<213> ORGANISM: Homo sapiens

<400> SEQUENCE: 585
tgcaggagac cggcttttgg gtccccttct tatacccctc          40

<210> SEQ ID NO 586
<211> LENGTH: 40
<212> TYPE: DNA
<213> ORGANISM: Homo sapiens

<400> SEQUENCE: 586
tgcaggagac cggcttttgg atactgctaa tcagtcctag          40

<210> SEQ ID NO 587
<211> LENGTH: 40
<212> TYPE: DNA
<213> ORGANISM: Homo sapiens

<400> SEQUENCE: 587
tcttgccaga gctgcccacg ctctccaccc tcagctgcct          40

<210> SEQ ID NO 588
<211> LENGTH: 40
<212> TYPE: DNA
<213> ORGANISM: Homo sapiens

<400> SEQUENCE: 588
tcttgccaga gctgcccacg cttctttcct tgctgctgga          40

<210> SEQ ID NO 589
<211> LENGTH: 40
<212> TYPE: DNA
<213> ORGANISM: Homo sapiens

<400> SEQUENCE: 589
gcaggctgcc cgggactctg gctctctttc tctcagggga          40

<210> SEQ ID NO 590
<211> LENGTH: 40
<212> TYPE: DNA
<213> ORGANISM: Homo sapiens

<400> SEQUENCE: 590
gcaggctgcc cgggactctg gggacatgaa gggacagtgg          40
```

```
<210> SEQ ID NO 591
<211> LENGTH: 40
<212> TYPE: DNA
<213> ORGANISM: Homo sapiens

<400> SEQUENCE: 591
gccagtccag agccctcaag tctttaccag acttgcaggg                              40

<210> SEQ ID NO 592
<211> LENGTH: 40
<212> TYPE: DNA
<213> ORGANISM: Homo sapiens

<400> SEQUENCE: 592
ttcccactgg tcgcctgcag gtatttctct ttagactggc                              40

<210> SEQ ID NO 593
<211> LENGTH: 40
<212> TYPE: DNA
<213> ORGANISM: Homo sapiens

<400> SEQUENCE: 593
ttcccactgg tcgcctgcag actggcatcc ttcgaaccaa                              40

<210> SEQ ID NO 594
<211> LENGTH: 40
<212> TYPE: DNA
<213> ORGANISM: Homo sapiens

<400> SEQUENCE: 594
tgtaaatggg gaagcgctgt tttctacaga ctgccattgc                              40

<210> SEQ ID NO 595
<211> LENGTH: 40
<212> TYPE: DNA
<213> ORGANISM: Homo sapiens

<400> SEQUENCE: 595
tgtaaatggg gaagcgctgt gcgacgactg taagggcaag                              40

<210> SEQ ID NO 596
<211> LENGTH: 40
<212> TYPE: DNA
<213> ORGANISM: Homo sapiens

<400> SEQUENCE: 596
tcaatgcaaa tatcatcatg gattttcttc ctaaatttct                              40

<210> SEQ ID NO 597
<211> LENGTH: 40
<212> TYPE: DNA
<213> ORGANISM: Homo sapiens

<400> SEQUENCE: 597
tcaatgcaaa tatcatcatg cctgaatttg aaaccaagtg                              40

<210> SEQ ID NO 598
<211> LENGTH: 40
<212> TYPE: DNA
<213> ORGANISM: Homo sapiens

<400> SEQUENCE: 598
acaaatcaac tggaaagcaa ttactgtttt caggcagtct                              40
```

<210> SEQ ID NO 599
<211> LENGTH: 40
<212> TYPE: DNA
<213> ORGANISM: Homo sapiens

<400> SEQUENCE: 599
acaaatcaac tggaaagcaa gcagtctgca gaactaaata                           40

<210> SEQ ID NO 600
<211> LENGTH: 40
<212> TYPE: DNA
<213> ORGANISM: Homo sapiens

<400> SEQUENCE: 600
caaagcgccc agccctgggg gctggaggct gagccccggc                           40

<210> SEQ ID NO 601
<211> LENGTH: 40
<212> TYPE: DNA
<213> ORGANISM: Homo sapiens

<400> SEQUENCE: 601
caaagcgccc agccctgggg atccggaaac ggcactcaag                           40

<210> SEQ ID NO 602
<211> LENGTH: 40
<212> TYPE: DNA
<213> ORGANISM: Homo sapiens

<400> SEQUENCE: 602
tgacacagcc ctgcaggcag gacctttccc cctccctagt                           40

<210> SEQ ID NO 603
<211> LENGTH: 40
<212> TYPE: DNA
<213> ORGANISM: Homo sapiens

<400> SEQUENCE: 603
agttgccatt ccattacatg tctttacttt cctgaagctt                           40

<210> SEQ ID NO 604
<211> LENGTH: 40
<212> TYPE: DNA
<213> ORGANISM: Homo sapiens

<400> SEQUENCE: 604
agttgccatt ccattacatg cttcaagctt agatgatgtt                           40

<210> SEQ ID NO 605
<211> LENGTH: 40
<212> TYPE: DNA
<213> ORGANISM: Homo sapiens

<400> SEQUENCE: 605
actgattaaa aatcttggtg gtgatttctc tttgccagtt                           40

<210> SEQ ID NO 606
<211> LENGTH: 40
<212> TYPE: DNA
<213> ORGANISM: Homo sapiens

<400> SEQUENCE: 606
actgattaaa aatcttggtg ttgatacaat acaaatggaa                           40

<210> SEQ ID NO 607
<211> LENGTH: 40
<212> TYPE: DNA
<213> ORGANISM: Homo sapiens

<400> SEQUENCE: 607
aggctattgt tgcagaccgg gctgttttcc ttacagatgg                    40

<210> SEQ ID NO 608
<211> LENGTH: 40
<212> TYPE: DNA
<213> ORGANISM: Homo sapiens

<400> SEQUENCE: 608
aggctattgt tgcagaccgg atggtagaaa tcctattcca                    40

<210> SEQ ID NO 609
<211> LENGTH: 40
<212> TYPE: DNA
<213> ORGANISM: Homo sapiens

<400> SEQUENCE: 609
cctttcaaga aaacaaaaag tcgcttttc cagtggcggt                     40

<210> SEQ ID NO 610
<211> LENGTH: 40
<212> TYPE: DNA
<213> ORGANISM: Homo sapiens

<400> SEQUENCE: 610
cctttcaaga aaacaaaaag gcaaagtgct cttaggagaa                    40

<210> SEQ ID NO 611
<211> LENGTH: 40
<212> TYPE: DNA
<213> ORGANISM: Homo sapiens

<400> SEQUENCE: 611
acacggagct caagaaacag tttcttccag aactaccagc                    40

<210> SEQ ID NO 612
<211> LENGTH: 40
<212> TYPE: DNA
<213> ORGANISM: Homo sapiens

<400> SEQUENCE: 612
acacggagct caagaaacag atggcaaacc aaaaagattt                    40

<210> SEQ ID NO 613
<211> LENGTH: 40
<212> TYPE: DNA
<213> ORGANISM: Homo sapiens

<400> SEQUENCE: 613
gacttcgaac atttaaacag tgtgttacag gtagaagaga                    40

<210> SEQ ID NO 614
<211> LENGTH: 40
<212> TYPE: DNA
<213> ORGANISM: Homo sapiens

<400> SEQUENCE: 614

```
gacttcgaac atttaaacag aggtatcctg ggcaagtcat                                  40
```

<210> SEQ ID NO 615
<211> LENGTH: 40
<212> TYPE: DNA
<213> ORGANISM: Homo sapiens

<400> SEQUENCE: 615

```
accacgaagg gtcacacaag tctatttggt ccaggggcag                                  40
```

<210> SEQ ID NO 616
<211> LENGTH: 40
<212> TYPE: DNA
<213> ORGANISM: Homo sapiens

<400> SEQUENCE: 616

```
accacgaagg gtcacacaag gggcagcctc acctgggcat                                  40
```

<210> SEQ ID NO 617
<211> LENGTH: 40
<212> TYPE: DNA
<213> ORGANISM: Homo sapiens

<400> SEQUENCE: 617

```
ttaacaaaca cgtgaatcta cagtgttttgg ccagcgcttg                                 40
```

<210> SEQ ID NO 618
<211> LENGTH: 40
<212> TYPE: DNA
<213> ORGANISM: Homo sapiens

<400> SEQUENCE: 618

```
tgctggcaca ccctgtggag cagtgtttgg ccagcgcttg                                  40
```

<210> SEQ ID NO 619
<211> LENGTH: 40
<212> TYPE: DNA
<213> ORGANISM: Homo sapiens

<400> SEQUENCE: 619

```
cgccccaggg caagcgaaag gtgttccttg acttgtgcgt                                  40
```

<210> SEQ ID NO 620
<211> LENGTH: 40
<212> TYPE: DNA
<213> ORGANISM: Homo sapiens

<400> SEQUENCE: 620

```
cgccccaggg caagcgaaag gtgatcaaca ctccggaaat                                  40
```

<210> SEQ ID NO 621
<211> LENGTH: 40
<212> TYPE: DNA
<213> ORGANISM: Homo sapiens

<400> SEQUENCE: 621

```
tggtacaact tcaggaaaag tctgtttgtt ttgcagtgtt                                  40
```

<210> SEQ ID NO 622
<211> LENGTH: 40
<212> TYPE: DNA
<213> ORGANISM: Homo sapiens

<400> SEQUENCE: 622
tggtacaact tcaggaaaag tgtttagccc tccaggccca                           40

<210> SEQ ID NO 623
<211> LENGTH: 40
<212> TYPE: DNA
<213> ORGANISM: Homo sapiens

<400> SEQUENCE: 623
tggatttgct cggcttttga ttttgattcc agccttccgc                           40

<210> SEQ ID NO 624
<211> LENGTH: 40
<212> TYPE: DNA
<213> ORGANISM: Homo sapiens

<400> SEQUENCE: 624
tggatttgct cggcttttga ctggaccgag tgactactat                           40

<210> SEQ ID NO 625
<211> LENGTH: 40
<212> TYPE: DNA
<213> ORGANISM: Homo sapiens

<400> SEQUENCE: 625
gatgaggacc cccacatagg tttccaaacc aggatggcca                           40

<210> SEQ ID NO 626
<211> LENGTH: 40
<212> TYPE: DNA
<213> ORGANISM: Homo sapiens

<400> SEQUENCE: 626
gatgaggacc cccacatagg gatggccata gcagccacaa                           40

<210> SEQ ID NO 627
<211> LENGTH: 40
<212> TYPE: DNA
<213> ORGANISM: Homo sapiens

<400> SEQUENCE: 627
tgttttaaat tccatagcag ctatttctac agtaaaccat                           40

<210> SEQ ID NO 628
<211> LENGTH: 40
<212> TYPE: DNA
<213> ORGANISM: Homo sapiens

<400> SEQUENCE: 628
tgttttaaat tccatagcag cattttcatc aatagctatt                           40

<210> SEQ ID NO 629
<211> LENGTH: 40
<212> TYPE: DNA
<213> ORGANISM: Homo sapiens

<400> SEQUENCE: 629
gctgggatgt tagggctcag cctgtcgttc caggacccag                           40

<210> SEQ ID NO 630
<211> LENGTH: 40
<212> TYPE: DNA
<213> ORGANISM: Homo sapiens

<400> SEQUENCE: 630
gctgggatgt tagggctcag ggaagaaaag tcagaagacc                    40

<210> SEQ ID NO 631
<211> LENGTH: 40
<212> TYPE: DNA
<213> ORGANISM: Homo sapiens

<400> SEQUENCE: 631
ctggttattg caaattaaag ctctttgccg tcccctccta                    40

<210> SEQ ID NO 632
<211> LENGTH: 40
<212> TYPE: DNA
<213> ORGANISM: Homo sapiens

<400> SEQUENCE: 632
ctggttattg caaattaaag gtcttcaacc ccaggattgg                    40

<210> SEQ ID NO 633
<211> LENGTH: 40
<212> TYPE: DNA
<213> ORGANISM: Homo sapiens

<400> SEQUENCE: 633
ggtcatgcta atgagacagg tctgttgttt ttttagattt                    40

<210> SEQ ID NO 634
<211> LENGTH: 40
<212> TYPE: DNA
<213> ORGANISM: Homo sapiens

<400> SEQUENCE: 634
ggtcatgcta atgagacagg atttgatgag gcgccaagaa                    40

<210> SEQ ID NO 635
<211> LENGTH: 40
<212> TYPE: DNA
<213> ORGANISM: Homo sapiens

<400> SEQUENCE: 635
gtcagcattt gcagactttg tttcttttgg cagatggaga                    40

<210> SEQ ID NO 636
<211> LENGTH: 40
<212> TYPE: DNA
<213> ORGANISM: Homo sapiens

<400> SEQUENCE: 636
gtcagcattt gcagactttg atggagatgg acacatggat                    40

<210> SEQ ID NO 637
<211> LENGTH: 40
<212> TYPE: DNA
<213> ORGANISM: Homo sapiens

<400> SEQUENCE: 637
gcagagctgt ggcttaccag acttctccct ttccaggccc                    40

<210> SEQ ID NO 638
<211> LENGTH: 40
<212> TYPE: DNA
<213> ORGANISM: Homo sapiens

```
<400> SEQUENCE: 638
tgcagctggc ccccgcccag gtctttctc tcccacaggc                             40

<210> SEQ ID NO 639
<211> LENGTH: 40
<212> TYPE: DNA
<213> ORGANISM: Homo sapiens

<400> SEQUENCE: 639
tgcagctggc ccccgcccag gccctgtct cccagcctga                             40

<210> SEQ ID NO 640
<211> LENGTH: 40
<212> TYPE: DNA
<213> ORGANISM: Homo sapiens

<400> SEQUENCE: 640
cacagcaagc accttctgag ttctttctt atttcaggct                             40

<210> SEQ ID NO 641
<211> LENGTH: 40
<212> TYPE: DNA
<213> ORGANISM: Homo sapiens

<400> SEQUENCE: 641
cacagcaagc accttctgag gctgatttgg agcaatataa                            40

<210> SEQ ID NO 642
<211> LENGTH: 40
<212> TYPE: DNA
<213> ORGANISM: Homo sapiens

<400> SEQUENCE: 642
tcacacctgt aggaactgag tgtattatga tacaggaaga                            40

<210> SEQ ID NO 643
<211> LENGTH: 40
<212> TYPE: DNA
<213> ORGANISM: Homo sapiens

<400> SEQUENCE: 643
tcacacctgt aggaactgag gaagaagtta tggcagaaga                            40

<210> SEQ ID NO 644
<211> LENGTH: 40
<212> TYPE: DNA
<213> ORGANISM: Homo sapiens

<400> SEQUENCE: 644
aaaattgact atggcaacaa tttttgcttt acagaatcct                            40

<210> SEQ ID NO 645
<211> LENGTH: 40
<212> TYPE: DNA
<213> ORGANISM: Homo sapiens

<400> SEQUENCE: 645
aaaattgact atggcaacaa aatccttgag cttgatttga                            40

<210> SEQ ID NO 646
<211> LENGTH: 40
<212> TYPE: DNA
```

<213> ORGANISM: Homo sapiens

<400> SEQUENCE: 646
acacggagct caagaaacag aactaccagc agatctagaa    40

<210> SEQ ID NO 647
<211> LENGTH: 40
<212> TYPE: DNA
<213> ORGANISM: Homo sapiens

<400> SEQUENCE: 647
gggaggaaaa gtaattaatg tttttgtttt tcttttttag    40

<210> SEQ ID NO 648
<211> LENGTH: 40
<212> TYPE: DNA
<213> ORGANISM: Homo sapiens

<400> SEQUENCE: 648
gggaggaaaa gtaattaatg gaagttatag aactaaccaa    40

<210> SEQ ID NO 649
<211> LENGTH: 40
<212> TYPE: DNA
<213> ORGANISM: Homo sapiens

<400> SEQUENCE: 649
agaaggagct gcagggccag tgtttccttc acagaatgtg    40

<210> SEQ ID NO 650
<211> LENGTH: 40
<212> TYPE: DNA
<213> ORGANISM: Homo sapiens

<400> SEQUENCE: 650
agaaggagct gcagggccag aatgtggagg ctgtggaccc    40

<210> SEQ ID NO 651
<211> LENGTH: 40
<212> TYPE: DNA
<213> ORGANISM: Homo sapiens

<400> SEQUENCE: 651
gctctggaga atctcaataa ggttttttctt cctttagggc    40

<210> SEQ ID NO 652
<211> LENGTH: 40
<212> TYPE: DNA
<213> ORGANISM: Homo sapiens

<400> SEQUENCE: 652
gctctggaga atctcaataa ggctctccta gcagacattg    40

<210> SEQ ID NO 653
<211> LENGTH: 40
<212> TYPE: DNA
<213> ORGANISM: Homo sapiens

<400> SEQUENCE: 653
catgcaatga acccaaaagg ttgattccag tgctaaaagg    40

<210> SEQ ID NO 654
<211> LENGTH: 40

<210> SEQ ID NO 654
<211> LENGTH: 40
<212> TYPE: DNA
<213> ORGANISM: Homo sapiens

<400> SEQUENCE: 654
catgcaatga acccaaaagg tcactctgag aggagtgata       40

<210> SEQ ID NO 655
<211> LENGTH: 40
<212> TYPE: DNA
<213> ORGANISM: Homo sapiens

<400> SEQUENCE: 655
tgcttccgga acagtgacag ccccatctct gcccctgcta       40

<210> SEQ ID NO 656
<211> LENGTH: 40
<212> TYPE: DNA
<213> ORGANISM: Homo sapiens

<400> SEQUENCE: 656
tgcttccgga acagtgacag ggacttcgct tttgtggcaa       40

<210> SEQ ID NO 657
<211> LENGTH: 40
<212> TYPE: DNA
<213> ORGANISM: Homo sapiens

<400> SEQUENCE: 657
tgggtttcag caagagaaca ttgttttct gattttctag        40

<210> SEQ ID NO 658
<211> LENGTH: 40
<212> TYPE: DNA
<213> ORGANISM: Homo sapiens

<400> SEQUENCE: 658
tgggtttcag caagagaaca ctggcagcct caggaaacaa       40

<210> SEQ ID NO 659
<211> LENGTH: 40
<212> TYPE: DNA
<213> ORGANISM: Homo sapiens

<400> SEQUENCE: 659
aggacatgga tttggtagag tgctctaatt tttgttttaa       40

<210> SEQ ID NO 660
<211> LENGTH: 40
<212> TYPE: DNA
<213> ORGANISM: Homo sapiens

<400> SEQUENCE: 660
aggacatgga tttggtagag gtgaatgaag cttttgctcc       40

<210> SEQ ID NO 661
<211> LENGTH: 40
<212> TYPE: DNA
<213> ORGANISM: Homo sapiens

<400> SEQUENCE: 661
atcacaaccg gaaccgcagg ctccttctgc cctgcccgca       40

<210> SEQ ID NO 662

```
<211> LENGTH: 40
<212> TYPE: DNA
<213> ORGANISM: Homo sapiens

<400> SEQUENCE: 662
atcacaaccg gaaccgcagg ctcatgatgg agcagtccaa                               40

<210> SEQ ID NO 663
<211> LENGTH: 40
<212> TYPE: DNA
<213> ORGANISM: Homo sapiens

<400> SEQUENCE: 663
caggaagcag ctagtctttt atgtttattc tctttgtaga                               40

<210> SEQ ID NO 664
<211> LENGTH: 40
<212> TYPE: DNA
<213> ORGANISM: Homo sapiens

<400> SEQUENCE: 664
caggaagcag ctagtctttt aggtaagaag tatggagaga                               40

<210> SEQ ID NO 665
<211> LENGTH: 40
<212> TYPE: DNA
<213> ORGANISM: Homo sapiens

<400> SEQUENCE: 665
gaaccaatgg aatggagaag gcacaggcgt tttgcaaagg                               40

<210> SEQ ID NO 666
<211> LENGTH: 40
<212> TYPE: DNA
<213> ORGANISM: Homo sapiens

<400> SEQUENCE: 666
gaaccaatgg aatggagaag gtcctatggc cgggctccga                               40

<210> SEQ ID NO 667
<211> LENGTH: 40
<212> TYPE: DNA
<213> ORGANISM: Homo sapiens

<400> SEQUENCE: 667
tgcttgtaaa attgaaatgg tgcttttaat tattatagtt                               40

<210> SEQ ID NO 668
<211> LENGTH: 40
<212> TYPE: DNA
<213> ORGANISM: Homo sapiens

<400> SEQUENCE: 668
tgcttgtaaa attgaaatgg ttgactacaa agaagaatat                               40

<210> SEQ ID NO 669
<211> LENGTH: 40
<212> TYPE: DNA
<213> ORGANISM: Homo sapiens

<400> SEQUENCE: 669
ccacctcacc atcacccagg cccctccaca gggcccctct                               40
```

```
<210> SEQ ID NO 670
<211> LENGTH: 40
<212> TYPE: DNA
<213> ORGANISM: Homo sapiens

<400> SEQUENCE: 670
cgtctccatg accatgcaag gtgtagacgc agtgctcccc                              40

<210> SEQ ID NO 671
<211> LENGTH: 40
<212> TYPE: DNA
<213> ORGANISM: Homo sapiens

<400> SEQUENCE: 671
cgtctccatg accatgcaag gcttcctgaa ctactacgat                              40

<210> SEQ ID NO 672
<211> LENGTH: 40
<212> TYPE: DNA
<213> ORGANISM: Homo sapiens

<400> SEQUENCE: 672
aggaggcaat taaggcaaag gcccttcccc tgctacaggt                              40

<210> SEQ ID NO 673
<211> LENGTH: 40
<212> TYPE: DNA
<213> ORGANISM: Homo sapiens

<400> SEQUENCE: 673
aggaggcaat taaggcaaag gtggggcagt acgtgtcccg                              40

<210> SEQ ID NO 674
<211> LENGTH: 40
<212> TYPE: DNA
<213> ORGANISM: Homo sapiens

<400> SEQUENCE: 674
ttacctccga aggatcgtgg ttctctttgt agggtctgcc                              40

<210> SEQ ID NO 675
<211> LENGTH: 40
<212> TYPE: DNA
<213> ORGANISM: Homo sapiens

<400> SEQUENCE: 675
ttacctccga aggatcgtgg ggtctgccac aaggtacctc                              40

<210> SEQ ID NO 676
<211> LENGTH: 40
<212> TYPE: DNA
<213> ORGANISM: Homo sapiens

<400> SEQUENCE: 676
aataagccct cagatggcag cctgtctgac ctgtgggccc                              40

<210> SEQ ID NO 677
<211> LENGTH: 40
<212> TYPE: DNA
<213> ORGANISM: Homo sapiens

<400> SEQUENCE: 677
aataagccct cagatggcag gcccaagtat ctggtggtga                              40
```

<210> SEQ ID NO 678
<211> LENGTH: 40
<212> TYPE: DNA
<213> ORGANISM: Homo sapiens

<400> SEQUENCE: 678
gcctggacct gtacttggag gtgcagatcc aggcgtacct                              40

<210> SEQ ID NO 679
<211> LENGTH: 40
<212> TYPE: DNA
<213> ORGANISM: Homo sapiens

<400> SEQUENCE: 679
gcctggacct gtacttggag aggcttcggc tcaccgagag                              40

<210> SEQ ID NO 680
<211> LENGTH: 40
<212> TYPE: DNA
<213> ORGANISM: Homo sapiens

<400> SEQUENCE: 680
ctgtaactac tagcccacag tttctttttt attcaaatag                              40

<210> SEQ ID NO 681
<211> LENGTH: 40
<212> TYPE: DNA
<213> ORGANISM: Homo sapiens

<400> SEQUENCE: 681
ctgtaactac tagcccacag agtgacatga tgagggagca                              40

<210> SEQ ID NO 682
<211> LENGTH: 40
<212> TYPE: DNA
<213> ORGANISM: Homo sapiens

<400> SEQUENCE: 682
ctctcaatgc agctttacag ttttcctgca gattgttcaa                              40

<210> SEQ ID NO 683
<211> LENGTH: 40
<212> TYPE: DNA
<213> ORGANISM: Homo sapiens

<400> SEQUENCE: 683
ctctcaatgc agctttacag gcttcaatgg ctgagaatag                              40

<210> SEQ ID NO 684
<211> LENGTH: 40
<212> TYPE: DNA
<213> ORGANISM: Homo sapiens

<400> SEQUENCE: 684
ggagcagttc cagaagactg ctgcttctcc atagggacca                              40

<210> SEQ ID NO 685
<211> LENGTH: 40
<212> TYPE: DNA
<213> ORGANISM: Homo sapiens

<400> SEQUENCE: 685
ggagcagttc cagaagactg ggaccattgt tgtggaaggc                              40

<210> SEQ ID NO 686
<211> LENGTH: 40
<212> TYPE: DNA
<213> ORGANISM: Homo sapiens

<400> SEQUENCE: 686
cctgctggac cattcttacg ttgtctcccc ctgttcctaa                                40

<210> SEQ ID NO 687
<211> LENGTH: 40
<212> TYPE: DNA
<213> ORGANISM: Homo sapiens

<400> SEQUENCE: 687
cctgctggac cattcttacg atttcaacca gctggatggt                                40

<210> SEQ ID NO 688
<211> LENGTH: 40
<212> TYPE: DNA
<213> ORGANISM: Homo sapiens

<400> SEQUENCE: 688
ggattttgat aatgaagaag ttgtgctctt tttccagagg                                40

<210> SEQ ID NO 689
<211> LENGTH: 40
<212> TYPE: DNA
<213> ORGANISM: Homo sapiens

<400> SEQUENCE: 689
ggattttgat aatgaagaag aggaacagtc agtccctccc                                40

<210> SEQ ID NO 690
<211> LENGTH: 40
<212> TYPE: DNA
<213> ORGANISM: Homo sapiens

<400> SEQUENCE: 690
cgtctccatg accatgcaag ggcaggtgta gacgcagtgc                                40

<210> SEQ ID NO 691
<211> LENGTH: 40
<212> TYPE: DNA
<213> ORGANISM: Homo sapiens

<400> SEQUENCE: 691
agtgccagct gcgggcccgg ctctcaccag tgacgccctc                                40

<210> SEQ ID NO 692
<211> LENGTH: 40
<212> TYPE: DNA
<213> ORGANISM: Homo sapiens

<400> SEQUENCE: 692
agtgccagct gcgggcccgg gaatcgtaca agtacttccc                                40

<210> SEQ ID NO 693
<211> LENGTH: 40
<212> TYPE: DNA
<213> ORGANISM: Homo sapiens

<400> SEQUENCE: 693 aacttactttgtttatgatgcttttattttagattcagag 40

<210> SEQ ID NO 694
<211> LENGTH: 40
<212> TYPE: DNA
<213> ORGANISM: Homo sapiens

<400> SEQUENCE: 694 aacttactttgtttatgatgagtatgaagatggtgatctg 40

<210> SEQ ID NO 695
<211> LENGTH: 40
<212> TYPE: DNA
<213> ORGANISM: Homo sapiens

<400> SEQUENCE: 695 atcatagcccacatgtccagttttctttctaggtaaaag 40

<210> SEQ ID NO 696
<211> LENGTH: 40
<212> TYPE: DNA
<213> ORGANISM: Homo sapiens

<400> SEQUENCE: 696 atcatagcccacatgtccaggtaaaagcagcgtttaatga 40

<210> SEQ ID NO 697
<211> LENGTH: 40
<212> TYPE: DNA
<213> ORGANISM: Homo sapiens

<400> SEQUENCE: 697 tgactccgctgctcgccatgactttcaggattaagcgatt 40

<210> SEQ ID NO 698
<211> LENGTH: 40
<212> TYPE: DNA
<213> ORGANISM: Homo sapiens

<400> SEQUENCE: 698 tgactccgctgctcgccatgtcttctcacaagactttcag 40

<210> SEQ ID NO 699
<211> LENGTH: 40
<212> TYPE: DNA
<213> ORGANISM: Homo sapiens

<400> SEQUENCE: 699 ccaagcacctgaaacagcagtttgcaggcttctattttag 40

<210> SEQ ID NO 700
<211> LENGTH: 40
<212> TYPE: DNA
<213> ORGANISM: Homo sapiens

<400> SEQUENCE: 700 ccaagcacctgaaacagcagatgctgaaaaagttcacttc 40

<210> SEQ ID NO 701
<211> LENGTH: 40
<212> TYPE: DNA
<213> ORGANISM: Homo sapiens

<400> SEQUENCE: 701
cgagctgttg gcatccttgg tttcttgtcc acaggagaag         40

<210> SEQ ID NO 702
<211> LENGTH: 40
<212> TYPE: DNA
<213> ORGANISM: Homo sapiens

<400> SEQUENCE: 702
cgagctgttg gcatccttgg gacctgccgc tgccaagcca         40

<210> SEQ ID NO 703
<211> LENGTH: 40
<212> TYPE: DNA
<213> ORGANISM: Homo sapiens

<400> SEQUENCE: 703
gctttctacg gaacatcaat gagcttctgt ctgcacacag         40

<210> SEQ ID NO 704
<211> LENGTH: 40
<212> TYPE: DNA
<213> ORGANISM: Homo sapiens

<400> SEQUENCE: 704
gctttctacg gaacatcaat gagtacctgg ccgtagtcga         40

<210> SEQ ID NO 705
<211> LENGTH: 40
<212> TYPE: DNA
<213> ORGANISM: Homo sapiens

<400> SEQUENCE: 705
caggaatacc tgcagataag atttcacaga atattcgcta         40

<210> SEQ ID NO 706
<211> LENGTH: 40
<212> TYPE: DNA
<213> ORGANISM: Homo sapiens

<400> SEQUENCE: 706
caggaatacc tgcagataag atgatagtta ctgatatata         40

<210> SEQ ID NO 707
<211> LENGTH: 40
<212> TYPE: DNA
<213> ORGANISM: Homo sapiens

<400> SEQUENCE: 707
ctacaccaag aagagaggac ctcttccctc gcgcagaatc         40

<210> SEQ ID NO 708
<211> LENGTH: 40
<212> TYPE: DNA
<213> ORGANISM: Homo sapiens

<400> SEQUENCE: 708
ctacaccaag aagagaggac agaggccaga cttcacagac         40

<210> SEQ ID NO 709
<211> LENGTH: 40
<212> TYPE: DNA
<213> ORGANISM: Homo sapiens

<400> SEQUENCE: 709
cggaggctgt ctcctctcag acttcctctc tcccaccagg                40

<210> SEQ ID NO 710
<211> LENGTH: 40
<212> TYPE: DNA
<213> ORGANISM: Homo sapiens

<400> SEQUENCE: 710
cggaggctgt ctcctctcag gaaatgctgc gctgcatttg                40

<210> SEQ ID NO 711
<211> LENGTH: 40
<212> TYPE: DNA
<213> ORGANISM: Homo sapiens

<400> SEQUENCE: 711
tcctgctgga gccacccaag cttttcttc ttcagaaaag                 40

<210> SEQ ID NO 712
<211> LENGTH: 40
<212> TYPE: DNA
<213> ORGANISM: Homo sapiens

<400> SEQUENCE: 712
tcctgctgga gccacccaag aaaagtgtga tgaagaccac                40

<210> SEQ ID NO 713
<211> LENGTH: 40
<212> TYPE: DNA
<213> ORGANISM: Homo sapiens

<400> SEQUENCE: 713
accaagcata cttccagatg ttctctctat ttaagggtca                40

<210> SEQ ID NO 714
<211> LENGTH: 40
<212> TYPE: DNA
<213> ORGANISM: Homo sapiens

<400> SEQUENCE: 714
accaagcata cttccagatg ggtcaatatt ctctcgagtt                40

<210> SEQ ID NO 715
<211> LENGTH: 40
<212> TYPE: DNA
<213> ORGANISM: Homo sapiens

<400> SEQUENCE: 715
cgggccgccc ccctgcccgg tgttcttctg ggcagtgcaa                40

<210> SEQ ID NO 716
<211> LENGTH: 40
<212> TYPE: DNA
<213> ORGANISM: Homo sapiens

<400> SEQUENCE: 716
cgggccgccc ccctgcccgg aggccggtcc ctgccaaggg                40

<210> SEQ ID NO 717
<211> LENGTH: 40
<212> TYPE: DNA
<213> ORGANISM: Homo sapiens

```
<400> SEQUENCE: 717
ggaggactgg ggtctgcaga catttcttgc agacagcacc                              40

<210> SEQ ID NO 718
<211> LENGTH: 40
<212> TYPE: DNA
<213> ORGANISM: Homo sapiens

<400> SEQUENCE: 718
ggaggactgg ggtctgcaga acagcacctt gtattctggc                              40

<210> SEQ ID NO 719
<211> LENGTH: 40
<212> TYPE: DNA
<213> ORGANISM: Homo sapiens

<400> SEQUENCE: 719
ctgccccctg cgccacacgg cctctttccc tgcagtgatg                              40

<210> SEQ ID NO 720
<211> LENGTH: 40
<212> TYPE: DNA
<213> ORGANISM: Homo sapiens

<400> SEQUENCE: 720
ctgccccctg cgccacacgg tgatggttca ttcgcatatg                              40

<210> SEQ ID NO 721
<211> LENGTH: 40
<212> TYPE: DNA
<213> ORGANISM: Homo sapiens

<400> SEQUENCE: 721
tgtaaatggg gaagcgctgt actgccattg ctatgcacgg                              40

<210> SEQ ID NO 722
<211> LENGTH: 40
<212> TYPE: DNA
<213> ORGANISM: Homo sapiens

<400> SEQUENCE: 722
ctgatgaaaa ctactacaag cagacacctt acaggccagg                              40

<210> SEQ ID NO 723
<211> LENGTH: 40
<212> TYPE: DNA
<213> ORGANISM: Homo sapiens

<400> SEQUENCE: 723
ctgatgaaaa ctactacaag gcccagaccc atggaaagtg                              40

<210> SEQ ID NO 724
<211> LENGTH: 40
<212> TYPE: DNA
<213> ORGANISM: Homo sapiens

<400> SEQUENCE: 724
ttcagctgcc cctgaagaag aaacatgttc tccttccttc                              40

<210> SEQ ID NO 725
<211> LENGTH: 40
<212> TYPE: DNA
```

<213> ORGANISM: Homo sapiens

<400> SEQUENCE: 725
ttcagctgcc cctgaagaag gaatgagtag cgacagtgac 40

<210> SEQ ID NO 726
<211> LENGTH: 40
<212> TYPE: DNA
<213> ORGANISM: Homo sapiens

<400> SEQUENCE: 726
tcccgaagcc acctcatgag cctctgcctt cccccaggtc 40

<210> SEQ ID NO 727
<211> LENGTH: 40
<212> TYPE: DNA
<213> ORGANISM: Homo sapiens

<400> SEQUENCE: 727
tcccgaagcc acctcatgag gtcgggcagt gtgatggagc 40

<210> SEQ ID NO 728
<211> LENGTH: 40
<212> TYPE: DNA
<213> ORGANISM: Homo sapiens

<400> SEQUENCE: 728
ccccggtgcg taaggaggag cctgcccccc tttggccctg 40

<210> SEQ ID NO 729
<211> LENGTH: 40
<212> TYPE: DNA
<213> ORGANISM: Homo sapiens

<400> SEQUENCE: 729
ccccggtgcg taaggaggag gaggacaatc ccaaggggga 40

<210> SEQ ID NO 730
<211> LENGTH: 40
<212> TYPE: DNA
<213> ORGANISM: Homo sapiens

<400> SEQUENCE: 730
agctggagaa aaaccttctt tttcttccag aactaccagc 40

<210> SEQ ID NO 731
<211> LENGTH: 40
<212> TYPE: DNA
<213> ORGANISM: Homo sapiens

<400> SEQUENCE: 731
agctggagaa aaaccttctt atggcaaacc aaaaagattt 40

<210> SEQ ID NO 732
<211> LENGTH: 40
<212> TYPE: DNA
<213> ORGANISM: Homo sapiens

<400> SEQUENCE: 732
ttcgttggca gcttctgctg agaccctgac ccccaccccc 40

<210> SEQ ID NO 733
<211> LENGTH: 40

```
<212> TYPE: DNA
<213> ORGANISM: Homo sapiens

<400> SEQUENCE: 733
ttcgttggca gcttctgctg cgtccacaga gaccctgacc                          40

<210> SEQ ID NO 734
<211> LENGTH: 40
<212> TYPE: DNA
<213> ORGANISM: Homo sapiens

<400> SEQUENCE: 734
gtgccaacga ggaccaggag ttctttattt cagatggaac                          40

<210> SEQ ID NO 735
<211> LENGTH: 40
<212> TYPE: DNA
<213> ORGANISM: Homo sapiens

<400> SEQUENCE: 735
gtgccaacga ggaccaggag atggaactag aagcattacg                          40

<210> SEQ ID NO 736
<211> LENGTH: 40
<212> TYPE: DNA
<213> ORGANISM: Homo sapiens

<400> SEQUENCE: 736
cctcacgatg caaggccacg agttcatgtc ccacagggag                          40

<210> SEQ ID NO 737
<211> LENGTH: 40
<212> TYPE: DNA
<213> ORGANISM: Homo sapiens

<400> SEQUENCE: 737
cctcacgatg caaggccacg ggagaagctg tgtacactgt                          40

<210> SEQ ID NO 738
<211> LENGTH: 40
<212> TYPE: DNA
<213> ORGANISM: Homo sapiens

<400> SEQUENCE: 738
aaaaataaag cctttcccag gcccagaccc atggaaagtg                          40

<210> SEQ ID NO 739
<211> LENGTH: 40
<212> TYPE: DNA
<213> ORGANISM: Homo sapiens

<400> SEQUENCE: 739
cgaggatgaa gacagagcag gtgaccaaga aaaaaagaa                           40

<210> SEQ ID NO 740
<211> LENGTH: 40
<212> TYPE: DNA
<213> ORGANISM: Homo sapiens

<400> SEQUENCE: 740
cgaggatgaa gacagagcag tacaggtgac caagaaaaaa                          40

<210> SEQ ID NO 741
```

```
<211> LENGTH: 40
<212> TYPE: DNA
<213> ORGANISM: Homo sapiens

<400> SEQUENCE: 741
aaaatgggct cagcagttag ggttttttgt tgtttgtttg                            40

<210> SEQ ID NO 742
<211> LENGTH: 40
<212> TYPE: DNA
<213> ORGANISM: Homo sapiens

<400> SEQUENCE: 742
aaaatgggct cagcagttag accttttcac agatgctgct                            40

<210> SEQ ID NO 743
<211> LENGTH: 40
<212> TYPE: DNA
<213> ORGANISM: Homo sapiens

<400> SEQUENCE: 743
aagcactggc ccagtgtcag gagccagatt ctgtgcgaga                            40

<210> SEQ ID NO 744
<211> LENGTH: 40
<212> TYPE: DNA
<213> ORGANISM: Homo sapiens

<400> SEQUENCE: 744
aagcactggc ccagtgtcag aaggagccag attctgtgcg                            40

<210> SEQ ID NO 745
<211> LENGTH: 40
<212> TYPE: DNA
<213> ORGANISM: Homo sapiens

<400> SEQUENCE: 745
ccactctcac aatgacccag gaggaccccc ggcggcgctt                            40

<210> SEQ ID NO 746
<211> LENGTH: 40
<212> TYPE: DNA
<213> ORGANISM: Homo sapiens

<400> SEQUENCE: 746
ccactctcac aatgacccag gctggatcaa gacctttgac                            40

<210> SEQ ID NO 747
<211> LENGTH: 40
<212> TYPE: DNA
<213> ORGANISM: Homo sapiens

<400> SEQUENCE: 747
cctttacttg gggctctcag caactgatgt tgccatgcag                            40

<210> SEQ ID NO 748
<211> LENGTH: 40
<212> TYPE: DNA
<213> ORGANISM: Homo sapiens

<400> SEQUENCE: 748
actcagatgc cgaaaactcg ccctcagtct gaggttctgt                            40
```

```
<210> SEQ ID NO 749
<211> LENGTH: 40
<212> TYPE: DNA
<213> ORGANISM: Homo sapiens

<400> SEQUENCE: 749
actcagatgc cgaaaactcg tgcatggagc ccatggagac                              40

<210> SEQ ID NO 750
<211> LENGTH: 40
<212> TYPE: DNA
<213> ORGANISM: Homo sapiens

<400> SEQUENCE: 750
gcctactctt aaccattagg gtggataggc atgtagacct                              40

<210> SEQ ID NO 751
<211> LENGTH: 40
<212> TYPE: DNA
<213> ORGANISM: Homo sapiens

<400> SEQUENCE: 751
tggagtgcgg atttgcaaca cttgcttcct tctcccacat                              40

<210> SEQ ID NO 752
<211> LENGTH: 40
<212> TYPE: DNA
<213> ORGANISM: Homo sapiens

<400> SEQUENCE: 752
tggagtgcgg atttgcaaca atcaaagatc tgcgagacca                              40

<210> SEQ ID NO 753
<211> LENGTH: 40
<212> TYPE: DNA
<213> ORGANISM: Homo sapiens

<400> SEQUENCE: 753
caactggagt tcattttcag gttttttgac agactatgta                              40

<210> SEQ ID NO 754
<211> LENGTH: 40
<212> TYPE: DNA
<213> ORGANISM: Homo sapiens

<400> SEQUENCE: 754
caactggagt tcattttcag actatgtatg agcacttggg                              40

<210> SEQ ID NO 755
<211> LENGTH: 40
<212> TYPE: DNA
<213> ORGANISM: Homo sapiens

<400> SEQUENCE: 755
caatgtgttg accatcgcag tccccctaca gccctgttca                              40

<210> SEQ ID NO 756
<211> LENGTH: 40
<212> TYPE: DNA
<213> ORGANISM: Homo sapiens

<400> SEQUENCE: 756
caatgtgttg accatcgcag cctctcctgc caacttacag                              40
```

```
<210> SEQ ID NO 757
<211> LENGTH: 40
<212> TYPE: DNA
<213> ORGANISM: Homo sapiens

<400> SEQUENCE: 757
cagctgctct caggagagag tggactggct ctgtaggtac            40

<210> SEQ ID NO 758
<211> LENGTH: 40
<212> TYPE: DNA
<213> ORGANISM: Homo sapiens

<400> SEQUENCE: 758
cagctgctct caggagagag gtacaaagaa gacccctggc            40

<210> SEQ ID NO 759
<211> LENGTH: 40
<212> TYPE: DNA
<213> ORGANISM: Homo sapiens

<400> SEQUENCE: 759
tctctagtgg gcccttctag ttctacaagg taaaactcta            40

<210> SEQ ID NO 760
<211> LENGTH: 40
<212> TYPE: DNA
<213> ORGANISM: Homo sapiens

<400> SEQUENCE: 760
tctctagtgg gcccttctag gaatgaccaa aagaagacaa            40

<210> SEQ ID NO 761
<211> LENGTH: 40
<212> TYPE: DNA
<213> ORGANISM: Homo sapiens

<400> SEQUENCE: 761
agctccgaga gggcaaggag ctccctccct cctagaaatg            40

<210> SEQ ID NO 762
<211> LENGTH: 40
<212> TYPE: DNA
<213> ORGANISM: Homo sapiens

<400> SEQUENCE: 762
agctccgaga gggcaaggag aaatgtgtcc actactggcc            40

<210> SEQ ID NO 763
<211> LENGTH: 40
<212> TYPE: DNA
<213> ORGANISM: Homo sapiens

<400> SEQUENCE: 763
gacgtggcag ctcatgtgag cattgtgtcg ttacaggctt            40

<210> SEQ ID NO 764
<211> LENGTH: 40
<212> TYPE: DNA
<213> ORGANISM: Homo sapiens

<400> SEQUENCE: 764
gacgtggcag ctcatgtgag gcttcagtgt catttgagga            40
```

<210> SEQ ID NO 765
<211> LENGTH: 40
<212> TYPE: DNA
<213> ORGANISM: Homo sapiens

<400> SEQUENCE: 765
aaggaagaac aagactttgt ttagtgtgac tctggatcca                                40

<210> SEQ ID NO 766
<211> LENGTH: 40
<212> TYPE: DNA
<213> ORGANISM: Homo sapiens

<400> SEQUENCE: 766
aatgttaagg agtcatcaag ttagtgtgac tctggatcca                                40

<210> SEQ ID NO 767
<211> LENGTH: 40
<212> TYPE: DNA
<213> ORGANISM: Homo sapiens

<400> SEQUENCE: 767
aggagaacac cttatttcag cttttatttt tatgtgataa                                40

<210> SEQ ID NO 768
<211> LENGTH: 40
<212> TYPE: DNA
<213> ORGANISM: Homo sapiens

<400> SEQUENCE: 768
aggagaacac cttatttcag aaaaggtgta ccatacctga                                40

<210> SEQ ID NO 769
<211> LENGTH: 40
<212> TYPE: DNA
<213> ORGANISM: Homo sapiens

<400> SEQUENCE: 769
ctgatgaaaa ctactacaag acaccttaca ggccaggaga                                40

<210> SEQ ID NO 770
<211> LENGTH: 40
<212> TYPE: DNA
<213> ORGANISM: Homo sapiens

<400> SEQUENCE: 770
ggggccacca ggttggccag cggccccctt tcccagggcc                                40

<210> SEQ ID NO 771
<211> LENGTH: 40
<212> TYPE: DNA
<213> ORGANISM: Homo sapiens

<400> SEQUENCE: 771
ggggccacca ggttggccag ggccatggct gagcacgcag                                40

<210> SEQ ID NO 772
<211> LENGTH: 40
<212> TYPE: DNA
<213> ORGANISM: Homo sapiens

<400> SEQUENCE: 772
tgcacacgcc tctcctacag agtctcttat gctggtccca                              40

<210> SEQ ID NO 773
<211> LENGTH: 40
<212> TYPE: DNA
<213> ORGANISM: Homo sapiens

<400> SEQUENCE: 773
tgcacacgcc tctcctacag gcagcccagc aaatcatcga                              40

<210> SEQ ID NO 774
<211> LENGTH: 40
<212> TYPE: DNA
<213> ORGANISM: Homo sapiens

<400> SEQUENCE: 774
gagctggaga ggaaggcgag aggcagctcg tcgggagcag                              40

<210> SEQ ID NO 775
<211> LENGTH: 40
<212> TYPE: DNA
<213> ORGANISM: Homo sapiens

<400> SEQUENCE: 775
gagctggaga ggaaggcgag gcaggcactg gtcgaccact                              40

<210> SEQ ID NO 776
<211> LENGTH: 40
<212> TYPE: DNA
<213> ORGANISM: Homo sapiens

<400> SEQUENCE: 776
ccgcctctgc cttcggatag gtctggcccc acctggagt                               40

<210> SEQ ID NO 777
<211> LENGTH: 40
<212> TYPE: DNA
<213> ORGANISM: Homo sapiens

<400> SEQUENCE: 777
ccgcctctgc cttcggatag gaaaggttga aagagccaac                              40

<210> SEQ ID NO 778
<211> LENGTH: 40
<212> TYPE: DNA
<213> ORGANISM: Homo sapiens

<400> SEQUENCE: 778
tttctcatat tgctcaacag ttcttttta ggtatcatct                               40

<210> SEQ ID NO 779
<211> LENGTH: 40
<212> TYPE: DNA
<213> ORGANISM: Homo sapiens

<400> SEQUENCE: 779
tttctcatat tgctcaacag gtatcatctt tatcagaaag                              40

<210> SEQ ID NO 780
<211> LENGTH: 40
<212> TYPE: DNA
<213> ORGANISM: Homo sapiens

<400> SEQUENCE: 780
agtggctttg gcgtcttatg gaggcttgct tgcagagggg    40

<210> SEQ ID NO 781
<211> LENGTH: 40
<212> TYPE: DNA
<213> ORGANISM: Homo sapiens

<400> SEQUENCE: 781
agtggctttg gcgtcttatg ggatggagga cgaaggttgg    40

<210> SEQ ID NO 782
<211> LENGTH: 40
<212> TYPE: DNA
<213> ORGANISM: Homo sapiens

<400> SEQUENCE: 782
ggtgacactc aacttcacag gtctctccct ctagtgccta    40

<210> SEQ ID NO 783
<211> LENGTH: 40
<212> TYPE: DNA
<213> ORGANISM: Homo sapiens

<400> SEQUENCE: 783
ggtgacactc aacttcacag tgcctactgg ggccagaagc    40

<210> SEQ ID NO 784
<211> LENGTH: 40
<212> TYPE: DNA
<213> ORGANISM: Homo sapiens

<400> SEQUENCE: 784
tttccattgg gccaatcaag atgcctggaa tgatgtcgtc    40

<210> SEQ ID NO 785
<211> LENGTH: 40
<212> TYPE: DNA
<213> ORGANISM: Homo sapiens

<400> SEQUENCE: 785
gagggccacc aatgggacaa atgcctggaa tgatgtcgtc    40

<210> SEQ ID NO 786
<211> LENGTH: 40
<212> TYPE: DNA
<213> ORGANISM: Homo sapiens

<400> SEQUENCE: 786
agagacaaag agaagaaaaa ctcttactgt tttacagtta    40

<210> SEQ ID NO 787
<211> LENGTH: 40
<212> TYPE: DNA
<213> ORGANISM: Homo sapiens

<400> SEQUENCE: 787
agagacaaag agaagaaaaa ttaactctgc tgtttgctgc    40

<210> SEQ ID NO 788
<211> LENGTH: 40
<212> TYPE: DNA
<213> ORGANISM: Homo sapiens

```
<400> SEQUENCE: 788
ctcaccagcg ccatcgtcag ctctaggagt tccagagcct                    40

<210> SEQ ID NO 789
<211> LENGTH: 40
<212> TYPE: DNA
<213> ORGANISM: Homo sapiens

<400> SEQUENCE: 789
ctcaccagcg ccatcgtcag atggcaaggt cagccccggc                    40

<210> SEQ ID NO 790
<211> LENGTH: 40
<212> TYPE: DNA
<213> ORGANISM: Homo sapiens

<400> SEQUENCE: 790
atcaggtgct catcctgagg tgtctgtctt taatacaggt                    40

<210> SEQ ID NO 791
<211> LENGTH: 40
<212> TYPE: DNA
<213> ORGANISM: Homo sapiens

<400> SEQUENCE: 791
atcaggtgct catcctgagg gtaatgcaga gctctcagaa                    40

<210> SEQ ID NO 792
<211> LENGTH: 40
<212> TYPE: DNA
<213> ORGANISM: Homo sapiens

<400> SEQUENCE: 792
tctggcagcc cacgatgctg caagatggca tcgagcagca                    40

<210> SEQ ID NO 793
<211> LENGTH: 40
<212> TYPE: DNA
<213> ORGANISM: Homo sapiens

<400> SEQUENCE: 793
tctggcagcc cacgatgctg ggagtcgggc tcacgtcctt                    40

<210> SEQ ID NO 794
<211> LENGTH: 40
<212> TYPE: DNA
<213> ORGANISM: Homo sapiens

<400> SEQUENCE: 794
agaattttaa gatacttcag attttgtctt gtaggtttta                    40

<210> SEQ ID NO 795
<211> LENGTH: 40
<212> TYPE: DNA
<213> ORGANISM: Homo sapiens

<400> SEQUENCE: 795
agaattttaa gatacttcag gttttatggg agaattgtag                    40

<210> SEQ ID NO 796
<211> LENGTH: 40
<212> TYPE: DNA
<213> ORGANISM: Homo sapiens
```

<400> SEQUENCE: 796
ccgcctctgc cttcggatag gctttattta ggtctggccc            40

<210> SEQ ID NO 797
<211> LENGTH: 40
<212> TYPE: DNA
<213> ORGANISM: Homo sapiens

<400> SEQUENCE: 797
gagctagtca gactttagag gaaacagtac tgctggagca            40

<210> SEQ ID NO 798
<211> LENGTH: 40
<212> TYPE: DNA
<213> ORGANISM: Homo sapiens

<400> SEQUENCE: 798
aaattcttga ccaatctagg gaaacagtac tgctggagca            40

<210> SEQ ID NO 799
<211> LENGTH: 40
<212> TYPE: DNA
<213> ORGANISM: Homo sapiens

<400> SEQUENCE: 799
cttcatctgt ggataagcag gtcatgtcct ccaggtttct            40

<210> SEQ ID NO 800
<211> LENGTH: 40
<212> TYPE: DNA
<213> ORGANISM: Homo sapiens

<400> SEQUENCE: 800
cttcatctgt ggataagcag tgcaggccaa ggcccctgc             40

<210> SEQ ID NO 801
<211> LENGTH: 40
<212> TYPE: DNA
<213> ORGANISM: Homo sapiens

<400> SEQUENCE: 801
agtatgggat attttaaaag attgttggac cttcagatgg            40

<210> SEQ ID NO 802
<211> LENGTH: 40
<212> TYPE: DNA
<213> ORGANISM: Homo sapiens

<400> SEQUENCE: 802
tcattcttat ttcaatgcag attgttggac cttcagatgg            40

<210> SEQ ID NO 803
<211> LENGTH: 40
<212> TYPE: DNA
<213> ORGANISM: Homo sapiens

<400> SEQUENCE: 803
ctttatctgt gcatgaacag tgcaggccaa ggcccctgc             40

<210> SEQ ID NO 804
<211> LENGTH: 40
<212> TYPE: DNA

<213> ORGANISM: Homo sapiens

<400> SEQUENCE: 804
aagtcgtcct cttcagaaag gccggagcct caacagaaag                     40

<210> SEQ ID NO 805
<211> LENGTH: 40
<212> TYPE: DNA
<213> ORGANISM: Homo sapiens

<400> SEQUENCE: 805
agagagaaac atccgaaaaa gccggagcct caacagaaag                     40

<210> SEQ ID NO 806
<211> LENGTH: 40
<212> TYPE: DNA
<213> ORGANISM: Homo sapiens

<400> SEQUENCE: 806
tgggctacct taaccctggg gtatttacac agagtcggcg                     40

<210> SEQ ID NO 807
<211> LENGTH: 40
<212> TYPE: DNA
<213> ORGANISM: Homo sapiens

<400> SEQUENCE: 807
tgggctacct taaccctggg gatttttgac cctcgtgtgg                     40

<210> SEQ ID NO 808
<211> LENGTH: 40
<212> TYPE: DNA
<213> ORGANISM: Homo sapiens

<400> SEQUENCE: 808
gactgcccta aaaggaaaag tttactgttt agactaaaga                     40

<210> SEQ ID NO 809
<211> LENGTH: 40
<212> TYPE: DNA
<213> ORGANISM: Homo sapiens

<400> SEQUENCE: 809
gactgcccta aaaggaaaag actaaagaag aaagacagtg                     40

<210> SEQ ID NO 810
<211> LENGTH: 40
<212> TYPE: DNA
<213> ORGANISM: Homo sapiens

<400> SEQUENCE: 810
tgatagttgg agcggagact cataatggca gaacctgttt                     40

<210> SEQ ID NO 811
<211> LENGTH: 40
<212> TYPE: DNA
<213> ORGANISM: Homo sapiens

<400> SEQUENCE: 811
tgatagttgg agcggagact tagcataatg gcagaacctg                     40

<210> SEQ ID NO 812
<211> LENGTH: 40

```
<212> TYPE: DNA
<213> ORGANISM: Homo sapiens

<400> SEQUENCE: 812
tcattcttat ttcaatgcag agacagggtc ttgctctgtt                          40

<210> SEQ ID NO 813
<211> LENGTH: 40
<212> TYPE: DNA
<213> ORGANISM: Homo sapiens

<400> SEQUENCE: 813
tgacggtgcc accgcggcgc ttttctccct tagatgcctt                          40

<210> SEQ ID NO 814
<211> LENGTH: 40
<212> TYPE: DNA
<213> ORGANISM: Homo sapiens

<400> SEQUENCE: 814
tgacggtgcc accgcggcgc agaggagtct gcaatgccga                          40

<210> SEQ ID NO 815
<211> LENGTH: 40
<212> TYPE: DNA
<213> ORGANISM: Homo sapiens

<400> SEQUENCE: 815
gcagtggctg gagatcaaag tttcaccccc agagggagcc                          40

<210> SEQ ID NO 816
<211> LENGTH: 40
<212> TYPE: DNA
<213> ORGANISM: Homo sapiens

<400> SEQUENCE: 816
gcagtggctg gagatcaaag agagagtgtg cctattgact                          40

<210> SEQ ID NO 817
<211> LENGTH: 40
<212> TYPE: DNA
<213> ORGANISM: Homo sapiens

<400> SEQUENCE: 817
ggacgatggg gatgagaaag atgacgagga ggataaagat                          40

<210> SEQ ID NO 818
<211> LENGTH: 40
<212> TYPE: DNA
<213> ORGANISM: Homo sapiens

<400> SEQUENCE: 818
ggacgatggg gatgagaaag aagatgacga ggaggataaa                          40

<210> SEQ ID NO 819
<211> LENGTH: 40
<212> TYPE: DNA
<213> ORGANISM: Homo sapiens

<400> SEQUENCE: 819
actcttatgc agtccccatg gactgaacca tcaagacacc                          40

<210> SEQ ID NO 820
```

<211> LENGTH: 40
<212> TYPE: DNA
<213> ORGANISM: Homo sapiens

<400> SEQUENCE: 820
gacccatgca tcctcctgtg ctcctcccac tgcagtgggc        40

<210> SEQ ID NO 821
<211> LENGTH: 40
<212> TYPE: DNA
<213> ORGANISM: Homo sapiens

<400> SEQUENCE: 821
gacccatgca tcctcctgtg tgggcacagt ggctcaggga        40

<210> SEQ ID NO 822
<211> LENGTH: 40
<212> TYPE: DNA
<213> ORGANISM: Homo sapiens

<400> SEQUENCE: 822
catcaagcag ctgttgcaat gtttagtccc aggaagcacc        40

<210> SEQ ID NO 823
<211> LENGTH: 40
<212> TYPE: DNA
<213> ORGANISM: Homo sapiens

<400> SEQUENCE: 823
catcaagcag ctgttgcaat ctgcccacaa agaatccagc        40

<210> SEQ ID NO 824
<211> LENGTH: 40
<212> TYPE: DNA
<213> ORGANISM: Homo sapiens

<400> SEQUENCE: 824
caatcattga caatattatg accctgcatg tgatggatca        40

<210> SEQ ID NO 825
<211> LENGTH: 40
<212> TYPE: DNA
<213> ORGANISM: Homo sapiens

<400> SEQUENCE: 825
caatcattga caatattatg gaactgactc agcgcaagaa        40

<210> SEQ ID NO 826
<211> LENGTH: 40
<212> TYPE: DNA
<213> ORGANISM: Homo sapiens

<400> SEQUENCE: 826
gggacactgt gccgaatgaa cttgcttgcc ttttgttttta       40

<210> SEQ ID NO 827
<211> LENGTH: 40
<212> TYPE: DNA
<213> ORGANISM: Homo sapiens

<400> SEQUENCE: 827
gggacactgt gccgaatgaa cagctgcagt atctcggaag        40

```
<210> SEQ ID NO 828
<211> LENGTH: 40
<212> TYPE: DNA
<213> ORGANISM: Homo sapiens

<400> SEQUENCE: 828 tcaggggcg cgtgctgaag gagctgcctg agttcgaggg                         40

<210> SEQ ID NO 829
<211> LENGTH: 40
<212> TYPE: DNA
<213> ORGANISM: Homo sapiens

<400> SEQUENCE: 829
tcgagccagg ctgcaaaaag gagctgcctg agttcgaggg                        40

<210> SEQ ID NO 830
<211> LENGTH: 40
<212> TYPE: DNA
<213> ORGANISM: Homo sapiens

<400> SEQUENCE: 830
ctacaaccag agcgaggctg ggtctcacac cctccaggga                        40

<210> SEQ ID NO 831
<211> LENGTH: 40
<212> TYPE: DNA
<213> ORGANISM: Homo sapiens

<400> SEQUENCE: 831
ctacaaccag agcgaggctg ggaatgaatg gctgcgacat                        40

<210> SEQ ID NO 832
<211> LENGTH: 40
<212> TYPE: DNA
<213> ORGANISM: Homo sapiens

<400> SEQUENCE: 832
tccaacaagc acctctgaag tcttctcatt cacaggttaa                        40

<210> SEQ ID NO 833
<211> LENGTH: 40
<212> TYPE: DNA
<213> ORGANISM: Homo sapiens

<400> SEQUENCE: 833
tccaacaagc acctctgaag gttaaggcta cctttccaga                        40

<210> SEQ ID NO 834
<211> LENGTH: 40
<212> TYPE: DNA
<213> ORGANISM: Homo sapiens

<400> SEQUENCE: 834
gttcccgagg ctgtcaccag ggtgttccct caggtcaatg                        40

<210> SEQ ID NO 835
<211> LENGTH: 40
<212> TYPE: DNA
<213> ORGANISM: Homo sapiens

<400> SEQUENCE: 835
gttcccgagg ctgtcaccag tggatactga ggctgtgtgg                        40
```

<210> SEQ ID NO 836
<211> LENGTH: 40
<212> TYPE: DNA
<213> ORGANISM: Homo sapiens

<400> SEQUENCE: 836
ccagatcaac acaattgata gtcgtactct ttcagatgtc        40

<210> SEQ ID NO 837
<211> LENGTH: 40
<212> TYPE: DNA
<213> ORGANISM: Homo sapiens

<400> SEQUENCE: 837
ccagatcaac acaattgata atgtcagcaa tatttccaac        40

<210> SEQ ID NO 838
<211> LENGTH: 40
<212> TYPE: DNA
<213> ORGANISM: Homo sapiens

<400> SEQUENCE: 838
cgtcctgccc ccaactgccg ctctgtcttc cctgttccca        40

<210> SEQ ID NO 839
<211> LENGTH: 40
<212> TYPE: DNA
<213> ORGANISM: Homo sapiens

<400> SEQUENCE: 839
cgtcctgccc ccaactgccg cctctcagcg agaaggacac        40

<210> SEQ ID NO 840
<211> LENGTH: 40
<212> TYPE: DNA
<213> ORGANISM: Homo sapiens

<400> SEQUENCE: 840
tgcaggggga gcagcccaag gaggccccac cgccactgtc        40

<210> SEQ ID NO 841
<211> LENGTH: 40
<212> TYPE: DNA
<213> ORGANISM: Homo sapiens

<400> SEQUENCE: 841
tgcaggggga gcagcccaag ccggccagcc ctgctgagga        40

<210> SEQ ID NO 842
<211> LENGTH: 40
<212> TYPE: DNA
<213> ORGANISM: Homo sapiens

<400> SEQUENCE: 842
gactgcccta aaaggaaaag cagtttactg tttagactaa        40

<210> SEQ ID NO 843
<211> LENGTH: 40
<212> TYPE: DNA
<213> ORGANISM: Homo sapiens

<400> SEQUENCE: 843
ctatgaggcc atgactgcag tggatactga ggctgtgtgg        40

<210> SEQ ID NO 844
<211> LENGTH: 40
<212> TYPE: DNA
<213> ORGANISM: Homo sapiens

<400> SEQUENCE: 844
cttctcaaga tcagtctcag gtgccacgtg tgccaacgca                       40

<210> SEQ ID NO 845
<211> LENGTH: 40
<212> TYPE: DNA
<213> ORGANISM: Homo sapiens

<400> SEQUENCE: 845
cttctcaaga tcagtctcag gaacctgaca gaacttcaca                       40

<210> SEQ ID NO 846
<211> LENGTH: 40
<212> TYPE: DNA
<213> ORGANISM: Homo sapiens

<400> SEQUENCE: 846
accttaacaa gatttatgag acttccttta ataagtgttg                       40

<210> SEQ ID NO 847
<211> LENGTH: 40
<212> TYPE: DNA
<213> ORGANISM: Homo sapiens

<400> SEQUENCE: 847
aatcactagg aactccagag acttccttta ataagtgttg                       40

<210> SEQ ID NO 848
<211> LENGTH: 40
<212> TYPE: DNA
<213> ORGANISM: Homo sapiens

<400> SEQUENCE: 848
actgggcttc caccgagcag aaacagcact tcttctcagt                       40

<210> SEQ ID NO 849
<211> LENGTH: 40
<212> TYPE: DNA
<213> ORGANISM: Homo sapiens

<400> SEQUENCE: 849
actgggcttc caccgagcag gagattacct ggggcaattg                       40

<210> SEQ ID NO 850
<211> LENGTH: 40
<212> TYPE: DNA
<213> ORGANISM: Homo sapiens

<400> SEQUENCE: 850
ctgaagacgg gattctttag ctctccccac ctggtgcagg                       40

<210> SEQ ID NO 851
<211> LENGTH: 40
<212> TYPE: DNA
<213> ORGANISM: Homo sapiens

<400> SEQUENCE: 851

```
ctgaagacgg gattctttag gttcgggagc ggatccgcat          40
```

<210> SEQ ID NO 852
<211> LENGTH: 40
<212> TYPE: DNA
<213> ORGANISM: Homo sapiens

<400> SEQUENCE: 852

```
atctcaggag cacctgaatg gtccctgcc tgtgcccttc          40
```

<210> SEQ ID NO 853
<211> LENGTH: 40
<212> TYPE: DNA
<213> ORGANISM: Homo sapiens

<400> SEQUENCE: 853

```
cccaccccctt caccctgcag gtccctgcc tgtgcccttc         40
```

<210> SEQ ID NO 854
<211> LENGTH: 40
<212> TYPE: DNA
<213> ORGANISM: Homo sapiens

<400> SEQUENCE: 854

```
ggccacacgc ctctgccaag cccctctccc ctggcacaga         40
```

<210> SEQ ID NO 855
<211> LENGTH: 40
<212> TYPE: DNA
<213> ORGANISM: Homo sapiens

<400> SEQUENCE: 855

```
ggccacacgc ctctgccaag acattgatga gtgtgagtct         40
```

<210> SEQ ID NO 856
<211> LENGTH: 40
<212> TYPE: DNA
<213> ORGANISM: Homo sapiens

<400> SEQUENCE: 856

```
gagtacgagg tctccagcag cctgccctgt gcctacagcc         40
```

<210> SEQ ID NO 857
<211> LENGTH: 40
<212> TYPE: DNA
<213> ORGANISM: Homo sapiens

<400> SEQUENCE: 857

```
gagtacgagg tctccagcag cctcgtgtgc atcaccgggg         40
```

<210> SEQ ID NO 858
<211> LENGTH: 40
<212> TYPE: DNA
<213> ORGANISM: Homo sapiens

<400> SEQUENCE: 858

```
agcgcatcgc agcttccaag tacttcttca cagctcccct         40
```

<210> SEQ ID NO 859
<211> LENGTH: 40
<212> TYPE: DNA
<213> ORGANISM: Homo sapiens

<400> SEQUENCE: 859
agcgcatcgc agcttccaag gctctcctcc atcagtactt         40

<210> SEQ ID NO 860
<211> LENGTH: 40
<212> TYPE: DNA
<213> ORGANISM: Homo sapiens

<400> SEQUENCE: 860
tgggcagccc cccgcagacg ttggtttttc agcagacctg         40

<210> SEQ ID NO 861
<211> LENGTH: 40
<212> TYPE: DNA
<213> ORGANISM: Homo sapiens

<400> SEQUENCE: 861
tgggcagccc cccgcagacg ctcaacatcc tggtggatac         40

<210> SEQ ID NO 862
<211> LENGTH: 40
<212> TYPE: DNA
<213> ORGANISM: Homo sapiens

<400> SEQUENCE: 862
aaccaagagg acccacacag gatggtcttc acaggttctc         40

<210> SEQ ID NO 863
<211> LENGTH: 40
<212> TYPE: DNA
<213> ORGANISM: Homo sapiens

<400> SEQUENCE: 863
aaccaagagg acccacacag gttctcaaag ctggcccaga         40

<210> SEQ ID NO 864
<211> LENGTH: 40
<212> TYPE: DNA
<213> ORGANISM: Homo sapiens

<400> SEQUENCE: 864
atattccttt tatttctaag tcttttgtct taggagttaa         40

<210> SEQ ID NO 865
<211> LENGTH: 40
<212> TYPE: DNA
<213> ORGANISM: Homo sapiens

<400> SEQUENCE: 865
atattccttt tatttctaag gagttaaaca tagatgtagc         40

<210> SEQ ID NO 866
<211> LENGTH: 40
<212> TYPE: DNA
<213> ORGANISM: Homo sapiens

<400> SEQUENCE: 866
ggtcctgaac gctgtgaaat aacttcgccc ccagcttcaa         40

<210> SEQ ID NO 867
<211> LENGTH: 40
<212> TYPE: DNA
<213> ORGANISM: Homo sapiens

<400> SEQUENCE: 867
ggtcctgaac gctgtgaaat tgtactgtca gaacttcgcc        40

<210> SEQ ID NO 868
<211> LENGTH: 40
<212> TYPE: DNA
<213> ORGANISM: Homo sapiens

<400> SEQUENCE: 868
tggagcagta tgccagcaag acttttcccc caggttcttc        40

<210> SEQ ID NO 869
<211> LENGTH: 40
<212> TYPE: DNA
<213> ORGANISM: Homo sapiens

<400> SEQUENCE: 869
tggagcagta tgccagcaag gttcttcatg acagccagat        40

<210> SEQ ID NO 870
<211> LENGTH: 40
<212> TYPE: DNA
<213> ORGANISM: Homo sapiens

<400> SEQUENCE: 870
tcgtgcagac cctggagaag atctcacaga tgtgcagtct        40

<210> SEQ ID NO 871
<211> LENGTH: 40
<212> TYPE: DNA
<213> ORGANISM: Homo sapiens

<400> SEQUENCE: 871
tcgtgcagac cctggagaag catggcttca gtgatattaa        40

<210> SEQ ID NO 872
<211> LENGTH: 40
<212> TYPE: DNA
<213> ORGANISM: Homo sapiens

<400> SEQUENCE: 872
ttgaagctca gtgagaaaag ttcttctgtt tatgtcttcc        40

<210> SEQ ID NO 873
<211> LENGTH: 40
<212> TYPE: DNA
<213> ORGANISM: Homo sapiens

<400> SEQUENCE: 873
ttgaagctca gtgagaaaag gatgatggag atagccaaag        40

<210> SEQ ID NO 874
<211> LENGTH: 40
<212> TYPE: DNA
<213> ORGANISM: Homo sapiens

<400> SEQUENCE: 874
cgccctgaca cacaatcagg acttctctat ctacaggctc        40

<210> SEQ ID NO 875
<211> LENGTH: 40
<212> TYPE: DNA
<213> ORGANISM: Homo sapiens

<400> SEQUENCE: 875
cgccctgaca cacaatcagg gctctgttgc aagaggcggt                    40

<210> SEQ ID NO 876
<211> LENGTH: 40
<212> TYPE: DNA
<213> ORGANISM: Homo sapiens

<400> SEQUENCE: 876
ttgctggcca tcggattggg cccttcgttt caggatggat                    40

<210> SEQ ID NO 877
<211> LENGTH: 40
<212> TYPE: DNA
<213> ORGANISM: Homo sapiens

<400> SEQUENCE: 877
ttgctggcca tcggattggg gatctatatt ggaaggcgtc                    40

<210> SEQ ID NO 878
<211> LENGTH: 40
<212> TYPE: DNA
<213> ORGANISM: Homo sapiens

<400> SEQUENCE: 878
ccattcgaga gcatcagaag attgggagga aggaccggct                    40

<210> SEQ ID NO 879
<211> LENGTH: 40
<212> TYPE: DNA
<213> ORGANISM: Homo sapiens

<400> SEQUENCE: 879
ccattcgaga gcatcagaag ctaaaccatt tcccaggctc                    40

<210> SEQ ID NO 880
<211> LENGTH: 40
<212> TYPE: DNA
<213> ORGANISM: Homo sapiens

<400> SEQUENCE: 880
tcaggagcag agaggaaaag tgcatttgcc cagtataaca                    40

<210> SEQ ID NO 881
<211> LENGTH: 40
<212> TYPE: DNA
<213> ORGANISM: Homo sapiens

<400> SEQUENCE: 881
ctcagggaag gggcagcaca tgcatttgcc cagtataaca                    40

<210> SEQ ID NO 882
<211> LENGTH: 40
<212> TYPE: DNA
<213> ORGANISM: Homo sapiens

<400> SEQUENCE: 882
gtgtggcaag tactttcaag tatctgccct tctattacag                    40

<210> SEQ ID NO 883
<211> LENGTH: 40
<212> TYPE: DNA

<213> ORGANISM: Homo sapiens

<400> SEQUENCE: 883
gtgtggcaag tactttcaag gccggggttt gaagtctcac    40

<210> SEQ ID NO 884
<211> LENGTH: 40
<212> TYPE: DNA
<213> ORGANISM: Homo sapiens

<400> SEQUENCE: 884
aaaatcattg attcccttga aattctcttt actctacctt    40

<210> SEQ ID NO 885
<211> LENGTH: 40
<212> TYPE: DNA
<213> ORGANISM: Homo sapiens

<400> SEQUENCE: 885
aaaatcattg attcccttga gtggttagac gatgctatta    40

<210> SEQ ID NO 886
<211> LENGTH: 40
<212> TYPE: DNA
<213> ORGANISM: Homo sapiens

<400> SEQUENCE: 886
tgctcagagg tgctttgaag cccatccaca acctgctcat    40

<210> SEQ ID NO 887
<211> LENGTH: 40
<212> TYPE: DNA
<213> ORGANISM: Homo sapiens

<400> SEQUENCE: 887
tgctcagagg tgctttgaag atgccggagg ccccgcctct    40

<210> SEQ ID NO 888
<211> LENGTH: 40
<212> TYPE: DNA
<213> ORGANISM: Homo sapiens

<400> SEQUENCE: 888
ccacggccac ggccgcatag ctttgtattc ctgcaggcaa    40

<210> SEQ ID NO 889
<211> LENGTH: 40
<212> TYPE: DNA
<213> ORGANISM: Homo sapiens

<400> SEQUENCE: 889
ccacggccac ggccgcatag gcaagcaccg gaagcacccc    40

<210> SEQ ID NO 890
<211> LENGTH: 40
<212> TYPE: DNA
<213> ORGANISM: Homo sapiens

<400> SEQUENCE: 890
catgccgggg ccagaggatg gctctttcca cctgtctgca    40

<210> SEQ ID NO 891
<211> LENGTH: 40

-continued

```
<212> TYPE: DNA
<213> ORGANISM: Homo sapiens

<400> SEQUENCE: 891
catgccgggg ccagaggatg ctctgcaccc gggacagtga                             40

<210> SEQ ID NO 892
<211> LENGTH: 40
<212> TYPE: DNA
<213> ORGANISM: Homo sapiens

<400> SEQUENCE: 892
ggccaagcaa gaacaaaaag tattttcttc taggatggaa                             40

<210> SEQ ID NO 893
<211> LENGTH: 40
<212> TYPE: DNA
<213> ORGANISM: Homo sapiens

<400> SEQUENCE: 893
ggccaagcaa gaacaaaaag tgaaatgcaa aatggaggac                             40

<210> SEQ ID NO 894
<211> LENGTH: 40
<212> TYPE: DNA
<213> ORGANISM: Homo sapiens

<400> SEQUENCE: 894
gaagaacagg atattaatag tatgttttttg tttttaggag                            40

<210> SEQ ID NO 895
<211> LENGTH: 40
<212> TYPE: DNA
<213> ORGANISM: Homo sapiens

<400> SEQUENCE: 895
gaagaacagg atattaatag gaggattctc tatgggagga                             40

<210> SEQ ID NO 896
<211> LENGTH: 40
<212> TYPE: DNA
<213> ORGANISM: Homo sapiens

<400> SEQUENCE: 896
caattcagta gattcaccct caacatctga atgaattgat                             40

<210> SEQ ID NO 897
<211> LENGTH: 40
<212> TYPE: DNA
<213> ORGANISM: Homo sapiens

<400> SEQUENCE: 897
aggtcttcct ggacctggag caacatctga atgaattgat                             40

<210> SEQ ID NO 898
<211> LENGTH: 40
<212> TYPE: DNA
<213> ORGANISM: Homo sapiens

<400> SEQUENCE: 898
agagggcacg ggacatccag cccctctgcc cctgcaggag                             40

<210> SEQ ID NO 899
```

```
<211> LENGTH: 40
<212> TYPE: DNA
<213> ORGANISM: Homo sapiens

<400> SEQUENCE: 899
agagggcacg ggacatccag gaggccgtgg agtcctgcct                    40

<210> SEQ ID NO 900
<211> LENGTH: 40
<212> TYPE: DNA
<213> ORGANISM: Homo sapiens

<400> SEQUENCE: 900
agatgattga ggcagccaag ctcttttctg tcttcttggt                    40

<210> SEQ ID NO 901
<211> LENGTH: 40
<212> TYPE: DNA
<213> ORGANISM: Homo sapiens

<400> SEQUENCE: 901
agatgattga ggcagccaag gccgtctata cccaggattg                    40

<210> SEQ ID NO 902
<211> LENGTH: 40
<212> TYPE: DNA
<213> ORGANISM: Homo sapiens

<400> SEQUENCE: 902
gctgctctct tcaatacaag tgcttctgct tccaggatac                    40

<210> SEQ ID NO 903
<211> LENGTH: 40
<212> TYPE: DNA
<213> ORGANISM: Homo sapiens

<400> SEQUENCE: 903
gctgctctct tcaatacaag gataccaagg gttcgagttt                    40

<210> SEQ ID NO 904
<211> LENGTH: 40
<212> TYPE: DNA
<213> ORGANISM: Homo sapiens

<400> SEQUENCE: 904
aatagaactt ccaactactg gcccttttc agtaaagtca                     40

<210> SEQ ID NO 905
<211> LENGTH: 40
<212> TYPE: DNA
<213> ORGANISM: Homo sapiens

<400> SEQUENCE: 905
aatagaactt ccaactactg taaagtcatc acctggcctt                    40

<210> SEQ ID NO 906
<211> LENGTH: 40
<212> TYPE: DNA
<213> ORGANISM: Homo sapiens

<400> SEQUENCE: 906
tgttactgca gtggctacag gtctctctct tgcaggtggt                    40
```

```
<210> SEQ ID NO 907
<211> LENGTH: 40
<212> TYPE: DNA
<213> ORGANISM: Homo sapiens

<400> SEQUENCE: 907
tgttactgca gtggctacag gtggtcctga caaccaagtc                             40

<210> SEQ ID NO 908
<211> LENGTH: 40
<212> TYPE: DNA
<213> ORGANISM: Homo sapiens

<400> SEQUENCE: 908
acatcacaaa gcaacctgtg gggttttgtt tttgttttag                             40

<210> SEQ ID NO 909
<211> LENGTH: 40
<212> TYPE: DNA
<213> ORGANISM: Homo sapiens

<400> SEQUENCE: 909
acatcacaaa gcaacctgtg gtgtacctga aggaaatctt                             40

<210> SEQ ID NO 910
<211> LENGTH: 40
<212> TYPE: DNA
<213> ORGANISM: Homo sapiens

<400> SEQUENCE: 910
ggtgctggct gcctgcgaaa ccctggctgc ccctgcaggc                             40

<210> SEQ ID NO 911
<211> LENGTH: 40
<212> TYPE: DNA
<213> ORGANISM: Homo sapiens

<400> SEQUENCE: 911
ggtgctggct gcctgcgaaa gcctgctcac cagccgccag                             40

<210> SEQ ID NO 912
<211> LENGTH: 40
<212> TYPE: DNA
<213> ORGANISM: Homo sapiens

<400> SEQUENCE: 912
cctctctgct cgagaaggag tgtgtgtctt tttgccaaca                             40

<210> SEQ ID NO 913
<211> LENGTH: 40
<212> TYPE: DNA
<213> ORGANISM: Homo sapiens

<400> SEQUENCE: 913
cctctctgct cgagaaggag ctggagcaga gccagaagga                             40

<210> SEQ ID NO 914
<211> LENGTH: 40
<212> TYPE: DNA
<213> ORGANISM: Homo sapiens

<400> SEQUENCE: 914
ctggaagctc aaggtactag atttttcctc tctctgtctt                             40
```

<210> SEQ ID NO 915
<211> LENGTH: 40
<212> TYPE: DNA
<213> ORGANISM: Homo sapiens

<400> SEQUENCE: 915
ctggaagctc aaggtactag tttgccaaag aaactagagt            40

<210> SEQ ID NO 916
<211> LENGTH: 40
<212> TYPE: DNA
<213> ORGANISM: Homo sapiens

<400> SEQUENCE: 916
cggcgatgac tcggacccag cttctctcca cagggctcct            40

<210> SEQ ID NO 917
<211> LENGTH: 40
<212> TYPE: DNA
<213> ORGANISM: Homo sapiens

<400> SEQUENCE: 917
cggcgatgac tcggacccag ggctccttca gtggtagatg            40

<210> SEQ ID NO 918
<211> LENGTH: 40
<212> TYPE: DNA
<213> ORGANISM: Homo sapiens

<400> SEQUENCE: 918
ccgccaggag aacaagccca tccccctcaca ggcagagata           40

<210> SEQ ID NO 919
<211> LENGTH: 40
<212> TYPE: DNA
<213> ORGANISM: Homo sapiens

<400> SEQUENCE: 919
ccgccaggag aacaagccca agttagtccc ctcacaggca            40

<210> SEQ ID NO 920
<211> LENGTH: 40
<212> TYPE: DNA
<213> ORGANISM: Homo sapiens

<400> SEQUENCE: 920
cagcagcagc tctgcttgag ctactgccaa caccactgct            40

<210> SEQ ID NO 921
<211> LENGTH: 40
<212> TYPE: DNA
<213> ORGANISM: Homo sapiens

<400> SEQUENCE: 921
cagcagcagc tctgcttgag gtgttggatc ctgaacaaaa            40

<210> SEQ ID NO 922
<211> LENGTH: 40
<212> TYPE: DNA
<213> ORGANISM: Homo sapiens

<400> SEQUENCE: 922
gcacttatgg tggtggcgtg agtttccaga ccttcagcat            40

<210> SEQ ID NO 923
<211> LENGTH: 40
<212> TYPE: DNA
<213> ORGANISM: Homo sapiens

<400> SEQUENCE: 923
gcacttatgg tggtggcgtg cacctgtcca gcccactggc          40

<210> SEQ ID NO 924
<211> LENGTH: 40
<212> TYPE: DNA
<213> ORGANISM: Homo sapiens

<400> SEQUENCE: 924
gtggctccag tatcagaaag agaccacaga gctgggcagc          40

<210> SEQ ID NO 925
<211> LENGTH: 40
<212> TYPE: DNA
<213> ORGANISM: Homo sapiens

<400> SEQUENCE: 925
gacctgctca agttcactca agaccacaga gctgggcagc          40

<210> SEQ ID NO 926
<211> LENGTH: 40
<212> TYPE: DNA
<213> ORGANISM: Homo sapiens

<400> SEQUENCE: 926
tgtgggcatg gagcgaaaag tgctgccctg ctttctctgt          40

<210> SEQ ID NO 927
<211> LENGTH: 40
<212> TYPE: DNA
<213> ORGANISM: Homo sapiens

<400> SEQUENCE: 927
tgtgggcatg gagcgaaaag ggtgtgctgt ccgacctcac          40

<210> SEQ ID NO 928
<211> LENGTH: 40
<212> TYPE: DNA
<213> ORGANISM: Homo sapiens

<400> SEQUENCE: 928
ttcctcttcc cctcatcaag tcctctcttt ctcctttgtc          40

<210> SEQ ID NO 929
<211> LENGTH: 40
<212> TYPE: DNA
<213> ORGANISM: Homo sapiens

<400> SEQUENCE: 929
ttcctcttcc cctcatcaag agctatctgt tccagctgct          40

<210> SEQ ID NO 930
<211> LENGTH: 40
<212> TYPE: DNA
<213> ORGANISM: Homo sapiens

<400> SEQUENCE: 930 gggggcactga cacggctact agcctctctg gcctcttcca                    40

<210> SEQ ID NO 931
<211> LENGTH: 40
<212> TYPE: DNA
<213> ORGANISM: Homo sapiens

<400> SEQUENCE: 931 gggggcactga cacggctact gtgttggaca tggccacgga                    40

<210> SEQ ID NO 932
<211> LENGTH: 40
<212> TYPE: DNA
<213> ORGANISM: Homo sapiens

<400> SEQUENCE: 932
aggctgtagc aggactccag ggttgggaag aacatggaaa                     40

<210> SEQ ID NO 933
<211> LENGTH: 40
<212> TYPE: DNA
<213> ORGANISM: Homo sapiens

<400> SEQUENCE: 933
aggctgtagc aggactccag gaagatgtta ccgagtactt                     40

<210> SEQ ID NO 934
<211> LENGTH: 40
<212> TYPE: DNA
<213> ORGANISM: Homo sapiens

<400> SEQUENCE: 934
ccgaggatgc taagggggcag tttctgttcc aggtgaaatc                    40

<210> SEQ ID NO 935
<211> LENGTH: 40
<212> TYPE: DNA
<213> ORGANISM: Homo sapiens

<400> SEQUENCE: 935
ccgaggatgc taagggggcag gattggatag ctttagtcaa                    40

<210> SEQ ID NO 936
<211> LENGTH: 40
<212> TYPE: DNA
<213> ORGANISM: Homo sapiens

<400> SEQUENCE: 936
gcctcccggt ccgcaagcag aatgaagaac tgcatgtggc                     40

<210> SEQ ID NO 937
<211> LENGTH: 40
<212> TYPE: DNA
<213> ORGANISM: Homo sapiens

<400> SEQUENCE: 937
gcctcccggt ccgcaagcag ttccagttat actccgtgta                     40

<210> SEQ ID NO 938
<211> LENGTH: 40
<212> TYPE: DNA
<213> ORGANISM: Homo sapiens

<400> SEQUENCE: 938

```
tcgtaacagg ggttgcacag gtgaagatca tgacggagaa                              40

<210> SEQ ID NO 939
<211> LENGTH: 40
<212> TYPE: DNA
<213> ORGANISM: Homo sapiens

<400> SEQUENCE: 939
ctgtgacggg tgtcgcccag gtgaagatca tgacggagaa                              40

<210> SEQ ID NO 940
<211> LENGTH: 40
<212> TYPE: DNA
<213> ORGANISM: Homo sapiens

<400> SEQUENCE: 940
gtttggggaa gtatggatgg agaaagctga tggtttgtgt                              40

<210> SEQ ID NO 941
<211> LENGTH: 40
<212> TYPE: DNA
<213> ORGANISM: Homo sapiens

<400> SEQUENCE: 941
gtttggggaa gtatggatgg gtacctggaa tggaaacaca                              40

<210> SEQ ID NO 942
<211> LENGTH: 40
<212> TYPE: DNA
<213> ORGANISM: Homo sapiens

<400> SEQUENCE: 942
taactaatcc ttctcagcag aaagagctgg gctccactga                              40

<210> SEQ ID NO 943
<211> LENGTH: 40
<212> TYPE: DNA
<213> ORGANISM: Homo sapiens

<400> SEQUENCE: 943
cagcctacca gaggcaccag aaagagctgg gctccactga                              40

<210> SEQ ID NO 944
<211> LENGTH: 40
<212> TYPE: DNA
<213> ORGANISM: Homo sapiens

<400> SEQUENCE: 944
cctgcgcaac tggtaccgag gcgcagccag tgtctttgga                              40

<210> SEQ ID NO 945
<211> LENGTH: 40
<212> TYPE: DNA
<213> ORGANISM: Homo sapiens

<400> SEQUENCE: 945
cctgcgcaac tggtaccgag gggacaaccc caacaagccc                              40

<210> SEQ ID NO 946
<211> LENGTH: 40
<212> TYPE: DNA
<213> ORGANISM: Homo sapiens
```

```
<400> SEQUENCE: 946
ataaaaattg cttagtaaag atttttgcct tctctcaggt                           40

<210> SEQ ID NO 947
<211> LENGTH: 40
<212> TYPE: DNA
<213> ORGANISM: Homo sapiens

<400> SEQUENCE: 947
ataaaaattg cttagtaaag gtcaaagatt ctaaactgcc                           40

<210> SEQ ID NO 948
<211> LENGTH: 40
<212> TYPE: DNA
<213> ORGANISM: Homo sapiens

<400> SEQUENCE: 948
tgagttcatg gatgatgcca aaattctttt taatctttcg                           40

<210> SEQ ID NO 949
<211> LENGTH: 40
<212> TYPE: DNA
<213> ORGANISM: Homo sapiens

<400> SEQUENCE: 949
tgagttcatg gatgatgcca acatgtgcat tgccattgcg                           40

<210> SEQ ID NO 950
<211> LENGTH: 40
<212> TYPE: DNA
<213> ORGANISM: Homo sapiens

<400> SEQUENCE: 950
agagttgaaa aacactggcg tctccttttc aggaatcaca                           40

<210> SEQ ID NO 951
<211> LENGTH: 40
<212> TYPE: DNA
<213> ORGANISM: Homo sapiens

<400> SEQUENCE: 951
agagttgaaa aacactggcg tttaattggt tgggtcaga                            40

<210> SEQ ID NO 952
<211> LENGTH: 40
<212> TYPE: DNA
<213> ORGANISM: Homo sapiens

<400> SEQUENCE: 952
tggggccaca aagacagatg ctggatacac agtatcgtcg                           40

<210> SEQ ID NO 953
<211> LENGTH: 40
<212> TYPE: DNA
<213> ORGANISM: Homo sapiens

<400> SEQUENCE: 953
tggggccaca aagacagatg aaaccccatg gcgactctag                           40

<210> SEQ ID NO 954
<211> LENGTH: 40
<212> TYPE: DNA
<213> ORGANISM: Homo sapiens
```

<400> SEQUENCE: 954
aacatggaat catcaggaag ttctccattt ctatttagcc                            40

<210> SEQ ID NO 955
<211> LENGTH: 40
<212> TYPE: DNA
<213> ORGANISM: Homo sapiens

<400> SEQUENCE: 955
aacatggaat catcaggaag ccaaggtgga agagcacctt                            40

<210> SEQ ID NO 956
<211> LENGTH: 40
<212> TYPE: DNA
<213> ORGANISM: Homo sapiens

<400> SEQUENCE: 956
cgtgcgtgtg tgtgctcttg ctatacacag aatgggattt                            40

<210> SEQ ID NO 957
<211> LENGTH: 40
<212> TYPE: DNA
<213> ORGANISM: Homo sapiens

<400> SEQUENCE: 957
cttaggaaag acaaagaact ctatacacag aatgggattt                            40

<210> SEQ ID NO 958
<211> LENGTH: 40
<212> TYPE: DNA
<213> ORGANISM: Homo sapiens

<400> SEQUENCE: 958
cccagcctgc tgtccagcag cctcttgcac tgtaccccca                            40

<210> SEQ ID NO 959
<211> LENGTH: 40
<212> TYPE: DNA
<213> ORGANISM: Homo sapiens

<400> SEQUENCE: 959
cccagcctgc tgtccagcag gcccccaccc ccgctgcccc                            40

<210> SEQ ID NO 960
<211> LENGTH: 40
<212> TYPE: DNA
<213> ORGANISM: Homo sapiens

<400> SEQUENCE: 960
acccaaggct cgtcctgaag tttctctgtt tccttctgca                            40

<210> SEQ ID NO 961
<211> LENGTH: 40
<212> TYPE: DNA
<213> ORGANISM: Homo sapiens

<400> SEQUENCE: 961
acccaaggct cgtcctgaag acgtggttaa cttggacctc                            40

<210> SEQ ID NO 962
<211> LENGTH: 40
<212> TYPE: DNA

<213> ORGANISM: Homo sapiens

<400> SEQUENCE: 962
gaacccggtg gtacccatag ttgctttgtc ccctcctcag                40

<210> SEQ ID NO 963
<211> LENGTH: 40
<212> TYPE: DNA
<213> ORGANISM: Homo sapiens

<400> SEQUENCE: 963
gaacccggtg gtacccatag gttgcctggc cacggcggcc                40

<210> SEQ ID NO 964
<211> LENGTH: 40
<212> TYPE: DNA
<213> ORGANISM: Homo sapiens

<400> SEQUENCE: 964
aatggaagta ccagcagaag aattttattt ttttcaagat                40

<210> SEQ ID NO 965
<211> LENGTH: 40
<212> TYPE: DNA
<213> ORGANISM: Homo sapiens

<400> SEQUENCE: 965
aatggaagta ccagcagaag attctactca acatgtccct                40

<210> SEQ ID NO 966
<211> LENGTH: 40
<212> TYPE: DNA
<213> ORGANISM: Homo sapiens

<400> SEQUENCE: 966
ggcagctgtt agccgagcaa gagctggacg aggtattgtg                40

<210> SEQ ID NO 967
<211> LENGTH: 40
<212> TYPE: DNA
<213> ORGANISM: Homo sapiens

<400> SEQUENCE: 967
ggcagctgtt agccgagcaa cttgctgatg accgtatggc                40

<210> SEQ ID NO 968
<211> LENGTH: 40
<212> TYPE: DNA
<213> ORGANISM: Homo sapiens

<400> SEQUENCE: 968
gtttagaaat ggaaaaatgt tttttgcttt tacagtaaca                40

<210> SEQ ID NO 969
<211> LENGTH: 40
<212> TYPE: DNA
<213> ORGANISM: Homo sapiens

<400> SEQUENCE: 969
gtttagaaat ggaaaaatgt taacaaatgt ggcaattatt                40

<210> SEQ ID NO 970
<211> LENGTH: 40

```
<212> TYPE: DNA
<213> ORGANISM: Homo sapiens

<400> SEQUENCE: 970
aaatctcgtg gacttctaag ttttctgttt gcccagaaag         40

<210> SEQ ID NO 971
<211> LENGTH: 40
<212> TYPE: DNA
<213> ORGANISM: Homo sapiens

<400> SEQUENCE: 971
aaatctcgtg gacttctaag aaagcgccat ggcctgtgct         40

<210> SEQ ID NO 972
<211> LENGTH: 40
<212> TYPE: DNA
<213> ORGANISM: Homo sapiens

<400> SEQUENCE: 972
agttccgggg ctacctgatg ccttcctctt tgcagaaatc         40

<210> SEQ ID NO 973
<211> LENGTH: 40
<212> TYPE: DNA
<213> ORGANISM: Homo sapiens

<400> SEQUENCE: 973
agttccgggg ctacctgatg aaatctctcc agacctcgct         40

<210> SEQ ID NO 974
<211> LENGTH: 40
<212> TYPE: DNA
<213> ORGANISM: Homo sapiens

<400> SEQUENCE: 974
aagaaggaat ccacgttcta gtcatttctt ttcaggattg         40

<210> SEQ ID NO 975
<211> LENGTH: 40
<212> TYPE: DNA
<213> ORGANISM: Homo sapiens

<400> SEQUENCE: 975
aagaaggaat ccacgttcta gattggccat ttgatgatgg         40

<210> SEQ ID NO 976
<211> LENGTH: 40
<212> TYPE: DNA
<213> ORGANISM: Homo sapiens

<400> SEQUENCE: 976
cgctggcacc atgaacccag gaccaagtga gcagagagaa         40

<210> SEQ ID NO 977
<211> LENGTH: 40
<212> TYPE: DNA
<213> ORGANISM: Homo sapiens

<400> SEQUENCE: 977 agccctgct tgacaaccag tttcatgtcc caccaggttg          40

<210> SEQ ID NO 978
```

```
<211> LENGTH: 40
<212> TYPE: DNA
<213> ORGANISM: Homo sapiens

<400> SEQUENCE: 978
agcccctgct tgacaaccag gttggtttta agaacatgca                    40

<210> SEQ ID NO 979
<211> LENGTH: 40
<212> TYPE: DNA
<213> ORGANISM: Homo sapiens

<400> SEQUENCE: 979
ttggctgtag gaaactcagg gtccagctgt agttcctctg                    40

<210> SEQ ID NO 980
<211> LENGTH: 40
<212> TYPE: DNA
<213> ORGANISM: Homo sapiens

<400> SEQUENCE: 980
ttggctgtag gaaactcagg cggcgttgac attccccagg                    40

<210> SEQ ID NO 981
<211> LENGTH: 40
<212> TYPE: DNA
<213> ORGANISM: Homo sapiens

<400> SEQUENCE: 981
tgtatctccg acactcagag actgtctctg gaggttatga                    40

<210> SEQ ID NO 982
<211> LENGTH: 40
<212> TYPE: DNA
<213> ORGANISM: Homo sapiens

<400> SEQUENCE: 982
tgtatctccg acactcagag gatttcccta gagattatga                    40

<210> SEQ ID NO 983
<211> LENGTH: 40
<212> TYPE: DNA
<213> ORGANISM: Homo sapiens

<400> SEQUENCE: 983
aggctgatct actgcaggag ccacgtcatg aatattttaa                    40

<210> SEQ ID NO 984
<211> LENGTH: 40
<212> TYPE: DNA
<213> ORGANISM: Homo sapiens

<400> SEQUENCE: 984
aggctgatct actgcaggag gaagctgaaa ccccacgtag                    40

<210> SEQ ID NO 985
<211> LENGTH: 40
<212> TYPE: DNA
<213> ORGANISM: Homo sapiens

<400> SEQUENCE: 985
gctcagcccc ctccccacag ggcccctaga agcctgtttc                    40
```

```
<210> SEQ ID NO 986
<211> LENGTH: 40
<212> TYPE: DNA
<213> ORGANISM: Homo sapiens

<400> SEQUENCE: 986
tgaccctgca gctcctcaaa ggcccctaga agcctgtttc                    40

<210> SEQ ID NO 987
<211> LENGTH: 40
<212> TYPE: DNA
<213> ORGANISM: Homo sapiens

<400> SEQUENCE: 987
gccgacccgc ctgcgacgct cttttcttgc ctggagaaga                    40

<210> SEQ ID NO 988
<211> LENGTH: 40
<212> TYPE: DNA
<213> ORGANISM: Homo sapiens

<400> SEQUENCE: 988
gccgacccgc ctgcgacgct gggaccgtga tgcccggccc                    40

<210> SEQ ID NO 989
<211> LENGTH: 40
<212> TYPE: DNA
<213> ORGANISM: Homo sapiens

<400> SEQUENCE: 989
tgcggagacc ccttcgggag gtgacagttc gtgatgctat                    40

<210> SEQ ID NO 990
<211> LENGTH: 40
<212> TYPE: DNA
<213> ORGANISM: Homo sapiens

<400> SEQUENCE: 990
tgcggagacc ccttcgggag gtctccgggc tgctgaagag                    40

<210> SEQ ID NO 991
<211> LENGTH: 40
<212> TYPE: DNA
<213> ORGANISM: Homo sapiens

<400> SEQUENCE: 991
ctatcagtag gttttagag atgaacatca ctcgaaaact                     40

<210> SEQ ID NO 992
<211> LENGTH: 40
<212> TYPE: DNA
<213> ORGANISM: Homo sapiens

<400> SEQUENCE: 992
gcattgatgt ggaagatgca atgaacatca ctcgaaaact                    40

<210> SEQ ID NO 993
<211> LENGTH: 40
<212> TYPE: DNA
<213> ORGANISM: Homo sapiens

<400> SEQUENCE: 993
gcattgatgt ggaagatgca gttttttcc tggcagaaga                     40
```

```
<210> SEQ ID NO 994
<211> LENGTH: 40
<212> TYPE: DNA
<213> ORGANISM: Homo sapiens

<400> SEQUENCE: 994
cagtgggcgg atgacatttg gtacagcctc ggaactggct                    40

<210> SEQ ID NO 995
<211> LENGTH: 40
<212> TYPE: DNA
<213> ORGANISM: Homo sapiens

<400> SEQUENCE: 995
cagtgggcgg atgacatttg ccctctgttg ctattctttg                    40

<210> SEQ ID NO 996
<211> LENGTH: 40
<212> TYPE: DNA
<213> ORGANISM: Homo sapiens

<400> SEQUENCE: 996
ggtgtccatg gcctgcactc ctataccttt ctgccgtgta                    40

<210> SEQ ID NO 997
<211> LENGTH: 40
<212> TYPE: DNA
<213> ORGANISM: Homo sapiens

<400> SEQUENCE: 997
ggtgtccatg gcctgcactc ttacgaaaag cggctgtact                    40

<210> SEQ ID NO 998
<211> LENGTH: 40
<212> TYPE: DNA
<213> ORGANISM: Homo sapiens

<400> SEQUENCE: 998
actgggaagt tcttaaaaag tccccctcta cacaagaatc                    40

<210> SEQ ID NO 999
<211> LENGTH: 40
<212> TYPE: DNA
<213> ORGANISM: Homo sapiens

<400> SEQUENCE: 999
actgggaagt tcttaaaaag gttcacagat gaagagtcta                    40

<210> SEQ ID NO 1000
<211> LENGTH: 40
<212> TYPE: DNA
<213> ORGANISM: Homo sapiens

<400> SEQUENCE: 1000
gctgagcggg gcgacccgag tcttctcatt cacaggttaa                    40

<210> SEQ ID NO 1001
<211> LENGTH: 40
<212> TYPE: DNA
<213> ORGANISM: Homo sapiens

<400> SEQUENCE: 1001
tgttccacct cctcctgcag ctcccccttt tcttccagtg                    40
```

<210> SEQ ID NO 1002
<211> LENGTH: 40
<212> TYPE: DNA
<213> ORGANISM: Homo sapiens

<400> SEQUENCE: 1002
tgttccacct cctcctgcag tgggccggat gtatccccg                    40

<210> SEQ ID NO 1003
<211> LENGTH: 40
<212> TYPE: DNA
<213> ORGANISM: Homo sapiens

<400> SEQUENCE: 1003
acccatgaga atgctcagag ctatgaagac cccgcggccc                    40

<210> SEQ ID NO 1004
<211> LENGTH: 40
<212> TYPE: DNA
<213> ORGANISM: Homo sapiens

<400> SEQUENCE: 1004
ctggcccctg agatccgcag ctatgaagac cccgcggccc                    40

<210> SEQ ID NO 1005
<211> LENGTH: 40
<212> TYPE: DNA
<213> ORGANISM: Homo sapiens

<400> SEQUENCE: 1005
caagctcgag tccatcgatg aacccatctg cgccgtcggc                    40

<210> SEQ ID NO 1006
<211> LENGTH: 40
<212> TYPE: DNA
<213> ORGANISM: Homo sapiens

<400> SEQUENCE: 1006
caagctcgag tccatcgatg gtgcccggta ccatgccctc                    40

<210> SEQ ID NO 1007
<211> LENGTH: 40
<212> TYPE: DNA
<213> ORGANISM: Homo sapiens

<400> SEQUENCE: 1007
cttcactgtc accgtcacag aaccccagt gcggatcata                    40

<210> SEQ ID NO 1008
<211> LENGTH: 40
<212> TYPE: DNA
<213> ORGANISM: Homo sapiens

<400> SEQUENCE: 1008
cttcactgtc accgtcacag agtcttacca aagtcaggac                    40

<210> SEQ ID NO 1009
<211> LENGTH: 40
<212> TYPE: DNA
<213> ORGANISM: Homo sapiens

<400> SEQUENCE: 1009
agaaacagaa accagcacag gatgtacctg gcaaagattc            40

<210> SEQ ID NO 1010
<211> LENGTH: 40
<212> TYPE: DNA
<213> ORGANISM: Homo sapiens

<400> SEQUENCE: 1010
agaaacagaa accagcacag aattatgatg acaatttcaa            40

<210> SEQ ID NO 1011
<211> LENGTH: 40
<212> TYPE: DNA
<213> ORGANISM: Homo sapiens

<400> SEQUENCE: 1011
ttctgcatct gtgggccgag tgatcctgcc atgaagcagt            40

<210> SEQ ID NO 1012
<211> LENGTH: 40
<212> TYPE: DNA
<213> ORGANISM: Homo sapiens

<400> SEQUENCE: 1012
aaaggagtgc ttatagaatg tgatcctgcc atgaagcagt            40

<210> SEQ ID NO 1013
<211> LENGTH: 40
<212> TYPE: DNA
<213> ORGANISM: Homo sapiens

<400> SEQUENCE: 1013
aggatcggca acatggcaag gcctctacta cgtggacagt            40

<210> SEQ ID NO 1014
<211> LENGTH: 40
<212> TYPE: DNA
<213> ORGANISM: Homo sapiens

<400> SEQUENCE: 1014
ctgggataag agaggccctg gcctctacta cgtggacagt            40

<210> SEQ ID NO 1015
<211> LENGTH: 40
<212> TYPE: DNA
<213> ORGANISM: Homo sapiens

<400> SEQUENCE: 1015
gttcaggaca caataagcag gttgcagagc ctgaggcctg            40

<210> SEQ ID NO 1016
<211> LENGTH: 40
<212> TYPE: DNA
<213> ORGANISM: Homo sapiens

<400> SEQUENCE: 1016
gggagggaga gaatacccag gttgcagagc ctgaggcctg            40

<210> SEQ ID NO 1017
<211> LENGTH: 40
<212> TYPE: DNA
<213> ORGANISM: Homo sapiens

<400> SEQUENCE: 1017
tacccggatg atggcatggg aagttcttgc tgtctttcag    40

<210> SEQ ID NO 1018
<211> LENGTH: 40
<212> TYPE: DNA
<213> ORGANISM: Homo sapiens

<400> SEQUENCE: 1018
tacccggatg atggcatggg gtatggcgac tacccgaagc    40

<210> SEQ ID NO 1019
<211> LENGTH: 40
<212> TYPE: DNA
<213> ORGANISM: Homo sapiens

<400> SEQUENCE: 1019
gacatatgag tcaaaggaag cccggtggcg cctgtccgtc    40

<210> SEQ ID NO 1020
<211> LENGTH: 40
<212> TYPE: DNA
<213> ORGANISM: Homo sapiens

<400> SEQUENCE: 1020
gacatatgag tcaaaggaag aagcccggtg gcgcctgtcc    40

<210> SEQ ID NO 1021
<211> LENGTH: 40
<212> TYPE: DNA
<213> ORGANISM: Homo sapiens

<400> SEQUENCE: 1021
cggatcaact tcgacaaata gtggttgtta cctcttccta    40

<210> SEQ ID NO 1022
<211> LENGTH: 40
<212> TYPE: DNA
<213> ORGANISM: Homo sapiens

<400> SEQUENCE: 1022
cggatcaact tcgacaaata ccacccaggc tactttggga    40

<210> SEQ ID NO 1023
<211> LENGTH: 40
<212> TYPE: DNA
<213> ORGANISM: Homo sapiens

<400> SEQUENCE: 1023
ttataggcgt gatgatagag tttcatttaa cttaggtccc    40

<210> SEQ ID NO 1024
<211> LENGTH: 40
<212> TYPE: DNA
<213> ORGANISM: Homo sapiens

<400> SEQUENCE: 1024
ttataggcgt gatgatagag gtccccccca aagacccaaa    40

<210> SEQ ID NO 1025
<211> LENGTH: 40
<212> TYPE: DNA
<213> ORGANISM: Homo sapiens

<400> SEQUENCE: 1025
tggaaatatt tctagacttg gtgtcagttg tacccgaggc				40

<210> SEQ ID NO 1026
<211> LENGTH: 40
<212> TYPE: DNA
<213> ORGANISM: Homo sapiens

<400> SEQUENCE: 1026
tcggcccaga agaaccccgc ctatacacag aatgggattt				40

<210> SEQ ID NO 1027
<211> LENGTH: 40
<212> TYPE: DNA
<213> ORGANISM: Homo sapiens

<400> SEQUENCE: 1027
gctgaaggga aaagacacca aaacacaaac agcagaatgg				40

<210> SEQ ID NO 1028
<211> LENGTH: 40
<212> TYPE: DNA
<213> ORGANISM: Homo sapiens

<400> SEQUENCE: 1028
gctgaaggga aaagacacca gttgcctggc agagcagtgg				40

<210> SEQ ID NO 1029
<211> LENGTH: 40
<212> TYPE: DNA
<213> ORGANISM: Homo sapiens

<400> SEQUENCE: 1029
catcatcaag tttttcaatg acgagctggt ccagccatcc				40

<210> SEQ ID NO 1030
<211> LENGTH: 40
<212> TYPE: DNA
<213> ORGANISM: Homo sapiens

<400> SEQUENCE: 1030
catcatcaag tttttcaatg aacgtgctga gcatcacgat				40

<210> SEQ ID NO 1031
<211> LENGTH: 40
<212> TYPE: DNA
<213> ORGANISM: Homo sapiens

<400> SEQUENCE: 1031
gagggcctgc tcattcaaag atgttctcag tgcagctgag				40

<210> SEQ ID NO 1032
<211> LENGTH: 40
<212> TYPE: DNA
<213> ORGANISM: Homo sapiens

<400> SEQUENCE: 1032
acatgcttca aataaatcag atgttctcag tgcagctgag				40

<210> SEQ ID NO 1033
<211> LENGTH: 40
<212> TYPE: DNA
<213> ORGANISM: Homo sapiens

```
<400> SEQUENCE: 1033
ctgaggctaa tgaaaaacag ggaagctgcc aaagaatgtc                    40

<210> SEQ ID NO 1034
<211> LENGTH: 40
<212> TYPE: DNA
<213> ORGANISM: Homo sapiens

<400> SEQUENCE: 1034
ctgaggctaa tgaaaaacag ggaagctgcc cgggagtgtc                    40

<210> SEQ ID NO 1035
<211> LENGTH: 40
<212> TYPE: DNA
<213> ORGANISM: Homo sapiens

<400> SEQUENCE: 1035
cggctgggac tcttccatgc gtggcactgg aagcagactg                    40

<210> SEQ ID NO 1036
<211> LENGTH: 40
<212> TYPE: DNA
<213> ORGANISM: Homo sapiens

<400> SEQUENCE: 1036
cggctgggac tcttccatgc agttgaaact ggttgacaac                    40

<210> SEQ ID NO 1037
<211> LENGTH: 40
<212> TYPE: DNA
<213> ORGANISM: Homo sapiens

<400> SEQUENCE: 1037
agtgaatgta gttgcaccag tgacaatact tgtatggagt                    40

<210> SEQ ID NO 1038
<211> LENGTH: 40
<212> TYPE: DNA
<213> ORGANISM: Homo sapiens

<400> SEQUENCE: 1038
agtgaatgta gttgcaccag gatttgtaca cacagatatg                    40

<210> SEQ ID NO 1039
<211> LENGTH: 40
<212> TYPE: DNA
<213> ORGANISM: Homo sapiens

<400> SEQUENCE: 1039
attcacacag agccacctag gccaggctac caacgtcttt                    40

<210> SEQ ID NO 1040
<211> LENGTH: 40
<212> TYPE: DNA
<213> ORGANISM: Homo sapiens

<400> SEQUENCE: 1040
tgaggatcaa tcctggggag gccaggctac caacgtcttt                    40

<210> SEQ ID NO 1041
<211> LENGTH: 40
<212> TYPE: DNA
```

<213> ORGANISM: Homo sapiens

<400> SEQUENCE: 1041
tggaaaagta taaaggcaaa attcttcaaa gaaggaacca                    40

<210> SEQ ID NO 1042
<211> LENGTH: 40
<212> TYPE: DNA
<213> ORGANISM: Homo sapiens

<400> SEQUENCE: 1042
tggaaaagta taaaggcaaa gtttcactag ttgtaaacgt                    40

<210> SEQ ID NO 1043
<211> LENGTH: 40
<212> TYPE: DNA
<213> ORGANISM: Homo sapiens

<400> SEQUENCE: 1043
atactaagaa caacaatttg aatgggacaa cagaagaagt                    40

<210> SEQ ID NO 1044
<211> LENGTH: 40
<212> TYPE: DNA
<213> ORGANISM: Homo sapiens

<400> SEQUENCE: 1044
atactaagaa caacaatttg cttcgtcagc aattgaagtg                    40

<210> SEQ ID NO 1045
<211> LENGTH: 40
<212> TYPE: DNA
<213> ORGANISM: Homo sapiens

<400> SEQUENCE: 1045
tggccttgac ctccaaccag gtcctgcacc cagacctcac                    40

<210> SEQ ID NO 1046
<211> LENGTH: 40
<212> TYPE: DNA
<213> ORGANISM: Homo sapiens

<400> SEQUENCE: 1046
tggccttgac ctccaaccag gagtacctgg acctgtccat                    40

<210> SEQ ID NO 1047
<211> LENGTH: 40
<212> TYPE: DNA
<213> ORGANISM: Homo sapiens

<400> SEQUENCE: 1047
tccttgaaca ctacaattag acctcttctt gggtgaattt                    40

<210> SEQ ID NO 1048
<211> LENGTH: 40
<212> TYPE: DNA
<213> ORGANISM: Homo sapiens

<400> SEQUENCE: 1048
tccttgaaca ctacaattag ctgttctgaa gcccagaaaa                    40

<210> SEQ ID NO 1049
<211> LENGTH: 40

<212> TYPE: DNA
<213> ORGANISM: Homo sapiens

<400> SEQUENCE: 1049
acaccattga ggagatccag gtgcggcagc tggtgcctcg					40

<210> SEQ ID NO 1050
<211> LENGTH: 40
<212> TYPE: DNA
<213> ORGANISM: Homo sapiens

<400> SEQUENCE: 1050
acaccattga ggagatccag ggactgacca cagcccatga					40

<210> SEQ ID NO 1051
<211> LENGTH: 40
<212> TYPE: DNA
<213> ORGANISM: Homo sapiens

<400> SEQUENCE: 1051
cccatgtata aggctttccg gatgtgctct ttgtcctcca					40

<210> SEQ ID NO 1052
<211> LENGTH: 40
<212> TYPE: DNA
<213> ORGANISM: Homo sapiens

<400> SEQUENCE: 1052
cccatgtata aggctttccg gagtgacagt tcattcaatt					40

<210> SEQ ID NO 1053
<211> LENGTH: 40
<212> TYPE: DNA
<213> ORGANISM: Homo sapiens

<400> SEQUENCE: 1053
ctcccagtgc tgtatatccc ggaattcctg gggaagtcgg					40

<210> SEQ ID NO 1054
<211> LENGTH: 40
<212> TYPE: DNA
<213> ORGANISM: Homo sapiens

<400> SEQUENCE: 1054
gagctgccac ggatactgag ggaattcctg gggaagtcgg					40

<210> SEQ ID NO 1055
<211> LENGTH: 40
<212> TYPE: DNA
<213> ORGANISM: Homo sapiens

<400> SEQUENCE: 1055
ggatgcgcgt ctggtcaagg gctgcagaga aggctggtat					40

<210> SEQ ID NO 1056
<211> LENGTH: 40
<212> TYPE: DNA
<213> ORGANISM: Homo sapiens

<400> SEQUENCE: 1056
agccgcagag catcctggcg gctgcagaga aggctggtat					40

<210> SEQ ID NO 1057

```
<211> LENGTH: 40
<212> TYPE: DNA
<213> ORGANISM: Homo sapiens

<400> SEQUENCE: 1057
acatgcttca aataaatcag cttctctcca agataaaatg                              40

<210> SEQ ID NO 1058
<211> LENGTH: 40
<212> TYPE: DNA
<213> ORGANISM: Homo sapiens

<400> SEQUENCE: 1058
aacaaagaaa taattcacag gatgaagatg ggtttcaaga                              40

<210> SEQ ID NO 1059
<211> LENGTH: 40
<212> TYPE: DNA
<213> ORGANISM: Homo sapiens

<400> SEQUENCE: 1059
ctgagtcttt atattttgag gatgaagatg ggtttcaaga                              40

<210> SEQ ID NO 1060
<211> LENGTH: 40
<212> TYPE: DNA
<213> ORGANISM: Homo sapiens

<400> SEQUENCE: 1060
tagccaccac tgtgtgccag ggatatcttc taaccatacc                              40

<210> SEQ ID NO 1061
<211> LENGTH: 40
<212> TYPE: DNA
<213> ORGANISM: Homo sapiens

<400> SEQUENCE: 1061
gggaaaagtc tttcaccctg ggatatcttc taaccatacc                              40

<210> SEQ ID NO 1062
<211> LENGTH: 40
<212> TYPE: DNA
<213> ORGANISM: Homo sapiens

<400> SEQUENCE: 1062
cctaccagcc acttcgggag gtatcagagt gctccatctc                              40

<210> SEQ ID NO 1063
<211> LENGTH: 40
<212> TYPE: DNA
<213> ORGANISM: Homo sapiens

<400> SEQUENCE: 1063
cctaccagcc acttcgggag gtattgccag ggaacagacg                              40

<210> SEQ ID NO 1064
<211> LENGTH: 40
<212> TYPE: DNA
<213> ORGANISM: Homo sapiens

<400> SEQUENCE: 1064
gtcccggctt cccctactc gcctggctca gaatctaacc                               40
```

```
<210> SEQ ID NO 1065
<211> LENGTH: 40
<212> TYPE: DNA
<213> ORGANISM: Homo sapiens

<400> SEQUENCE: 1065
gtcccggctt cccctactc agtgaagaag ccaccctcag                    40

<210> SEQ ID NO 1066
<211> LENGTH: 40
<212> TYPE: DNA
<213> ORGANISM: Homo sapiens

<400> SEQUENCE: 1066
cttaagcata tatttaaagg gtgaagatgc ttttgatgcc                   40

<210> SEQ ID NO 1067
<211> LENGTH: 40
<212> TYPE: DNA
<213> ORGANISM: Homo sapiens

<400> SEQUENCE: 1067
cttaagcata tatttaaagg gagatgttttt tgattcagcc                  40

<210> SEQ ID NO 1068
<211> LENGTH: 40
<212> TYPE: DNA
<213> ORGANISM: Homo sapiens

<400> SEQUENCE: 1068
caggaacaag tatctgacag aaaatatctt tcaggcctgg                   40

<210> SEQ ID NO 1069
<211> LENGTH: 40
<212> TYPE: DNA
<213> ORGANISM: Homo sapiens

<400> SEQUENCE: 1069
caggaacaag tatctgacag tcaagtccta attcgaagca                   40

<210> SEQ ID NO 1070
<211> LENGTH: 40
<212> TYPE: DNA
<213> ORGANISM: Homo sapiens

<400> SEQUENCE: 1070
gaagttctga ggaaaagcag aatgctgtgt cctctgaaga                   40

<210> SEQ ID NO 1071
<211> LENGTH: 40
<212> TYPE: DNA
<213> ORGANISM: Homo sapiens

<400> SEQUENCE: 1071
gaagttctga ggaaaagcag ctttacaaca aatacccaga                   40

<210> SEQ ID NO 1072
<211> LENGTH: 40
<212> TYPE: DNA
<213> ORGANISM: Homo sapiens

<400> SEQUENCE: 1072
atctccctct tggtgtacaa attgttttca gaaaacacaa                   40
```

<210> SEQ ID NO 1073
<211> LENGTH: 40
<212> TYPE: DNA
<213> ORGANISM: Homo sapiens

<400> SEQUENCE: 1073
atctccctct tggtgtacaa aaaacacaag gaatacaacc                                40

<210> SEQ ID NO 1074
<211> LENGTH: 40
<212> TYPE: DNA
<213> ORGANISM: Homo sapiens

<400> SEQUENCE: 1074
tgcgagtact gcttcaccag aaagaagatt ggcccatgca                                40

<210> SEQ ID NO 1075
<211> LENGTH: 40
<212> TYPE: DNA
<213> ORGANISM: Homo sapiens

<400> SEQUENCE: 1075
tgcgagtact gcttcaccag gaaagaagga ttgtccaaat                                40

<210> SEQ ID NO 1076
<211> LENGTH: 40
<212> TYPE: DNA
<213> ORGANISM: Homo sapiens

<400> SEQUENCE: 1076
tccagaaagt gaaactaaaa ttttaatcca ggtgctggtt                                40

<210> SEQ ID NO 1077
<211> LENGTH: 40
<212> TYPE: DNA
<213> ORGANISM: Homo sapiens

<400> SEQUENCE: 1077
tccagaaagt gaaactaaaa gagcgtcagg aagcagagaa                                40

<210> SEQ ID NO 1078
<211> LENGTH: 40
<212> TYPE: DNA
<213> ORGANISM: Homo sapiens

<400> SEQUENCE: 1078
agattctaca gataaatcag atttcggaaa cttctggcag                                40

<210> SEQ ID NO 1079
<211> LENGTH: 40
<212> TYPE: DNA
<213> ORGANISM: Homo sapiens

<400> SEQUENCE: 1079
agattctaca gataaatcag ctgcacttag tgcattggaa                                40

<210> SEQ ID NO 1080
<211> LENGTH: 40
<212> TYPE: DNA
<213> ORGANISM: Homo sapiens

<400> SEQUENCE: 1080
tggctggctt cagtggacca aattttcagg atggctgtat                                40

<210> SEQ ID NO 1081
<211> LENGTH: 40
<212> TYPE: DNA
<213> ORGANISM: Homo sapiens

<400> SEQUENCE: 1081
tggctggctt cagtggacca gccttcatgg tgaaacacct                              40

<210> SEQ ID NO 1082
<211> LENGTH: 40
<212> TYPE: DNA
<213> ORGANISM: Homo sapiens

<400> SEQUENCE: 1082
ccctgctcat cacctacggg gaacccagaa tgggggcttc                              40

<210> SEQ ID NO 1083
<211> LENGTH: 40
<212> TYPE: DNA
<213> ORGANISM: Homo sapiens

<400> SEQUENCE: 1083
ggcagccacc acgggctcgg acaatttatg aaaaccgaat                              40

<210> SEQ ID NO 1084
<211> LENGTH: 40
<212> TYPE: DNA
<213> ORGANISM: Homo sapiens

<400> SEQUENCE: 1084
tgataattgg gcctccaaga acaatttatg aaaaccgaat                              40

<210> SEQ ID NO 1085
<211> LENGTH: 40
<212> TYPE: DNA
<213> ORGANISM: Homo sapiens

<400> SEQUENCE: 1085
accgccctgc actgctacag gagtcctccg ctctgccaca                              40

<210> SEQ ID NO 1086
<211> LENGTH: 40
<212> TYPE: DNA
<213> ORGANISM: Homo sapiens

<400> SEQUENCE: 1086
accgccctgc actgctacag gaagggcctg accttcgtct                              40

<210> SEQ ID NO 1087
<211> LENGTH: 40
<212> TYPE: DNA
<213> ORGANISM: Homo sapiens

<400> SEQUENCE: 1087
tcacaattat aggggaagag ctcgtggtct gggttgatcc                              40

<210> SEQ ID NO 1088
<211> LENGTH: 40
<212> TYPE: DNA
<213> ORGANISM: Homo sapiens

<400> SEQUENCE: 1088

```
gtgctattaa agaagaagat ctcgtggtct gggttgatcc                        40

<210> SEQ ID NO 1089
<211> LENGTH: 40
<212> TYPE: DNA
<213> ORGANISM: Homo sapiens

<400> SEQUENCE: 1089
ctcgtctatg atatcaccag atgcccgaat gctagcgagc                        40

<210> SEQ ID NO 1090
<211> LENGTH: 40
<212> TYPE: DNA
<213> ORGANISM: Homo sapiens

<400> SEQUENCE: 1090
ctcgtctatg atatcaccag ccgagaaacc tacaatgcgc                        40

<210> SEQ ID NO 1091
<211> LENGTH: 40
<212> TYPE: DNA
<213> ORGANISM: Homo sapiens

<400> SEQUENCE: 1091
caatgccaca gggcaggctg aaggctggg atgcatggga                         40

<210> SEQ ID NO 1092
<211> LENGTH: 40
<212> TYPE: DNA
<213> ORGANISM: Homo sapiens

<400> SEQUENCE: 1092
caatgccaca gggcaggctg actgcaaagc ccaggatgag                        40

<210> SEQ ID NO 1093
<211> LENGTH: 40
<212> TYPE: DNA
<213> ORGANISM: Homo sapiens

<400> SEQUENCE: 1093
tcagaagaga aaatcggatg acaggcggac ccacaggccc                        40

<210> SEQ ID NO 1094
<211> LENGTH: 40
<212> TYPE: DNA
<213> ORGANISM: Homo sapiens

<400> SEQUENCE: 1094
tcagaagaga aaatcggatg gaccttgacc ctgctgttca                        40

<210> SEQ ID NO 1095
<211> LENGTH: 40
<212> TYPE: DNA
<213> ORGANISM: Homo sapiens

<400> SEQUENCE: 1095
tgactgccgc tttctctcag gcccggaaac aaaactcatg                        40

<210> SEQ ID NO 1096
<211> LENGTH: 40
<212> TYPE: DNA
<213> ORGANISM: Homo sapiens

<400> SEQUENCE: 1096
```
ctaaagcctt ctataaaact gcccggaaac aaaactcatg    40

<210> SEQ ID NO 1097
<211> LENGTH: 40
<212> TYPE: DNA
<213> ORGANISM: Homo sapiens

<400> SEQUENCE: 1097
atgcagatac acaaagcaag ccatgcagtt tggtcagctc    40

<210> SEQ ID NO 1098
<211> LENGTH: 40
<212> TYPE: DNA
<213> ORGANISM: Homo sapiens

<400> SEQUENCE: 1098
atgcagatac acaaagcaag gtgcaccagc tatatgaaac    40

<210> SEQ ID NO 1099
<211> LENGTH: 40
<212> TYPE: DNA
<213> ORGANISM: Homo sapiens

<400> SEQUENCE: 1099
tactgatcat attgtccaag tcaaagtaaa caagtatgga    40

<210> SEQ ID NO 1100
<211> LENGTH: 40
<212> TYPE: DNA
<213> ORGANISM: Homo sapiens

<400> SEQUENCE: 1100
aagagtgcca aaaaagaag tcaaagtaaa caagtatgga    40

<210> SEQ ID NO 1101
<211> LENGTH: 40
<212> TYPE: DNA
<213> ORGANISM: Homo sapiens

<400> SEQUENCE: 1101
tgtcatccat tgtggaagag ccccgaaaca cagcagagct    40

<210> SEQ ID NO 1102
<211> LENGTH: 40
<212> TYPE: DNA
<213> ORGANISM: Homo sapiens

<400> SEQUENCE: 1102
tgtcatccat tgtggaagag ctgctggatc agtgcctggc    40

<210> SEQ ID NO 1103
<211> LENGTH: 40
<212> TYPE: DNA
<213> ORGANISM: Homo sapiens

<400> SEQUENCE: 1103
taccggaaac ctaggaaaag gcgccaagcc catctttgtg    40

<210> SEQ ID NO 1104
<211> LENGTH: 40
<212> TYPE: DNA
<213> ORGANISM: Homo sapiens

```
<400> SEQUENCE: 1104
gctgccaaag ccttagacaa gcgccaagcc catctttgtg                              40

<210> SEQ ID NO 1105
<211> LENGTH: 40
<212> TYPE: DNA
<213> ORGANISM: Homo sapiens

<400> SEQUENCE: 1105
aggatatcgg tttcattaag aaagacctga gctgtcttcc                              40

<210> SEQ ID NO 1106
<211> LENGTH: 40
<212> TYPE: DNA
<213> ORGANISM: Homo sapiens

<400> SEQUENCE: 1106
aggatatcgg tttcattaag ttggactaaa tgctcttcct                              40

<210> SEQ ID NO 1107
<211> LENGTH: 40
<212> TYPE: DNA
<213> ORGANISM: Homo sapiens

<400> SEQUENCE: 1107
gcggcgggca gtggcggcag gtgtacattt ttatctttca                              40

<210> SEQ ID NO 1108
<211> LENGTH: 40
<212> TYPE: DNA
<213> ORGANISM: Homo sapiens

<400> SEQUENCE: 1108
gcggcgggca gtggcggcag aatgttggct accagggtat                              40

<210> SEQ ID NO 1109
<211> LENGTH: 40
<212> TYPE: DNA
<213> ORGANISM: Homo sapiens

<400> SEQUENCE: 1109
tatccagcac tgaccacatg gacagacgtt gaaagatacc                              40

<210> SEQ ID NO 1110
<211> LENGTH: 40
<212> TYPE: DNA
<213> ORGANISM: Homo sapiens

<400> SEQUENCE: 1110
cctgattctc cccaccagag gacagacgtt gaaagatacc                              40

<210> SEQ ID NO 1111
<211> LENGTH: 40
<212> TYPE: DNA
<213> ORGANISM: Homo sapiens

<400> SEQUENCE: 1111
ttcatcatgg tgtggtggag ctctcctctt gtttttcagg                              40

<210> SEQ ID NO 1112
<211> LENGTH: 40
<212> TYPE: DNA
<213> ORGANISM: Homo sapiens
```

```
<400> SEQUENCE: 1112
ttcatcatgg tgtggtggag gttgacgccg ctgtcacccc                              40

<210> SEQ ID NO 1113
<211> LENGTH: 40
<212> TYPE: DNA
<213> ORGANISM: Homo sapiens

<400> SEQUENCE: 1113
tgaaatcaga aaaaaatatg tttattttgt ttcaggcctg                              40

<210> SEQ ID NO 1114
<211> LENGTH: 40
<212> TYPE: DNA
<213> ORGANISM: Homo sapiens

<400> SEQUENCE: 1114
tgaaatcaga aaaaaatatg gcctgtttaa agaagaaaac                              40

<210> SEQ ID NO 1115
<211> LENGTH: 40
<212> TYPE: DNA
<213> ORGANISM: Homo sapiens

<400> SEQUENCE: 1115
gcaaggatat ataataactg ctgctttatt tttccacaga                              40

<210> SEQ ID NO 1116
<211> LENGTH: 40
<212> TYPE: DNA
<213> ORGANISM: Homo sapiens

<400> SEQUENCE: 1116
gcaaggatat ataataactg attggtgtgc ccgtttaata                              40

<210> SEQ ID NO 1117
<211> LENGTH: 40
<212> TYPE: DNA
<213> ORGANISM: Homo sapiens

<400> SEQUENCE: 1117
gaactgcaaa ggcttcagag gatttgtaca cacagatatg                              40

<210> SEQ ID NO 1118
<211> LENGTH: 40
<212> TYPE: DNA
<213> ORGANISM: Homo sapiens

<400> SEQUENCE: 1118
ttggagatca ggacgcaaag gtcaccatca gaaaagctaa                              40

<210> SEQ ID NO 1119
<211> LENGTH: 40
<212> TYPE: DNA
<213> ORGANISM: Homo sapiens

<400> SEQUENCE: 1119
gatctggatt ctcgtttcag gtcaccatca gaaaagctaa                              40

<210> SEQ ID NO 1120
<211> LENGTH: 40
<212> TYPE: DNA
```

<213> ORGANISM: Homo sapiens

<400> SEQUENCE: 1120
tggaagaggc tacctctggg gtcaatgaga gtgaaatggc    40

<210> SEQ ID NO 1121
<211> LENGTH: 40
<212> TYPE: DNA
<213> ORGANISM: Homo sapiens

<400> SEQUENCE: 1121
tggaagaggc tacctctggg gtaaccccg ggactttgcc    40

<210> SEQ ID NO 1122
<211> LENGTH: 40
<212> TYPE: DNA
<213> ORGANISM: Homo sapiens

<400> SEQUENCE: 1122
tctggagcca tacgtgacag tgacctgacc aacggtgcag    40

<210> SEQ ID NO 1123
<211> LENGTH: 40
<212> TYPE: DNA
<213> ORGANISM: Homo sapiens

<400> SEQUENCE: 1123
tctggagcca tacgtgacag aaatggctca gggaactgtt    40

<210> SEQ ID NO 1124
<211> LENGTH: 40
<212> TYPE: DNA
<213> ORGANISM: Homo sapiens

<400> SEQUENCE: 1124
ctgcagtatc tgtaaccgag gtctccaggc accaggagcc    40

<210> SEQ ID NO 1125
<211> LENGTH: 40
<212> TYPE: DNA
<213> ORGANISM: Homo sapiens

<400> SEQUENCE: 1125
ctgcagtatc tgtaaccgag gtttctcctc tgcctcctac    40

<210> SEQ ID NO 1126
<211> LENGTH: 40
<212> TYPE: DNA
<213> ORGANISM: Homo sapiens

<400> SEQUENCE: 1126
tgatttcaag tttgaacaag gggttggcat ctgcacatcc    40

<210> SEQ ID NO 1127
<211> LENGTH: 40
<212> TYPE: DNA
<213> ORGANISM: Homo sapiens

<400> SEQUENCE: 1127
tgatgagact ccagacagag gggttggcat ctgcacatcc    40

<210> SEQ ID NO 1128
<211> LENGTH: 40

<212> TYPE: DNA
<213> ORGANISM: Homo sapiens

<400> SEQUENCE: 1128
agcgagctcc tcagcctcag gcatctgcat ctgggaccga                               40

<210> SEQ ID NO 1129
<211> LENGTH: 40
<212> TYPE: DNA
<213> ORGANISM: Homo sapiens

<400> SEQUENCE: 1129
ccggggattg ccggcgccag gcatctgcat ctgggaccga                               40

<210> SEQ ID NO 1130
<211> LENGTH: 40
<212> TYPE: DNA
<213> ORGANISM: Homo sapiens

<400> SEQUENCE: 1130
agtttctact agtccagttg gtgactctcc tattccatct                               40

<210> SEQ ID NO 1131
<211> LENGTH: 40
<212> TYPE: DNA
<213> ORGANISM: Homo sapiens

<400> SEQUENCE: 1131
agtttctact agtccagttg ggttaccatc cattgaccca                               40

<210> SEQ ID NO 1132
<211> LENGTH: 40
<212> TYPE: DNA
<213> ORGANISM: Homo sapiens

<400> SEQUENCE: 1132
ggaaaggaca gcaagcacag gtgagactgt ggagatgaga                               40

<210> SEQ ID NO 1133
<211> LENGTH: 40
<212> TYPE: DNA
<213> ORGANISM: Homo sapiens

<400> SEQUENCE: 1133
tgaggtgccc taagcacaag gtgagactgt ggagatgaga                               40

<210> SEQ ID NO 1134
<211> LENGTH: 40
<212> TYPE: DNA
<213> ORGANISM: Homo sapiens

<400> SEQUENCE: 1134
agttgcatgt tgactttagg gagtctgtgt gaagcagcac                               40

<210> SEQ ID NO 1135
<211> LENGTH: 40
<212> TYPE: DNA
<213> ORGANISM: Homo sapiens

<400> SEQUENCE: 1135
agttgcatgt tgactttagg aacgtgaagc tcttggagca                               40

<210> SEQ ID NO 1136

```
<211> LENGTH: 40
<212> TYPE: DNA
<213> ORGANISM: Homo sapiens

<400> SEQUENCE: 1136
ccgcccccgt tccatccacg ggggagctca gtgtgaacac                             40

<210> SEQ ID NO 1137
<211> LENGTH: 40
<212> TYPE: DNA
<213> ORGANISM: Homo sapiens

<400> SEQUENCE: 1137
ccgcccccgt tccatccacg gacgagtgtg aggacgccaa                             40

<210> SEQ ID NO 1138
<211> LENGTH: 40
<212> TYPE: DNA
<213> ORGANISM: Homo sapiens

<400> SEQUENCE: 1138
tggagccgaa caacatcgtg ctcagcgatg cctgccgctt                             40

<210> SEQ ID NO 1139
<211> LENGTH: 40
<212> TYPE: DNA
<213> ORGANISM: Homo sapiens

<400> SEQUENCE: 1139
tggagccgaa caacatcgtg gttctgctcc agacgagccc                             40

<210> SEQ ID NO 1140
<211> LENGTH: 40
<212> TYPE: DNA
<213> ORGANISM: Homo sapiens

<400> SEQUENCE: 1140
gcctggaaag ctaccaaaag gagctgtcca gacagctggt                             40

<210> SEQ ID NO 1141
<211> LENGTH: 40
<212> TYPE: DNA
<213> ORGANISM: Homo sapiens

<400> SEQUENCE: 1141
gcctggaaag ctaccaaaag ggatctctgc aggagctgtc                             40

<210> SEQ ID NO 1142
<211> LENGTH: 40
<212> TYPE: DNA
<213> ORGANISM: Homo sapiens

<400> SEQUENCE: 1142
tgttattgta gattctgggg gtggacttct caaaccaaca                             40

<210> SEQ ID NO 1143
<211> LENGTH: 40
<212> TYPE: DNA
<213> ORGANISM: Homo sapiens

<400> SEQUENCE: 1143
tgttattgta gattctgggg gctttgatga actaggtgga                             40
```

```
<210> SEQ ID NO 1144
<211> LENGTH: 40
<212> TYPE: DNA
<213> ORGANISM: Homo sapiens

<400> SEQUENCE: 1144
ggggaccaag aaaagcagca tggttgcact gaaaagactg                              40

<210> SEQ ID NO 1145
<211> LENGTH: 40
<212> TYPE: DNA
<213> ORGANISM: Homo sapiens

<400> SEQUENCE: 1145
ggggaccaag aaaagcagca ccatgaatga cctggtgcag                              40

<210> SEQ ID NO 1146
<211> LENGTH: 40
<212> TYPE: DNA
<213> ORGANISM: Homo sapiens

<400> SEQUENCE: 1146
caaaaaagac caaaactgag gaactccctc ggccacagtc                              40

<210> SEQ ID NO 1147
<211> LENGTH: 40
<212> TYPE: DNA
<213> ORGANISM: Homo sapiens

<400> SEQUENCE: 1147
caaaaaagac caaaactgag caggaactcc ctcggccaca                              40

<210> SEQ ID NO 1148
<211> LENGTH: 40
<212> TYPE: DNA
<213> ORGANISM: Homo sapiens

<400> SEQUENCE: 1148
ccaaagcaga gacccaggag gtgtacatgg acatcaagat                              40

<210> SEQ ID NO 1149
<211> LENGTH: 40
<212> TYPE: DNA
<213> ORGANISM: Homo sapiens

<400> SEQUENCE: 1149
ccaaagcaga gacccaggag ggagagccca ttgctaaaaa                              40

<210> SEQ ID NO 1150
<211> LENGTH: 40
<212> TYPE: DNA
<213> ORGANISM: Homo sapiens

<400> SEQUENCE: 1150
gccgaatcac ctgatctaag gagattacct ggggcaattg                              40

<210> SEQ ID NO 1151
<211> LENGTH: 40
<212> TYPE: DNA
<213> ORGANISM: Homo sapiens

<400> SEQUENCE: 1151
acgccgcaag tcctccagag gaacagcagc acaatggacc                              40
```

```
<210> SEQ ID NO 1152
<211> LENGTH: 40
<212> TYPE: DNA
<213> ORGANISM: Homo sapiens

<400> SEQUENCE: 1152
agcacccatg ggtgcagggg gaacagcagc acaatggacc                              40

<210> SEQ ID NO 1153
<211> LENGTH: 40
<212> TYPE: DNA
<213> ORGANISM: Homo sapiens

<400> SEQUENCE: 1153
aaccagtaac aacggaacct cagagtccag atctgaacga                              40

<210> SEQ ID NO 1154
<211> LENGTH: 40
<212> TYPE: DNA
<213> ORGANISM: Homo sapiens

<400> SEQUENCE: 1154
aaccagtaac aacggaacct agtccagatc tgaacgatgc                              40

<210> SEQ ID NO 1155
<211> LENGTH: 40
<212> TYPE: DNA
<213> ORGANISM: Homo sapiens

<400> SEQUENCE: 1155
gagaccgcgt gcgaggaccg cagcaatgca gagtccctgg                              40

<210> SEQ ID NO 1156
<211> LENGTH: 40
<212> TYPE: DNA
<213> ORGANISM: Homo sapiens

<400> SEQUENCE: 1156
gagaccgcgt gcgaggaccg caatgcagag tccctggaca                              40

<210> SEQ ID NO 1157
<211> LENGTH: 40
<212> TYPE: DNA
<213> ORGANISM: Homo sapiens

<400> SEQUENCE: 1157
gtctctggca agtaatccag aacttcttaa tcttccatcc                              40

<210> SEQ ID NO 1158
<211> LENGTH: 40
<212> TYPE: DNA
<213> ORGANISM: Homo sapiens

<400> SEQUENCE: 1158
gtctctggca agtaatccag taattaagaa gaaagttcat                              40

<210> SEQ ID NO 1159
<211> LENGTH: 40
<212> TYPE: DNA
<213> ORGANISM: Homo sapiens

<400> SEQUENCE: 1159
aagcatgtag aaagccggaa caggtactta aaatgaatgc                              40
```

<210> SEQ ID NO 1160
<211> LENGTH: 40
<212> TYPE: DNA
<213> ORGANISM: Homo sapiens

<400> SEQUENCE: 1160
aagcatgtag aaagccggaa ggataaagaa atggagaaga                40

<210> SEQ ID NO 1161
<211> LENGTH: 40
<212> TYPE: DNA
<213> ORGANISM: Homo sapiens

<400> SEQUENCE: 1161
agcacccatg ggtgcagggg caagctccag aaaagggact                40

<210> SEQ ID NO 1162
<211> LENGTH: 40
<212> TYPE: DNA
<213> ORGANISM: Homo sapiens

<400> SEQUENCE: 1162
tccacaagag cgaggaggcg aagcgggtgc tgcggtatta                40

<210> SEQ ID NO 1163
<211> LENGTH: 40
<212> TYPE: DNA
<213> ORGANISM: Homo sapiens

<400> SEQUENCE: 1163
aggcggtgag tgtcggacag aagcgggtgc tgcggtatta                40

<210> SEQ ID NO 1164
<211> LENGTH: 40
<212> TYPE: DNA
<213> ORGANISM: Homo sapiens

<400> SEQUENCE: 1164
tccgccccac agtccacgag actttaccag aatgcaggac                40

<210> SEQ ID NO 1165
<211> LENGTH: 40
<212> TYPE: DNA
<213> ORGANISM: Homo sapiens

<400> SEQUENCE: 1165
ggcggagaca tggaccagag actttaccag aatgcaggac                40

<210> SEQ ID NO 1166
<211> LENGTH: 40
<212> TYPE: DNA
<213> ORGANISM: Homo sapiens

<400> SEQUENCE: 1166
ttgatcttcg gccccacacg aacagcagag aggggcagca                40

<210> SEQ ID NO 1167
<211> LENGTH: 40
<212> TYPE: DNA
<213> ORGANISM: Homo sapiens

<400> SEQUENCE: 1167
ttgatcttcg gccccacacg cagagagggg cagcaggatg                        40

<210> SEQ ID NO 1168
<211> LENGTH: 40
<212> TYPE: DNA
<213> ORGANISM: Homo sapiens

<400> SEQUENCE: 1168
gaaaaacttt ccagccattg gggggacagg ccccacctcg                        40

<210> SEQ ID NO 1169
<211> LENGTH: 40
<212> TYPE: DNA
<213> ORGANISM: Homo sapiens

<400> SEQUENCE: 1169
gaaaaacttt ccagccattg gaggttgtcg ggacatttca                        40

<210> SEQ ID NO 1170
<211> LENGTH: 40
<212> TYPE: DNA
<213> ORGANISM: Homo sapiens

<400> SEQUENCE: 1170
gcgctcgccc gggcggcaga ctgtgaggtg gagcagtggg                        40

<210> SEQ ID NO 1171
<211> LENGTH: 40
<212> TYPE: DNA
<213> ORGANISM: Homo sapiens

<400> SEQUENCE: 1171
ccgcaggata cccgccgagg ctgtgaggtg gagcagtggg                        40

<210> SEQ ID NO 1172
<211> LENGTH: 40
<212> TYPE: DNA
<213> ORGANISM: Homo sapiens

<400> SEQUENCE: 1172
cgggacgact tctacgacag gctcttcgac taccggggcc                        40

<210> SEQ ID NO 1173
<211> LENGTH: 40
<212> TYPE: DNA
<213> ORGANISM: Homo sapiens

<400> SEQUENCE: 1173
gcagcatctg ccatatacag gctcttcgac taccggggcc                        40

<210> SEQ ID NO 1174
<211> LENGTH: 40
<212> TYPE: DNA
<213> ORGANISM: Homo sapiens

<400> SEQUENCE: 1174
actgaagcag caacacgcct ctctgcgtac gtgtcctatg                        40

<210> SEQ ID NO 1175
<211> LENGTH: 40
<212> TYPE: DNA
<213> ORGANISM: Homo sapiens

<400> SEQUENCE: 1175

```
actgaagcag caacacgcct gctgagattg agagctgctg                              40

<210> SEQ ID NO 1176
<211> LENGTH: 40
<212> TYPE: DNA
<213> ORGANISM: Homo sapiens

<400> SEQUENCE: 1176
ctgccggcgg agaatataag gagatggaca aaccgtgtgg                              40

<210> SEQ ID NO 1177
<211> LENGTH: 40
<212> TYPE: DNA
<213> ORGANISM: Homo sapiens

<400> SEQUENCE: 1177
ctgccggcgg agaatataag gtgtgtgtga ccatggaacg                              40

<210> SEQ ID NO 1178
<211> LENGTH: 40
<212> TYPE: DNA
<213> ORGANISM: Homo sapiens

<400> SEQUENCE: 1178
caacctctaa gactggagcg gttcttcttc cgcagtggga                              40

<210> SEQ ID NO 1179
<211> LENGTH: 40
<212> TYPE: DNA
<213> ORGANISM: Homo sapiens

<400> SEQUENCE: 1179
caacctctaa gactggagcg tgggaacatc gagcacccgg                              40

<210> SEQ ID NO 1180
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1180
gcgagacaca ctggtattaa g                                                 21

<210> SEQ ID NO 1181
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1181
tgtggatgag cagcagaaag t                                                 21

<210> SEQ ID NO 1182
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1182
```
gatgagcagc atgaagttcg g                                          21

<210> SEQ ID NO 1183
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1183
gacttccttc tttattgccc ttc                                        23

<210> SEQ ID NO 1184
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1184
agcactgatg gtccgaactt tc                                         22

<210> SEQ ID NO 1185
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1185
gtgtgcaaaa gcaagaagtc c                                          21

<210> SEQ ID NO 1186
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1186
gcactgatgg tccgaacttc a                                          21

<210> SEQ ID NO 1187
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1187
gcttggcggt gggaaagaga aattg                                      25

<210> SEQ ID NO 1188
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1188
aaccagtcat accacccaaa ggtgttg                                          27

<210> SEQ ID NO 1189
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1189
ggcacccagc acaatgaaga tcaag                                            25

<210> SEQ ID NO 1190
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1190
actcgtcata ctcctgcttg ctgatc                                           26

<210> SEQ ID NO 1191
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1191
actctcttcc gcatcgctgt                                                  20

<210> SEQ ID NO 1192
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1192
ccgacgggtt tccgatccaa                                                  20

<210> SEQ ID NO 1193
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1193
ctgttgggct cgcggttg                                                    18

<210> SEQ ID NO 1194
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1194
tcttgtctac ctctggttcc t                                                21

<210> SEQ ID NO 1195
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1195
ccttcttgtt gatgtgcctt tc                                              22

<210> SEQ ID NO 1196
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1196
cagtcttcgc ccctcttttc ttag                                            24

<210> SEQ ID NO 1197
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1197
cggtggtgca agtggaa                                                    17

<210> SEQ ID NO 1198
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1198
gccttggtgt cctcatttct                                                 20

<210> SEQ ID NO 1199
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1199
cttgaggttt catttccccc tccc                                            24

<210> SEQ ID NO 1200
<211> LENGTH: 1304
<212> TYPE: PRT
<213> ORGANISM: Homo sapiens

<400> SEQUENCE: 1200

Met Ala Lys Ile Ala Lys Thr His Glu Asp Ile Glu Ala Gln Ile Arg
1               5                   10                  15

Glu Ile Gln Gly Lys Lys Ala Ala Leu Asp Glu Ala Gln Gly Val Gly
            20                  25                  30

-continued

```
Leu Asp Ser Thr Gly Tyr Tyr Asp Gln Glu Ile Tyr Gly Gly Ser Asp
         35                  40                  45

Ser Arg Phe Ala Gly Tyr Val Thr Ser Ile Ala Ala Thr Glu Leu Glu
 50                  55                  60

Asp Asp Asp Asp Asp Tyr Ser Ser Ser Thr Ser Leu Leu Gly Gln Lys
 65                  70                  75                  80

Lys Pro Gly Tyr His Ala Pro Val Ala Leu Leu Asn Asp Ile Pro Gln
                 85                  90                  95

Ser Thr Glu Gln Tyr Asp Pro Phe Ala Glu His Arg Pro Pro Lys Ile
            100                 105                 110

Ala Asp Arg Glu Asp Glu Tyr Lys Lys His Arg Arg Thr Met Ile Ile
            115                 120                 125

Ser Pro Glu Arg Leu Asp Pro Phe Ala Asp Gly Gly Lys Thr Pro Asp
        130                 135                 140

Pro Lys Met Asn Ala Arg Thr Tyr Met Asp Val Met Arg Glu Gln His
145                 150                 155                 160

Leu Thr Lys Glu Glu Arg Glu Ile Arg Gln Gln Leu Ala Glu Lys Ala
                165                 170                 175

Lys Ala Gly Glu Leu Lys Val Val Asn Gly Ala Ala Ser Gln Pro
            180                 185                 190

Pro Ser Lys Arg Lys Arg Arg Trp Asp Gln Thr Ala Asp Gln Thr Pro
        195                 200                 205

Gly Ala Thr Pro Lys Lys Leu Ser Ser Trp Asp Gln Ala Glu Thr Pro
    210                 215                 220

Gly His Thr Pro Ser Leu Arg Trp Asp Glu Thr Pro Gly Arg Ala Lys
225                 230                 235                 240

Gly Ser Glu Thr Pro Gly Ala Thr Pro Gly Ser Lys Ile Trp Asp Pro
                245                 250                 255

Thr Pro Ser His Thr Pro Ala Gly Ala Ala Thr Pro Gly Arg Gly Asp
            260                 265                 270

Thr Pro Gly His Ala Thr Pro Gly His Gly Ala Thr Ser Ser Ala
        275                 280                 285

Arg Lys Asn Arg Trp Asp Glu Thr Pro Lys Thr Glu Arg Asp Thr Pro
    290                 295                 300

Gly His Gly Ser Gly Trp Ala Glu Thr Pro Arg Thr Asp Arg Gly Gly
305                 310                 315                 320

Asp Ser Ile Gly Glu Thr Pro Thr Pro Gly Ala Ser Lys Arg Lys Ser
                325                 330                 335

Arg Trp Asp Glu Thr Pro Ala Ser Gln Met Gly Gly Ser Thr Pro Val
            340                 345                 350

Leu Thr Pro Gly Lys Thr Pro Ile Gly Thr Pro Ala Met Asn Met Ala
        355                 360                 365

Thr Pro Thr Pro Gly His Ile Met Ser Met Thr Pro Glu Gln Leu Gln
    370                 375                 380

Ala Trp Arg Trp Glu Arg Glu Ile Asp Glu Arg Asn Arg Pro Leu Ser
385                 390                 395                 400

Asp Glu Glu Leu Asp Ala Met Phe Pro Glu Gly Tyr Lys Val Leu Pro
                405                 410                 415

Pro Pro Ala Gly Tyr Val Pro Ile Arg Thr Pro Ala Arg Lys Leu Thr
            420                 425                 430

Ala Thr Pro Thr Pro Leu Gly Gly Met Thr Gly Phe His Met Gln Thr
        435                 440                 445
```

```
Glu Asp Arg Thr Met Lys Ser Val Asn Asp Gln Pro Ser Gly Asn Leu
    450                 455                 460
Pro Phe Leu Lys Pro Asp Asp Ile Gln Tyr Phe Asp Lys Leu Leu Val
465                 470                 475                 480
Asp Val Asp Glu Ser Thr Leu Ser Pro Glu Glu Gln Lys Glu Arg Lys
                485                 490                 495
Ile Met Lys Leu Leu Leu Lys Ile Lys Asn Gly Thr Pro Pro Met Arg
            500                 505                 510
Lys Ala Ala Leu Arg Gln Ile Thr Asp Lys Ala Arg Glu Phe Gly Ala
        515                 520                 525
Gly Pro Leu Phe Asn Gln Ile Leu Pro Leu Leu Met Ser Pro Thr Leu
530                 535                 540
Glu Asp Gln Glu Arg His Leu Leu Val Lys Val Ile Asp Arg Ile Leu
545                 550                 555                 560
Tyr Lys Leu Asp Asp Leu Val Arg Pro Tyr Val His Lys Ile Leu Val
                565                 570                 575
Val Ile Glu Pro Leu Leu Ile Asp Glu Asp Tyr Tyr Ala Arg Val Glu
            580                 585                 590
Gly Arg Glu Ile Ile Ser Asn Leu Ala Lys Ala Ala Gly Leu Ala Thr
        595                 600                 605
Met Ile Ser Thr Met Arg Pro Asp Ile Asp Asn Met Asp Glu Tyr Val
610                 615                 620
Arg Asn Thr Thr Ala Arg Ala Phe Ala Val Val Ala Ser Ala Leu Gly
625                 630                 635                 640
Ile Pro Ser Leu Leu Pro Phe Leu Lys Ala Val Cys Lys Ser Lys Lys
                645                 650                 655
Ser Trp Gln Ala Arg His Thr Gly Ile Lys Ile Val Gln Gln Ile Ala
            660                 665                 670
Ile Leu Met Gly Cys Ala Ile Leu Pro His Leu Arg Ser Leu Val Glu
        675                 680                 685
Ile Ile Glu His Gly Leu Val Asp Glu Gln Gln Lys Val Arg Thr Ile
690                 695                 700
Ser Ala Leu Ala Ile Ala Ala Leu Ala Glu Ala Ala Thr Pro Tyr Gly
705                 710                 715                 720
Ile Glu Ser Phe Asp Ser Val Leu Lys Pro Leu Trp Lys Gly Ile Arg
                725                 730                 735
Gln His Arg Gly Lys Gly Leu Ala Ala Phe Leu Lys Ala Ile Gly Tyr
            740                 745                 750
Leu Ile Pro Leu Met Asp Ala Glu Tyr Ala Asn Tyr Tyr Thr Arg Glu
        755                 760                 765
Val Met Leu Ile Leu Ile Arg Glu Phe Gln Ser Pro Asp Glu Glu Met
770                 775                 780
Lys Lys Ile Val Leu Lys Val Val Lys Gln Cys Cys Gly Thr Asp Gly
785                 790                 795                 800
Val Glu Ala Asn Tyr Ile Lys Thr Glu Ile Leu Pro Pro Phe Phe Lys
                805                 810                 815
His Phe Trp Gln His Arg Met Ala Leu Asp Arg Arg Asn Tyr Arg Gln
            820                 825                 830
Leu Val Asp Thr Thr Val Glu Leu Ala Asn Lys Val Gly Ala Ala Glu
        835                 840                 845
Ile Ile Ser Arg Ile Val Asp Asp Leu Lys Asp Glu Ala Glu Gln Tyr
850                 855                 860
Arg Lys Met Val Met Glu Thr Ile Glu Lys Ile Met Gly Asn Leu Gly
```

-continued

```
865                 870                 875                 880
Ala Ala Asp Ile Asp His Lys Leu Glu Glu Gln Leu Ile Asp Gly Ile
                885                 890                 895
Leu Tyr Ala Phe Gln Glu Gln Thr Thr Glu Asp Ser Val Met Leu Asn
                900                 905                 910
Gly Phe Gly Thr Val Val Asn Ala Leu Gly Lys Arg Val Lys Pro Tyr
                915                 920                 925
Leu Pro Gln Ile Cys Gly Thr Val Leu Trp Arg Leu Asn Asn Lys Ser
                930                 935                 940
Ala Lys Val Arg Gln Gln Ala Ala Asp Leu Ile Ser Arg Thr Ala Val
945                 950                 955                 960
Val Met Lys Thr Cys Gln Glu Lys Leu Met Gly His Leu Gly Val
                965                 970                 975
Val Leu Tyr Glu Tyr Leu Gly Glu Glu Tyr Pro Glu Val Leu Gly Ser
                980                 985                 990
Ile Leu Gly Ala Leu Lys Ala Ile Val Asn Val Ile Gly Met His Lys
                995                 1000                1005
Met Thr Pro Pro Ile Lys Asp Leu Leu Pro Arg Leu Thr Pro Ile
    1010                1015                1020
Leu Lys Asn Arg His Glu Lys Val Gln Glu Asn Cys Ile Asp Leu
    1025                1030                1035
Val Gly Arg Ile Ala Asp Arg Gly Ala Glu Tyr Val Ser Ala Arg
    1040                1045                1050
Glu Trp Met Arg Ile Cys Phe Glu Leu Leu Glu Leu Leu Lys Ala
    1055                1060                1065
His Lys Lys Ala Ile Arg Arg Ala Thr Val Asn Thr Phe Gly Tyr
    1070                1075                1080
Ile Ala Lys Ala Ile Gly Pro His Asp Val Leu Ala Thr Leu Leu
    1085                1090                1095
Asn Asn Leu Lys Val Gln Glu Arg Gln Asn Arg Val Cys Thr Thr
    1100                1105                1110
Val Ala Ile Ala Ile Val Ala Glu Thr Cys Ser Pro Phe Thr Val
    1115                1120                1125
Leu Pro Ala Leu Met Asn Glu Tyr Arg Val Pro Glu Leu Asn Val
    1130                1135                1140
Gln Asn Gly Val Leu Lys Ser Leu Ser Phe Leu Phe Glu Tyr Ile
    1145                1150                1155
Gly Glu Met Gly Lys Asp Tyr Ile Tyr Ala Val Thr Pro Leu Leu
    1160                1165                1170
Glu Asp Ala Leu Met Asp Arg Asp Leu Val His Arg Gln Thr Ala
    1175                1180                1185
Ser Ala Val Val Gln His Met Ser Leu Gly Val Tyr Gly Phe Gly
    1190                1195                1200
Cys Glu Asp Ser Leu Asn His Leu Leu Asn Tyr Val Trp Pro Asn
    1205                1210                1215
Val Phe Glu Thr Ser Pro His Val Ile Gln Ala Val Met Gly Ala
    1220                1225                1230
Leu Glu Gly Leu Arg Val Ala Ile Gly Pro Cys Arg Met Leu Gln
    1235                1240                1245
Tyr Cys Leu Gln Gly Leu Phe His Pro Ala Arg Lys Val Arg Asp
    1250                1255                1260
Val Tyr Trp Lys Ile Tyr Asn Ser Ile Tyr Ile Gly Ser Gln Asp
    1265                1270                1275
```

-continued

```
Ala Leu Ile Ala His Tyr Pro Arg Ile Tyr Asn Asp Asp Lys Asn
    1280            1285            1290

Thr Tyr Ile Arg Tyr Glu Leu Asp Tyr Ile Leu
    1295            1300
```

SPLICE VARIANTS ASSOCIATED WITH NEOMORPHIC SF3B1 MUTANTS

The present application is a continuation of U.S. patent application Ser. No. 15/755,225, filed Feb. 26, 2018, which is a national stage application under 35 U.S.C. § 371 of international application number PCT/US2016/049490, filed Aug. 30, 2016, which designated the U.S. and claims the benefit of priority to U.S. Provisional Patent Application No. 62/212,876, filed Sep. 1, 2015, the contents of which are hereby incorporated by reference herein in their entirety.

The instant application contains a Sequence Listing which has been submitted electronically in ASCII format and is hereby incorporated by reference in its entirety. The ASCII copy, created on May 16, 2014, is named 12636.6-304_SL.txt and is 183 kilobytes in size.

RNA splicing, a highly regulated molecular event orchestrated by the spliceosome, results in the removal of intronic sequences from pre-mRNA to generate mature mRNA. Dysregulation of RNA splicing has been identified as a causative defect in several diseases. In addition, dysregulated splicing has been proposed to play an important role in tumorigenesis and resistance to therapy; however, the molecular causes of dysregulated splicing in cancer have remained elusive.

SF3B1 is a protein involved in RNA splicing. It forms part of the U2 snRNP complex which binds to the pre-mRNA at a region containing the branchpoint site and is involved in early recognition and stabilization of the spliceosome at the 3' splice site (3'ss). A thorough and systematic analysis of the effects of SF3B1 mutations is needed to define their effects on RNA splicing in cells and may lead to novel therapeutic approaches for SF3B1 mutant cancers.

The description provided herein demonstrates that certain SF3B1 mutations result in neomorphic activity with the production of known and novel splicing alterations. In addition, lineage-specific splicing aberrations were identified in chronic lymphocytic leukemia (CLL), melanoma, and breast cancer. Furthermore, treatment of SF3B1-mutant cancer cell lines, xenografts, and CLL patient samples with modulators of SF3B1 reduced aberrant splicing and induced tumor regression.

SUMMARY

The methods described herein involve detecting or quantifying the expression of one or more splice variants in a cell containing a neomorphic mutant SF3B1 protein. Various embodiments of the invention include detecting or quantifying splice variants to determine whether a patient has a cancer with one or more neomorphic SF3B1 mutations. Additional embodiments include measuring the amount of a splice variant to evaluate the effects of a compound on a mutant SF3B1 protein. Further embodiments include methods of treating a patient who has cancer cells with a neomorphic mutant SF3B1 protein.

Various embodiments encompass a method of detecting one or more splice variants selected from rows 1-790 of Table 1 in a biological sample, comprising:
 a) providing a biological sample suspected of containing one or more splice variants;
 b) contacting the biological sample with one or more nucleic acid probes capable of specifically hybridizing to the one or more splice variants, and
 c) detecting the binding of the one or more probes to the one or more splice variants.

In some embodiments, the one or more nucleic acid probes capable of specifically hybridizing to the one or more splice variants each comprise a label. In some embodiments, the method of detecting one or more splice variants selected from rows 1-790 of Table 1 in a biological sample further comprises contacting the biological sample with one or more additional nucleic acid probes, wherein the additional probes are each labeled with a molecular barcode.

Embodiments further encompass a method of modulating the activity of a neomorphic mutant SF3B1 protein in a target cell, comprising applying an SF3B1-modulating compound to the target cell, wherein the target cell has been determined to express one or more aberrant splice variants selected from rows 1-790 of Table 1 at a level that is increased or decreased relative to the level in a cell not having the neomorphic mutant SF3B1 protein.

Embodiments also encompass a method for evaluating the ability of a compound to modulate the activity of a neomorphic mutant SF3B1 protein in a target cell, comprising the steps of:
 a) providing a target cell having a mutant SF3B1 protein;
 b) applying the compound to the target cell; and
 c) measuring the expression level of one or more splice variants selected from row 1-790 of Table 1.

In some embodiments, the method for evaluating the ability of a compound to modulate the activity of a neomorphic mutant SF3B1 protein in a target cell further comprises the step of measuring the expression level of one or more splice variants selected from row 1-790 of Table 1 before step (b).

In some embodiments, the neomorphic mutant SF3B1 protein is selected from K700E, K666N, R625C, G742D, R625H, E622D, H662Q, K666T, K666E, K666R, G740E, Y623C, T663I, K741N, N626Y, T663P, H662R, G740V, D781E, or R625L. In some embodiments, the neomorphic mutant SF3B1 protein is selected from E622D, E622K, E622Q, E622V, Y623C, Y623H, Y623S, R625C, R625G, R625H, R625L, R625P, R625S, N626D, N626H, N626I, N626S, N626Y, H662D, H662L, H662Q, H662R, H662Y, T663I, T663P, K666E, K666M, K666N, K666Q, K666R, K666S, K666T, K700E, V701A, V701F, V701I, I704F, I704N, I704S, I704V, G740E, G740K, G740R, G740V, K741N, K741Q, K741T, G742D, D781E, D781G, or D781N.

In some embodiments, the step of measuring the expression level of one or more splice variants comprises using an assay to quantify nucleic acid selected from nucleic acid barcoding (e.g. NanoString®), RT-PCR, microarray, nucleic acid sequencing, nanoparticle probes (e.g. SmartFlare™), and in situ hybridization (e.g. RNAscope®).

In some embodiments, the step of measuring the expression level of one or more splice variants comprises measuring the number of copies of the one or more splice variant RNAs in the target cell.

In further embodiments, the compound is selected from a small molecule, an antibody, an antisense molecule, an aptamer, an RNA molecule, and a peptide. In further embodiments, the small molecule is selected from pladienolide and a pladienolide analog. In additional embodiments, the pladienolide analog is selected from pladienolide B, pladienolide D, E7107, a compound of formula 1:

a compound of formula 2:

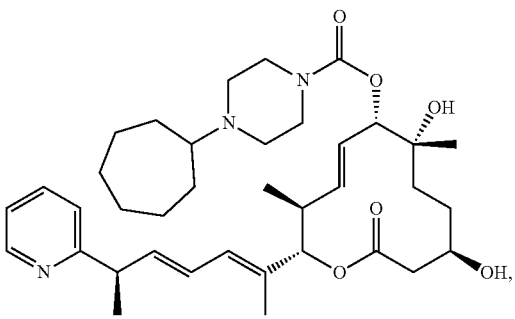

a compound of formula 3:

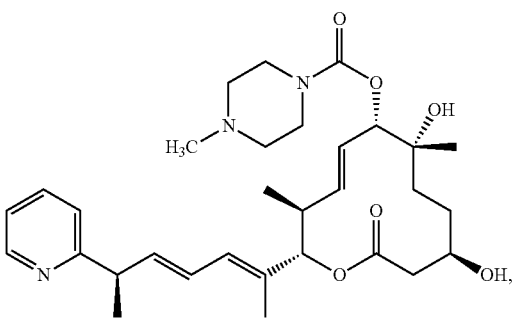

or a compound of formula 4:

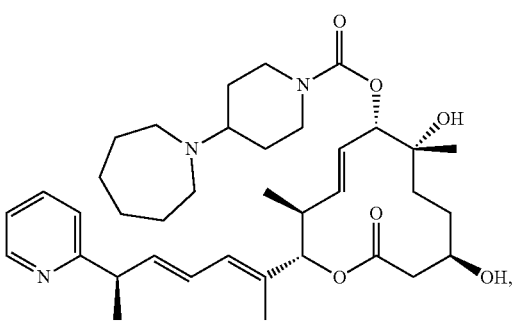

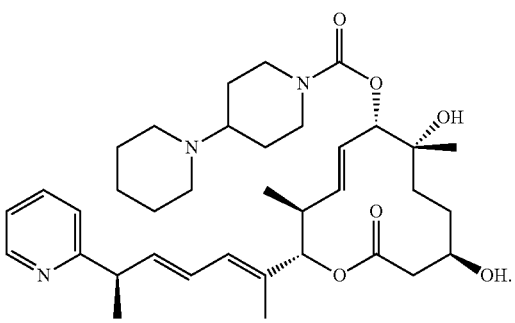

In some embodiments, the target cell is obtained from a patient suspected of having myelodysplastic syndrome, chronic lymphocytic leukemia, chronic myelomonocytic leukemia, or acute myeloid leukemia. In some embodiments, the target cell is obtained from a sample selected from blood or a blood fraction or is a cultured cell derived from a cell obtained from a sample chosen from blood or a blood fraction. In some embodiments, the target cell is a lymphocyte.

In further embodiments, the target cell is obtained from a solid tumor. In some embodiments, the target cell is a breast tissue cell, pancreatic cell, lung cell, or skin cell.

In some embodiments, one or more of the aberrant variants are selected from rows 1, 7, 9, 10, 13, 15, 16, 18, 21, 24, 27, 28, 30, 31, 33, 34, 48, 51, 62, 65, 66, 71, 72, 81, 84, 89, 91, 105, 107, 121, 135, 136, 152, 178, 235, 240, 247, 265, 267, 272, 276, 279, 282, 283, 286, 292, 295, 296, 298, 302, 306, 329, 330, 331, 343, 350, 355, 356, 360, 364, 372, 378, 390, 391, 423, 424, 425, 426, 431, 433, 438, 439, 443, 445, 447, 448, 451, 452, 458, 459, 460, 462, 468, 469, 472, 500, 508, 517, 519, 521, 524, 525, 527, 528, 530, 533, 536, 540, 543, 548, 545, 554, 556, 559, 571, 573, 580, 582, 583, 597, 601, 615, 617, 618, 639, 640, 654, 657, 666, 670, 680, 727, 730, 750, 758, 767, or 774 of Table 1.

In some embodiments, one or more of the aberrant variants are selected from rows 21, 31, 51, 81, 118, 279, 372, 401, 426, 443, 528, 543, 545, 548 or 566 of Table 1.

Embodiments further encompass a method for treating a patient with a neoplastic disorder, comprising administering a therapeutically effective amount of an SF3B1-modulating compound to the patient, wherein a cell from the patient has been determined to:

a) contain a neomorphic mutant SF3B1 protein; and
b) express one or more aberrant splice variants selected from rows 1-790 of Table 1 at a level that is increased or decreased relative to the level in a cell not having the neomorphic mutant SF3B1 protein.

Additional embodiments are set forth in the description which follows.

It is to be understood that both the foregoing general description and the following detailed description are exemplary and explanatory only and are not restrictive of the invention, as claimed.

BRIEF DESCRIPTION OF THE DRAWINGS

FIGS. 15A and 15B are a set of graphs showing the level of splicing of pre-mRNA Ad2 substrate in nuclear extracts from (FIG. 15A) 293F cells expressing Flag-tag SF3B1$^{WT}$ or SF3B1$^{K700E}$ (left and right panels [circles and triangles], respectively) and (FIG. 15B) Nalm-6 (SF3B1$^{WT}$) and Nalm-6 SF3B1$^{K700E}$ cells (left and right panels [circles and triangles], respectively) treated with varying concentrations of E7101. Data are represented as mean±SD, n=2.

FIG. 16B depicts lower panels, a pair of graphs showing the levels of abnormally spliced isoforms of abnormally spliced genes COASY (triangles) and ZDHHC16 (diamonds) in Nalm-6 SF3B1$^{K700K}$ cells (left panel) and Nalm-6 SF3B1$^{K700E}$ cells (right panel) treated with varying concentrations of E7107, as measured by qPCR. qPCR data in (FIG. 16B) are represented as mean±SD (n=3).

DESCRIPTION OF THE EMBODIMENTS

In certain aspects, the methods of the invention provide assays for measuring the amount of a splice variant in a cell, thereby determining whether a patient has a cancer with a neomorphic SF3B1 mutation. In some embodiments, at least one of the measured splice variants is an aberrant splice variant associated with a neomorphic mutation in an SF3B1 protein. In additional aspects, the measurement of a splice variant in a cell may be used to evaluate the ability of a compound to modulate a mutant neomorphic SF3B1 protein in a cell.

To assist in understanding the present invention, certain terms are first defined. Additional definitions are provided throughout the application.

As used herein, the term "mutant SF3B1 protein" includes SF3B1 proteins that differ in amino acid sequence from the human wild type SF3B1 protein set forth in SEQ ID NO:1200 (GenBank Accession Number NP_036565, Version NP_036565.2) (S. Bonnal, L. Vigevani, and J. Valcárcel, "The spliceosome as a target of novel antitumour drugs," *Nat. Rev. Drug Discov.* 11:847-59 [2012]). Certain mutant SF3B1 proteins are "neomorphic" mutants, which refers to mutant SF3B1 proteins that are associated with differential expression of aberrant splice variants. In certain embodiments, neomorphic SF3B1 mutants include K700E, K666N, R625C, G742D, R625H, E622D, H662Q, K666T, K666E, K666R, G740E, Y623C, T663I, K741N, N626Y, T663P, H662R, G740V, D781E, or R625L. In other embodiments, neomophic SF3B1 mutants include E622D, E622K, E622Q, E622V, Y623C, Y623H, Y623S, R625C, R625G, R625H, R625L, R625P, R625S, N626D, N626H, N626I, N626S, N626Y, H662D, H662L, H662Q, H662R, H662Y, T663I, T663P, K666E, K666M, K666N, K666Q, K666R, K666S, K666T, K700E, V701A, V701F, V701I, I704F, I704N, I704S, I704V, G740E, G740K, G740R, G740V, K741N, K741Q, K741T, G742D, D781E, D781G, or D781N. Certain SF3B1 mutations are not associated with expression of aberrant splice variants, including K700R.

Figure 1:
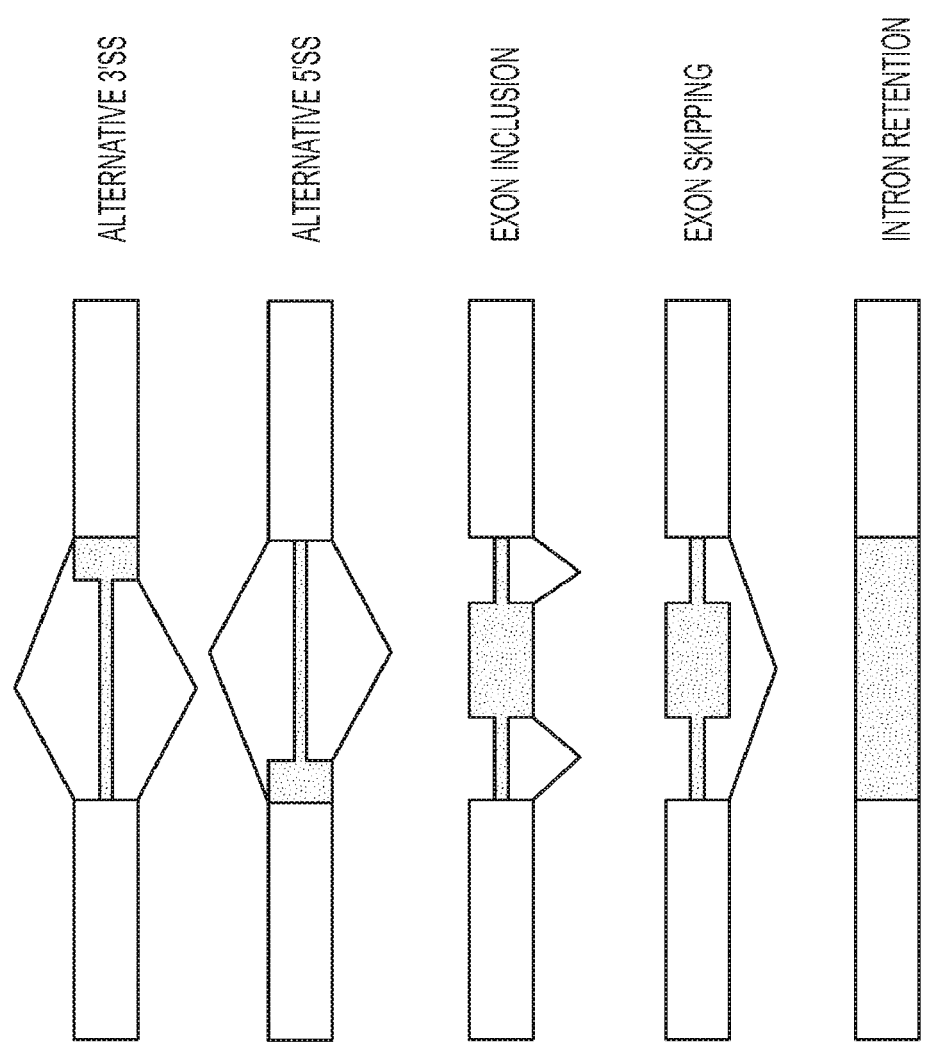
FIG. 1 is a schematic diagram depicting modes of alternative splicing.

The term "splice variant" as used herein includes nucleic acid sequences that span a junction either between two exon sequences or across an intron-exon boundary in a gene, where the junction can be alternatively spliced. Alternative splicing includes alternate 3' splice site selection ("3'ss"), alternate 5' splice site selection ("5'ss"), differential exon inclusion, exon skipping, and intron retention (FIG. 1). Certain splice variants associated with a given genomic location may be referred to as wild type, or "canonical," variants. These splice variants are most abundantly expressed in cells that do not contain a neomorphic SF3B1 mutant protein. Additional splice variants may be referred to as "aberrant" splice variants, which differ from the canonical splice variant and are primarily associated with the presence of a neomorphic SF3B1 mutant protein in a cell. Aberrant splice variants may alternatively be referred to as "abnormal" or "noncanonical" splice variants. In certain circumstances, cells with a wild type or non-neomorphic SF3B1 protein have low or undetected amounts of an aberrant splice variant, while cells with a neomorphic SF3B1 protein have levels of an aberrant splice variant that are elevated relative to the low or undetected levels in the wild type SF3B1 cells. In some cases, an aberrant splice variant is a splice variant that is present in a wild type SF3B1 cell but is differentially expressed in a cell that has a neomorphic SF3B1 mutant, whereby the latter cell has a level of the aberrant splice variant that is elevated or reduced relative to the level in the wild type SF3B1 cell. Different types of cells containing a neomorphic SF3B1 mutant, such as different types of cancer cells, may have differing levels of expression of certain aberrant splice variants. In addition, certain aberrant splice variants present in one type of cell containing a neomorphic SF3B1 mutant may not be present in other types of cells containing a neomorphic SF3B1 mutant. In some cases, patients with a neomorphic SF3B1 mutant protein may not express an aberrant splice variant or may express an aberrant splice variant at lower levels, due to low allelic frequency of the neomorphic SF3B1 allele. The identity and relative expression levels of aberrant splice variants associated with various types of cells containing neomorphic SF3B1 mutants, such as certain cancer cells, will be apparent from the description and examples provided herein.

The term "evaluating" includes determining the ability of a compound to treat a disease associated with a neomorphic SF3B1 mutation. In some instances, "evaluating" includes determining whether or to what degree a compound modulates aberrant splicing events associated with a neomorphic SF3B1 protein. Modulation of the activity of an SF3B1 protein may encompass up-regulation or down-regulation of aberrant splice variant expression associated with a neomorphic SF3B1 protein. Additionally, "evaluating" includes distinguishing patients that may be successfully treated with a compound that modulates the expression of splice variants associated with a neomorphic SF3B1 protein.

The use of the word "a", "an" or "the" when used in conjunction with the term "comprising" in the claims or the specification may mean "one," but it is also consistent with the meaning of "one or more," "at least one," and "one or more than one." "Or" is to be read inclusively to mean "and/or" unless explicitly indicated to refer to alternatives only, such as where alternatives are mutually exclusive.

Splice Variants

Splice variants of the invention are listed in Table 1. Table 1 provides the genomic location of each canonical ("WT") and aberrant ("Ab.") splice junction, as well as the sequence. Each sequence listed in the table contains 20 nucleotides from each of the 3' and 5' sides of a splice junction (i.e., the splice junction is at the midpoint of the listed nucleotide sequence). The "Avg WT %" and "Avg Ab. %" columns provide the average percentage count that the canonical (WT) or aberrant splice variant, respectively, represented out of the total counts of all splice variants that utilize a shared splice site, where the counts were determined as set forth in Example 1. The "$Log_2$ Fold Change" column provides the $log_2$ of the fold change observed between percentage counts of canonical and aberrant cohorts (see Example 1). The "FDR Q-Value" column provides, as a measure of statistical significance, q-values calculated using the Benjamin-Hochberg procedure from p-values, which in turn were determined using the moderated t-test defined in the Bioconductor's limma package (see Example 1). The "Event" column indicates the nature of the aberrant splice variant, where "3'ss" indicates alternate 3' splice site selection, "5'ss" indicates alternate 5' splice site selection, "exon incl." indicates differential exon inclusion, and "exon skip" indicates exon skipping. The "Type" column refers to the cancer type of the sample in which the aberrant splice variant was identified, where "Br." indicates breast cancer, "CLL" indicates chronic lymphocytic leukemia, and "Mel." indicates melanoma.

TABLE 1

| | Aberrant junction | WT junction | Aberrant sequence (SEQ ID NO) | WT sequence (SEQ ID NO) | Avg WT % | Avg Ab. % | $Log_2$ Fold Diff. | FDR Q-Value | Event | Type |
|---|---|---|---|---|---|---|---|---|---|---|
| 1 | chr2: 109102364- 109102954 | chr2: 109102364- 109102966 | AGCAAGTAGAAG TCTATAAATTT ACCCCCAGATAC AGCT (1) | AGCAAGTAGAAG TCTATAAATAC AGCTGGCTGAAA TAAC (2) | 0 | 56 | 5.83 | 6.30E-07 | 3'ss | Br. |

TABLE 1-continued

| | Aberrant junction | WT junction | Aberrant sequence (SEQ ID NO) | WT sequence (SEQ ID NO) | Avg WT % | Avg Ab. % | Log$_2$ Fold Diff. | FDR Q-Value | Event | Type |
|---|---|---|---|---|---|---|---|---|---|---|
| 2 | chr16: 708344-708509 | chr16: 708344-708524 | CGGGCCGCATCA TCCGGGAGAGCA CTGTGTTCCAGC TGCC (3) | CGGGCCGCATCA TCCGGGAGCTGC CCGGTGTCCACC CTGA (4) | 0 | 51 | 5.70 | 2.38E-07 | 3'ss | Br. |
| 3 | chr3: 50380021-50380348 | chr3: 50380000-50380348 | CTGGAGCCGGCG GGAAGGAGTGTG CTGGTTCCTCTC CCCA (5) | CTGGAGCCGGCG GGAAGGAGGCAA GCTGCAGCAGTT CGAG (6) | 0 | 51 | 5.70 | 2.19E-07 | 3'ss | Br. |
| 4 | chr19: 57908542-57909780 | chr19: 57908542-57909797 | GGCCCTTTTGTC CTCACTAGCATT TCTGTTCTGACA GGTT (7) | GGCCCTTTTGTC CTCACTAGGTTC TTGGCATGGAGC TGAG (8) | 0 | 48 | 5.61 | 2.32E-06 | 3'ss | Br. |
| 5 | chr2: 97285513-97297048 | chr2: 97285499-97297048 | TGGGAGGAGCAT GTCAACAGAGTT TCCCTTATAGGA CTGG (9) | TGGGAGGAGCAT GTCAACAGGACT GGCTGGACAATG GCCC (10) | 0 | 47 | 5.58 | 7.79E-07 | 3'ss | Br. |
| 6 | chr19: 23545541-23556543 | chr19: 23545527-23556543 | GATGGTGGATGA ACCGACAGTTTT TTTTTTTCAGGT ATAT (11) | GATGGTGGATGA ACCCACAGGTAT ATGTCCTCATTT TCCT (12) | 0 | 46 | 5.55 | 1.10E-05 | 3'ss | Br. |
| 7 | chr10: 99214556-99215395 | chr10: 99214556-99215416 | TACCTCTGGTTC CTGTGCAGTCTT CGCCCCTCTTTT CTTA (13) | TACCTCTGGTTC CTGTGCAGTTCT GTGGCACTTGCC CTGG (14) | 0 | 46 | 5.55 | 3.63E-09 | 3'ss | Br. |
| 8 | chr18: 683395-685920 | chr18: 683380-685920 | TTGGACCGGAAA AGACTTTGAGTC TCTTTTTGCAGA TGAT (15) | TTGGACCGGAAA AGACTTTGATGA TGGATGCCAACC AGCG (16) | 0 | 44 | 5.49 | 4.30E-09 | 3'ss | Br. |
| 9 | chr17: 40714237-40714373 | chr17: 40714237-40714629 | ACCCAAGCCTTG AGGTTTCATTTC CCCTCCCAGGA TTTC (17) | ACCCAAGCCTTG AGGTTTCAGCCT GGGCAGCATGGC CGTA (18) | 0 | 44 | 5.49 | 1.50E-07 | exon incl. | Br. |
| 10 | chr5: 139815842-139818078 | chr5: 139815842-139818045 | AGCATTGCTAGA AGCAGCAGCTTT TGCAGATCCTGA GGTA (19) | AGCATTGCTAGA AGCAGCAGGAAT TGGCAAATTGTC AACT (20) | 0 | 41 | 5.39 | 4.86E-09 | 3'ss | Br. |
| 11 | chr1: 245246990-245288006 | chr1: 245246990-245250546 | CAAGTATATGAC TGAAGAAGATCC TGAATTCCAGCA AAAC (21) | CAAGTATATGAC TGAAGAAGGTGA GCCTTTTTCTCA AGAG (22) | 0 | 39 | 5.32 | 1.31E-10 | 3'ss | Br. |
| 12 | chr3: 9960293-9962150 | chr3: 9960293-9962174 | TGCAGTTTGGTC AGTCTGTGCCTT CCTCACCCCTCT CCTC (23) | TGCAGTTTGGTC AGTCTGTGGGCT CTGTGGTATATG ACTG (24) | 0 | 36 | 5.21 | 9.63E-09 | 3'ss | Br. |
| 13 | chr1: 101458310-101460665 | chr1: 101458296-101460665 | TCTTTGGAAAAT CTAATCAATTTT CTGCCTATAGGG GAAG (25) | TCTTTGGAAAAT CTAATCAAGGGA AGGAAGATCTAT GAAC (26) | 0 | 29 | 4.91 | 3.27E-07 | 3'ss | Br. |
| 14 | chr7: 94157562-94162500 | chr7: 94157562-94162516 | GTATCAAAGTGT GGACTGAGATTT GTCTTCCTTTAG GATT (27) | GTATCAAAGTGT GGACTGAGGATT CCATTGCAAAGC CACA (28) | 0 | 28 | 4.86 | 5.02E-05 | 3'ss | Br. |
| 15 | chr20: 62701988-62703210 | chr20: 62701988-62703222 | AGAACTGCACCT ACACACAGCCCT GTTCACAGGTGC AGAC (29) | AGAACTGCACCT ACACACAGGTGC AGACCCGCAGCT CTGA (30) | 0 | 27 | 4.81 | 1.50E-07 | 3'ss | Br. |
| 16 | chr17: 71198039-71199162 | chr17: 71198039-71199138 | GGAGCAGTGCAG TTGTGAAATCAT TACTTCTAGATG ATGC (31) | GGAGCAGTGCAG TTGTGAAAGTTT TGATTCATGGAT TCAC (32) | 0 | 25 | 4.70 | 9.63E-06 | 3'ss | Br. |

TABLE 1-continued

| | Aberrant junction | WT junction | Aberrant sequence (SEQ ID NO) | WT sequence (SEQ ID NO) | Avg WT % | Avg Ab. % | Log$_2$ Fold Diff. | FDR Q-Value | Event | Type |
|---|---|---|---|---|---|---|---|---|---|---|
| 17 | chr17: 7131030-7131295 | chr17: 7131102-7131295 | CTATTTCACTCT CCCCCGAACCTA TCCAGGTTCCTC CTCC (33) | CTATTTCACTCT CCCCCGAAATGA GCCCATCCAGCC AATT (34) | 0 | 25 | 4.70 | 5.99E-08 | 3'ss | Br. |
| 18 | chr20: 35282126-35284762 | chr20: 35282104-35284762 | TTTGCAGGGAAT GGGCTACATCCC CTTGGTTCTCTG TTAC (35) | TTTGCAGGGAAT GGGCTACATCC ATCTGCCAGCAT GACT (36) | 0 | 25 | 4.70 | 2.72E-07 | 3'ss | Br. |
| 19 | chr2: 232196609-232209660 | chr2: 232196609-232209686 | TGACCACGGAGT ACCTGGGGCCCT TTTTTCTCTTTC CTTC (37) | TGACCACGGAGT ACCTGGGGATCA TGACCAACACGG GGAA (38) | 0 | 25 | 4.70 | 1.61E-06 | 3'ss | Br. |
| 20 | chr17: 62574712-62576906 | chr17: 62574694-62576906 | AGACCTACCAGA AGGTATGTGTT TATTAATTTTAC AGAA (39) | AGACCTACCAGA AGGCTATGAACA GAGGACAACGCA ACAA (40) | 0 | 24 | 4.64 | 7.16E-06 | 3'ss | Br. |
| 21 | chr12: 105601825-105601935 | chr12: 105601807-105601935 | ATTTGGACTCGC TAGCAATGATGT CTGTTTATTTTT AGAG (41) | ATTTGGACTCGC TAGCAATGAGCA TGACCTCTCAAT GGCA (42) | 0 | 23 | 4.58 | 8.14E-08 | 3'ss | Br. |
| 22 | chr12: 53836517-53837270 | chr12: 53836517-53837174 | CATGTGGAATCC CAATGCCGGCCC CTGTCCTCCTCC CCCA (43) | CATGTGGAATCC CAATGCCGGGCA GCAGGGCCAAA TCCA (44) | 0 | 22 | 4.52 | 1.87E-04 | 3'ss | Br. |
| 23 | chr22: 19044699-19050714 | chr22: 19044675-19050714 | CTGGGAGGTGGC ATTCAAAGCCCC ACCTTTTGTCTC CCCA (45) | CTGGGAGGTGGC ATTCAAAGGCTC TTCAGAGGTGTT CCTG (46) | 0 | 22 | 4.52 | 2.76E-08 | 3'ss | Br. |
| 24 | chr11: 71939542-71939690 | chr11: 71939542-71939770 | GGATGACCGGGA TGCCTCAGTCAC TTTACAGCTGCA TCGT (47) | GGATGACCGGGA TGCCTCAGATGG GGAGGATGAGAA GCCC (48) | 0 | 21 | 4.46 | 4.61E-08 | 3'ss | Br. |
| 25 | chr20: 34144042-34144725 | chr20: 34144042-34144743 | ACATGAAGGTGG ACGGAGAGGCTC CCCTCCCACCCC AGGT (49) | ACATGAAGGTGG ACGGAGAGGTAC TGAGGACAAATC AGTT (50) | 0 | 21 | 4.46 | 2.63E-08 | 3'ss | Br. |
| 26 | chr6: 31919381-31919565 | chr6: 31919381-31919651 | AGAGAAGTCGTT TCATTCAAGTCA GCTAAGACACAA GCAG (51) | AGAGAAGTCGTT TCATTCAAGTTG GTGTAATCAGCT GGGG (52) | 2 | 64 | 4.44 | 2.91E-10 | 3'ss | Br. |
| 27 | chr1: 179835004-179846373 | chr1: 179834989-179846373 | TCACTCAAACAG TAAACGAGTTTT ATCATTTACAGG TATG (53) | TCACTCAAACAG TAAACGAGGTAT GTGACGCATTCC CAGA (54) | 0 | 20 | 4.39 | 9.99E-07 | 3'ss | Br. |
| 28 | chr1: 52880319-52880412 | chr1: 52880319-52880433 | CGATCTCCCAAA AGGAGAAGTCTG ACCAGTCTTTTC TACA (55) | CGATCTCCCAAA AGGAGAAGCCCC TCCCCTGCCGA GAAA (56) | 0 | 20 | 4.39 | 1.35E-09 | 3'ss | Br. |
| 29 | chr8: 38095145-38095624 | chr8: 38095145-38095606 | TTATTTACACA ATCCAAAGCCAG TTGCAGGGTCTG ATGA (57) | TTATTTACACA ATCCAAAGCTTA TGGTGCATTACC AGCC (58) | 0 | 20 | 4.39 | 1.49E-09 | 3'ss | Br. |
| 30 | chr19: 14031735-14034130 | chr19: 14031735-14034145 | TGCCTGTGGACA TCACCAAGCCTC GTCCTCCCCAGG TGCC (59) | TGCCTGTGGACA TCACCAAGGTGC CGCCTGCCCCTG TCAA (60) | 0 | 19 | 4.32 | 2.37E-05 | 3'ss | Br. |
| 31 | chr14: 74358911-74360478 | chr14: 74358911-74360499 | AGTTAGAATCCA AACCAGAGTGTT GTCTTTTCTCCC CCCA (61) | AGTTAGAATCCA AACCAGAGCTCC TGGTACAGTTTG TTCA (62) | 0 | 18 | 4.25 | 1.65E-10 | 3'ss | Br. |

TABLE 1-continued

| | Aberrant junction | WT junction | Aberrant sequence (SEQ ID NO) | WT sequence (SEQ ID NO) | Avg WT % | Avg Ab. % | Log₂ Fold Diff. | FDR Q-Value | Event | Type |
|---|---|---|---|---|---|---|---|---|---|---|
| 32 | chr19: 45314603-45315482 | chr19: 45314603-45315419 | ATATGCTGGAATGGTTCCTTGTCACAATGCACGACACCCG (63) | ATATGCTGGAATGGTTCCTTACCGACCGCTCGGGAGCTCG (64) | 0 | 18 | 4.25 | 8.07E-08 | 3'ss | Br. |
| 33 | chr1: 212515622-212519131 | chr1: 212515622-212519144 | ATCAGAAATTCGTACAACAGGTTTCTTTTAAAGCTCCTGG (65) | ATCAGAAATTCGTACAACAGCTCCTGGAGCTTTTGATAG (66) | 0 | 18 | 4.25 | 4.25E-08 | 3'ss | Br. |
| 34 | chr9: 125759640-125760854 | chr9: 125759640-125760875 | AAATGAAGAAACTCCTAAAGCCTCTCTCTTTCTTTGTTTA (67) | AAATGAAGAAACTCCTAAAGATAAAGTCCTGTTTATGACC (68) | 0 | 18 | 4.25 | 1.31E-10 | 3'ss | Br. |
| 35 | chr11: 4104212-4104471 | chr11: 4104212-4104492 | CATAAAATTCTAACAGCTAATTCTCTTTCCTCTGTCTTCA (69) | CATAAAATTCTAACAGCTAAGCAAGCACTGAGCGAGGTGA (70) | 0 | 17 | 4.17 | 1.35E-06 | 3'ss | Br. |
| 36 | chr12: 113346629-113348840 | chr12: 113346629-113348855 | GCCTGCCTTTGATGCCCTGGATTTTGCCCGAACAGGTCAG (71) | GCCTGCCTTTGATGCCCTGGGTCAGTTGACTGGCGGCTAT (72) | 0 | 17 | 4.17 | 3.58E-07 | 3'ss | Br. |
| 37 | chr17: 78188582-78188831 | chr17: 78188564-78188831 | CCAAGCTGGTGTGCGCACAGGCCTCTCTTCCCGCCCAGGC (73) | CCAAGCTGGTGTGCGCACAGGCATCATCGGGAAGAAGCAC (74) | 0 | 17 | 4.17 | 4.19E-04 | 3'ss | Br. |
| 38 | chr20: 45354963-45355453 | chr20: 45354963-45355502 | CTCCTTTGGGTTTGGGCCAGGCCCCAGGTCCCACCACAGC (75) | CTCCTTTGGGTTTGGGCCAGTGACCTGGCTTGTCCTCAGC (76) | 0 | 17 | 4.17 | 2.67E-07 | 3'ss | Br. |
| 39 | chr12: 116413154-116413319 | chr12: 116413118-116413319 | AATATTGCTTTACCAAACAGGGACCCCTTCCCCTTCCCCA (77) | AATATTGCTTTACCAAACAGGTCACGGAGGAGTAAAGTAT (78) | 0 | 16 | 4.09 | 2.79E-07 | 3'ss | Br. |
| 40 | chr14: 71059726-71060012 | chr14: 71059705-71060012 | CAGTTATAAACTCTAGAGTGAGTTTATTTTCCTTTTACAA (79) | CAGTTATAAACTCTAGAGTGCTTACTGCAGTGCATGGTAT (80) | 0 | 16 | 4.09 | 4.46E-07 | 3'ss | Br. |
| 41 | chr16: 30012851-30016688 | chr16: 30012851-30016541 | GCCTGCCCCGGAAACTCAAGATGTTCAGCGATGCAGGTAG (81) | GCCTGCCCCGGAAACTCAAGATGGCGGTGGGACCCCCCGA (82) | 0 | 15 | 4.00 | 7.77E-06 | 3'ss | Br. |
| 42 | chr17: 57148329-57153007 | chr17: 57148308-57153007 | TTCAGGAGGTGGAGCACCAGATAATTTTTTTTCCTCACACA (83) | TTCAGGAGGTGGAGCACCAGTTGCGGTCTTGTAGTAAGAG (84) | 0 | 15 | 4.00 | 3.26E-05 | 3'ss | Br. |
| 43 | chr16: 1402307-1411686 | chr16: 1402307-1411743 | GGATCCTTCACCCGTGTCTGTCTTTGCAGACAGGTTCTGT (85) | GGATCCTTCACCCGTGTCTGGACCCGTGCATCTCTTCCGA (86) | 0 | 14 | 3.91 | 3.01E-07 | 3'ss | Br. |
| 44 | chr3: 196792335-196792578 | chr3: 196792319-196792578 | ATTTGGATCCTGTGTTCCTCTTTTTTTCTGTTAAAGATAC (87) | ATTTGGATCCTGTGTTCCTCATACAACTAGACCAAAACGA (88) | 0 | 14 | 3.91 | 8.71E-07 | 3'ss | Br. |
| 45 | chr14: 75356052-75356580 | chr14: 75356052-75356599 | AGATGTCAGGTGGGAGAAAGCCTTTGATTGTCTTTTCAGC (89) | AGATGTCAGGTGGGAGAAAGCTGTTGGAGACACAGTTGCA (90) | 0 | 13 | 3.81 | 1.55E-05 | 3'ss | Br. |
| 46 | chr18: 33605641-33606862 | chr18: 33573263-33606862 | AGAAAGAGCATAAATTGGAAATATTGGACATGGGCGTATC (91) | AGAAAGAGCATAAATTGGAAGAGTACAAGCGCAAGCTAGC (92) | 0 | 13 | 3.81 | 9.84E-07 | 3'ss | Br. |

TABLE 1-continued

| | Aberrant junction | WT junction | Aberrant sequence (SEQ ID NO) | WT sequence (SEQ ID NO) | Avg WT % | Avg Ab. % | Log$_2$ Fold Diff. | FDR Q-Value | Event | Type |
|---|---|---|---|---|---|---|---|---|---|---|
| 47 | chr1: 226036315-226036597 | chr1: 226036255-226036597 | TCAGCCCTCTGAACTACAAAGGTGTTTGTTCACAGAGATC (93) | TCAGCCCTCTGAACTACAAAACAGAAGAGCCTGCAAGTGA (94) | 0 | 13 | 3.81 | 6.10E-07 | 3'ss | Br. |
| 48 | chr6: 10723474-10724788 | chr6: 10723474-10724802 | CCGGGGCCTTCGTGAGACCGCTTGTTTTCTGCAGGTGCAG (95) | CCGGGGCCTTCGTGAGACCGGTGCAGGCCTGGGGTAGTCT (96) | 3 | 51 | 3.70 | 1.35E-09 | 3'ss | Br. |
| 49 | chr2: 132288400-132289210 | chr2: 132288400-132289236 | CAAGTCCATCTCTAATTCAGGGTCTGACTTGCAGCCAACT (97) | CAAGTCCATCTCTAATTCAGGCAAGGCCAGGCCCCAGCCC (98) | 0 | 12 | 3.70 | 5.71E-03 | 3'ss | Br. |
| 50 | chr2: 170669034-170671986 | chr2: 170669016-170671986 | CAAGATAGATATTATAGCAGGTGGCTTTTGTTTTACAGAA (99) | CAAGATAGATATTATAGCAGAACTTCGATATGACCTGCCA (100) | 0 | 12 | 3.70 | 4.26E-06 | 3'ss | Br. |
| 51 | chr15: 59209219-59224554 | chr15: 59209198-59224554 | GAAACCAACTAAAGGCAAAGCCCATTTTCCTTCTTTCGCA (101) | GAAACCAACTAAAGGCAAAGGTAAAAAACATGAAGCAGAT (102) | 1 | 24 | 3.64 | 4.30E-09 | 3'ss | Br. |
| 52 | chr11: 57100545-57100908 | chr11: 57100623-57100908 | GGGGACAGTGAAATTTGGTGGCAAGAATGAGGTGACACTG (103) | GGGGACAGTGAAATTTGGTGGGCAGCTGCTTTCCTTTGAC (104) | 0 | 11 | 3.58 | 5.99E-08 | 3'ss | Br. |
| 53 | chr1: 35871069-35873587 | chr1: 35871069-35873608 | CTCAGAGCCAGGCTGTAGAGATGTTTTCTACCTTTCCACA (105) | CTCAGAGCCAGGCTGTAGAGTCCGCTCTATCAAGCTGAAG (106) | 0 | 11 | 3.58 | 3.15E-07 | 3'ss | Br. |
| 54 | chr2: 220044485-220044888 | chr2: 220044485-220044831 | GAGGAGCCACACTCTGACAGATACCTGGCTGAGAGCTGGC (107) | GAGGAGCCACACTCTGACAGTGAGGGTGCGGGGTCAGGCG (108) | 0 | 11 | 3.58 | 2.22E-07 | 3'ss | Br. |
| 55 | chr5: 150411955-150413168 | chr5: 150411944-150413168 | ACTCGCGCCTCTTCCATCTGTTTTGTCGCAGCCGGAATAC (109) | ACTCGCGCCTCTTCCATCTGCCGGAATACACCTGGCGTCT (110) | 0 | 11 | 3.58 | 7.04E-07 | 3'ss | Br. |
| 56 | chrX: 47059013-47059808 | chrX: 47059013-47060292 | ACTTCCTTAGTGGTTTCCAGGTTGCCAGGGCACTGCAGCT (111) | ACTTCCTTAGTGGTTTCCAGGTGGTGGTGCTCACCAACAC (112) | 0 | 11 | 3.58 | 7.37E-07 | 3'ss | Br. |
| 57 | chrX: 47059943-47060292 | chrX: 47059013-47060292 | GTCTTGAGAATTGGAAGCAGGTGGTGGTGCTCACCAACAC (113) | ACTTCCTTAGTGGTTTCCAGGTGGTGGTGCTCACCAACAC (112) | 0 | 11 | 3.58 | 6.70E-06 | 5'ss | Br. |
| 58 | chr20: 330007-330259 | chr20: 330007-330281 | TCCAGAGCCCACAGTCCCAGCTGCACCTTACCTGCTCCCC (114) | TCCAGAGCCCACAGTCCCAGGGGTCCATGATGCCGAGCTG (115) | 2 | 34 | 3.54 | 4.87E-09 | 3'ss | Br. |
| 59 | chr18: 224200-224923 | chr18: 224179-224923 | CCAAGTTTTGTGAAAGAAAGTGTATGTTTTGTTCACGACA (116) | CCAAGTTTTGTGAAAGAAAGAACATCAGATACCAAACCTA (117) | 1 | 22 | 3.52 | 1.96E-05 | 3'ss | Br. |
| 60 | chr11: 47195466-47196565 | chr11: 47195391-47196565 | TCTTCACAGAACACACTCAAGTGCTTGTAGGTCTTGGTGC (118) | TCTTCACAGAACACACTCAACCCCCTGCCTGGGATGCGCC (119) | 0 | 10 | 3.46 | 2.99E-08 | 3'ss | Br. |
| 61 | chr12: 56604352-56606779 | chr12: 56604352-56607741 | GAGAAGCTCACGATTACCAGGCACCTCATTGTGAACATGC (120) | TCTTGGAGGAGCCAGTACAGGCACCTCATTGTGAACATGC (121) | 0 | 10 | 3.46 | 4.11E-02 | exon incl. | Br. |

TABLE 1-continued

| | Aberrant junction | WT junction | Aberrant sequence (SEQ ID NO) | WT sequence (SEQ ID NO) | Avg WT % | Avg Ab. % | Log$_2$ Fold Diff. | FDR Q-Value | Event | Type |
|---|---|---|---|---|---|---|---|---|---|---|
| 62 | chr14: 23237380-23238985 | chr14: 23237380-23238999 | GTGGGGGGCCAT TGCTGCATTTTG TATTTTCCAGGT ACAG (122) | GTGGGGGGCCAT TGCTGCATGTAC AGTCTTTGCCCG CTGC (123) | 0 | 10 | 3.46 | 3.25E-08 | 3'ss | Br. |
| 63 | chr17: 34942628-34943454 | chr17: 34942628-34943426 | TACTGAAATGTG ATGAACATATCC AGGTAATCGAGA GACC (124) | TACTGAAATGTG ATGAACATATCC AGAAGCTTGGAA GCTG (125) | 0 | 10 | 3.46 | 2.49E-05 | 3'ss | Br. |
| 64 | chr1: 145581564-145583935 | chr1: 145581564-145583914 | GAATCTCTTATC ATTGATGGTTCC TGTTCAGATTGT GATG (126) | GAATCTCTTATC ATTGATGGTTTA TTTATGGAGATT CTTA (127) | 0 | 10 | 3.46 | 2.93E-06 | 3'ss | Br. |
| 65 | chr5: 869519-870587 | chr5: 865696-870587 | CTCCATGCTCAG CTCTCTGGTTTC TTTCAGGGCCTG CCAT (128) | CTCCATGCTCAG CTCTCTGGGAA GGTGAAGAAGGA GCTG (129) | 1 | 20 | 3.39 | 6.76E-06 | 3'ss | Br. |
| 66 | chr12: 107378993-107380746 | chr12: 107379003-107380746 | CTTGGAGCTGAC GCCGACGGGGAA CTGACAAGATCA CATT (130) | CTTGGAGCTGAC GCCGACGGTTTA TTGCAGGGAACT GACA (131) | 7 | 79 | 3.32 | 1.30E-08 | 3'ss | Br. |
| 67 | chr7: 8261028-8267267 | chr7: 8261028-8268230 | TCCAGCCTGGGC GACAGAAGTCTT GTCTCAAGAAGA AAAC (132) | CTATCAAAAGAG GATATGTTTCTT GTCTCAAGAAGA AAAC (133) | 1 | 19 | 3.32 | 4.35E-08 | exon incl. | Br. |
| 68 | chr10: 5497081-5498027 | chr10: 5497081-5498049 | TGCGGAGCAAGA GTGGACATCGTT TGTTTCCCATTT CTCC (134) | TGCGGAGCAAGA GTGGACATAAAC TTTACATTTTCC TGTT (135) | 0 | 9 | 3.32 | 1.37E-04 | 3'ss | Br. |
| 69 | chr11: 64900740-64900940 | chr11: 64900723-64900940 | AGTCCAGCCCCA GCATGGCACCTC TCCCCACTCCTA GGTC (136) | AGTCCAGCCCCA GCATGGCAGTCC TGTACATCCAGG CCTT (137) | 0 | 9 | 3.32 | 4.66E-07 | 3'ss | Br. |
| 70 | chr19: 5595521-5598803 | chr19: 5595508-5598803 | CAAGCAGGTCCA AAGAGAGATTTT GGTAAACAGAGC TCCA (138) | CAAGCAGGTCCA AAGAGAGAAGCT CCAAGAGTCAGG ATCG (139) | 0 | 9 | 3.32 | 1.49E-09 | 3'ss | Br. |
| 71 | chr22: 39064137-39066874 | chr22: 39064137-39066888 | CTCTCTCCAACC TGCATTCTCATC TCGCCCACAGTT GGAT (140) | CTCTCTCCAACC TGCATTCTTTGG ATCGATCAACCC GGGA (141) | 0 | 9 | 3.32 | 8.58E-06 | 3'ss | Br. |
| 72 | chr9: 125023777-125026993 | chr9: 125023787-125026993 | CACCACGCCGAG GCCACGAGACAT TGATGGAAGCAG AAAC (142) | CACCACGCCGAG GCCACGAGTATT TCATAGACATTG ATGG (143) | 2 | 28 | 3.27 | 2.13E-08 | 3'ss | Br. |
| 73 | chr15: 25207356-25212175 | chr15: 25207356-25213078 | GCCTCACTGAGC AACCAAGAGTAG TGACTTGTCAGG AGGA (144) | GCCTCACTGAGC AACCAAGAGTGT CAGTTGTACCCG AGGC (145) | 1 | 18 | 3.25 | 5.94E-09 | exon incl. | Br. |
| 74 | ch19: 35813153-35813262 | chr9: 35813142-35813262 | GGGAGATGGATA CCGACTTGCTCA ATTTCAGTGATC AACG (146) | GGGAGATGGATA CCGACTTGTGAT CAACGATGGGAA GCTG (147) | 3 | 35 | 3.17 | 6.19E-08 | 3'ss | Br. |
| 75 | chr6: 31602334-31602574 | chr6: 31602334-31602529 | AGGATGTGGCTG GCACAGAAGTGT CATCAGGTCCCT GCAG (148) | AGGATGTGGCTG GCACAGAAATGA GTCAGTCTGACA GTGG (149) | 1 | 17 | 3.17 | 5.18E-06 | 3'ss | Br. |
| 76 | chr11: 125442465-125445146 | chr11: 125442465-125445158 | TTCTCCAGGACC TTGCCAGACCTT TTCTATAGGGAA TCAA (150) | TTCTCCAGGACC TTGCCAGAGGAA TCAAAGACTCCA TCTG (151) | 0 | 8 | 3.17 | 6.00E-04 | 3'ss | Br. |

TABLE 1-continued

| | Aberrant junction | WT junction | Aberrant sequence (SEQ ID NO) | WT sequence (SEQ ID NO) | Avg WT % | Avg Ab. % | Log₂ Fold Diff. | FDR Q-Value | Event | Type |
|---|---|---|---|---|---|---|---|---|---|---|
| 77 | chr13: 113915073-113917776 | chr13: 113915073-113917800 | AGCTGAAATTTC CAGTAAAGGGGG GTTTTATTCTTC TTTT (152) | AGCTGAAATTTC CAGTAAAGCCTG GAGATTTGAAAA AGAG (153) | 0 | 8 | 3.17 | 1.20E-06 | 3'ss | Br. |
| 78 | chr16: 14966186-14968874 | chr16: 14966186-14968892 | GATGTCACTGTG ACTATCAAGGGC CGTCTTTCTTCT AGGT (154) | GATGTCACTGTG ACTATCAAGTCT TCCATCGACAGT GAAC (155) | 0 | 8 | 3.17 | 4.76E-02 | 3'ss | Br. |
| 79 | c11r2: 178096758-178097119 | chr2: 178096736-178097119 | TATCCATTCCTG AGTTACAGTATA AACTTCCTTCTC ATGC (156) | TATCCATTCCTG AGTTACAGTGTC TTAATATTGAAA ATGA (157) | 0 | 8 | 3.17 | 2.22E-07 | 3'ss | Br. |
| 80 | chrX: 153699660-153699819 | chrX: 153699660-153699830 | TACAAGAGCTGG GTGGAGAGGGTC CCAACAGGTATT ATCG (158) | TACAAGAGCTGG GTGGAGAGGTAT TATCGAGACATT GCAA (159) | 0 | 8 | 3.17 | 2.14E-05 | 3'ss | Br. |
| 81 | chr19: 9728842-9730107 | chr19: 9728855-9730107 | AGCCATTTATTT GTCCCGTGGGAA CCAATCTGCCCT TTTG (160) | AGCCATTTATTT GTCCCGTGGGTT TTTTCCAGGGA ACCA (161) | 3 | 31 | 3.00 | 7.42E-06 | 3'ss | Br. |
| 82 | chr1: 185056772-185060696 | chr1: 185056772-185060710 | AGTTACAACGAA CACCTCAGTGAC TCTTTTACAGGA GGCA (162) | AGTTACAACGAA CACCTCAGGAGG CAATAACAGATG GCTT (163) | 2 | 23 | 3.00 | 8.51E-06 | 3'ss | Br. |
| 83 | chr15: 25212299-25213078 | chr15: 25207356-25213078 | TCACACAGGATA ATTTGAAAGTGT CAGTTGTACCCG AGGC (164) | GCCTCACTGAGC AACCAAGAGTGT CAGTTGTACCCG AGGC (145) | 1 | 15 | 3.00 | 3.25E-08 | exon incl. | Br. |
| 84 | chr11: 62648919-62649352 | chr11: 62648919-62649364 | CGGCGCGGGCAA CCTGGCGGCCCC CATTTCAGGTCT GAAG (165) | CGGCGCGGGCAA CCTGGCGGGTCT GAAGGGCGTCT CGAT (166) | 0 | 7 | 3.00 | 1.28E-08 | 3'ss | Br. |
| 85 | chr11: 64877395-64877934 | chr11: 64877395-64877953 | CCACCGCCATCG ACGTGCAGTACC TCTTTTTACCAC CAGG (167) | CCACCGCCATCG ACGTGCAGGTGG GGCTCCTGTACG AAGA (168) | 0 | 7 | 3.00 | 4.87E-09 | 3'ss | Br. |
| 86 | chr19: 41084118-41084353 | chr19: 41084118-41084367 | CTATGGGCTCAC TCCTCTGGTCCT CCTGTTGCAGTT CGTC (169) | CTATGGGCTCAC TCCTCTGGTTCG TCGCCTGCAGCT TCGA (170) | 0 | 7 | 3.00 | 1.24E-03 | 3'ss | Br. |
| 87 | chr1: 35917392-35919157 | chr1: 35917377-35919157 | TATCTCTGGGAA AAAACACATTTC TTTTTTTGCAGG GGAC (171) | TATCTCTGGGAA AAAACACAGGGA CCTGATGGGGTG CAGC (172) | 0 | 7 | 3.00 | 3.66E-06 | 3'ss | Br. |
| 88 | chr22: 50966161-50966940 | chr22: 50966146-50966940 | TCATCCAGAGCC CAGAGCAGGGGA TGTCTGACCAGA TGCA (173) | TCATCCAGAGCC CAGAGCAGATGC AAGTGCTGCTGG ACCA (174) | 0 | 7 | 3.00 | 1.95E-06 | 3'ss | Br. |
| 89 | chr9: 139837449-139837800 | chr9: 139837395-139837800 | CCAAGGACTGCA CTGTGAAGGCCC CCGCCCCGCGAC CTGG (175) | CCAAGGACTGCA CTGTGAAGATCT GGAGCAACGACC TGAC (176) | 0 | 7 | 3.00 | 8.14E-08 | 3'ss | Br. |
| 90 | chr1: 3548881-3549961 | chr1: 3548902-3549961 | CCCGAGCTCAGA GAGTAAATTCTC CTTACAGACACT GAAA (177) | CCCGAGCTCAGA GAGTAAATATGA GATCGCCTCTGT CCCA (178) | 4 | 38 | 2.96 | 2.79E-08 | 3'ss | Br. |
| 91 | chr19: 55776746-55777253 | chr19: 55776757-55777253 | GTGCTTGGAGCC CTGTGCAGACTT TCCGCAGGGTGT GCGC (179) | GTGCTTGGAGCC CTGTGCAGCCTG GTGACAGACTTT CCGC (180) | 3 | 29 | 2.91 | 3.56E-07 | 3'ss | Br. |

TABLE 1-continued

| | Aberrant junction | WT junction | Aberrant sequence (SEQ ID NO) | WT sequence (SEQ ID NO) | Avg WT % | Avg Ab. % | Log$_2$ Fold Diff. | FDR Q-Value | Event | Type |
|---|---|---|---|---|---|---|---|---|---|---|
| 92 | chr1: 39332671-39338689 | chr1: 39333282-39338689 | GCTGGACACGCT GACCAAGGCATC ACTTAGGAGCTG CTAC (181) | GCTGGACACGCT GACCAAGGTGTT GGTAGCCTTATA TGAA (182) | 1 | 14 | 2.91 | 2.38E-07 | exon skip | Br. |
| 93 | chr2: 27260570-27260682 | chr2: 27260570-27261013 | CCCCTGAGATGA AGAAAGAGCTCC CTGTTGACAGCT GCCT (183) | CCCCTGAGATGA AGAAAGAGCTCC TGAGCAGCCTGA CTGA (184) | 1 | 14 | 2.91 | 1.82E-07 | exon incl. | Br. |
| 94 | chr2: 233599948-233600472 | chr2: 233599948-233612324 | CTGAACTTTGGG CCTGAATGATGT GTTTGGACCCCG AATA (185) | CTGAACTTTGGG CCTGAATGGCTC CGAGCTCTGTCC AGTG (186) | 3 | 28 | 2.86 | 7.09E-06 | 3'ss | Br. |
| 95 | chr11: 3697619-3697738 | chr11: 3697606-3697738 | AGATCGCCTGGC TCAGTCAGTTTT TCTCTCTAGACA TGGC (187) | AGATCGCCTGGC TCAGTCAGACAT GGCCAAACGTGT AGCC (188) | 0 | 6 | 2.81 | 4.87E-09 | 3'ss | Br. |
| 96 | chr11: 68363686-68367788 | chr11: 68363686-68367808 | GGAGGTGGACCT GAGTGAACAATT TCTCCCCTCTTT TTAG (189) | GGAGGTGGACCT GAGTGAACCACC CAACTGGTCAGC TAAC (190) | 0 | 6 | 2.81 | 1.25E-06 | 3'ss | Br. |
| 97 | chr12: 72315234-72316743 | chr12: 72315234-72316762 | TACAGATGGTAA AATGCAAGTTTG ATTTTTCATATC CAGG (191) | TACAGATGGTAA AATGCAAGGAAT TGCCACAAGCAG TCTG (192) | 0 | 6 | 2.81 | 8.19E-07 | 3'ss | Br. |
| 98 | chr16: 685022-685280 | chr16: 684956-685280 | CCCTGCTCATCA CCTACGGGTCTG TCCCAGGCTCTC TGGG (193) | CCCTGCTCATCA CCTACGGGCCCT ATGCCATCAATG GGAA (194) | 0 | 6 | 2.81 | 5.11E-07 | 3'ss | Br. |
| 99 | chr1: 155630724-155631097 | chr1: 155630704-155631097 | GGCTCCCATTCT GGTTAAAGAGTG TTCTCATTTCCA ATAG (195) | GGCTCCCATTCT GGTTAAAGGCCA GTCTGCCATCCA TCCA (196) | 0 | 6 | 2.81 | 3.43E-04 | 3'ss | Br. |
| 100 | chr1: 47108988-47110832 | chr1: 47108973-47110832 | CTGCACTTATAA ATATTCAGTGTT CCACCTTGCAGA CCCG (197) | CTGCACTTATAA ATATTCAGACCC GAGGGGAAGCTG CAGC (198) | 0 | 6 | 2.81 | 1.50E-06 | 3'ss | Br. |
| 101 | chr22: 36627480-36629198 | chr22: 36627512-36629198 | CGCTGGCACCAT GAACCCAGTATT TCCAGGACCAAG TGAG (199) | CGCTGGCACCAT GAACCCAGAGAG CAGTATCTTTAT TGAG (200) | 0 | 6 | 2.81 | 1.29E-02 | 3'ss | Br. |
| 102 | chr6: 31919565-31919651 | chr6: 31919381-31919651 | CCCTAGTCTGAT TCCTTTAGGTTG GTGTAATCAGCT GGGG (201) | AGAGAAGTCGTT TCATTCAAGTTG GTGTAATCAGCT GGGG (52) | 0 | 6 | 2.81 | 6.01E-04 | 5'ss | Br. |
| 103 | chr1: 19480448-19481411 | chr1: 19480433-19481411 | TTCCCCATCAAC ATCAAAAGTTTT GTTGTCTGCAGT TCCA (202) | TTCCCCATCAAC ATCAAAAGTTCC AATGGTGGCAGT AAGA (203) | 3 | 26 | 2.75 | 6.26E-07 | 3'ss | Br. |
| 104 | chr11: 67161081-67161193 | chr11: 67161081-67161161 | CCAGCTGCATTG CAAGTTCGGACT GTGAGTCCCTGC AGGC (204) | CCAGCTGCATTG CAAGTTCGGGGT GCGGAAGACTCA CAAC (205) | 4 | 32 | 2.72 | 6.93E-04 | 3'ss | Br. |
| 105 | chr12: 120934019-120934204 | chr12: 120934019-120934218 | GGCCAGCCCCCT TCTCCACGGCCT TGCCCACTAGGT AACC (206) | GGCCAGCCCCCT TCTCCACGGTAA CCATGTGCGACC GAAA (207) | 6 | 41 | 2.58 | 1.26E-09 | 3'ss | Br. |
| 106 | chr14: 75348719-75352288 | chr14: 75349327-75352288 | CGCTCTCCGCCT TCCAGAGGGGGT CTCCTTATGCCA GGGA (208) | AGGGAGACGTTC CCTGCCTGGGGT CTCCTTATGCCA GGGA (209) | 2 | 17 | 2.58 | 1.96E-05 | exon skip | Br. |

TABLE 1-continued

| | Aberrant junction | WT junction | Aberrant sequence (SEQ ID NO) | WT sequence (SEQ ID NO) | Avg WT % | Avg Ab. % | Log₂ Fold Diff. | FDR Q-Value | Event | Type |
|---|---|---|---|---|---|---|---|---|---|---|
| 107 | chr1: 23398690- 23399766 | chr1: 23398690- 23399784 | TTGGAAGCGAAT CCCCCAAGTCCT TTGTTCTTTTGC AGTG (210) | TTGGAAGCGAAT CCCCCAAGTGAT GTATATCTCTCA TCAA (211) | 1 | 11 | 2.58 | 1.14E-07 | | 3'ss Br. |
| 108 | chr11: 44957237- 44958353 | chr11: 44957213- 44958353 | CTACGGCGGTGC CCTCCTCACCCC CTTTTCATCCCC CGCC (212) | CTACGGCGGTGC CCTCCTCAGCAT CTCCCTGATCAT GTGG (213) | 0 | 5 | 2.58 | 1.09E-07 | | 3'ss Br. |
| 109 | chr12: 57494682- 57496072 | chr12: 57493873- 57496072 | CCTGGTCGCAGT TCAACAAGATGA GGAATCTGATGC TCAG (214) | CCTGGTCGCAGT TCAACAAGGAGA TCCTGCTGGGCC GTGG (215) | 0 | 5 | 2.58 | 9.89E-04 | exon incl. | Br. |
| 110 | chr16: 15129410- 15129852 | chr16: 15129410- 15129872 | CACCAAGCAGAG GCTTCCAGTCTG TCTGCCCTTTCT GTAG (216) | CACCAAGCAGAG GCTTCCAGGCCA GAAGCCTTTTAA AAGG (217) | 0 | 5 | 2.58 | 1.04E-07 | | 3'ss Br. |
| 111 | chr17: 41164294- 41164946 | chr17: 41164294- 41165063 | GGGACTCCCCCA AAGCACAAGCTTT TCTTTCAGTAAA TGTA (218) | GGGACTCCCCCA AAGCACAAGGTCC CATTTTCAGTGC CCAA (219) | 0 | 5 | 2.58 | 9.75E-05 | | 3'ss Br. |
| 112 | chr17: 61511981- 61512446 | chr17: 61511955- 61512446 | GCACTGCTGTTC AACCTCGGCTTC TCCCTTCCTCTC ACCC (220) | GCACTGCTGTTC AACCTCGGGGGC AAGTATAGCGCA TTTG (221) | 0 | 5 | 2.58 | 1.25E-05 | | 3'ss Br. |
| 113 | chr19: 2247021- 2247564 | chr19: 2247021- 2247592 | ACGAGACCATTG CCTTCAAGGAGC CCTCTCTGTCCC CCGC (222) | ACGAGACCATTG CCTTCAAGGTGC CGAGCAGAGAGA TCGA (223) | 0 | 5 | 2.58 | 1.71E-05 | | 3'ss Br. |
| 114 | chr21: 38570326- 38572514 | chr21: 38570326- 38572532 | AAGATGTCCCTG TGAGGATTGTGT GTTTGTTTCCAC AGGC (224) | AAGATGTCCCTG TGAGGATTGCAC TGGGTGCAAGTT CCTG (225) | 0 | 5 | 2.58 | 5.11E-07 | | 3'ss Br. |
| 115 | chr6: 31919381- 31919551 | chr6: 31919381- 31919651 | AGAGAAGTCGTT TCATTCAATCTG ATTCCTTTAGGT CAGC (226) | AGAGAAGTCGTT TCATTCAAGTTG GTGTAATCAGCT GGGG (52) | 0 | 5 | 2.58 | 2.67E-07 | | 3'ss Br. |
| 116 | chrX: 48751114- 48751182 | chrX: 48751100- 48751182 | AGCCCAGCAGTT CCGAAATGTCTC CCTTCTCCAGCG CCCC (227) | AGCCCAGCAGTT CCGAAATGCGCC CCCATTCCTGGA GGAC (228) | 0 | 5 | 2.58 | 5.15E-07 | | 3'ss Br. |
| 117 | chr17: 40714505- 40714629 | chr17: 40714237- 40714629 | CCCTCCCCCGGC TCCTGTCGGCCT GGGCAGCATGGC CGTA (229) | ACCCAAGCCTTG AGGTTTCAGCCT GGGCAGCATGGC CGTA (18) | 2 | 16 | 2.5 | 3.35E-04 | exon incl. | Br. |
| 118 | chr15: 25213229- 25219533 | chr15: 25213229- 25219457 | TGATTCCAAGCA AAAACCAGCCTT CCCCTAGGTCTT CAGA (230) | TGATTCCAAGCA AAAACCAGGCTC CATCTACTCTTT GAAG (231) | 1 | 10 | 2.46 | 1.54E-06 | | 3'ss Br. |
| 119 | chr2: 132288400- 132289224 | chr2: 132288400- 132289236 | CAAGTCCATCTC TAATTCAGCCAA CTCTCAAGGCAA GGCC (232) | CAAGTCCATCTC TAATTCAGGCAA GGCCAGGCCCCA GCCC (98) | 2 | 15 | 2.42 | 6.24E-03 | | 3'ss Br. |
| 120 | chr7: 8267481- 8268230 | chr7: 8261028- 8268230 | CTATCAAAAGAG GATATGTTCATT TTAGGAGGCCAA GGCA (233) | CTATCAAAAGAG GATATGTTTCTT GTCTCAAGAAGA AAAC (133) | 2 | 15 | 2.42 | 9.00E-05 | exon incl. | Br. |
| 121 | chr3: 148759467- 148759952 | chr3: 148759455- 148759952 | GTCTTCCAATGG CCCCTCAGCCTT TTCTCTAGGAAA TGAT (234) | GTCTTCCAATGG CCCCTCAGGAAA TGATACACCTGA AGAA (235) | 7 | 41 | 2.39 | 2.38E-07 | | 3'ss Br. |

TABLE 1-continued

| | Aberrant junction | WT junction | Aberrant sequence (SEQ ID NO) | WT sequence (SEQ ID NO) | Avg WT % | Avg Ab. % | Log$_2$ Fold Diff. | FDR Q-Value | Event | Type |
|---|---|---|---|---|---|---|---|---|---|---|
| 122 | chr8: 144873910-144874045 | chr8: 144873610-144874045 | GCACCTCCCGG GACGCCTGCCCT TGTCTGGAAAGA AGTT (236) | GCACCTCCCGG GACGCCTGTCAC CGGACTTTGCTG AGGA (237) | 4 | 25 | 2.38 | 3.96E-02 | exon incl. | Br. |
| 123 | chr17: 3828735-3831533 | chr17: 3828735-3831956 | TGGACCCCAGAC CACACCGGAAGA AATGAGCCAGAA GTGA (238) | GTCCCGGAACCA CATGCACGAAGA AATGAGCCAGAA GTGA (239) | 1 | 9 | 2.32 | 5.71E-03 | exon incl. | Br. |
| 124 | chr11: 66040546-66043274 | chr11: 66039931-66043274 | TCTGTGTTCCCA TCGCACAGGAAT CCTACGCCAACG TGAA (240) | TGTATGACGTCA CTGACCAGGAAT CCTACGCCAACG TGAA (241) | 0 | 4 | 2.32 | 2.08E-03 | 5'ss | Br. |
| 125 | chr12: 15272132-15273996 | chr12: 15264351-15273996 | GGAATATGATCC CACCCTCGTACT TCTCAAAGAGGA TGGC (242) | GGAATATGATCC CACCCTCGAATC AACCTACCGACA CCAA (243) | 0 | 4 | 2.32 | 6.10E-04 | 3'ss | Br. |
| 126 | chr16: 313774-313996 | chr16: 313774-314014 | GAACTGGCACCG ACAGACAGTGTC CCCTCCCTCCCC AGAT (244) | GAACTGGCACCG ACAGACAGATCC TGTTTCTGGACC TTGG (245) | 0 | 4 | 2.32 | 1.02E-06 | 3'ss | Br. |
| 127 | chr19: 44116292-44118380 | chr19: 44112259-44118380 | TGATGAAGACCT TTCCCCAGATCT CTTAGGTGAAGA CATG (246) | TGATGAAGACCT TTCCCCAGGCCC CGAGCATTCCTC TGAT (247) | 0 | 4 | 2.32 | L.48E-03 | 3'ss | Br. |
| 128 | chr1: 228335400-228336058 | chr1: 228335400-228336071 | CCAGGCCGACAT GGAGAGCAGCCC CACCCACAGGCA AGGA (248) | CCAGGCCGACAT GGAGAGCAGCAA GGAGCCCGGCCT GTTT (249) | 0 | 4 | 2.32 | 4.27E-07 | 3'ss | Br. |
| 129 | chr20: 34144042-34144761 | chr20: 34144042-34144743 | ACATGAAGGTGG ACGGAGAGTTCT CTGTGACCAGAC ATGA (250) | ACATGAAGGTGG ACGGAGAGGTAC TGAGGACAAATC AGTT (50) | 0 | 4 | 2.32 | 5.15E-07 | 3'ss | Br. |
| 130 | chr2: 198267783-198268308 | chr2: 198267759-198268308 | TTCGTCCATATG TGCATAAGCTTC TTCTCTTTTCTC TTTT (251) | TTCGTCCATATG TGCATAAGATCC TCGTGGTCATTG AACC (252) | 0 | 4 | 2.32 | 2.38E-03 | 3'ss | Br. |
| 131 | chr3: 47969840-47981988 | chr3: 47969840-48019354 | AGGGATGGCCAG TGGTAGTGGGTC TCCAACTGAATT CCTT (253) | AGAAGGGAGCGA TACTACAGGGTC TCCAACTGAATT CCTT (254) | 0 | 4 | 2.32 | 8.01E-04 | 5'ss | Br. |
| 132 | chr4: 38907482-38910197 | chr4: 38907482-38910212 | CCAATGTGGTTC AAAACACATTAT CTCATCTGCAGG GTAA (255) | CCAATGTGGTTC AAAACACAGGTA AAAGTGTCTTAA CTGG (256) | 0 | 4 | 2.32 | 1.00E-05 | 3'ss | Br. |
| 133 | ch17: 94227316-94228086 | chr7: 94218044-94228086 | CCATTGATGCAA ACGCAGCAATGG AGTTTCGCTCCT GTTG (257) | CCATTGATGCAA ACGCAGCAGAAC TTGCCACATCAG ACTC (258) | 0 | 4 | 2.32 | 7.45E-03 | exon incl. | Br. |
| 134 | chr8: 17873340-17882869 | chr8: 17872349-17882869 | GCTGCATCTGGA GGTCCTGGGAAG CAGAATCTGGTA ATAT (259) | CAGTGTTAGTGA ATGACTATGAAG CAGAATCTGGTA ATAT (260) | 0 | 4 | 2.32 | 6.84E-03 | 5'ss | Br. |
| 135 | chr17: 73518592-73519333 | chr17: 73518292-73519333 | ACAAGGACACAG AAAACAAGCCTT CCCACACAGGCC CTGC (261) | ACAAGGACACAG AAAACAAGCTGG AGCACCGCTGCA CCTC (262) | 10 | 53 | 2.30 | 5.76E-06 | 3'ss | Br. |
| 136 | chr16: 47495337-47497792 | chr16: 47495337-47497809 | AGCTCGGACCAA GCGCTCAGTTTT AAAATTGCTATA GCTT (263) | AGCTCGGACCAA GCGCTCAGCTTA GCCTGCGACGCT TATG (264) | 9 | 48 | 2.29 | 1.29E-03 | 3'ss | Br. |

TABLE 1-continued

| | Aberrant junction | WT junction | Aberrant sequence (SEQ ID NO) | WT sequence (SEQ ID NO) | Avg WT % | Avg Ab. % | Log₂ Fold Diff. | FDR Q-Value | Event | Type |
|---|---|---|---|---|---|---|---|---|---|---|
| 137 | chr6: 91269953-91271340 | chr6: 91269933-91271340 | AGGGGGCTCTTT ATATAATGTTTG TGCCTTTCTTTC GCAG (265) | AGGGGGCTCTTT ATATAATGTGCT GCATGGTGCTGA ACCA (266) | 6 | 32 | 2.24 | 3.39E-03 | 3'ss | Br. |
| 138 | chr15: 41130464-41130740 | chr15: 41128480-41130740 | GCCCCCAACTGA GAAGCTGGGCTG GAGTGCTGTGGC ACAA (267) | GCCCCCAACTGA GAAGCTGGTGCC CTTGGTGTGGTG GAAG (268) | 2 | 13 | 2.22 | 4.76E-03 | exon incl. | Br. |
| 139 | chr17: 2276080-2276246 | chr17: 2275782-2276246 | GAACGAGATCTC ATCCCACTAACT ACAAAGAGCTGG AGCT (269) | AGTATCAGAAGG ACAAAAGAACT ACAAAGAGCTGG AGCT (270) | 4 | 21 | 2.14 | 6.40E-03 | 5'ss | Br. |
| 140 | chr17: 4885470-4886051 | chr17: 4885455-4886051 | TGAAGGTCCAGG GCATGGAGCCTG TCTCCTGGCAGT GTCT (271) | TGAAGGTCCAGG GCATGGAGTGTC TCTATGGCTGCT ACGT (272) | 8 | 35 | 2.00 | 4.45E-02 | 3'ss | Br. |
| 141 | chr16: 1728357-1733509 | chr16: 1728357-1735439 | GGCGGCCGCGCC GGCTCCAGGAAA TGGCAACTGCTG ACAG (273) | GGCGGCCGCGCC GGCTCCAGGGCC ATGAAGCCCCCA GGAG (274) | 2 | 11 | 2.00 | 3.29E-02 | exon incl. | Br. |
| 142 | chr11: 2993509-2997253 | chr11: 2993473-2997253 | CCTTCCAGCTAC ATCGAAACGCAT GAGGATGTTGTA TTTC (275) | CCTTCCAGCTAC ATCGAAACTTTA CCTAAAGCAGTA AAAA (276) | 1 | 7 | 2.00 | 1.25E-04 | 3'ss | Br. |
| 143 | chr10: 69583150-69595149 | chr10: 69583150-69597691 | CTTTTCTCTTCT TTTTATAGGTTG AACAAATCCTGG CAGA (277) | GATGTGATGAAC TATCTTCGGTTG AACAAATCCTGG CAGA (278) | 0 | 3 | 2.00 | 2.72E-03 | 5'ss | Br. |
| 144 | chr11: 66053068-66053171 | chr11: 66053007-66053171 | GCACTGGGCATT CAGAAAAGTCTC TCTTCCTCACCC CTGC (279) | GCACTGGGCATT CAGAAAAGGTTC TCCCCGGAGGTG CTGG (280) | 0 | 3 | 2.00 | 1.28E-07 | 3'ss | Br. |
| 145 | chr11: 77090454-77090938 | chr11: 77090433-77090938 | CTGTCACAGGGG AGTTTACGTCTT GCATGTCTCTCT TACA (281) | CTGTCACAGGGG AGTTTACGGGAA TGCCAGAGCAGT GGGC (282) | 0 | 3 | 2.00 | 2.18E-03 | 3'ss | Br. |
| 146 | chr12: 57032980-57033763 | chr12: 57033091-57033763 | GGGTGCAAAAGA TCCTGCAGCCAT TCCAGGTTGCTG AGGT (283) | GGGTGCAAAAGA TCCTGCAGGACT ACAAATCCCTCC AGGA (284) | 0 | 3 | 2.00 | 2.66E-07 | 3'ss | Br. |
| 147 | chr12: 58109976-58110164 | chr12: 58109976-58110194 | GGCACCCCAAAA GATGGCAGATCA GTCTCTCCCTGT TCTC (285) | GGCACCCCAAAA GATGGCAGGTGC GAGCCCGACCAA GGAT (286) | 0 | 3 | 2.00 | 9.82E-07 | 3'ss | Br. |
| 148 | chr17: 16344444-16344670 | chr17: 16344444-16344681 | GCATCTCAGCCC AAGAGAAGTTTC TTTGCAGGTTAT ATTC (287) | GCATCTCAGCCC AAGAGAAGGTTA TATTCCCAGAGG ATGT (288) | 0 | 3 | 2.00 | 2.72E-07 | 3'ss | Br. |
| 149 | chr1: 154246074-154246225 | chr1: 154246074-154246249 | CTTGCCTTCCCA TCCTCCTGCAAA CACCTGCCACCT TTCT (289) | CTTGCCTTCCCA TCCTCCTGAACT TCCAGGTCCTGA GTCA (290) | 0 | 3 | 2.00 | 2.32E-04 | 3'ss | Br. |
| 150 | chr1: 32096333-32098095 | chr1: 32096443-32098095 | CTACACAGAGCT GCAGCAAGGTGT GCACCCAGCTGC AGGT (291) | CTACACAGAGCT GCAGCAAGCTCT GTCCCAAATGGG CTAC (292) | 0 | 3 | 2.00 | 8.14E-08 | 3'ss | Br. |
| 151 | chr2: 101622533-101635459 | chr2: 101622533-101622811 | ACCTGTTACCAC TTTCAAAATTTC TGTGCTAAACAG TGTT (293) | ACCTGTTACCAC TTTCAAAAATCT ACAGACAGTCAA TGTG (294) | | | | | | |

TABLE 1-continued

| | Aberrant junction | WT junction | Aberrant sequence (SEQ ID NO) | WT sequence (SEQ ID NO) | Avg WT % | Avg Ab. % | Log$_2$ Fold Diff. | FDR Q-Value | Event | Type |
|---|---|---|---|---|---|---|---|---|---|---|
| 152 | chr2: 26437445-26437921 | chr2: 26437430-26437921 | AGACAAGGGATT GGTGGAAACATT TTATTTTACAGA ATTG (295) | AGACAAGGGATT GGTGGAAAAATT GACAGCGTATGC CATG (296) | 0 | 3 | 2.00 | 3.82E-06 | 3'ss | Br. |
| 153 | chr3: 101401353-101401614 | chr3: 101401336-101401614 | CAACGAGAACAA GCTATCAGTTAC TTTTACCCCACA GGGC (297) | CAACGAGAACAA GCTATCAGGGCT GCTAAGGAAGCA AAAA (298) | 0 | 3 | 2.00 | 2.29E-07 | 3'ss | Br. |
| 154 | chr5: 177576859-177577888 | chr5: 177576839-177577888 | TCTATATCCCCT CTAAGACGCACT TCTTTCCCCTCT GTAG (299) | TCTATATCCCCT CTAAGACGGACC TGGGTGCAGCCG CAGG (300) | 0 | 3 | 2.00 | 1.27E-06 | 3'ss | Br. |
| 155 | chr6: 31506716-31506923 | chr6: 31506632-31506923 | TGGAGCCAGTTA CTGGGCAGGTGT GTTTTTGTGACA GTCA (301) | TGGAGCCAGTTA CTGGGCAGGTGT CTGTACTGGTGA TGTG (302) | 0 | 3 | 2.00 | 9.28E-04 | 3'ss | Br. |
| 156 | chrX: 129771378-129790554 | chrX: 129771384-129790554 | AAAAGAAACTGA GGAATCAGTATC ACAGGCAGAAGC TCTG (303) | AAAAGAAACTGA GGAATCAGCCTT AGTATCACAGGC AGAA (304) | 13 | 54 | 1.97 | 1.08E-05 | 3'ss | Br. |
| 157 | chrX: 135758876-135761693 | chrX: 135760115-135761693 | CAGCACTAGGTT ATAAAGAGGAGT CTAGTAAAAGCC CTAA (305) | CAGCACTAGGTT ATAAAGAGAGGA TGTCTTATATCT TAAA (306) | 7 | 30 | 1.95 | 8.04E-04 | exon skip | Br. |
| 158 | chr6: 31936315-31936399 | chr6: 31936315-31936462 | GCCCCCGTTTTC CTGCCCAGCCCT TGTCCTCAGTGC ACCC (307) | GCCCCCGTTTTC CTGCCCAGTACC TGAAGCTGCGGG AGCG (308) | 4 | 18 | 1.93 | 9.28E-05 | 3'ss | Br. |
| 159 | chr2: 97757449-97760437 | chr2: 97757449-97757599 | GCCGCCGCCGCC GCCGCCAGGCTC TGATGCTGGTGT CTGG (309) | CACCTTATGAAG TATAGCAGGCTC TGATGCTGGTGT CTGG (310) | 10 | 40 | 1.90 | 4.22E-03 | 5'ss | Br. |
| 160 | chr19: 6731065-6731209 | chr19: 6731122-6731209 | AGTGGCAGTGGC TGTACCAGCCCA CAGGAAACAACC CGTA (311) | AGTGGCAGTGGC TGTACCAGCTCT TGGTGGAGGGCT CCAC (312) | 6 | 25 | 1.89 | 2.97E-03 | 3'ss | Br. |
| 161 | chr16: 54954250-54957496 | chr16: 54954322-54957496 | GAGATTCTGAAG ATAAGGAGTTCT CTTGTAGGATGC CACT (313) | GAGATTCTGAAG ATAAGGAGGTAA AACCTGTTTAGA AATT (314) | 4 | 16 | 1.77 | 5.02E-05 | 3'ss | Br. |
| 162 | chr2: 27260760-27261013 | chr2: 27260570-27261013 | CCAAGAGACAGC ACATTCAGCTCC TGAGCAGCCTGA CTGA (315) | CCCCTGAGATGA AGAAAGAGCTCC TGAGCAGCCTGA CTGA (184) | 4 | 16 | 1.77 | 3.39E-06 | exon incl. | Br. |
| 163 | chr10: 75290593-75294357 | chr10: 75290593-75296026 | TCAGAGCAGTCG GGACACAGGACA CCTGACTGATAG TGAA (316) | CTACGACAGTGA AGATTCAGGACA CCTGACTGATAG TGAA (317) | 10 | 35 | 1.71 | 1.55E-02 | 5'ss | Br. |
| 164 | chr1: 155278867-155279833 | chr1: 155278867-155279854 | CTGTTGTGTCCG TTTTGAAGAGCC CTTTGCTCCTCC CTCA (318) | CTGTTGTGTCCG TTTTGAAGAATG AACGGAGACCAG AATT (319) | 19 | 63 | 1.68 | 5.06E-05 | 3'ss | Br. |
| 165 | chr16: 630972-632882 | chr16: 632309-632882 | CCGGCCCTACAG GCTGGCGGATAA ACCCACTGCCCT ACAG (320) | CCCTCCGCCTCC TGATGCAGATAA ACCCACTGCCCT ACAG (321) | 6 | 21 | 1.65 | 3.26E-02 | exon skip | Br. |
| 166 | chr16: 54954239-54957496 | chr16: 54954322-54957496 | GAGATTCTGAAG ATAAGGAGGATG CCACTGGAAATG TTGA (322) | GAGATTCTGAAG ATAAGGAGGTAA AACCTGTTTAGA AATT (314) | 18 | 57 | 1.61 | 6.30E-07 | 3'ss | Br. |

TABLE 1-continued

| | Aberrant junction | WT junction | Aberrant sequence (SEQ ID NO) | WT sequence (SEQ ID NO) | Avg WT % | Avg Ab. % | Log$_2$ Fold Diff. | FDR Q-Value | Event | Type |
|---|---|---|---|---|---|---|---|---|---|---|
| 167 | chr14: 39734625-39746137 | chr14: 39736726-39746137 | TGAAAAGTCCAGAGGAAGAGGTTGTGGCAGCACTGCCTGA (323) | TCCTGGAGGAGCTACGCAGGGTTGTGGCAGCACTGCCTGA (324) | 15 | 47 | 1.58 | 1.41E-02 | 5'ss | Br. |
| 168 | chr13: 21157158-21165105 | chr13: 21164006-21165105 | GTCATGGCAGAAGACCTCCATCCAAGACATCTCTGGCATC (325) | CTATAGCTACTGGATATGGGTCCAAGACATCTCTGGCATC (326) | 10 | 32 | 1.58 | 1.25E-02 | exon skip | Br. |
| 169 | chr17: 45229302-45232037 | chr17: 45229284-45232037 | CCGGAGCCCCTTCAAAAAAGACTTTTCGTGTTTTACAGTC (327) | CCGGAGCCCCTTCAAAAAAGTCTGTTGCCAGAATCGGCCA (328) | 5 | 17 | 1.58 | 4.45E-02 | 3'ss | Br. |
| 170 | chr16: 47484364-47485306 | chr16: 47462809-47485306 | CCACAGATACTATTAGGAGGCCATACCACCCTGAACGCGC (329) | CCACAGATACTATTAGGAGGAATTTATCATGGCATCCAG (330) | 3 | 11 | 1.58 | 1.99E-02 | 3'ss | Br. |
| 171 | chr12: 57493873-57494628 | chr12: 57493873-57496072 | TGTTCAAGTTCCCAAAGCAGGAGATCCTGCTGGGCCGTGG (331) | CCTGGTCGCAGTTCAACAAGGAGATCCTGCTGGGCCGTGG (215) | 1 | 5 | 1.58 | 1.50E-04 | exon incl. | Br. |
| 172 | chr16: 56403209-56419830 | chr16: 56403239-56419830 | ACTCCCAGCTCAATGCAATGGTTCCATACCATCTGGTACT (332) | ACTCCCAGCTCAATGCAATGGCTCATCAGATTCAAGAGAT (333) | 0 | 2 | 1.58 | 6.10E-05 | 3'ss | Br. |
| 173 | chr17: 80013701-80013861 | chr17: 80013701-80013876 | ATCACTGTGACTTCCCTGAGGTCTCTGCTCCTCAGCTGCT (334) | ATCACTGTGACTTCCCTGAGCTGCTGTCCCCAGCAACGT (335) | 0 | 2 | 1.58 | 4.98E-05 | 3'ss | Br. |
| 174 | chr18: 51729496-51731367 | chr18: 51715381-51731367 | ATCCTCTCAATCAAAATAAGTTTGTGTGCACTTTTCTGCT (336) | ATCCTCTCAATCAAAATAAGGGTAAACCAGACTTGAATAC (337) | 0 | 2 | 1.58 | 4.76E-02 | 3'ss | Br. |
| 175 | chr1: 145109684-145112354 | chr1: 145109684-145112372 | CTATTCCTTTATTGAATTTGTTTTCTTCATCATTCTAGAT (338) | CTATTCCTTTATTGAATTTGATACTTTCATTCAGAAAACC (339) | 0 | 2 | 1.58 | 5.34E-04 | 3'ss | Br. |
| 176 | chr2: 242274627-242275373 | chr2: 242274627-242275389 | AGTCATACCTGGAGCAGCAGTTTGTTTCTTTTCTAGAAAA (340) | AGTCATACCTGGAGCAGCAGAAAAATTGAAAGAACTGTC (341) | 0 | 2 | 1.58 | 3.46E-03 | 3'ss | Br. |
| 177 | chr3: 49395199-49395459 | chr3: 493951S0-49395459 | GCAACCAGTTTGGGCATCAGCTGCCCTTCTCTCCTGTAGG (342) | GCAACCAGTTTGGGCATCAGGAGAACGCCAAGAACGAAGA (343) | 0 | 2 | 1.58 | 1.37E-04 | 3'ss | Br. |
| 178 | chr4: 152022314-152024139 | chr4: 152022314-152024022 | CCATGGTCAAAAAATGGCAGCACCAACAGGTCCGCCAAAT (344) | CCATGGTCAAAAAATGGCAGACAATGATTGAAGCTCACGT (345) | 0 | 2 | 1.58 | 3.60E-05 | 3'ss | Br. |
| 179 | chr5: 1323984-1325865 | chr5: 1324928-1325865 | GCCTGATGCCCGAATTTCAGGCCATGAAGTACTTGTCATA (346) | GCCTGATGCCCGAATTTCAGTTTGGCACTTACAGCGAATC (347) | 0 | 2 | 1.58 | 1.29E-02 | exon skip | Br. |
| 180 | chr5: 132439718-132439902 | chr5: 132439718-132439924 | AGATTGAAGCTAAAATTAAGTTTTCTGTCTTACCCATTCC (348) | AGATTGAAGCTAAAATTAAGGAGCTGACAAGTACTTGTAG (349) | 0 | 2 | 1.58 | 6.18E-06 | 3'ss | Br. |
| 181 | chr5: 44813384-44814996 | chr5: 44813384-44815014 | AGCACAAGCTATGTATCAAGCATAACTTTCTTCTACAGGA (350) | AGCACAAGCTATGTATCAAGGATTCTGGAGTGAAGCAGAT (351) | 0 | 2 | 1.58 | 5.76E-06 | 3'ss | Br. |

TABLE 1-continued

| | Aberrant junction | WT junction | Aberrant sequence (SEQ ID NO) | WT sequence (SEQ ID NO) | Avg WT % | Avg Ab. % | Log₂ Fold Diff. | FDR Q-Value | Event | Type |
|---|---|---|---|---|---|---|---|---|---|---|
| 182 | chr6: 52546712-52548863 | chr6: 52546712-52548875 | AGATGTAAAAGT GTCACTGTTTTG GTTTTCAGTTAC AGCT (352) | AGATGTAAAAGT GTCACTGTTTAC AGCTTTCTTCCT GGCT (353) | 0 | 2 | 1.58 | 5.43E-04 | 3'ss | Br. |
| 183 | chr7: 94218044-94227241 | chr7: 94218044-94228086 | CTGCAGCCTCCG CCTCCCAGGAAC TTGCCACATCAG ACTC (354) | CCATTGATGCAA ACGCAGCAGAAC TTGCCACATCAG ACTC (258) | 0 | 2 | 1.58 | 8.78E-03 | exon incl. | Br. |
| 184 | chr15: 59373483-59376300 | chr15: 59373483-59376327 | AGGATGATGCAG CATCCAACTGGT CTTTTTGTGTTC TGTG (355) | AGGATGATGCAG CATCCAACGCGG GCACATGAACGC CCCC (356) | 10 | 28 | 1.4 | 1.70E-03 | 3'ss | Br. |
| 185 | chr1: 153925126-153925280 | chr1: 153925111-153925280 | TGGTGAAATGGA CCCCAAAGTCTT TCTCTTTCAAGT ACCT (357) | TGGTGAAATGGA CCCCAAAGTACC TGCTATTGAGGA GAAC (358) | 12 | 33 | 1.39 | 1.25E-03 | 3'ss | Br. |
| 186 | chr1: 151739775-151742647 | chr1: 151740709-151742647 | AGCTTAAAGAAC TGTATTCGTTTG ACTGCAACCCTG GAGT (359) | GATCAAGGCAAC CGGGAAAGTTTG ACTGCAACCCTG GAGT (360) | 9 | 25 | 1.38 | 3.31E-02 | exon skip | Br. |
| 187 | chr19: 47342877-47349249 | chr19: 47342835-47349249 | AACACACCAACT TTGTGGAGGTCC TGGCAATCTCCG TTGC (361) | AACACACCAACT TTGTGGAGTTCC GGAACTTTAAGA TCAT (362) | 1 | 4 | 1.32 | 8.52E-04 | 3'ss | Br. |
| 188 | chr15: 75631685-75632305 | chr15: 75632219-75632305 | GCGGGTCTGCAG CCTACGCAAACT GAAGCAGGGCCA GACC (363) | GTTCCAGGTCCT CCTGGCAGAACT GAAGCAGGGCCA GACC (364) | 5 | 13 | 1.22 | 5.55E-04 | exon skip | Br. |
| 189 | chr1: 212459633-212506838 | chr1: 212502673-212506838 | CCCGCTGCCCCA GCTCAAAGATCA GTGCTAACATCT TCCG (365) | ATTCTGATATAG TAAAAATGATCA GTGCTAACATCT TCCG (366) | 5 | 13 | 1.22 | 1.52E-02 | exon skip | Br. |
| 190 | chr22: 30976673-30976998 | chr22: 30976688-30976998 | ATGAGTTTCCCA CCGATGGGGAGG AAGACCGCAGGA AGGA (367) | ATGAGTTTCCCA CCGATGGGGAGA TGTCAGCGCAGG AGGA (368) | 2 | 6 | 1.22 | 1.59E-03 | 3'ss | Br. |
| 191 | chr7: 80535232-80545994 | chr7: 80458061-80545994 | AGTTTATTTAAC ATTTGATGAGCC TACCTTGTACAA TGCT (369) | AGTTTATTTAAC ATTTGATGAACT TCGAGAAACCAA GACC (370) | 2 | 6 | 1.22 | 3.40E-02 | exon incl. | Br. |
| 192 | chr8: 145153766-145153768 | chr8: 145153691-145153768 | CCACCTAGCAGC CACCAGAGACCA GAGGTGGCACAG GCAG (371) | CCACCTAGCAGC CACCAGAGGTTA CAAGGGGAGAGT GGCC (372) | 2 | 6 | 1.22 | 1.17E-03 | intron retention | Br. |
| 193 | chr9: 96285645-96289436 | chr9: 96278551-96289436 | TCCAGGATCCTG AGGCATGGCCAT ATCAGCGGGAAC AAGA (373) | GGCAGCGGAGGG GCGACAAACCAT ATCAGCGGGAAC AAGA (374) | 2 | 6 | 1.22 | 8.61E-03 | exon incl. | Br. |
| 194 | chr2: 106781255-106782511 | chr2: 106781240-106782511 | GGCAACTTCGTT AATATGAGCTTT CTACTCAACAGG TCTA (375) | GGCAACTTCGTT AATATGAGGTCT ATCCAGGAAAAT GGTG (376) | 20 | 47 | 1.19 | 5.26E-03 | 3'ss | Br. |
| 195 | chr19: 7976215-7976299 | chr19: 7976215-7976320 | GGAGCCTGGGCA TCTCGTTGCCCT GCCCGTCTCCCT CCCA (377) | GGAGCCTGGGCA TCTCGTTGGTGG AGCTGGCAACAG GACA (378) | 6 | 15 | 1.19 | 1.98E-02 | 3'ss | Br. |
| 196 | chr11: 9161795-9163486 | chr11: 9161401-9163486 | CTGGTGTGCTTG GGAGCCAGGGTT ATCATGAAGATT AAAT (379) | CTGGTGTGCTTG GGAGCCAGAGAT CACCTCCTACAC CACT (380) | 3 | 8 | 1.17 | 4.87E-02 | exon incl. | Br. |

TABLE 1-continued

| | Aberrant junction | WT junction | Aberrant sequence (SEQ ID NO) | WT sequence (SEQ ID NO) | Avg WT % | Avg Ab. % | Log₂ Fold Diff. | FDR Q-Value | Event | Type |
|---|---|---|---|---|---|---|---|---|---|---|
| 197 | chr1: 160252899-160254844 | chr1: 160253429-160254844 | ATTGGAGGAGCTTCTGGAAAGATGCCCTCTTCGCTTCCCA (381) | ATTGGAGGAGCTTCTGGAAAGTGCTCTTGATGATTTCGAT (382) | 10 | 23 | 1.13 | 3.12E-03 | exon skip | Br. |
| 198 | chr19: 16641724-16643408 | chr19: 16641691-16643408 | AATGACGTGCTGCACCACTGGGCCCTGACGCGCGGAAAGT (383) | AATGACGTGCTGCACCACTGCCAGCGCAAGCAGGCCCGGG (384) | 7 | 16 | 1.09 | 1.69E-02 | 3'ss | Br. |
| 199 | chr3: 39141945-39142237 | chr3: 39141994-39142237 | GCCTGGGGTGGAGAGGGCAGCCCCCCAGCTACCACAAGAA (385) | GCCTGGGGTGGAGAGGGCAGTCTGGGATGTGGCATTGGCT (386) | 9 | 20 | 1.07 | 3.01E-02 | exon skip | Br. |
| 200 | chr2: 230657846-230659894 | chr2: 230657861-230659894 | GGAAATGGGACAGGAGGCAGAGGATCACAGGCTTTAAAAT (387) | GGAAATGGGACAGGAGGCAGCTTTTCTCTCAACAGAGGAT (388) | 11 | 24 | 1.06 | 3.05E-03 | 3'ss | Br. |
| 201 | chr10: 123718925-123719872 | chr10: 123719110-123719872 | AGACCGACTGCCAGTAATAGGAGATTGTGAAGACCTTTGA (389) | AGACCGACTGCCAGTAATAGAGCCTGTTAGTATTAATGAA (390) | 5 | 11 | 1.00 | 2.09E-02 | exon skip | Br. |
| 202 | chr1: 44064584-44067741 | chr1: 44064584-44069086 | TCATGCTAGCCGAGGCCCAGTGGCGGCCAGAGGAGTCCGA (391) | TCATGCTAGCCGAGGCCCAGGAAACCACTATCAGCGGCCT (392) | 5 | 11 | 1.00 | 3.31E-02 | exon incl. | Br. |
| 203 | chr1: 11131045-11132143 | chr1: 11131030-11132143 | GAAGGCAGCTGAGCAAACAGTTCTCTCCCTTGCAGCTGCC (393) | GAAGGCAGCTGAGCAAACAGCTGCCCGGGACAGGCAAAG (394) | 4 | 9 | 1.00 | 1.37E-03 | 3'ss | Br. |
| 204 | ch16: 109690220-109697276 | chr6: 109691670-109697276 | GCCAACAGCCAATTCTACAGGTACAACAAATAACACTGTG (395) | GCCAACAGCCAATTCTACAGCTAAACCCACAGTTCAGCCC (396) | 3 | 7 | 1.00 | 6.32E-03 | exon skip | Br. |
| 205 | chr17: 37873733-37879571 | chr17: 37873733-37876039 | CCCATCAACTGCACCCACTCCCCTCTGACGTCCATCATCT (397) | CCCATCAACTGCACCCACTCCTGTGTGGACCTGGATGACA (398) | 2 | 5 | 1.00 | 4.46E-02 | exon skip | Br. |
| 206 | chr17: 5250220-5253766 | chr17: 5250220-5253745 | GCGGAAAGAATTGCATGAAGAGCGACAACAACACAACCAG (399) | GCGGAAAGAATTGCATGAAGTTTGCCATCTCTTGGAGCAA (400) | 2 | 5 | 1.00 | 4.49E-02 | 3'ss | Br. |
| 207 | chr1: 27260910-27267947 | chr1: 27250657-27267947 | TGTGGGAATTACAATTCAAGCTTATCACACAGACTTTCAG (401) | AAGAAGGGATGGCAGAGAAGCTTATCACACAGACTTTCAG (402) | 2 | 5 | 1.00 | 7.58E-03 | exon incl. | Br. |
| 208 | chr5: 176759270-176761284 | chr5: 176759247-176761284 | CTTCCTCAAGTCGCCCAAAGCTCCCCCGTTTCTTCTCCCC (403) | CTTCCTCAAGTCGCCCAAAGACAACGTGGACGACCCCACG (404) | 1 | 3 | 1.00 | 1.35E-02 | 3'ss | Br. |
| 209 | chr7: 44619227-44621047 | chr7: 44620838-44621047 | TCTTCGCTGGTGGCAAACTGTATCGTGAAGAGCGCTTCCG (405) | TCTTCGCTGGTGGCAAACTGCGGGTGCATCTCGACATCCA (406) | 1 | 3 | 1.00 | 8.43E-03 | exon skip | Br. |
| 210 | chr1: 165619201-165620230 | chr1: 165619201-165620250 | GCAAGAAGTACAAAGTGGAGTATGTGCTTTGTTGTGACAG (407) | GCAAGAAGTACAAAGTGGAGTATCCTATCATGTACAGCAC (408) | 0 | 1 | 1.00 | 9.69E-03 | 3'ss | Br. |
| 211 | chr3: 42826828-42827519 | chr3: 42826812-42827519 | TGTAGGAGCAATGACTGTTGCATTCTTTTTCTTTAGGTAT (409) | TGTAGGAGCAATGACTGTTGGTATGGGCTATTCCATGTAT (410) | 0 | 1 | 1.00 | 2.54E-04 | 3'ss | Br. |

TABLE 1-continued

| Aberrant junction | WT junction | Aberrant sequence (SEQ ID NO) | WT sequence (SEQ ID NO) | Avg WT % | Avg Ab. % | Log$_2$ Fold Diff. | FDR Q-Value | Event | Type |
|---|---|---|---|---|---|---|---|---|---|
| 212 chr8: 117738411-117746515 | chr8: 117738411-117767904 | CCTTCCTGGATCCCCCTAAGGTGGTATTAAAGATAATCAA (411) | AAGTGCAGATAGATGGCCTTGTGGTATTAAAGATAATCAA (412) | 0 | 1 | 1.00 | 5.33E-04 | exon incl. | Br. |
| 213 chrX: 54835809-54836550 | chrX: 54835809-54836154 | CAGGTCTAACTCGCTTCCAGGCCCCAGCAGATGAACCTGA (413) | CAGGTCTAACTCGCTTCCAGGCTGAAGCTTCAGAAAAGGA (414) | 0 | 1 | 1.00 | 1.53E-02 | 3'ss | Br. |
| 214 chr16: 30012361-30016541 | chr16: 30012851-30016541 | CCTCCCCATACCTGAGCTCGATGGCGGTGGGACCCCCCGA (415) | GCCTGCCCCGGAAACTCAAGATGGCGGTGGGACCCCCCGA (82) | 10 | 20 | 0.93 | 3.40E-02 | exon skip | Br. |
| 215 chr6: 43006222-43006303 | chr6: 43006210-43006303 | GCAAAAGGATATACCAGGAGCATTTATTTCAGGGGTCCTC (416) | GCAAAAGGATATACCAGGAGGGGTCCTCAAGATTCGAGAT (417) | 10 | 20 | 0.93 | 2.78E-02 | 3'ss | Br. |
| 216 chr6: 135517140-135518098 | chr6: 135517140-135520045 | CACTCCAATTTATAGATTCTGATTCTTCATCATGGTGTGA (418) | CACTCCAATTTATAGATTCTTTCTTAAACACTTCCAGTAA (419) | 9 | 18 | 0.93 | 1.40E-02 | exon incl. | Br. |
| 217 chr7: 99943591-99947339 | chr7: 99943591-99947421 | TGAGAGTCTTCAGTTACTAGTTTGTCTTTCCTAGATCCAG (420) | TGAGAGTCTTCAGTTACTAGAGGCGGATTTCCCTGACTGA (421) | 45 | 85 | 0.90 | 3.07E-04 | 3'ss | Br. |
| 218 chr12: 111085013-111085015 | chr12: 111082934-111085015 | TTAACAGCATTTTGTTTTGCGATTCCTGCCAGCTCCCAGG (422) | CCCAGTCATTCAACAGGAAGGATTCCTGCCAGCTCCCAGG (423) | 10 | 19 | 0.86 | 1.21E-02 | intron retention | Br. |
| 219 chr4: 141300346-141302115 | chr4: 141300346-141300722 | GATGAATGCTGACATGGATGATCTCTCTGCAAGAGTAGAT (424) | GATGAATGCTGACATGGATGCAGTTGATGCTGAAAATCAA (425) | 4 | 8 | 0.85 | 2.40E-02 | exon skip | Br. |
| 220 chr10: 114905856-114910741 | chr10: 114905856-114910756 | GTCAATGCTTCCATGTCCAGCTTTCTGTCTTCTAGGTTCC (426) | GTCAATGCTTCCATGTCCAGGTTCCCTCCCCATATGGTCC (427) | 18 | 33 | 0.84 | 3.71E-02 | 3'ss | Br. |
| 221 chr16: 30767593-30767675 | chr16: 30767593-30767687 | TATGGCAAGGAGGTCGACTTCTCTTTCCCAGCTGGGCCT (428) | TATGGCAAGGAGGTCGACCTCTGGGCCTGTGGGGTGATCT (429) | 7 | 13 | 0.81 | 2.25E-02 | 3'ss | Br. |
| 222 chr3: 128890351-128890476 | chr3: 128890381-128890476 | TGGTTTTACCTCGGATAGAGACATTTGTTATCGCTGTGGT (430) | TGGTTTTACCTCGGATAGAGGTTTCCAGTTTGTTTCCTCG (431) | 7 | 13 | 0.81 | 5.98E-03 | 3'ss | Br. |
| 223 chr1: 155278756-155279833 | chr1: 155278756-155279854 | GAATCCGTATCTGGGAACAGAGCCCTTTGCTCCTCCCTCA (432) | GAATCCGTATCTGGGAACAGAATGAACGGAGACCAGAATT (433) | 34 | 60 | 0.80 | 2.74E-04 | 3'ss | Br. |
| 224 chr20: 264722-270899 | chr20: 264722-270199 | TCCAGGAGTTCAAGGTTCCGTGTTTCACTTCAAGCCCACT (434) | TTTGACTAGGGTCCAACCAGTGTTTCACTTCAAGCCCACT (435) | 22 | 39 | 0.80 | 1.59E-02 | exon skip | Br. |
| 225 chr1: 53370762-53373539 | chr1: 53372283-53373539 | GGGCCTGATGAATGACATCGCTTCCTCGGCAGTCATGGGA (436) | GGGCCTGATGAATGACATCGCAGCCTTCCCTGCACCCACC (437) | 30 | 52 | 0.77 | 2.84E-03 | exon skip | Br. |
| 226 chr4: 5815889-5825343 | chr4: 5815889-5819937 | AGCCCCAGGATGCCTCGCAGCTCTCGGAAGAACTGGTTGT (438) | AGCCCCAGGATGCCTCGCAGACGTGCTTCTGCCATGATT (439) | 16 | 28 | 0.77 | 1.45E-02 | exon skip | Br. |

TABLE 1-continued

| | Aberrant junction | WT junction | Aberrant sequence (SEQ ID NO) | WT sequence (SEQ ID NO) | Avg WT % | Avg Ab. % | Log$_2$ Fold Diff. | FDR Q-Value | Event | Type |
|---|---|---|---|---|---|---|---|---|---|---|
| 227 | chr20: 47741142-47752369 | chr20: 47741124-47752369 | ACTTGCCTGTGA ATTTCGAGTCTT TCCCTCTGAAAC AGGT (440) | ACTTGCCTGTGA ATTTCGAGGTGG CCCGGGAGAGTG GCCC (441) | 15 | 26 | 0.75 | 1.83E-03 | 3'ss | Br. |
| 228 | chrX: 48933637-48934088 | chrX: 48933604-48934088 | TACCCGGGACAA CCCCAAGGCCGC CCACCCCACCCC CCAT (442) | TACCCGGGACAA CCCCAAGGGGCT CTGTGACCTCTG CCCC (443) | 2 | 4 | 0.74 | 4.57E-02 | 3'ss | Br. |
| 229 | chr1: 67890660-67890765 | chr1: 67890642-67890765 | CATAGTGGAAGT GATAGATCTTCT TTTTCACATTAC AGTG (444) | CATAGTGGAAGT GATAGATCTGGC CTGAAGCACGAG GACA (445) | 39 | 64 | 0.70 | 4.20E-07 | 3'ss | Br. |
| 230 | chr1: 156705701-156706410 | chr1: 156705701-156706423 | GCTGTACCTTCA GGAACAGGCCCT TTCTCCCAGGTT TCCA (446) | GCTGTACCTTCA GGAACAGGGTTT CCATGCTGAGCT CCTG (447) | 18 | 29 | 0.66 | 2.84E-03 | 3'ss | Br. |
| 231 | chr10: 101507147-101514285 | chr10: 101507147-101510125 | TAAAGCGACTCA TTGAGCAGGAGG TGGTATAACAGA CAGA (448) | TAAAGCGACTCA TTGAGCAGGCAA AAGGCAGGATTG TGGT (449) | 29 | 46 | 0.65 | 1.78E-02 | exon skip | Br. |
| 232 | chr12: 117595889-117603289 | chr12: 117595868-117603289 | TGGGAATCTGGC CAGAGAGTCTT TCTGTCTTGTTT TGAA (450) | TGGGAATCTGGC CAGAGAGGTGC TTGACATCCTCC AGCA (451) | 31 | 49 | 0.64 | 3.09E-04 | 3'ss | Br. |
| 233 | chr2: 114472772-114476730 | chr2: 114475427-114476730 | AGAAAACATCGA ATTCAGAGCTTG ATAATGGAACTA TACA (452) | AGAAAACATCGA ATTCAGAGAGTT CCAGAAGACAGC GAAC (453) | 8 | 13 | 0.64 | 2.66E-02 | exon skip | Br. |
| 234 | chr1l: 504996-507112 | chr11: 504996-506608 | CGTCCGCCAGTC GTCCCGAGGCAT GAAGAACTCTTG ACTG (454) | AGCCGGGCGTTG GGGGAAAGGCAT GAAGAACTCTTG ACTG (455) | 34 | 53 | 0.63 | 1.78E-02 | 5'ss | Br. |
| 235 | chrX: 123224814-123227867 | chrX: 123224614-123227867 | ACTAATCTTCAG CATGCCATTCGG CGTGGCACAAGC CTAA (456) | CAAACACCTCTT GATTATAATCGG CGTGGCACAAGC CTAA (457) | 14 | 22 | 0.62 | 2.22E-04 | exon incl. | Br. |
| 236 | chr9: 140622981-140637822 | chr9: 140622981-140637843 | CACCACAAAATC ACAGACAGCTTG CTTGCCTTTTGT TTTA (458) | CACCACAAAATC ACAGACAGCAGC TGCAGTATCTCG GAAG (459) | 37 | 57 | 0.61 | 6.00E-04 | 3'ss | Br. |
| 237 | chr2: 152324660-152325154 | chr2: 152325065-152325154 | CTCCTACTACAC AATCTAAGATTT CAGAAATGGCCA AAGA (460) | AGAGCTCAAAGA AGTGTTTAATTT CAGAAATGGCCA AAGA (461) | 34 | 52 | 0.60 | 2.66E-02 | exon skip | Br. |
| 238 | chr12: 95660408-95663814 | chr12: 95660408-95663826 | ATTTCCAGAGGA TTTACACTTTTG CTTGACAGGGTC AGTG (462) | ATTTCCAGAGGA TTTACACTGGTC AGTGCTGCTTGC CCAT (463) | 49 | 74 | 0.58 | 1.10E-04 | 3'ss | Br. |
| 239 | chr7: 44880611-44887567 | chr7: 44880611-44882875 | GAGTCGGCGCCG AGAACATGTTTC CTGTGGGCCGCA TCCA (464) | CACAGAGAGCTG GGCTACAGTTTC CTGTGGGCCGCA TCCA (465) | 5 | 8 | 0.58 | 4.45E-02 | exon skip | Br. |
| 240 | chr10: 75554088-75554298 | chr10: 75554088-75554313 | TGACGTTCTCTG TGCTCCAGTGGT TTCTCCCACAGG TTCC (466) | TGACGTTCTCTG TGCTCCAGGTTC CCGGCCCCCAAG TCGC (467) | 46 | 68 | 0.55 | 4.09E-04 | 3'ss | Br. |
| 241 | chrX: 123224614-123224703 | chrX: 123224614-123227867 | CAAACACCTCTT GATTATAACACG CAGGTAACATGG ATGT (468) | CAAACACCTCTT GATTATAATCGG CGTGGCACAAGC CTAA (457) | 14 | 21 | 0.55 | 2.21E-02 | exon incl. | Br. |

TABLE 1-continued

| | Aberrant junction | WT junction | Aberrant sequence (SEQ ID NO) | WT sequence (SEQ ID NO) | Avg WT % | Avg Ab. % | $\text{Log}_2$ Fold Diff. | FDR Q-Value | Event | Type |
|---|---|---|---|---|---|---|---|---|---|---|
| 242 | chr2: 86398468-86400772 | chr2: 86398435-86400772 | TACTCCAGCTTCAGCAACAGCACCTACAGAAGCGGCTCAA (469) | TACTCCAGCTTCAGCAACAGCAGGTGATACCCTGTCGGTC (470) | 30 | 44 | 0.54 | 8.18E-03 | 3'ss | Br. |
| 243 | chr17: 47882807-47888837 | chr17: 47886570-47888837 | TCTCAGCTGACGAATGCAAGGCACCAACGGAGAGACAGCT (471) | GGCATGCAACCAGGCACCAGGCACCAACGGAGAGACAGCT (472) | 13 | 19 | 0.51 | 4.21E-03 | exon skip | Br. |
| 244 | chr1: 109743522-109745534 | chr1: 109743522-109745565 | TCAAATCATTTACCTCCAAGCAGCCAGCTCCTGTCACCAT (473) | TCAAATCATTTACCTCCAAGAGGACTCCTGATGGATTTGA (474) | 9 | 13 | 0.49 | 3.77E-02 | 3'ss | Br. |
| 245 | chr11: 502249-504823 | chr11: 502181-504823 | AGCAAAAGGGGTGTCTCAGAATCTCCGGCCTGTGAAACT (475) | AGCAAAAGGGGTGTCTCAGGCCACTCTTCACCTCCACCA (476) | 35 | 49 | 0.47 | 2.40E-02 | 3'ss | Br. |
| 246 | chr6: 31611971-31612083 | chr6: 31611971-31612301 | TGTTGCCTCCGCGGCCGCAGGACAGCAGGTGCCAGGCTTC (477) | TGGTCATGGCCAAACCCTGGGACAGCAGGTGCCAGGCTTC (478) | 44 | 60 | 0.44 | 5.91E-04 | exon incl. | Br. |
| 247 | chr20: 30310151-30310420 | chr20: 30310133-30310420 | TGCCTAAGGCGGATTTGAATCTCTTTCTCTCCCTTCAGAA (479) | TGCCTAAGGCGGATTTGAATAATCTTATCTTGGCTTTGGA (480) | 63 | 84 | 0.41 | 4.16E-05 | 3'ss | Br. |
| 248 | chr6: 31612191-31612301 | chr6: 31611971-31612301 | TGGTCATGGCCAAACCCTGGGCTCCACCCTCATCCAGCTG (481) | TGGTCATGGCCAAACCCTGGGACAGCAGGTGCCAGGCTTC (478) | 51 | 68 | 0.41 | 4.27E-03 | exon incl. | Br. |
| 249 | chr10: 34649187-34661425 | chr10: 34649187-34663801 | TGCAGATTCCAAAAGAAACGAAAGCAGAAGATGAGGATAT (482) | CCTTCCACCCAAGGGAACTGAAAGCAGAAGATGAGGATAT (483) | 49 | 63 | 0.36 | 4.56E-02 | exon incl. | Br. |
| 250 | chr4: 860289-860743 | chr4: 860322-860743 | AGGAGGGCCCCCTGCCGCTGGCAACAACTCCCAGCCCTGC (484) | AGGAGGGCCCCCTGCCGCTGCTGACCCCTTTGGCCCGCTT (485) | 43 | 54 | 0.32 | 1.35E-02 | 3'ss | Br. |
| 251 | chr8: 99054946-99057170 | chr8: 99055003-99057170 | AACAACTGCCCAGCTTTGAGTGGCAATAATATTGAACTGG (486) | AACAACTGCCCAGCTTTGAGGAAATCTGAAATAGAGTACT (487) | 3 | 4 | 0.32 | 4.44E-02 | 3'ss | Br. |
| 252 | chr8: 48694815-48694938 | chr8: 48691654-48694938 | GTTGTGCCCATGACCTCCAGGTTAGGATTAATTGAGTGGC (488) | GTTGTGCCCATGACCTCCAGTGATCCCAGGGCACCCCGT (489) | 66 | 81 | 0.29 | 4.37E-02 | exon incl. | Br. |
| 253 | chr20: 57470739-57473995 | chr20: 57470739-57478585 | GTTAATGGGTTTAATGGAGAGGGCGGCGAAGAGGACCCGC (490) | GTTAATGGGTTTAATGGAGATGAGAAGGCAACCAAAGTGC (491) | 57 | 68 | 0.25 | 2.24E-02 | exon incl. | Br. |
| 254 | chr20: 57474040-57478585 | chr20: 57470739-57478585 | GCAAGGAGCAACAGCGATGGTGAGAAGGCAACCAAAGTGC (492) | GTTAATGGGTTTAATGGAGATGAGAAGGCAACCAAAGTGC (491) | 59 | 69 | 0.22 | 4.34E-03 | exon incl. | Br. |
| 255 | chr19: 17339118-17339611 | chr19: 17339118-17339817 | AGTTGAGATGAAGCGAATGGATCCTGGCTTCCTGGACAA (493) | AGTTGAGATGAAGCGAATGCTCCCCTACCAGGGGTCGC (494) | 79 | 91 | 0.2 | 2.28E-02 | exon incl. | Br. |
| 256 | chrX: 2209644-2326785 | chrX: 2310515-2326785 | AGAAACCTTGAACGACAAAGTGGAATTTTTATACTGTGAC (495) | AGAAACCTTGAACGACAAAGAGACGTGAGTCTTGCTGTGT (496) | 84 | 95 | 0.18 | 4.29E-02 | exon skip | Br. |

TABLE 1-continued

| | Aberrant junction | WT junction | Aberrant sequence (SEQ ID NO) | WT sequence (SEQ ID NO) | Avg WT % | Avg Ab. % | Log$_2$ Fold Diff. | FDR Q-Value | Event | Type |
|---|---|---|---|---|---|---|---|---|---|---|
| 257 | chrY: 2159644-2276785 | chrY: 2260515-2276785 | AGAAACCTTGAA CGACAAAGTGGA ATTTTTATACTG TGAC (495) | AGAAACCTTGAA CGACAAAGAGAC GTGAGTCTTGCT GTGT (496) | 84 | 95 | 0.18 | 4.29E-02 | exon skip | Br. |
| 258 | chr11: 67815439-67815553 | chr11: 67815439-67816345 | ACCCCTTTGGCA TCGATCCTGCCC TTTCCTCAGCAC AAGA (497) | ACCCCTTTGGCA TCGATCCTATTT GGAGCCTGGCTG CCAA (498) | 0 | 60 | 5.93 | 5.12E-05 | 3'ss | CLL |
| 259 | chr2: 97285513-97297048 | chr2: 97285499-97297048 | TGGGAGGAGCAT GTCAACAGAGTT TCCCTTATAGGA CTGG (9) | TGGGAGGAGCAT GTCAACAGGACT GGCTGGACAATG GCCC (10) | 0 | 59 | 5.91 | 7.08E-07 | 3'ss | CLL |
| 260 | chr10: 93244412-93244921 | chr10: 93244412-93244936 | TAAAGTGTTGGC TTTACTTAAATT TATCTTTACAGA TACT (499) | TAAAGTGTTGGC TTTACTTAATAC TGCAAACAATTT AGTT (500) | 0 | 51 | 5.7 | 5.10E-07 | 3'ss | CLL |
| 261 | chr21: 47970657-47971529 | chr21: 47970657-47971546 | ACCTCGTCAGAA ACAACCAGAGTT CCCCCGTTTCTA GAGG (501) | ACCTCGTCAGAA ACAACCAGAGGT TGGACCAGCCTC AATG (502) | 0 | 48 | 5.61 | 2.38E-05 | 3'ss | CLL |
| 262 | chr22: 50966161-50966940 | chr22: 50966146-50966940 | TCATCCAGAGCC CAGAGCAGGGGA TGTCTGACCAGA TGCA (173) | TCATCCAGAGCC CAGAGCAGATGC AAGTGCTGCTGG ACCA (174) | 0 | 48 | 5.61 | 3.58E-03 | 3'ss | CLL |
| 263 | chr13: 26970491-26971275 | chr13: 26970491-26971289 | AAAGATTTCAGA AGAAATACTATT TCTCTTTCAGGT ATAC (503) | AAAGATTTCAGA AGAAATACGTAT ACCAACTGCAGC CTTA (504) | 0 | 39 | 5.32 | 1.50E-02 | 3'ss | CLL |
| 264 | chr5: 865696-869359 | chr5: 865696-870587 | CCAAAAGAGGGG ATAATGAGGGAA GGTGAAGAAGGA GCTG (505) | CTCCATGCTCAG CTCTCTGGGGAA GGTGAAGAAGGA GCTG (129) | 0 | 39 | 5.32 | 4.28E-05 | exon incl. | CLL |
| 265 | chr22: 39064137-39066874 | chr22: 39064137-39066888 | CTCTCTCCAACC TGCATTCTCATC TCGCCCACAGTT GGAT (140) | CTCTCTCCAACC TGCATTCTTTGG ATCGATCAACCC GGGA (141) | 0 | 38 | 5.29 | 4.92E-04 | 3'ss | CLL |
| 266 | chr10: 89519557-89527429 | chr10: 89516679-89527429 | TCATCTTGAAAA ATGAAAATTCCT ATTTTACAGCTG AGGA (506) | TCATCTTGAAAA ATGAAAATGTGG ATAGGCATGTAG ACCT (507) | 0 | 34 | 5.13 | 3.62E-05 | 3'ss | CLL |
| 267 | chr20: 35282126-35284762 | chr20: 35282104-35284762 | TTTGCAGGGAAT GGGCTACATCCC CTTGGTTCTCTG TTAC (35) | TTTGCAGGGAAT GGGCTACATACC ATCTGCCAGCAT GACT (36) | 0 | 34 | 5.13 | 3.01E-05 | 3'ss | CLL |
| 268 | chr10: 102276734-102286155 | chr10: 102276717-102286155 | ACCCTGTCTACC AGCCTGTGTTTT CTGCCACCTACA GGAT (508) | ACCCTGTCTACC AGCCTGTGGATA GACCATGAAGCT GAAG (509) | 1 | 64 | 5.02 | 4.28E-05 | 3'ss | CLL |
| 269 | chr14: 75356052-75356580 | chr14: 75356052-75356599 | AGATGTCAGGTG GGAGAAAGCCTT TGATTGTCTTTT CAGC (89) | AGATGTCAGGTG GGAGAAAGCTGT TGGAGACACAGT TGCA (90) | 1 | 62 | 4.98 | 8.04E-09 | 3'ss | CLL |
| 270 | chr19: 16264018-16265147 | chr19: 16264018-16265208 | TGACACAGCCCT GCAGGCAGGGTC CGTGCAGGACCT TTCC (510) | TGACACAGCCCT GCAGGCAGAGGG ATCCCGCAAACG TGGA (511) | 1 | 59 | 4.91 | 4.19E-04 | 3'ss | CLL |
| 271 | chr7: 102074108-102076648 | chr7: 10207410S-102076671 | GCGGGGCGAGGG CAGCTCCGCGTT TCTCTGAATTCT CCCC (512) | GCGGGGCGAGGG CAGCTCCGGGAA GGAACGTCCAG GGAT (513) | 1 | 59 | 4.91 | 8.04E-09 | 3'ss | CLL |

TABLE 1-continued

| | Aberrant junction | WT junction | Aberrant sequence (SEQ ID NO) | WT sequence (SEQ ID NO) | Avg WT % | Avg Ab. % | Log₂ Fold Diff. | FDR Q-Value | Event | Type |
|---|---|---|---|---|---|---|---|---|---|---|
| 272 | chr1: 1014583J0-101460665 | chr1: 101458296-101460665 | TCTTTGGAAAATCTAATCAATTTTCTGCCTATAGGGGAAG (25) | TCTTTGGAAAATCTAATCAAGGGAAGGAAGATCTATGAAC (26) | 0 | 29 | 4.91 | 3.49E-03 | 3'ss | CLL |
| 273 | ch17: 99954506-99955849 | chr7: 99954506-99955842 | CCACCTCACCATCACCCAGGGCAGCCCCTCCACAGGGCCC (514) | CCACCTCACCATCACCCAGGCCCTCAGGCAGCCCCTCCAC (515) | 0 | 29 | 4.91 | 1.26E-02 | 3'ss | CLL |
| 274 | chr19: 23545541-23556543 | chr19: 23545527-23556543 | GATGGTGGATGAACCCACAGTTTTTTTTTTTCAGGTATAT (11) | GATGGTGGATGAACCCACAGGTATATGTCCTCATTTTCCT (12) | 1 | 57 | 4.86 | 7.10E-04 | 3'ss | CLL |
| 275 | chr3: 108403188-108405274 | chr3: 108403188-108405291 | GCCAACCTAGAGCCCCCCTGCTCTCTGCCTCTTACAGATG (516) | GCCAACCTAGAGCCCCCCTGATGACTGGCATAGCCTGGGC (517) | 1 | 56 | 4.83 | 2.18E-05 | 3'ss | CLL |
| 276 | chr17: 71198039-71199162 | chr17: 71198039-71199138 | GGAGCAGTGCAGTTGTGAAATCATTACTTCTAGATGATGC (31) | GGAGCAGTGCAGTTGTGAAAGTTTTGATTCATGGATTCAC (32) | 0 | 27 | 4.81 | 1.14E-04 | 3'ss | CLL |
| 277 | chr6: 41040823-41046743 | chr6: 41040823-41046767 | AACCGGGGGAGCGAGGCACGTTTCTTTCCCCACCTTTCTA (518) | AACCGGGGGAGCGAGGCACGGAGTGTACCTCACAGCCTTC (519) | 0 | 27 | 4.81 | 8.95E-03 | 3'ss | CLL |
| 278 | chr11: 62376298-62376433 | chr11: 62376277-62376433 | CACACAGACTGCGTTCGATGAGTGTCTTCCCCCTGCCTTA (520) | CACACAGACTGCGTTCGATGCCTTGCTGTTCACCCTGATG (521) | 1 | 54 | 4.78 | 3.38E-06 | 3'ss | CLL |
| 279 | chr14: 74358911-74360478 | chr14: 74358911-74360499 | AGTTAGAATCCAAACCAGAGTGTTGTCTTTTCTCCCCCA (61) | AGTTAGAATCCAAACCAGAGCTCCTGGTACAGTTTGTTCA (62) | 0 | 26 | 4.75 | 9.14E-07 | 3'ss | CLL |
| 280 | chr11: 4104212-4104471 | chr11: 4104212-4104492 | CATAAAATTCTAACAGCTAATTCTCTTTCCTCTGTCTTCA (69) | CATAAAATTCTAACAGCTAAGCAAGCACTGAGCGAGGTGA (70) | 2 | 79 | 4.74 | 1.89E-06 | 3'ss | CLL |
| 281 | chr17: 62574712-62576906 | chr17: 62574694-62576906 | AGACCTACCAGAAGGCTATGTGTTTATTAATTTTACAGAA (39) | AGACCTACCAGAAGGCTATGAACAGAGGCAACGCAACAA (40) | 0 | 25 | 4.70 | 1.18E-02 | 3'ss | CLL |
| 282 | ch17: 76943820-76950041 | chr7: 76943806-76950041 | gtttttacctctGCCTCCTGATCTCTCATCCTAGGTTTTC (522) | GTTTTTACCTCTGCCTCCTGGTTTTCATACTCTGCACACC (523) | 1 | 49 | 4.64 | 1.80E-08 | 3'ss | CLL |
| 283 | chr20: 62701988-62703210 | chr20: 62701988-62703222 | AGAACTGCACCTACACACAGCCCTGTTCACAGGTGCAGAC (29) | AGAACTGCACCTACACACAGGTGCAGACCCGCAGCTCTGA (30) | 0 | 24 | 4.64 | 3.30E-05 | 3'ss | CLL |
| 284 | chr3: 129284872-129285369 | chr3: 129284860-129285369 | CACTGCTGGGAGAGTGGAAGTTGCTTCCACAGATTCCTGA (524) | CACTGCTGGGAGAGTGGAAGATTCCTGAGAGCTGCCGGCC (525) | 0 | 24 | 4.64 | 1.42E-07 | 3'ss | CLL |
| 285 | chr11: 33080641-33083060 | chr11: 33080641-33083075 | GATTTTGGAGAGGCAACCAACTTTGTTTTTCACAGATTCC (526) | GATTTTGGAGAGGCAACCAAATTCCCTGGACTTTGTCACC (527) | 0 | 23 | 4.58 | 1.27E-04 | 3'ss | CLL |
| 286 | chr1: 179835004-179846373 | chr1: 179834989-179846373 | TCACTCAAACAGTAAACGAGTTTTATCATTTACAGGTATG (53) | TCACTCAAACAGTAAACGAGGTATGTGACGCATTCCCAGA (54) | 0 | 23 | 4.58 | 1.48E-03 | 3'ss | CLL |

TABLE 1-continued

| | Aberrant junction | WT junction | Aberrant sequence (SEQ ID NO) | WT sequence (SEQ ID NO) | Avg WT % | Avg Ab. % | Log$_2$ Fold Diff. | FDR Q-Value | Event | Type |
|---|---|---|---|---|---|---|---|---|---|---|
| 287 | chr2: 23977668-23980287 | chr2: 23977644-23980287 | TGCAGAACTGGA TAAAGAAGTGTA TTTTTTTGTCTC AATT (528) | TGCAGAACTGGA TAAAGAAGGTGC TTCTAAAGTAAA GAAA (529) | 0 | 23 | 4.58 | 2.35E-02 | 3'ss | CLL |
| 288 | chr5: 1579622-1585098 | chr5: 1581810-1585098 | ACTCTTATGCAG TCCCCATGAGGT TATGCTTATGTT TCTC (530) | ACTCTTATGCAG TCCCCATGAGGA GATCCTAGTCTC ACCA (531) | 0 | 23 | 4.58 | 4.37E-03 | 3'ss | CLL |
| 289 | chr6: 30884736-30884871 | chr6: 30884736-30884881 | AGTGTTTTACCA TGGATGTTGTCA TTCCAGGGCTCC TCAG (532) | AGTGTTTTACCA TGGATGTTGGCT CCTCAGTGGCTG TGAC (533) | 0 | 23 | 4.58 | 2.41E-04 | 3'ss | CLL |
| 290 | chr6: 49416664-49419178 | chr6: 49416640-49419178 | TTTATGATGCTG CTTTAAAGTTTT GTTAATGTTTTT CTTT (534) | TTTATGATGCTG CTTTAAAGCTCA TTAATGAAATTG AAGA (535) | 0 | 23 | 4.58 | 1.66E-02 | 3'ss | CLL |
| 291 | chr8: 61741365-61742868 | chr8: 61741365-61742880 | ATCTAAAAACAG AAGAGCAGGTCC TTTTTTAGGTGC AAAA (536) | ATCTAAAAACAG AAGAGCAGGTGC AAAAACTTCAAG CTAT (537) | 0 | 23 | 4.58 | 3.15E-03 | 3'ss | CLL |
| 292 | chr2: 109102364-109102954 | chr2: 109102364-109102966 | AGCAAGTAGAAG TCTATAAAATTT ACCCCCAGATAC AGCT (1) | AGCAAGTAGAAG TCTATAAAATAC AGCTGGCTGAAA TAAC (2) | 2 | 68 | 4.52 | 3.76E-08 | 3'ss | CLL |
| 293 | chr15: 72859518-72862504 | chr15: 72859518-72862517 | GGATTGCAGCCA ACACAAAGTTTC TCTTCATAGGAA TGTC (538) | GGATTGCAGCCA ACACAAAGGAAT GTCCCAAATGCC ATGT (539) | 0 | 22 | 4.52 | 5.30E-05 | 3'ss | CLL |
| 294 | chr5: 109181707-109183328 | chr5: 109181707-109183357 | GGTTTCGAGTTT GAATAGTGTTTT GCTTGTTTGTTT GTTT (540) | GGTTTCGAGTTT GAATAGTGGTCA GATTGAAGTTAT CATG (541) | 0 | 22 | 4.52 | 1.57E-02 | 3'ss | CLL |
| 295 | chr9: 125759640-125760854 | chr9: 125759640-125760875 | AAATGAAGAAAC TCCTAAAGCCTC TCTCTTTCTTTG TTTA (67) | AAATGAAGAAAC TCCTAAAGATAA AGTCCTGTTTAT GACC (68) | 0 | 22 | 4.52 | 5.36E-04 | 3'ss | CLL |
| 296 | chr11: 71939542-71939690 | chr11: 71939542-71939770 | GGATGACCGGGA TGCCTCAGTCAC TTTACAGCTGCA TCGT (47) | GGATGACCGGGA TGCCTCAGATGG GGAGGATGAGAA GCCC (48) | 2 | 65 | 4.46 | 7.66E-06 | 3'ss | CLL |
| 297 | chr11: 64877395-64877934 | chr11: 64877395-64877953 | CCACCGCCATCG ACGTGCAGTACC TCTTTTTACCAC CAGG (167) | CCACCGCCATCG ACGTGCAGGTGG GGCTCCTGTACG AAGA (168) | 2 | 65 | 4.46 | 2.31E-08 | 3'ss | CLL |
| 298 | chr19: 14031735-14034130 | chr19: 14031735-14034145 | TGCCTGTGGACA TCACCAAGCCTC GTCCTCCCCAGG TGCC (59) | TGCCTGTGGACA TCACCAAGGTGC CGCCTGCCCCTG TCAA (60) | 0 | 21 | 4.46 | 1.50E-04 | 3'ss | CLL |
| 299 | chr11: 64676597-64676742 | chr11: 64676622-64676742 | CGCAAGTACTTC CTGCCCCATCCA GCAGCACACAGT GGGA (542) | CGCAAGTACTTC CTGCCCCAGGTA GTGGTGACTGTG AACC (543) | 0 | 20 | 4.39 | 2.24E-03 | 3'ss | CLL |
| 300 | chr22: 24210086-24210667 | chr22: 24204389-24210667 | TTCATAACAAAC CAGTAAATCACA TTCAGGAATTCA CCAA (544) | TCATCAATGCCC CGACCTTGCACA TTCAGGAATTCA CCAA (545) | 0 | 20 | 4.39 | 1.08E-04 | 5'ss | CLL |
| 301 | chr2: 24207701-24222524 | chr2: 24207701-24222541 | AAATTTAACATT ACTCATAGTTTT TGCTGTTTTACA GAGT (546) | AAATTTAACATT ACTCATAGAGTA AGCCATATCAAA GACT (547) | 0 | 20 | 4.39 | 2.96E-02 | 3'ss | CLL |

TABLE 1-continued

| | Aberrant junction | WT junction | Aberrant sequence (SEQ ID NO) | WT sequence (SEQ ID NO) | Avg WT % | Avg Ab. % | Log₂ Fold Diff. | FDR Q-Value | Event | Type |
|---|---|---|---|---|---|---|---|---|---|---|
| 302 | chr11: 64119858-64120198 | chr11: 64119858-64120215 | CACCGGGAGCTG CAGGGCCGCCCC TTGTCCATCCCA GGCA (548) | CACCGGGAGCTG CAGGGCCGGCAC GAGCAGCTGCAG GCCC (549) | 2 | 59 | 4.32 | 8.17E-07 | 3'ss | CLL |
| 303 | chr11: 68363686-68367788 | chr11: 68363686-68367808 | GGAGGTGGACCT GAGTGAACAATT TCTCCCCTCTTT TTAG (189) | GGAGGTGGACCT GAGTGAACCACC CAACTGGTCAGC TAAC (190) | 0 | 19 | 4.32 | 5.52E-04 | 3'ss | CLL |
| 304 | chr11: 984190-984644 | chr11: 981299-984644 | ATTGGACACAGA GATGGGATATCG TGACGTCTGCAT CCAC (550) | CTGTCTCTAGGC TAAGCAGAATCG TGACGTCTGCAT CCAC (551) | 0 | 19 | 4.32 | 5.03E-04 | 5'ss | CLL |
| 305 | chr17: 43522984-43527983 | chr17: 43523029-43527983 | GGGACCTCACCA AGCGCCCGCCCC TCATCAACCTGC AGAT (552) | GGGACCTCACCA AGCGCCCGATCT GCAGGCCAGGCCC TGAA (553) | 0 | 19 | 4.32 | 5.14E-03 | 3'ss | CLL |
| 306 | chr9: 139837449-139837800 | chr9: 139837395-139837800 | CCAAGGACTGCA CTGTGAAGGCCC CCGCCCCGCGAC CTGG (175) | CCAAGGACTGCA CTGTGAAGATCT GGAGCAACGACC TGAC (176) | 2 | 57 | 4.27 | 1.96E-04 | 3'ss | CLL |
| 307 | chr4: 56874548-56875878 | chr4: 56874548-56875900 | GAGTGTGAATCA TCTGTGAATTTC ACATCACTCATT TAAC (554) | GAGTGTGAATCA TCTGTGAACCAG CTGAAAGAAACA TTGG (555) | 2 | 56 | 4.25 | 3.01E-02 | 3'ss | CLL |
| 308 | chr5: 139815842-139818078 | chr5: 139815842-139818045 | AGCATTGCTAGA AGCAGCAGCTTT TGCAGATCCTGA GGTA (19) | AGCATTGCTAGA AGCAGCAGGAAT TGGCAAATTGTC AACT (20) | 1 | 37 | 4.25 | 3.83E-05 | 3'ss | CLL |
| 309 | chr22: 24204389-24209938 | chr22: 24204389-24210667 | TCATCAATGCCC CGACCTTGGTTC ATGAACACATTG AGGT (556) | TCATCAATGCCC CGACCTTGCACA TTCAGGAATTCA CCAA (545) | 0 | 18 | 4.25 | 3.60E-04 | 3'ss | CLL |
| 310 | chr3: 38038678-38038959 | chr3: 38038678-38038973 | GCATTTCTGAGA AGGCTCGGGTCC TCTCCCGCAGGG GCTG (557) | GCATTTCTGAGA AGGCTCGGGGGC TGGCTTTGACCT ACAG (558) | 0 | 18 | 4.25 | 3.30E-03 | 3'ss | CLL |
| 311 | chr6: 109767078-109767338 | chr6: 109767065-109767338 | GCCAGTCCAGAG CCCTCAAGTTCT TCTTCTCAGCTC TTGT (559) | GCCAGTCCAGAG CCCTCAAGCTCT TGTGGCCATGGA GAAG (560) | 1 | 36 | 4.21 | 6.38E-07 | 3'ss | CLL |
| 312 | chr1: 16803042-16803424 | chr1: 16802999-16803424 | TGGCCGAGGCGC TGACCAAGACCT TACTCAGGGGAT CCTC (561) | TGGCCGAGGCGC TGACCAAGGCTG AGGGCAGAGGAG GCCT (562) | 2 | 54 | 4.20 | 1.35E-04 | 3'ss | CLL |
| 313 | chr2: 103348885-103353104 | chr2: 103348868-103353104 | TCTACTTGGTGG GCTTCTTGCATT TATTTTGTTTTA GGAT (563) | TCTACTTGGTGG GCTTCTTGGATT TGTTTGGTGTCA GCAT (564) | 3 | 72 | 4.19 | 1.68E-04 | 3'ss | CLL |
| 314 | chr14: 78203438-78205120 | chr14: 78203418-78205120 | GCTCCTGCTCAG TATATCCGTTTT TATCTGCTTTCT TCAG (565) | GCTCCTGCTCAG TATATCCGATAC ACACCATCTCAG CAAG (566) | 0 | 17 | 4.17 | 3.99E-04 | 3'ss | CLL |
| 315 | chr3: 122152652-122156016 | chr3: 122152635-122156016 | GAAATAGGGCAC AGATCCAGTTTT TCTTTAATTTTA GACT (567) | GAAATAGGGCAC AGATCCAGACTG TGATAGATGCCA ACAT (568) | 0 | 17 | 4.17 | 7.71E-03 | 3'ss | CLL |
| 316 | chr18: 33724997-33725896 | chr18: 33724997-33725910 | GCAACCTGTGTT TTACAAAGGTTT TATTTTTTAGAT GGTG (569) | GCAACCTGTGTT TTACAAAGATGG TGTCCTACAGCA GCCA (570) | 1 | 33 | 4.09 | 3.11E-03 | 3'ss | CLL |

TABLE 1-continued

| | Aberrant junction | WT junction | Aberrant sequence (SEQ ID NO) | WT sequence (SEQ ID NO) | Avg WT % | Avg Ab. % | Log$_2$ Fold Diff. | FDR Q-Value | Event | Type |
|---|---|---|---|---|---|---|---|---|---|---|
| 317 | chr7: 94157562- 94162500 | chr7: 94157562- 94162516 | GTATCAAAGTGT GGACTGAGATTT GTCTTCCTTTAG GATT (27) | GTATCAAAGTGT GGACTGAGGATT CCATTGCAAAGC CACA (28) | 1 | 33 | 4.09 | 4.37E-04 | 3'ss | CLL |
| 318 | chr4: 39868635- 39871013 | chr4: 39868617- 39871013 | CCCCTGAAGTAC TAGCAAAGCATG TTAATATTTTAT AGGT (571) | CCCCTGAAGTAC TAGCAAAGGTAC AGGCAATTAAAC TTCT (572) | 0 | 16 | 4.09 | 1.12E-04 | 3'ss | CLL |
| 319 | chr10: 99502921- 99504468 | chr10: 99502921- 99504485 | GTTCCTCACTTT GAATGAGGTGTT TTTGATTCTGCA GGTG (573) | GTTCCTCACTTT GAATGAGGGTGC ATGGTACTCAGT AGGT (574) | 1 | 31 | 4.00 | 1.17E-04 | 3'ss | CLL |
| 320 | chr1: 226036315- 226036597 | chr1: 226036255- 226036597 | TCAGCCCTCTGA ACTACAAAGGTG TTTGTTCACAGA GATC (93) | TCAGCCCTCTGA ACTACAAAACAG AAGAGCCTGCAA GTGA (94) | 0 | 15 | 4.00 | 6.99E-03 | 3'ss | CLL |
| 321 | chr20: 31983014- 31984566 | chr20: 31982922- 31984566 | TCTTGGAAGGCA GAGAAAAGATAT TTCTAGAGCATT TGGG (575) | TCTTGGAAGGCA GAGAAAGTCTA CCTCGAGACCTA TGGC (576) | 0 | 15 | 4.00 | 4.25E-03 | 3'ss | CLL |
| 322 | chr2: 64456774- 64456978 | chr2: 64456774- 64478252 | AACCCGGAGAGA AAAGGGAGTTTG TTTTTAGGTCAG AGTC (577) | AACCCGGAGAGA AAAGGGAGCAAC TGATGTTGCCAT GCAG (578) | 0 | 15 | 4.00 | 5.64E-03 | 3'ss | CLL |
| 323 | chr11: 92887382- 92895871 | chr11: 92887443- 92895871 | AATCTTCCCGAA GATGTATGTTCT ATGTTCCAGCAG AGAT (579) | AATCTTCCCCAA GATGTATGGTTA TATCAATCAGTG AAAA (580) | 1 | 30 | 3.95 | 7.37E-04 | 3'ss | CLL |
| 324 | chr18: 43459192- 43460039 | chr18: 43459179- 43460039 | CTCTCTTGTCAG ACAAGCAGTTGT CTCTTCCAGGTA ATGG (581) | CTCTCTTGTCAG ACAAGCAGGTAA TGGAGACTATAC AGTG (582) | 1 | 30 | 3.95 | 2.23E-02 | 3'ss | CLL |
| 325 | chr5: 138724290- 138725368 | chr5: 138724274- 138725368 | GCAGAGCTGTGG CTTACCAGTCCC TCCTTGTTCCAG ATGT (583) | GCAGAGCTGTGG CTTACCAGATGT GGCAAAATCTGG CAAA (584) | 1 | 30 | 3.95 | 1.23E-03 | 3'ss | CLL |
| 326 | chr17: 58163509- 58165557 | chr17: 58163487- 58165557 | TGCAGGAGACCG GCTTTTGGGTCC CCTTCTTATACC CCTC (585) | TGCAGGAGACCG GCTTTTGGATAC TGCTAATCAGTC CTAG (586) | 1 | 29 | 3.91 | 7.83E-03 | 3'ss | CLL |
| 327 | chr1: 185056772- 185060696 | chr1: 185056772- 185060710 | AGTTACAACGAA CACCTCAGTGAC TCTTTTACAGGA GGCA (162) | AGTTACAACGAA CACCTCAGGAGG CAATAACAGATG GCTT (163) | 1 | 29 | 3.91 | 2.95E-05 | 3'ss | CLL |
| 328 | chr10: 99219232- 99219415 | chr10: 99219283- 99219415 | TCTTGCCAGAGC TGCCCACGCTCT CCACCCTCAGCT GCCT (587) | TCTTGCCAGAGC TGCCCACGCTTC TTTTCCTTGCTGC TGGA (588) | 0 | 14 | 3.91 | 5.04E-05 | 3'ss | CLL |
| 329 | chr4: 152022314- 152024139 | chr4: 152022314- 152024022 | CCATGGTCAAAA AATGGCAGCACC AACAGGTCCGCC AAAT (344) | CCATGGTCAAAA AATGGCAGACAA TGATTGAAGCTC ACGT (345) | 0 | 14 | 3.91 | 4.36E-02 | 3'ss | CLL |
| 330 | chr1: 212515622- 212519131 | chr1: 212515622- 212519144 | ATCAGAAATTCG TACAACAGGTTT CTTTTAAAGCTC CTGG (65) | ATCAGAAATTCG TACAACAGCTCC TGGAGCTTTTTG ATAG (66) | 3 | 57 | 3.86 | 4.89E-06 | 3'ss | CLL |
| 331 | chr1: 156552962- 156553113 | chr1: 156552962- 156553129 | GCAGGCTGCCCG GGACTCTGGCTC TCTTTCTCTCAG GGGA (589) | GCAGGCTGCCCG GGACTCTGGGGA CATGAAGGGACA GTGG (590) | 4 | 69 | 3.81 | 2.04E-07 | 3'ss | CLL |

TABLE 1-continued

| | Aberrant junction | WT junction | Aberrant sequence (SEQ ID NO) | WT sequence (SEQ ID NO) | Avg WT % | Avg Ab. % | Log₂ Fold Diff. | FDR Q-Value | Event | Type |
|---|---|---|---|---|---|---|---|---|---|---|
| 332 | chr6: 109767165- 109767338 | chr6: 109767065- 109767338 | GCCAGTCCAGAG CCCTCAAGTCTT TACCAGACTTGC AGGG (591) | GCCAGTCCAGAG CCCTCAAGCTCT TGTGGCCATGGA GAAG (560) | 2 | 41 | 3.81 | 4.40E-03 | 3'ss | CLL |
| 333 | chr20: 34144042- 34144725 | chr20: 34144042- 34144743 | ACATGAAGGTGG ACGGAGAGGCTC CCCTCCCACCCC AGGT (49) | ACATGAAGGTGG ACGGAGAGGTAC TGAGGACAAATC AGTT (50) | 5 | 81 | 3.77 | 1.48E-08 | 3'ss | CLL |
| 334 | chr17: 7131030- 7131295 | chr17: 7131102- 7131295 | CTATTTCACTCT CCCCCGAACCTA TCCAGGTTCCTC CTCC (33) | CTATTTCACTCT CCCCCGAAATGA GCCCATCCAGCC AATT (34) | 1 | 25 | 3.70 | 2.79E-05 | 3'ss | CLL |
| 335 | ch16: 110085185- 110086201 | ch16: 110085185- 110086215 | TTCCCACTGGTC GCCTGCAGGTAT TTCTCTTTAGAC TGGC (592) | TTCCCACTGGTC GCCTGCAGACTG GCATCCTTCGAA CCAA (593) | 1 | 25 | 3.70 | 3.91E-03 | 3'ss | CLL |
| 336 | chr7: 889240- 889468 | chr7: 889240- 889559 | TGTAAATGGGGA AGCGCTGTTTTC TACAGACTGCCA TTGC (594) | TGTAAATGGGGA AGCGCTGTGCGA CGACTGTAAGGG CAAG (595) | 1 | 25 | 3.70 | 2.18E-05 | 3'ss | CLL |
| 337 | chr12: 112915534- 112915638 | chr12: 112915534- 112915660 | TCAATGCAAATA TCATCATGGATT TTCTTCCTAAAT TTCT (596) | TCAATGCAAATA TCATCATGCCTG AATTTGAAACCA AGTG (597) | 0 | 12 | 3.70 | 1.92E-03 | 3'ss | CLL |
| 338 | chr14: 56100059- 56101230 | chrU: 56100059- 56101243 | ACAAATCAACTG GAAAGCAATTAC TGTTTTCAGGCA GTCT (598) | ACAAATCAACTG GAAAGCAAGCAG TCTGCAGAACTA AATA (599) | 0 | 12 | 3.70 | 1.38E-03 | 3'ss | CLL |
| 339 | chr17: 2266428- 2266727 | chr17: 2266428- 2266758 | CAAAGCGCCCAG CCCTGGGGGCTG GAGGCTGAGCCC CGGC (600) | CAAAGCGCCCAG CCCTGGGGATCC GGAAACGGCACT CAAG (601) | 0 | 12 | 3.70 | 2.10E-02 | 3'ss | CLL |
| 340 | chr19: 16264018- 16265158 | chr19: 16264018- 16265208 | TGACACAGCCCT GCAGGCAGGACC TTTCCCCCTCCC TAGT (602) | TGACACAGCCCT GCAGGCAGAAGG ATCCCGCAAACG TGGA (511) | 0 | 12 | 3.70 | 4.53E-05 | 3'ss | CLL |
| 341 | chr1: 186324917- 186325417 | chr1: 186324900- 186325417 | AGTTGCCATTCC ATTACATGTCTT TACTTTCCTGAA GCTT (603) | AGTTGCCATTCC ATTACATGCTTC AAGCTTAGATGA TGTT (604) | 0 | 12 | 3.70 | 4.52E-03 | 3'ss | CLL |
| 342 | chr3: 56649300- 56649931 | chr3: 56649300- 56649949 | ACTGATTAAAAA TCTTGGTGGTGA TTTCTCTTTGCC AGTT (605) | ACTGATTAAAAA TCTTGGTGTTGA TACAATACAAAT GGAA (606) | 4 | 62 | 3.66 | 9.33E-05 | 3'ss | CLL |
| 343 | chr6: 10723474- 10724788 | chr6: 10723474- 10724802 | CCGGGGCCTTCG TGAGACCGCTTG TTTTCTGCAGGT GCAG (95) | CCGGGGCCTTCG TGAGACCGGTGC AGGCCTGGGGTA GTCT (96) | 4 | 58 | 3.56 | 3.53E-06 | 3'ss | CLL |
| 344 | chr3: 184587316- 184588487 | chr3: 184587316- 184588503 | AGGCTATTGTTG CAGACCGGGCTG TTTTCCTTACAG ATGG (607) | AGGCTATTGTTG CAGACCGGATGG TAGAAATCCTAT TCCA (608) | 1 | 22 | 3.52 | 2.36E-03 | 3'ss | CLL |
| 345 | chr4: 3124663- 3125976 | chr4: 3124663- 3127275 | CCTTTCAAGAAA ACAAAAAGTCGC TTTTTCCAGTGG CGGT (609) | CCTTTCAAGAAA ACAAAAAGGCAA AGTGCTCTTAGG AGAA (610) | 1 | 22 | 3.52 | 1.60E-02 | 3'ss | CLL |
| 346 | chr9: 123933826- 123935634 | chr9: 123933826- 123935520 | ACACGGAGCTCA AGAAACAGTTTC TTCCAGAACTAC CAGC (611) | ACACGGAGCTCA AGAAACAGATGG CAAACCAAAAAG ATTT (612) | 2 | 33 | 3.50 | 1.45E-05 | 3'ss | CLL |

TABLE 1-continued

| | Aberrant junction | WT junction | Aberrant sequence (SEQ ID NO) | WT sequence (SEQ ID NO) | Avg WT % | Avg Ab. % | Log$_2$ Fold Diff. | FDR Q-Value | Event | Type |
|---|---|---|---|---|---|---|---|---|---|---|
| 347 | chr19: 5595521-5598803 | chr19: 5595508-5598803 | CAAGCAGGTCCA AAGAGAGATTTT GGTAAACAGAGC TCCA (138) | CAAGCAGGTCCA AAGAGAGAAGCT CCAAGAGTCAGG ATCG (139) | 6 | 76 | 3.46 | 9.28E-05 | 3'ss | CLL |
| 348 | chr5: 78608321-78610192 | chr5: 78608321-78610079 | GACTTCGAACAT TTAAACAGTGTG TTACAGGTAGAA GAGA (613) | GACTTCGAACAT TTAAACAGAGGT ATCCTGGGCAAG TCAT (614) | 4 | 54 | 3.46 | 7.66E-03 | 3'ss | CLL |
| 349 | chr2: 231050873-231065600 | chr2: 231050859-231065600 | ACCACGAAGGGT CACACAAGTCTA TTTGGTCCAGGG GCAG (615) | ACCACGAAGGGT CACACAAGGGGC AGCCTCACCTGG GCAT (616) | 2 | 32 | 3.46 | 1.25E-02 | 3'ss | CLL |
| 350 | chr1: 52880319-52880412 | chr1: 52880319-52880433 | CGATCTCCCAAA AGGAGAAGTCTG ACCAGTCTTTTC TACA(55) | CGATCTCCCAAA AGGAGAACCCC TCCCCTCGCCGA GAAA{56) | 1 | 21 | 3.46 | 1.57E-05 | 3'ss | CLL |
| 351 | chr2: 69015785-69034404 | chr2: 69015088-69034404 | TTAACAAACACG TGAATCTACAGT GTTTGGCCAGCG CTTG{617) | TGCTGGCACACC CTGTGGAGCAGT GTTTGGCCAGCG CTTG{618) | 0 | 10 | 3.46 | 8.22E-03 | 5'ss | CLL |
| 352 | chr5: 156915521-156916109 | chr5: 156915497-156916109 | CGCCCCAGGGCA AGCGAAAGGTGT TCCTTGACTTGT GCGT (619) | CGCCCCAGGGCA AGCGAAAGGTGA TCAACACTCCGG AAAT{620) | 0 | 10 | 3.46 | 1.97E-03 | 3'ss | CLL |
| 353 | chr9: 115934002-115935732 | chr9: 115933986-115935732 | TGGTACAACTTC AGGAAAAGTCTG TTTGTTTTGCAG TGTT(621) | TGGTACAACTTC AGGAAAAGTGTT TAGCCCTCCAGG CCCA(622) | 0 | 10 | 3.46 | 6.70E-03 | 3'ss | CLL |
| 354 | chr14: 50808004-50808849 | chr14: 50807950-50808849 | TGGATTTGCTCG gcttttgattt GATTCCAGCCTT CCGC{623) | TGGATTTGCTCG GCTTTTGACTGG ACCGAGTGACTA CTAT{624) | 1 | 20 | 3.39 | 1.52E-04 | 3'ss | CLL |
| 355 | chr18: 9133520-9136361 | chr18: 9133508-9136361 | GATGAGGACCCC CACATAGGTTTC CAAACCAGGATG GCCA{625) | GATGAGGACCCC CACATAGGGATG GCCATAGCAGCC ACAA{626) | 5 | 61 | 3.37 | 3.06E-06 | 3'ss | CLL |
| 356 | chr10: 99214556-99215395 | chr10: 99214556-99215416 | TACCTCTGGTTC CTGTGCAGTCTT CGCCCCTCTTTT CTTA{13) | TACCTCTGGTTC CTGTGCAGTTCT GTGGCACTTGCC CTGG{14) | 3 | 39 | 3.32 | 2.21E-05 | 3'ss | CLL |
| 357 | chr2: 225670231-225670842 | chr2: 225670246-225670842 | TGTTTTAAATTC CATAGCAGCTAT TTCTACAGTAAA CCAT{627) | TGTTTTAAATTC CATAGCAGCATT TTCATCAATAGC TATT{628) | 2 | 29 | 3.32 | 8.44E-06 | 3'ss | CLL |
| 358 | chrX: 153323986-153357641 | chrX: 153298008-153357641 | GCTGGGATGTTA GGGCTCAGCCTG TCGTTCCAGGAC CCAG{629) | GCTGGGATGTTA GGGCTCAGGGAA GAAAAGTCGAAA GACC{630) | 1 | 19 | 3.32 | 2.06E-02 | 3'ss | CLL |
| 359 | chr16: 72139523-72139882 | chr16: 72139523-72139903 | CTGGTTATTGCA AATTAAAGCTCT TTGCCGTCCCCT CCTA{631) | CTGGTTATTGCA AATTAAAGGTCT TCAACCCCAGGA TTGG{632) | 0 | 9 | 3.32 | 6.10E-05 | 3'ss | CLL |
| 360 | chr5: 869519-870587 | chr5: 865696-870587 | CTCCATGCTCAG CTCTCTGGTTTC TTTCAGGGCCTG CCAT{128) | CTCCATGCTCAG CTCTCTGGGGAA GGTGAAGAAGGA GCTG{129) | 4 | 48 | 3.29 | 1.01E-06 | exon incl. | CLL |
| 361 | chrX: 70516897-70517210 | chrX: 70516897-70517226 | GGTCATGCTAAT GAGACAGGTCTG TTGTTTTTTAG ATTT{633) | GGTCATGCTAAT GAGACAGGATTT GATGAGGCGCCA AGAA{634) | 8 | 82 | 3.21 | 5.22E-07 | 3'ss | CLL |

TABLE 1-continued

| | Aberrant junction | WT junction | Aberrant sequence (SEQ ID NO) | WT sequence (SEQ ID NO) | Avg WT % | Avg Ab. % | Log$_2$ Fold Diff. | FDR Q-Value | Event | Type |
|---|---|---|---|---|---|---|---|---|---|---|
| 362 | chr16: 47347747-47399698 | chr16: 47347734-47399698 | GTCAGCATTTGC AGACTTTGTTTC TTTTGGCAGATG GAGA{635} | GTCAGCATTTGC AGACTTTGATGG AGATGGACACAT GGAT{636} | 2 | 26 | 3.17 | 7.43E-04 | 3'ss | CLL |
| 363 | chr5: 138725125-138725368 | chr5: 138724274-138725368 | GCAGAGCTGTGG CTTACCAGACTT CTCCCTTTCCAG GCCC{637} | GCAGAGCTGTGG CTTACCAGATGT GGCAAAATCTGG CAAA{584} | 2 | 26 | 3.17 | 1.17E-03 | 3'ss | CLL |
| 364 | chr11: 62648919-62649352 | chr11: 62648919-62649364 | CGGCGCGGGCAA CCTGGCGGCCCC CATTTCAGGTCT GAAG (165) | CGGCGCGGGCAA CCTGGCGGGTCT GAAGGGGCGTCT CGAT (166) | 0 | 8 | 3.17 | 6.70E-03 | 3'ss | CLL |
| 365 | chr11: 64002365-64002911 | chr11: 64002365-64002929 | TGCAGCTGGCCC CCGCCCAGGTCT TTTCTCTCCCAC AGGC (638) | TGCAGCTGGCCC CCGCCCAGGCCC CTGTCTCCCAGC CTGA (639) | 0 | 8 | 3.17 | 2.22E-02 | 3'ss | CLL |
| 366 | chr14: 31169464-31171484 | chrU: 31169464-31171501 | CACAGCAAGCAC CTTCTGAGTTCT TTTCTTATTTCA GGCT (640) | CACAGCAAGCAC CTTCTGAGGCTG ATTTGGAGCAAT ATAA (641) | 0 | 8 | 3.17 | 3.01E-05 | 3'ss | CLL |
| 367 | chr1: 186300728-186301326 | chr1: 186300711-186301326 | TCACACCTGTAG GAACTGAGTGTA TTATGATACAGG AAGA (642) | TCACACCTGTAG GAACTGAGGAAG AAGTTATGGCAG AAGA (643) | 0 | 8 | 3.17 | 9.33E-05 | 3'ss | CLL |
| 368 | chr5: 169101449-169108733 | chr5: 169101449-169108747 | AAAATTGACTAT GGCAACAATTTT TGCTTTACAGAA TCCT (644) | AAAATTGACTAT GGCAACAAAATC CTTGAGCTTGAT TTGA (645) | 0 | 8 | 3.17 | 7.30E-03 | 3'ss | CLL |
| 369 | chr9: 123933826-123935644 | chr9: 123933826-123935520 | ACACGGAGCTCA AGAAACAGAACT ACCAGCAGATCT AGAA (646) | ACACGGAGCTCA AGAAACAGATGG CAAACCAAAAAG ATTT (612) | 0 | 8 | 3.17 | 5.42E-04 | 3'ss | CLL |
| 370 | chr10: 112058568-112060304 | chr10: 112058548-112060304 | GGGAGGAAAAGT AATTAATGTTTT TGTTTTTCTTTT TTAG (647) | GGGAGGAAAAGT AATTAATGGAAG TTATAGAACTAA CCAA (648) | 5 | 52 | 3.14 | 1.27E-03 | 3'ss | CLL |
| 371 | chr3: 196792335-196792578 | chr3: 196792319-196792578 | ATTTGGATCCTG TGTTCCTCTTTT TTTCTGTTAAAG ATAC (87) | ATTTGGATCCTG TGTTCCTCATAC AACTAGACCAAA ACGA (88) | 4 | 43 | 3.14 | 1.46E-04 | 3'ss | CLL |
| 372 | chr12: 105601825-105601935 | chr12: 105601807-105601935 | ATTTGGACTCGC TAGCAATGATGT CTGTTTATTTTT AGAG (41) | ATTTGGACTCGC TAGCAATGAGCA TGACCTCTCAAT GGCA (42) | 3 | 34 | 3.13 | 1.20E-04 | 3'ss | CLL |
| 373 | chr19: 41084118-41084353 | chr19: 41084118-41084367 | CTATGGGCTCAC TCCTCTGGTCCT CCTGTTGCAGTT CGTC (169) | CTATGGGCTCAC TCCTCTGGTTCG TCGCCTGCAGCT TCGA (170) | 7 | 67 | 3.09 | 2.90E-04 | 3'ss | CLL |
| 374 | chr11: 125442465-125445146 | chr11: 125442465-125445158 | TTCTCCAGGACC TTGCCAGACCTT TTCTATAGGGAA TCAA (150) | TTCTCCAGGACC TTGCCAGAGGAA TCAAAGACTCCA TCTG (151) | 1 | 16 | 3.09 | 4.69E-03 | 3'ss | CLL |
| 375 | chr12: 110437589-110449795 | chr12: 110437589-110449809 | AGAAGGAGCTGC AGGGCCAGTGTT TCCTTCACAGAA TGTG (649) | AGAAGGAGCTGC AGGGCCAGAATG TGGAGGCTGTGG ACCC (650) | 1 | 16 | 3.09 | 2.88E-03 | 3'ss | CLL |
| 376 | chr8: 126051218-126052036 | chr8: 126051201-126052036 | GCTCTGGAGAAT CTCAATAAGGTT TTTCTTCCTTTA GGGC (651) | GCTCTGGAGAAT CTCAATAAGGCT CTCCTAGAGCAC ATTG (652) | 4 | 41 | 3.07 | 6.90E-07 | 3'ss | CLL |

TABLE 1-continued

| | Aberrant junction | WT junction | Aberrant sequence (SEQ ID NO) | WT sequence (SEQ ID NO) | Avg WT % | Avg Ab. % | Log$_2$ Fold Diff. | FDR Q-Value | Event | Type |
|---|---|---|---|---|---|---|---|---|---|---|
| 377 | chr3: 42674315-42675109 | chr3: 42674315-42675071 | CATGCAATGAACCCAAAAGGTTGATTCCAGTGCTAAAAGG (653) | CATGCAATGAACCCAAAAGGTCACTCTGAGAGGAGTGATA (654) | 2 | 24 | 3.06 | 7.00E-06 | 3'ss | CLL |
| 378 | chr5: 139941307-139941428 | chr5: 139941286-139941428 | TGCTTCCGGAACAGTGACAGCCCCATCTCTGCCCCTGCTA (655) | TGCTTCCGGAACAGTGACAGGGACTTCGCTTTTGTGGCAA (656) | 6 | 57 | 3.05 | 3.26E-05 | 3'ss | CLL |
| 379 | chr12: 64199184-64202434 | chr12: 64199184-64202454 | TGGGTTTCAGCAAGAGAACATTGTTTTTCTGATTTTCTAG (657) | TGGGTTTCAGCAAGAGAACACTGGCAGCCTCAGGAAACAA (658) | 0 | 7 | 3.00 | 4.31E-03 | 3'ss | CLL |
| 380 | chr18: 47311742-47313660 | chr18: 47311721-47313660 | AGGACATGGATTTGGTAGAGTGCTCTAATTTTTGTTTTAA (659) | AGGACATGGATTTGGTAGAGGTGAATGAAGCTTTTGCTCC (660) | 0 | 7 | 3.00 | 4.13E-03 | 3'ss | CLL |
| 381 | chr19: 15491444-15507960 | chr19: 15491423-15507960 | ATCACAACCGGAACCGCAGGCTCCTTCTGCCCTGCCCGCA (661) | ATCACAACCGGAACCGCAGGCTCATGATGGAGCAGTCCAA (662) | 0 | 7 | 3.00 | 2.46E-02 | 3'ss | CLL |
| 382 | chr1: 46068037-46070588 | chr1: 46068037-46070607 | CAGGAAGCAGCTagtcttttatgtTTATTCTCTTTGTAGA (663) | CAGGAAGCAGCTAGTCTTTTAGGTAAGAAGTATGGAGAGA (664) | 0 | 7 | 3.00 | 7.09E-04 | 3'ss | CLL |
| 383 | chr21: 45452053-45452682 | chr21: 45452053-45457672 | GAACCAATGGAATGGAGAAGGCACAGGCGTTTTGCAAAGG (665) | GAACCAATGGAATGGAGAAGGTCCTATGGCCGGGCTCCGA (666) | 0 | 7 | 3.00 | 1.40E-02 | 3'ss | CLL |
| 384 | chr2: 160673561-160676236 | chr2: 160673543-160676236 | TGCTTGTAAAATTGAAATGGTGCTTTTAATTATTATAGTT (667) | TGCTTGTAAAATTGAAATGGTTGACTACAAAGAAGAATAT (668) | 0 | 7 | 3.00 | 1.13E-02 | 3'ss | CLL |
| 385 | chr5: 150411955-150413168 | chr5: 150411944-150413168 | ACTCGCGCCTCTTCCATCTGTTTTGTCGCAGCCGGAATAC (109) | ACTCGCGCCTCTTCCATCTGCCGGAATACACCTGGCGTCT (110) | 0 | 7 | 3.00 | 4.59E-02 | 3'ss | CLL |
| 386 | ch17: 99954506-99955853 | chr7: 99954506-99955842 | CCACCTCACCATCACCCAGGCCCCTCCACAGGGCCCCTCT (669) | CCACCTCACCATCACCCAGGCCCTCAGGCAGCCCCTCCAC (515) | 0 | 7 | 3.00 | 2.08E-02 | 3'ss | CLL |
| 387 | chr4: 995351-995438 | chr4: 995351-995466 | CGTCTCCATGACCATGCAAGGTGTAGACGCAGTGCTCCCC (670) | CGTCTCCATGACCATGCAAGGCTTCCTGAACTACTACGAT (671) | 6 | 54 | 2.97 | 7.33E-05 | 3'ss | CLL |
| 388 | chr15: 75131104-75131350 | chr15: 75131086-75131350 | AGGAGGCAATTAAGGCAAAGGCCCTTTCCCTGCTACAGGT (672) | AGGAGGCAATTAAGGCAAAGGTGGGGCAGTACGTGTCCCG (673) | 8 | 68 | 2.94 | 1.81E-04 | 3'ss | CLL |
| 389 | chrX: 153699660-153699819 | chrX: 153699660-153699830 | TACAAGAGCTGGGTGGAGAGGGTCCCAACAGGTATTATCG (158) | TACAAGAGCTGGGTGGAGAGGTATTATCGAGACATTGCAA (159) | 2 | 22 | 2.94 | 1.26E-04 | 3'ss | CLL |
| 390 | chr9: 125023777-125026993 | chr9: 125023787-125026993 | CACCACGCCGAGGCCACGAGACATTGATGGAAGCAGAAAC (142) | CACCACGCCGAGGCCACGAGTATTCATAGACATTGATGG (143) | 5 | 43 | 2.87 | 3.76E-08 | 3'ss | CLL |
| 391 | chr14: 23242937-23243141 | chr14: 23242925-23243141 | TTACCTCCGAAGGATCGTGGTTCTCTTTGTAGGGTCTGCC (674) | TTACCTCCGAAGGATCGTGGGGTCTGCCACAAGGTACCTC (675) | 10 | 79 | 2.86 | 3.40E-05 | 3'ss | CLL |

TABLE 1-continued

| | Aberrant junction | WT junction | Aberrant sequence (SEQ ID NO) | WT sequence (SEQ ID NO) | Avg WT % | Avg Ab. % | Log$_2$ Fold Diff. | FDR Q-Value | Event | Type |
|---|---|---|---|---|---|---|---|---|---|---|
| 392 | chr11: 67376193-67376896 | chr11: 67376193-67376922 | AATAAGCCCTCAGATGGCAGCCTGTCTGACCTGTGGGCCC (676) | AATAAGCCCTCAGATGGCAGGCCCAAGTATCTGGTGGTGA (677) | 0 | 6 | 2.81 | 1.66E-02 | 3'ss | CLL |
| 393 | chr16: 56403209-56419830 | chr16: 56403239-56419830 | ACTCCCAGCTCAATGCAATGGTTCCATACCATCTGGTACT (332) | ACTCCCAGCTCAATGCAATGGCTCATCAGATTCAAGAGAT (333) | 0 | 6 | 2.81 | 1.49E-02 | 3'ss | CLL |
| 394 | chr17: 43316432-43317875 | chr17: 43316432-43317842 | GCCTGGACCTGTACTTGGAGGTGCAGATCCAGGCGTACCT (678) | GCCTGGACCTGTACTTGGAGAGGCTTCGGCTCACCGAGAG (679) | 0 | 6 | 2.81 | 4.26E-02 | 3'ss | CLL |
| 395 | chr21: 47655360-47656742 | chr21: 47655340-47656742 | CTGTAACTACTAGCCCACAGTTTCTTTTTTATTCAAATAG (680) | CTGTAACTACTAGCCCACAGAGTGACATGATGAGGGAGCA (681) | 0 | 6 | 2.81 | 3.47E-04 | 3'ss | CLL |
| 396 | chr3: 71019345-71019886 | chr3: 71015207-71019886 | CTCTCAATGCAGCTTTACAGTTTTCCTGCAGATTGTTCAA (682) | CTCTCAATGCAGCTTTACAGGCTTCAATGGCTGAGAATAG (683) | 0 | 6 | 2.81 | 1.49E-03 | 3'ss | CLL |
| 397 | chr9: 95007367-95009658 | chr9: 95007353-95009658 | GGAGCAGTTCCAGAAGACTGCTGCTTCTCCATAGGGACCA (684) | GGAGCAGTTCCAGAAGACTGGGACCATTGTTGTGGAAGGC (685) | 0 | 6 | 2.81 | 4.44E-03 | 3'ss | CLL |
| 398 | chrX: 48340103-48340769 | chrX: 48340103-48340796 | CCTGCTGGACCATTCTTACGTTGTCTCCCCCTGTTCCTAA (686) | CCTGCTGGACCATTCTTACGATTTCAACCAGCTGGATGGT (687) | 0 | 6 | 2.81 | 1.25E-02 | 3'ss | CLL |
| 399 | chr20: 36631195-36634598 | chr20: 36631178-36634598 | GGATTTTGATAATGAAGAAGTTGTGCTCTTTTTCCAGAGG (688) | GGATTTTGATAATGAAGAAGAGGAACAGTCAGTCCCTCCC (689) | 7 | 53 | 2.75 | 1.01E-03 | 3'ss | CLL |
| 400 | chr4: 995351-995433 | chr4: 995351-995466 | CGTCTCCATGACCATGCAAGGGCAGGTGTAGACGCAGTGC (690) | CGTCTCCATGACCATGCAAGGCTTCCTGTAACTACTACGAT (671) | 3 | 26 | 2.75 | 5.89E-04 | 3'ss | CLL |
| 401 | chr15: 25213229-25219533 | chr15: 25213229-25219457 | TGATTCCAAGCAAAAACCAGCCTTCCCCTAGGTCTTCAGA (230) | TGATTCCAAGCAAAAACCAGGCTCCATCTACTCTTTGAAG (231) | 2 | 19 | 2.74 | 3.63E-05 | 3'ss | CLL |
| 402 | chr18: 47811617-47812118 | chr18: 47811721-47812118 | AGTGCCAGCTGCGGGCCCGGCTCTCACCAGTGACGCCCTC (691) | AGTGCCAGCTGCGGGCCCGGGAATCGTACAAGTACTTCCC (692) | 2 | 19 | 2.74 | 1.04E-03 | exon skip | CLL |
| 403 | chr18: 66356291-66358531 | chr18: 66355002-66358531 | AACTTACTTTGTTTATGATGCTTTTATTTTAGATTCAGAG (693) | AACTTACTTTGTTTATGATGAGTATGAAGATGGTGATCTG (694) | 2 | 19 | 2.74 | 1.46E-04 | 3'ss | CLL |
| 404 | chr21: 37416267-37417879 | chr21: 37416254-37417879 | ATCATAGCCCACATGTCCAGTTTTTCTTTCTAGGTAAAAG (695) | ATCATAGCCCACATGTCCAGGTAAAAGCAGCGTTTAATGA (696) | 3 | 25 | 2.7 | 2.17E-02 | 3'ss | CLL |
| 405 | chrX: 118923962-118925536 | chrX: 118923974-118925536 | TGACTCCGCTGCTCGCCATGACTTTCAGGATTAAGCGATT (697) | TGACTCCGCTGCTCGCCATGTCTTCTCACAAGACTTTCAG (698) | 1 | 12 | 2.7 | 2.07E-02 | 3'ss | CLL |
| 406 | chr1: 100606070-100606400 | chr1: 100606070-100606522 | CCAAGCACCTGAAACAGCAGTTTGCAGGCTTCTATTTTAG (699) | CCAAGCACCTGAAACAGCAGATGCTGAAAAAGTTCACTTC (700) | 7 | 50 | 2.67 | 1.87E-03 | 3'ss | CLL |

TABLE 1-continued

| | Aberrant junction | WT junction | Aberrant sequence (SEQ ID NO) | WT sequence (SEQ ID NO) | Avg WT % | Avg Ab. % | Log₂ Fold Diff. | FDR Q-Value | Event | Type |
|---|---|---|---|---|---|---|---|---|---|---|
| 407 | chr12: 113346629-113348840 | chr12: 113346629-113348855 | GCCTGCCTTTGA TGCCCTGGATTT TGCCCGAACAGG TCAG (71) | GCCTGCCTTTGA TGCCCTGGGTCA GTTGACTGGCGG CTAT (72) | 13 | 88 | 2.67 | 1.74E-07 | 3'ss | CLL |
| 408 | ch17: 149547427-149549949 | chr7: 149547427-149556510 | CGAGCTGTTGGC ATCCTTGGTTTC TTGTCCACAGGA GAAG (701) | CGAGCTGTTGGC ATCCTTGGGACC TGCCGCTGCCAA GCCA (702) | 7 | 49 | 2.64 | 2.27E-05 | 3'ss | CLL |
| 409 | chr11: 126142974-126143210 | chr11: 126142974-126143230 | GCTTTCTACGGA ACATCAATGAGC TTCTGTCTGCAC ACAG (703) | GCTTTCTACGGA ACATCAATGAGT ACCTGGCCGTAG TCGA (704) | 3 | 24 | 2.64 | 1.08E-04 | 3'ss | CLL |
| 410 | chr8: 38095145-38095624 | chr8: 38095145-38095606 | TTATTTTACACA ATCCAAAGCCAG TTGCAGGGTCTG ATGA (57) | TTATTTTACACA ATCCAAAGCTTA TGGTGCATTACC AGCC (58) | 3 | 24 | 2.64 | 2.89E-05 | 3'ss | CLL |
| 411 | chr12: 62783294-62783413 | chr12: 62783294-62783384 | CAGGAATACCTG CAGATAAGATTT CACAGAATATTC GCTA (705) | CAGGAATACCTG CAGATAAGATGA TAGTTACTGATA TATA (706) | 1 | 11 | 2.58 | 2.06E-06 | 3'ss | CLL |
| 412 | chr17: 18007203-18007857 | chr17: 18007203-18007936 | CTACACCAAGAA GAGAGGACCTCT TCCCTCGCGCAG AATC (707) | CTACACCAAGAA GAGAGGACAGAG GCCAGACTTCAC AGAC (708) | 1 | 11 | 2.58 | 2.56E-03 | 3'ss | CLL |
| 413 | chr17: 73486839-73487110 | chr17: 73486839-73487129 | CGGAGGCTGTCT CCTCTCAGACTT CCTCTCTCCCAC CAGG (709) | CGGAGGCTGTCT CCTCTCAGGAAA TGCTGCGCTGCA TTTG (710) | 1 | 11 | 2.58 | 4.39E-03 | 3'ss | CLL |
| 414 | chr11: 68331900-68334466 | chr11: 68331900-68334481 | TCCTGCTGGAGC CACCCAAGCTTT TTCTTCTTCAGA AAAG (711) | TCCTGCTGGAGC CACCCAAGAAAA GTGTGATGAAGA CCAC (712) | 0 | 5 | 2.58 | 5.77E-03 | 3'ss | CLL |
| 415 | chr13: 113915073-113917776 | chr13: 113915073-113917800 | AGCTGAAATTTC CAGTAAAGGGGG gttttattcttc TTTT (152) | AGCTGAAATTTC CAGTAAAGCCTG GAGATTTGAAAA AGAG (153) | 0 | 5 | 2.58 | 3.85E-02 | 3'ss | CLL |
| 416 | chr13: 20656270-20656905 | chr13: 20656270-20656920 | ACCAAGCATACT TCCAGATGTTCT CTCTATTTAAGG GTCA (713) | ACCAAGCATACT TCCAGATGGGTC AATATTCTCTCG AGTT (714) | 0 | 5 | 2.58 | 1.04E-02 | 3'ss | CLL |
| 417 | chr19: 36231397-36231924 | chr19: 36230989-36231924 | CGGGCCGCCCCC CTGCCCGGTGTT CTTCTGGGCAGT GCAA (715) | CGGGCCGCCCCC CTGCCCGGAGGC CGGTCCCTGCCA AGGG (716) | 0 | 5 | 2.58 | 1.76E-03 | 3'ss | CLL |
| 418 | chr20: 34144042-34144761 | chr20: 34144042-34144743 | ACATGAAGGTGG ACGGAGAGTTCT CTGTGACCAGAC ATGA (250) | ACATGAAGGTGG ACGGAGAGGTAC TGAGGACAAATC AGTT (50) | 0 | 5 | 2.58 | 3.36E-03 | 3'ss | CLL |
| 419 | chr21: 38570326-38572514 | chr21: 38570326-38572532 | AAGATGTCCCTG TGAGGATTGTGT GTTTGTTTCCAC AGGC (224) | AAGATGTCCCTG TGAGGATTGCAC TGGGTGCAAGTT CCTG (225) | 0 | 5 | 2.58 | 3.03E-02 | 3'ss | CLL |
| 420 | chr6: 32095539-32095893 | chr6: 32095527-32095893 | GGAGGACTGGGG TCTGCAGACATT TCTTGCAGACAG CACC (717) | GGAGGACTGGGG TCTGCAGAACAG CACCTTGTATTC TGGC (718) | 0 | 5 | 2.58 | 2.97E-03 | 3'ss | CLL |
| 421 | chr7: 44795898-44796008 | chr7: 44795898-44796023 | CTGCCCCCTGCG CCACACGGCCTC TTTCCCTGCAGT GATG (719) TGTAAATGGGGA | CTGCCCCCTGCG CCACACGGTGAT GGTTCATTCGCA TATG (720) TGTAAATGGGGA | 0 0 | 5 5 | 2.58 2.58 | 7.48E-03 2.68E-02 | 3'ss 3'ss | CLL CLL |

TABLE 1-continued

| | Aberrant junction | WT junction | Aberrant sequence (SEQ ID NO) | WT sequence (SEQ ID NO) | Avg WT % | Avg Ab. % | Log$_2$ Fold Diff. | FDR Q-Value | Event | Type |
|---|---|---|---|---|---|---|---|---|---|---|
| 422 | chr7: 889240-889477 | chr7: 889240-889559 | AGCGCTGTACTG CCATTGCTATGC ACGG (721) GGCCAGCCCCCT | AGCGCTGTGCGA CGACTGTAAGGG CAAG (595) GGCCAGCCCCCT | 10 | 62 | 2.52 | 1.37E-08 | 3'ss | CLL |
| 423 | chr12: 120934019-120934204 | chr12: 120934019-120934218 | TCTCCACGGCCT TGCCCACTAGGT AACC (206) CTGATGAAAACT | TCTCCACGGTAA CCATGTGCGACC GAAA (207) CTGATGAAAACT | 11 | 66 | 2.48 | 1.51E-04 | 3'ss | CLL |
| 424 | chr9: 93641235-93648124 | chr9: 93641235-93650030 | ACTACAAGCAGA CACCTTACAGGC CAGG (722) TTCAGCTGCCCC | ACTACAAGGCCC AGACCCATGGAA AGTG (723) TTCAGCTGCCCC | 8 | 49 | 2.47 | 1.42E-05 | 3'ss | CLL |
| 425 | chr17: 57079102-57089688 | chr17: 57079075-57089688 | TGAAGAAGAAAC ATGTTCTCCTTC CTTC (724) GAAACCAACTAA | TGAAGAAGGAAT GAGTAGCGACAG TGAC (725) GAAACCAACTAA | 3 | 21 | 2.46 | 9.18E-03 | 3'ss | CLL |
| 426 | chr15: 59209219-59224554 | chr15: 59209198-59224554 | AGGCAAAGCCCA TTTTCCTTCTTT CGCA (101) TCCCGAAGCCAC | AGGCAAAGGTAA AAAACATGAAGC AGAT (102) TCCCGAAGCCAC | 3 | 21 | 2.46 | 4.67E-04 | 3'ss | CLL |
| 427 | chr7: 99752804-99752884 | chr7: 99752787-99752884 | CTCATGAGCCTC TGCCTTCCCCCA GGTC (726) CCCCGGTGCGTA | CTCATGAGGTCG GGCAGTGTGATG GAGC (727) CCCCGGTGCGTA | 1 | 10 | 2.46 | 2.22E-02 | 3'ss | CLL |
| 428 | chr8: 145624052-145624168 | chr8: 145624028-145624168 | AGGAGGAGCCTG CCCCCCTTTGGC CCTG (728) AGCTGGAGAAAA | AGGAGGAGGAGG ACAATCCCAAGG GGGA (729) AGCTGGAGAAAA | 1 | 10 | 2.46 | 3.34E-04 | 3'ss | CLL |
| 429 | chr9: 123932094-123935634 | chr9: 123932094-123935520 | ACCTTCTTTTTC TTCCAGAACTAC CAGC (730) TTCGTTGGCAGC | ACCTTCTTATGG CAAACCAAAAAG ATTT (731) TTCGTTGGCAGC | 6 | 37 | 2.44 | 2.59E-04 | 3'ss | CLL |
| 430 | chr15: 77327904-77328151 | chr15: 77327904-77328142 | TTCTGCTGAGAC CCTGACCCCCAC CCCC (732) GTGCTTGGAGCC | TTCTGCTGCGTC CACAGAGACCCT GACC (733) GTGCTTGGAGCC | 5 | 31 | 2.42 | 4.69E-03 | 3'ss | CLL |
| 431 | chr19: 55776746-55777253 | chr19: 55776757-55777253 | CTGTGCAGACTT TCCGCAGGGTGT GCGC (179) GTGCCAACGAGG | CTGTGCAGCCTG GTGACAGACTTT CCGC (180) GTGCCAACGAGG | 10 | 57 | 2.4 | 1.64E-03 | 3'ss | CLL |
| 432 | chr4: 184577127-184580081 | chr4: 184577114-184580081 | ACCAGGAGTTCT TTATTTCAGATG GAAC (734) CCTCACGATGCA | ACCAGGAGATGG AACTAGAAGCAT TACG (735) CCTCACGATGCA | 7 | 40 | 2.36 | 8.53E-04 | 3'ss | CLL |
| 433 | chr16: 67692735-67692830 | chr16: 67692719-67692830 | AGGCCACGAGTT CATGTCCCACAG GGAG (736) | AGGCCACGGGAG AAGCTGTGTACA CTGT (737) | | | | | | |
| 434 | chr6: 91269953-91271340 | chr6: 91269933-91271340 | AGGGGGCTCTTT ATATAATGTTTG TGCCTTTCTTTC GCAG (265) | AGGGGGCTCTTT ATATAATGTGCT GCATGGTGCTGA ACCA (266) | 14 | 75 | 2.34 | 3.51E-06 | 3'ss | CLL |
| 435 | chr15: 25212299-25213078 | chr15: 25207356-25213078 | TCACACAGGATA ATTTGAAAGTGT CAGTTGTACCCG AGGC (164) | GCCTCACTGAGC AACCAAGAGTGT CAGTTGTACCCG AGGC (145) | 2 | 14 | 2.32 | 4.92E-03 | exon incl. | CLL |
| 436 | chr9: 93648256-93650030 | chr9: 93641235-93650030 | AAAAATAAAGCC TTTCCCAGGCCC AGACCCATGGAA AGTG (738) | CTGATGAAAACT ACTACAAGGCCC AGACCCATGGAA AGTG (723) | 1 | 9 | 2.32 | 3.99E-03 | 5'ss | CLL |

TABLE 1-continued

| | Aberrant junction | WT junction | Aberrant sequence (SEQ ID NO) | WT sequence (SEQ ID NO) | Avg WT % | Avg Ab. % | Log$_2$ Fold Diff. | FDR Q-Value | Event | Type |
|---|---|---|---|---|---|---|---|---|---|---|
| 437 | chr14: 34998676- 35002649 | chr14: 34998681- 35002649 | CGAGGATGAAGA CAGAGCAGGTGA CCAAGAAAAAAA AGAA (739) | CGAGGATGAAGA CAGAGCAGTACA GGTGACCAAGAA AAAA (740) | 0 | 4 | 2.32 | 4.50E-03 | 3'ss | CLL |
| 438 | chr2: 26437445- 26437921 | chr2: 26437430- 26437921 | AGACAAGGGATT GGTGGAAACATT TTATTTTACAGA ATTG (295) | AGACAAGGGATT GGTGGAAAAATT GACAGCGTATGC CATG (296) | 0 | 4 | 2.32 | 1.21E-02 | 3'ss | CLL |
| 439 | chrX: 129771378- 129790554 | chrX: 129771384- 129790554 | AAAAGAAACTGA GGAATCAGTATC ACAGGCAGAAGC TCTG (303) | AAAAGAAACTGA GGAATCAGCCTT AGTATCACAGGC AGAA (304) | 16 | 82 | 2.29 | 2.84E-08 | 3'ss | CLL |
| 440 | chr1: 19480448- 19481411 | chr1: 19480433- 19481411 | TTCCCCATCAAC ATCAAAAGTTTT GGTGTCTGCAGT TCCA (202) | TTCCCCATCAAC ATCAAAAGTTCC AATGGTGGCAGT AAGA (203) | 5 | 28 | 2.27 | 4.85E-06 | 3'ss | CLL |
| 441 | chr3: 141896447- 141900302 | chr3: 141896418- 141900302 | AAAATGGGCTCA GCAGTTAGGGTT TTTTGTTGTTTG TTTG (741) | AAAATGGGCTCA GCAGTTAGACCT TTTCACAGATGC TGCT (742) | 10 | 52 | 2.27 | 1.39E-04 | 3'ss | CLL |
| 442 | chr1: 156553242- 156553591 | chr1: 156553242- 156553588 | AAGCACTGGCCC AGTGTCAGGAGC CAGATTCTGTGC GAGA (743) | AAGCACTGGCCC AGTGTCAGAAGG AGCCAGATTCTG TGCG (744) | 4 | 22 | 2.20 | 2.08E-02 | 3'ss | CLL |
| 443 | chr19: 9728842- 9730107 | chr19: 9728855- 9730107 | AGCCATTTATTT GTCCCGTGGGAA CCAATCTGCCCT TTTG (160) | AGCCATTTATTT GTCCCGTGGGTT TTTTCCAGGGA ACCA (161) | 11 | 53 | 2.17 | 2.14E-08 | 3'ss | CLL |
| 444 | chr15: 91448953- 91449151 | chr15: 91448953- 91449074 | CCACTCTCACAA TGACCCAGGAGG ACCCCCGGCGGC GCTT (745) | CCACTCTCACAA TGACCCAGGCTG GATCAAGACCTT TGAC (746) | 1 | 8 | 2.17 | 1.41E-02 | 3'ss | CLL |
| 445 | chr1: 23398690- 23399766 | chr1: 23398690- 23399784 | TTGGAAGCGAAT CCCCCAAGTCCT TTGTTCTTTTGC AGTG (210) | TTGGAAGCGAAT CCCCCAAGTGAT GTATATCTCTCA TCAA (211) | 1 | 8 | 2.17 | 4.59E-02 | 3'ss | CLL |
| 446 | chr2: 64457092- 64478252 | chr2: 64456774- 64478252 | CCTTTACTTGGG GCTCTCAGCAAC TGATGTTGCCAT GCAG (747) | AACCCGGAGAGA AAAGGGAGCAAC TGATGTTGCCAT GCAG (578) | 1 | 8 | 2.17 | 4.13E-02 | 5'ss | CLL |
| 447 | chr14: 23237380- 23238985 | chr14: 23237380- 23238999 | GTGGGGGGCCAT TGCTGCATTTTG TATTTTCCAGGT ACAG (122) | GTGGGGGGCCAT TGCTGCATGTAC AGTCTTTGCCCG CTGC (123) | 16 | 75 | 2.16 | 9.79E-09 | 3'ss | CLL |
| 448 | chr15: 74326871- 74327483 | chr15: 74326871- 74327512 | ACTCAGATGCCG AAAACTCGCCCT CAGTCTGAGGTT CTGT (748) | ACTCAGATGCCG AAAACTCGTGCA TGGAGCCCATGG AGAC (749) | 14 | 65 | 2.14 | 1.32E-05 | 3'ss | CLL |
| 449 | chr10: 89516679- 89519457 | chr10: 89516679- 89527429 | GCCTACTCTTAA CCATTAGGGTGG ATAGGCATGTAG ACCT (750) | TCATCTTGAAAA ATGAAAATGTGG ATAGGCATGTAG ACCT (507) | 7 | 34 | 2.13 | 4.92E-03 | exon incl. | CLL |
| 450 | chr20: 33703761- 33706400 | chr20: 33703736- 33706400 | TGGAGTGCGGAT TTGCAACACTTG CTTCCTTCTCCC ACAT (751) | TGGAGTGCGGAT TTGCAACAATCA AAGATCTGCGAG ACCA (752) | 2 | 12 | 2.12 | 4.37E-03 | 3'ss | CLL |
| 451 | chr12: 105514375- 105514866 | chr12: 105514375- 105514878 | CAACTGGAGTTC ATTTTCAGGTTT TTGACAGACTA TGTA (753) | CAACTGGAGTTC ATTTTCAGACTA TGTATGAGCACT TGGG (754) | 12 | 53 | 2.05 | 3.67E-06 | 3'ss | CLL |

TABLE 1-continued

| Aberrant junction | WT junction | Aberrant sequence (SEQ ID NO) | WT sequence (SEQ ID NO) | Avg WT % | Avg Ab. % | Log$_2$ Fold Diff. | FDR Q-Value | Event | Type |
|---|---|---|---|---|---|---|---|---|---|
| 452 chr1: 155237988- 155238083 | chr1: 155237937- 155238083 | CAATGTGTTGAC CATCGCAGTCCC CCTACAGCCCTG TTCA (755) | CAATGTGTTGAC CATCGCAGCCTC TCCTGCCAACTT ACAG (756) | 14 | 61 | 2.05 | 1.87E-03 | 3'ss | CLL |
| 453 chr15: 89870310- 89870397 | chr15: 89870294- 89870397 | CAGCTGCTCTCA GGAGAGAGTGGA CTGGCTCTGTAG GTAC (757) | CAGCTGCTCTCA GGAGAGAGGTAC AAAGAAGACCCC TGGC (758) | 16 | 67 | 2.00 | 7.47E-04 | 3'ss | CLL |
| 454 chr3: 141272782- 141274647 | chr3: 141272782- 141274681 | TCTCTAGTGGGC CCTTCTAGTTCT ACAAGGTAAAAC TCTA (759) | TCTCTAGTGGGC CCTTCTAGGAAT GACCAAAAGAAG ACAA (760) | 8 | 35 | 2.00 | 7.53E-03 | 3'ss | CLL |
| 455 chr1: 202122978- 202123313 | chr1: 202122963- 202123313 | AGCTCCGAGAGG GCAAGGAGCTCC CTCCCTCCTAGA AATG (761) | AGCTCCGAGAGG GCAAGGAGAAAT GTGTCCACTACT GGCC (762) | 2 | 11 | 2.00 | 6.28E-03 | 3'ss | CLL |
| 456 chrX: 47315813- 47326808 | chrX: 47315797- 47326808 | GACGTGGCAGCT CATGTGAGCATT GTGTCGTTACAG GCTT (763) | GACGTGGCAGCT CATGTGAGGCTT CAGTGTCATTTG AGGA (764) | 19 | 73 | 1.89 | 1.20E-04 | 3'ss | CLL |
| 457 chr6: 25975158- 25983391 | chr6: 25973513- 25983391 | AAGGAAGAACAA GACTTTGTTTAG TGTGACTCTGGA TCCA (765) | AATGTTAAGGAG TCATCAAGTTAG TGTGACTCTGGA TCCA (766) | 2 | 10 | 1.87 | 4.93E-04 | exon incl. | CLL |
| 458 chr11: 10876665- 10877690 | chr11: 10876633- 10877690 | AGGAGAACACCT TATTTCAGCTTT TATTTTTATGTG ATAA (767) | AGGAGAACACCT TATTTCAGAAAA GGTGTACCATAC CTGA (768) | 15 | 55 | 1.81 | 1.53E-04 | 3'ss | CLL |
| 459 chr9: 93641235- 93648127 | chr9: 93641235- 93650030 | CTGATGAAAACT ACTACAAGACAC CTTACAGGCCAG GAGA (769) | CTGATGAAAACT ACTACAAGGCCC AGACCCATGGAA AGTG (723) | 12 | 43 | 1.76 | 4.16E-05 | 3'ss | CLL |
| 460 chr8: 145313817- 145314126 | chr8: 145313817- 145314142 | GGGGCCACCAGG TTGGCCAGCGGC CCCCTTTCCCAG GGCC (770) | GGGGCCACCAGG TTGGCCAGGGCC ATGGCTGAGCAC GCAG (771) | 21 | 72 | 1.73 | 2.11E-05 | 3'ss | CLL |
| 461 chr7: 98579583- 98580862 | chr7: 98579583- 98580886 | TGCACACGCCTC TCCTACAGAGTC TCTTATGCTGGT CCCA (772) | TGCACACGCCTC TCCTACAGGCAG CCCAGCAAATCA TCGA (773) | 4 | 15 | 1.68 | 2.26E-02 | 3'ss | CLL |
| 462 chr22: 50660983- 50662569 | chr22: 50661021- 50662569 | GAGCTGGAGAGG AAGGCGAGAGGC AGCTCGTCGGGA GCAG (774) | GAGCTGGAGAGG AAGGCGAGGCAG CCACTGGTCGAC CACT (775) | 14 | 46 | 1.65 | 2.74E-04 | 3'ss | CLL |
| 463 chr6: 31936315- 31936399 | chr6: 31936315- 31936462 | GCCCCGTTTTC CTGCCCAGCCCT TGTCCTCAGTGC ACCC (307) | GCCCCGTTTTC CTGCCCAGTACC TGAAGCTGCGGG AGCG (308) | 17 | 55 | 1.64 | 1.17E-04 | 3'ss | CLL |
| 464 chr7: 64139714- 64150776 | chr7: 64139714- 64144464 | CCGCCTCTGCCT TCGGATAGGTCT GGCCCCACCCTG GAGT (776) | CCGCCTCTGCCT TCGGATAGGAAA GGTTGAAAGAGC CAAC (777) | 8 | 26 | 1.58 | 3.53E-03 | 3'ss | CLL |
| 465 chr12: 51174021- 51189680 | chr12: 51174021- 51189691 | TTTCTCATATTG CTCAACAGTTCT TTTTTAGGTATC ATCT (778) | TTTCTCATATTG CTCAACAGGTAT CATCTTTATCAG AAAG (779) | 5 | 17 | 1.58 | 4.42E-03 | 3'ss | CLL |
| 466 chr11: 126144916- 126144918 | chr11: 126144916- 126145221 | AGTGGCTTTGGG GTCTTATGGAGG CTTGCTTGCAGA GGGG (780) | AGTGGCTTTGGG GTCTTATGGGAT GGAGGACGAAGG TTGG (781) | 15 | 46 | 1.55 | 1.99E-03 | intron retention | CLL |

TABLE 1-continued

| | Aberrant junction | WT junction | Aberrant sequence (SEQ ID NO) | WT sequence (SEQ ID NO) | Avg WT % | Avg Ab. % | Log₂ Fold Diff. | FDR Q-Value | Event | Type |
|---|---|---|---|---|---|---|---|---|---|---|
| 467 | chr1: 67890660-67890765 | chr1: 67890642-67890765 | CATAGTGGAAGT GATAGATCTTCT TTTTCACATTAC AGTG (444) | CATAGTGGAAGT GATAGATCTGGC CTGAAGCACGAG GACA (445) | 20 | 60 | 1.54 | 6.97E-06 | 3'ss | CLL |
| 468 | chr1: 157771381-157771704 | chr1: 157771367-157771704 | GGTGACACTCAA CTTCACAGGTCT CTCCCTCTAGTG CCTA (782) | GGTGACACTCAA CTTCACAGTGCC TACTGGGGCCAG AAGC (783) | 22 | 65 | 1.52 | 1.10E-05 | 3'ss | CLL |
| 469 | chr2: 106781255-106782511 | chr2: 106781240-106782511 | GGCAACTTCGTT AATATGAGCTTT CTACTCAACAGG TCTA (375) | GGCAACTTCGTT AATATGAGGTCT ATCCAGGAAAAT GGTG (376) | 27 | 76 | 1.46 | 7.08E-07 | 3'ss | CLL |
| 470 | chr14: 75348719-75352288 | chr14: 75349327-75352288 | CGCTCTCCGCCT TCCAGAAGGGGT CTCCTTATGCCA GGGA (208) | AGGGAGACGTTC CCTGCCTGGGGT CTCCTTATGCCA GGGA (209) | 19 | 54 | 1.46 | 2.09E-04 | exon skip | CLL |
| 471 | chr2: 153551136-153571063 | chr2: 153551136-153572508 | TTTCCATTGGGC CAATCAAGATGC CTGGAATGATGT CGTC (784) | GAGGGCCACCAA TGGGACAAATGC CTGGAATGATGT CGTC (785) | 3 | 10 | 1.46 | 4.35E-02 | exon incl. | CLL |
| 472 | chrX: 118759359-118763280 | chrX: 118759342-118763280 | AGAGACAAAGAG AAGAAAAACTCT TACTGTTTTACA GTTA (786) | AGAGACAAAGAG AAGAAAAATTAA CTCTGCTGTTTG CTGC (787) | 33 | 92 | 1.45 | 4.85E-06 | 3'ss | CLL |
| 473 | chr17: 27238402-27239499 | chr17: 27238255-27239499 | CTCACCAGCGCC ATCGTCAGCTCT AGGAGTTCCAGA GCCT (788) | CTCACCAGCGCC ATCGTCAGATGG CAAGGTCAGCCC CGGC (789) | 5 | 15 | 1.42 | 1.43E-03 | exon incl. | CLL |
| 474 | chr12: 50821692-50822699 | chr12: 50821692-50822717 | ATCAGGTGCTCA TCCTGAGGTGTC TGTCTTTAATAC AGGT (790) | ATCAGGTGCTCA TCCTGAGGGTAA TGCAGAGCTCTC AGAA (791) | 11 | 30 | 1.37 | 9.13E-04 | 3'ss | CLL |
| 475 | chr6: 43152643-43153228 | chr6: 43152643-43153193 | TCTGGCAGCCCA CGATGCTGCAAG ATGGCATGCAGC AGCA (792) | TCTGGCAGCCCA CGATGCTGGGAG TCGGGCTCACGT CCTT (793) | 17 | 45 | 1.35 | 1.98E-04 | 3'ss | CLL |
| 476 | chr3: 3186394-3188099 | chr3: 3186394-3188113 | AGAATTTTAAGA TACTTCAGATTT TGTCTTGTAGGT TTTA (794) | AGAATTTTAAGA TACTTCAGGTTT TATGGGAGAATT GTAG (795) | 11 | 29 | 1.32 | 1.64E-03 | 3'ss | CLL |
| 477 | chr7: 64139714-64150765 | chr7: 64139714-64144464 | CCGCCTCTGCCT TCGGATAGGCTT TATTTAGGTCTG GCCC (796) | CCGCCTCTGCCT TCGGATAGGAAA GGTTGAAAGAGC CAAC (777) | 1 | 4 | 1.32 | 2.43E-02 | 3'ss | CLL |
| 478 | chr3: 56606456-56626997 | chr3: 56605330-56626997 | GAGCTAGTCAGA CTTTAGAGGAAA CAGTACTGCTGG AGCA (797) | AAATTCTTGACC AATCTAGGGAAA CAGTACTGCTGG AGCA (798) | 15 | 38 | 1.29 | 1.66E-02 | exon incl. | CLL |
| 479 | chr22: 24043032-24047615 | chr22: 24037704-24047615 | CTTCATCTGTGG ATAAGCAGGTCA TGTCCTCCAGGT TTCT (799) | CTTCATCTGTGG ATAAGCAGTGCA GGCCAAGGCCCC CTGC (800) | 25 | 61 | 1.25 | 5.02E-06 | 3'ss | CLL |
| 480 | chr17: 45229302-45232037 | chr17: 45229284-45232037 | CCGGAGCCCCTT CAAAAAGACTTT TCGTGTTTTAC AGTC (327) | CCGGAGCCCCTT CAAAAAGTCTGG TTGCCAGAATCG GCCA (328) | 8 | 20 | 1.22 | 1.07E-02 | 3'ss | CLL |
| 481 | chr1: 62149218-62152463 | chr1: 62149218-62160368 | AGTATGGGATAT TTTAAAAGATTG TTGGACCTTCAG ATGG (801) | TCATTCTTATTT CAATGCAGATTG TTGGACCTTCAG ATGG (802) | 8 | 20 | 1.22 | 2.03E-02 | exon incl. | CLL |

TABLE 1-continued

| | Aberrant junction | WT junction | Aberrant sequence (SEQ ID NO) | WT sequence (SEQ ID NO) | Avg WT % | Avg Ab. % | Log₂ Fold Diff. | FDR Q-Value | Event | Type |
|---|---|---|---|---|---|---|---|---|---|---|
| 482 | chr22: 24037704-24042912 | chr22: 24037704-24047615 | CTTTATCTGTGCATGAACAGTGCAGGCCAAGGCCCCCTGC (803) | CTTCATCTGTGGATAAGCAGTGCAGGCCAAGGCCCCCTGC (800) | 31 | 73 | 1.21 | 1.26E-05 | exon incl. | CLL |
| 483 | chr7: 104844232-104909252 | chr7: 104844232-105029094 | AAGTCGTCCTCTTCAGAAAGGCCGGAGCCTCAACAGAAAG (804) | AGAGAGAAACATCCGAAAAGCCGGAGCCTCAACAGAAAG (805) | 18 | 42 | 118 | 2.78E-02 | exon incl. | CLL |
| 484 | chr2: 85779690-85780061 | chr2: 85779104-85780061 | TGGGCTACCTTAACCCTGGGGTATTTACACAGAGTCGGCG (806) | TGGGCTACCTTAACCCTGGGGATTTTTGACCCTCGTGTGG (807) | 23 | 53 | 1.17 | 3.28E-02 | exon incl. | CLL |
| 485 | chr1: 52902647-52903891 | chr1: 52902635-52903891 | GACTGCCCTAAAAGGAAAAGTTTACTGTTTAGACTAAAGA (808) | GACTGCCCTAAAAGGAAAAGACTAAAGAAGAAAGACAGTG (809) | 10 | 23 | 1.13 | 4.92E-03 | 3'ss | CLL |
| 486 | chr3: 179065598-179066635 | chr3: 179065598-179066632 | TGATAGTTGGAGCGGAGACTCATAATGGCAGAACCTGTTT (810) | TGATAGTTGGAGCGGAGACTTAGCATAATGGCAGAACCTG (811) | 11 | 25 | 1.12 | 3.47E-03 | 3'ss | CLL |
| 487 | chr1: 62152593-62160368 | chr1: 62149218-62160368 | TCATTCTTATTTCAATGCAGAGACAGGGTCTTGCTCTGTT (812) | TCATTCTTATTTCAATGCAGATTGTTGGACCTTCAGATGG (802) | 5 | 12 | 112 | 3.19E-02 | exon incl. | CLL |
| 488 | chr19: 53935281-53936832 | chr19: 53935281-53945048 | TGACGGTGCCACCGCGGCGCTTTTCTCCCTTAGATGCCTT (813) | TGACGGTGCCACCGCGGCGCAGAGGAGTCTGCAATGCCGA (814) | 30 | 65 | 1.09 | 4.13E-02 | exon incl. | CLL |
| 489 | chr19: 19414656-19416657 | chr19: 19414721-19416657 | GCAGTGGCTGGAGATCAAAGTTTCACCCCCAGAGGGAGCC (815) | GCAGTGGCTGGAGATCAAAGAGAGAGTGTGCCTATTGACT (816) | 42 | 85 | 1.00 | 4.02E-05 | 3'ss | CLL |
| 490 | chrX: 47103949-47104083 | chrX: 47103949-47104080 | GGACGATGGGGATGAGAAAGATGACGAGGAGGATAAAGAT (817) | GGACGATGGGGATGAGAAAGAAGATGACGAGGAGGATAAA (818) | 3 | 7 | 1.00 | 8.68E-03 | 3'ss | CLL |
| 491 | chr5: 1579599-1585098 | chr5: 1581810-1585098 | ACTCTTATGCAGTCCCCATGGACTGAACCATCAAGACACC (819) | ACTCTTATGCAGTCCCCATGAGGAGATCCTAGTCTCACCA (531) | 24 | 48 | 0.97 | 7.63E-03 | 3'ss | CLL |
| 492 | chr17: 73587327-73587681 | chr17: 73587327-73587696 | GACCCATGCATCCTCCTGTGCTCCTCCCACTGCAGTGGGC (820) | GACCCATGCATCCTCCTGTGTGGGCACAGTGGCTCAGGGA (821) | 47 | 93 | 0.97 | 2.22E-02 | 3'ss | CLL |
| 493 | chr18: 224200-224923 | chr18: 224179-224923 | CCAAGTTTTGTGAAAGAAAGTGTATGTTTTGTTCACGACA (116) | CCAAGTTTTGTGAAAGAAAGAACATCAGATACCAAACCTA (117) | 38 | 75 | 0.96 | 7.90E-03 | 3'ss | CLL |
| 494 | chr16: 57473207-57474683 | chr16: 57473246-57474683 | CATCAAGCAGCTGTTGCAATGTTTAGTCCCAGGAAGCACC (822) | CATCAAGCAGCTGTTGCAATCTGCCCACAAAGAATCCAGC (823) | 10 | 20 | 0.93 | 2.86E-02 | 3'ss | CLL |
| 495 | chr7: 99943591-99947339 | chr7: 99943591-99947421 | TGAGAGTCTTCAGTTACTAGTTTGTCTTTCCTAGATCCAG (420) | TGAGAGTCTTCAGTTACTAGAGGCGGATTTCCCTGACTGA (421) | 45 | 86 | 0.92 | 7.69E-08 | 3'ss | CLL |
| 496 | chr12: 47599928-47600293 | chr12: 47599852-47600293 | CAATCATTGACAATATTATGACCCTGCATGTGATGGATCA (824) | CAATCATTGACAATATTATGGAACTGACTCAGCGCAAGAA (825) | 29 | 54 | 0.87 | 3.27E-02 | 3'ss | CLL |

TABLE 1-continued

| | Aberrant junction | WT junction | Aberrant sequence (SEQ ID NO) | WT sequence (SEQ ID NO) | Avg WT % | Avg Ab. % | Log₂ Fold Diff. | FDR Q-Value | Event | Type |
|---|---|---|---|---|---|---|---|---|---|---|
| 497 | chr9: 140633231-140637822 | chr9: 140633231-140637843 | GGGACACTGTGCCGAATGAACTTGCTTGCCTTTTGTTTTA(826) | GGGACACTGTGCCGAATGAACAGCTGCAGTATCTCGGAAG(827) | 43 | 72 | 0.73 | 1.74E-02 | 3'ss | CLL |
| 498 | chr19: 17654242-17657494 | chr19: 17654440-17657494 | TCAGGGGGCGCGTGCTGAAGGAGCTGCCTGAGTTCGAGGG(828) | TCGAGCCAGGCTGCAAAAGGAGCTGCCTGAGTTCGAGGG(829) | to | 17 | 0.71 | 2.37E-02 | exon skip | CLL |
| 499 | chr6: 29691704-29691949 | chr6: 29691704-29691966 | CTACAACCAGAGCGAGGCTGGGTCTCACACCCTCCAGGGA(830) | CTACAACCAGAGCGAGGCTGGGAATGGCTGCGACAT(831) | 57 | 92 | 0.68 | 2.50E-03 | 3'ss | CLL |
| 500 | chr20: 30310151-30310420 | chr20: 30310133-30310420 | TGCCTAAGGCGGATTTGAATCTCTTTCTCTCCCTTCAGAA(479) | TGCCTAAGGCGGATTTGAATAATCTTATCTTGGCTTTGGA(480) | 54 | 87 | 0.68 | 4.59E-02 | 3'ss | CLL |
| 501 | chr4: 17806394-17806729 | chr4: 17806379-17806729 | TCCAACAAGCACCTCTGAAGTCTTCTCATTCACAGGTTAA(832) | TCCAACAAGCACCTCTGAAGGTTAAGGCTACCTTTCCAGA(833) | 55 | 87 | 0.65 | 1.64E-04 | 3'ss | CLL |
| 502 | chr9: 140622981-140637822 | chr9: 140622981-140637843 | CACCACAAAATCACAGACAGCTTGCTTGCCTTTTGTTTTA(458) | CACCACAAAATCACAGACAGCAGCTGCAGTATCTCGGAAG(459) | 41 | 65 | 0.65 | 4.07E-03 | 3'ss | CLL |
| 503 | chr1: 155278756-155279833 | chr1: 155278756-155279854 | GAATCCGTATCTGGGAACAGAGCCCTTTGCTCCTCCCTCA(432) | GAATCCGTATCTGGGAACAGAATGAACGGAGACCAGAATT(433) | 45 | 70 | 0.63 | 4.59E-02 | 3'ss | CLL |
| 504 | chr17: 40690773-40692967 | chr17: 40690773-40695045 | GTTCCCGAGGCTGTCACCAGGGTGTTCCCTCAGGTCAATG(834) | GTTCCCGAGGCTGTCACCAGTGGATACTGAGGCTGTGTGG(835) | 60 | 90 | 0.58 | 8.49E-05 | 3'ss | CLL |
| 505 | chr12: 95660408-95663814 | chr12: 95660408-95663826 | ATTTCCAGAGGATTTACACTTTTGCTTGACAGGGTCAGTG(462) | ATTTCCAGAGGATTTACACTGGTCAGTGCTGCTTGCCCAT(463) | 51 | 76 | 0.57 | 1.45E-05 | 3'ss | CLL |
| 506 | chr3: 133371473-133372188 | chr3: 133371458-133372188 | CCAGATCAACACAATTGATAGTCGTACTCTTTCAGATGTC(836) | CCAGATCAACACAATTGATAATGTCAGCAATATTTCCAAC(837) | 44 | 65 | 0.55 | 2.77E-02 | 3'ss | CLL |
| 507 | chr19: 7075116-7075665 | chr19: 7075116-7075686 | CGTCCTGCCCCCAACTGCCGCTCTGTCTTCCCTGTTCCCA(838) | CGTCCTGCCCCCAACTGCCGCCTCTCAGCGAGAAGGACAC(839) | 67 | 94 | 0.48 | 2.30E-02 | 3'ss | CLL |
| 508 | chr10: 75554088-75554298 | chr10: 75554088-75554313 | TGACGTTCTCTGTGCTCCAGTGGTTTCTCCCACAGGTTCC(466) | TGACGTTCTCTGTGCTCCAGGTTCCCGGCCCCAAGTCGC(467) | 53 | 74 | 0.47 | 2.22E-03 | 3'ss | CLL |
| 509 | chr19: 11558433-11558507 | chr19: 11558433-11558537 | TGCAGGGGAGCAGCCCAAGGAGGCCCCACCGCCACTGTC(840) | TGCAGGGGAGCAGCCCAAGCCGGCCAGCCCTGCTGAGGA(841) | 48 | 66 | 0.45 | 6.62E-03 | 3'ss | CLL |
| 510 | chr1: 52902650-52903891 | chr1: 52902635-52903891 | GACTGCCCTAAAAGGAAAAGCAGTTTACTGTTTAGACTAA(842) | GACTGCCCTAAAAGGAAAAGACTAAAGAAGAAAGACAGTG(809) | 55 | 74 | 0.42 | 8.74E-03 | 3'ss | CLL |
| 511 | chr17: 40693224-40695045 | chr17: 40690773-40695045 | CTATGAGGCCATGACTGCAGTGGATACTGAGGCTGTGTGG(843) | GTTCCCGAGGCTGTCACCAGTGGATACTGAGGCTGTGTGG(835) | 68 | 87 | 0.35 | 1.45E-03 | exon incl. | CLL |

TABLE 1-continued

| | Aberrant junction | WT junction | Aberrant sequence (SEQ ID NO) | WT sequence (SEQ ID NO) | Avg WT % | Avg Ab. % | Log₂ Fold Diff. | FDR Q-Value | Event | Type |
|---|---|---|---|---|---|---|---|---|---|---|
| 512 | chr5: 139865317-139866542 | chr5: 139865317-139866590 | CTTCTCAAGATC AGTCTCAGGTGC CACGTGTGCCAA CGCA (844) | CTTCTCAAGATC AGTCTCAGGAAC CTGACAGAACTT CACA (845) | 70 | 86 | 0.29 | 2.73E-02 | 3'ss | CLL |
| 513 | chr6: 127636041-127637594 | chr6: 127636041-127648146 | ACCTTAACAAGA TTTATGAGACTT CCTTTAATAAGT GTTG (846) | AATCACTAGGAA CTCCAGAGACTT CCTTTAATAAGT GTTG (847) | 58 | 71 | 0.29 | 1.38E-02 | exon incl. | CLL |
| 514 | chr4: 54266006-54280781 | chr4: 54266006-54292038 | ACTGGGCTTCCA CCGAGCAGAAAC AGCACTTCTTCT CAGT (848) | ACTGGGCTTCCA CCGAGCAGGAGA TTACCTGGGGCA ATTG (849) | 60 | 72 | 0.26 | 4.54E-02 | exon incl. | CLL |
| 515 | chr9: 130566979-130569251 | chf9: 130566979-130569270 | CTGAAGACGGGA TTCTTTAGCTCT CCCCACCTGGTG CAGG (850) | CTGAAGACGGGA TTCTTTAGGTTC GGGAGCGGATCC GCAT (851) | 87 | 92 | 0.08 | 2.80E-02 | 3'ss | CLL |
| 516 | chr17: 72759659-72763074 | chr17: 72760785-72763074 | ATCTCAGGAGCA CCTGAATGGTCC CCTGCCTGTGCC CTTC (852) | CCCACCCCTTCA CCCTGCAGGTCC CCTGCCTGTGCC CTTC (853) | 93 | 98 | 0.07 | 4.18E-03 | 5'ss | CLL |
| 517 | chr2: 109102364-109102954 | chr2: 109102364-109102966 | AGCAAGTAGAAG TCTATAAAATTT ACCCCCAGATAC AGCT (1) | AGCAAGTAGAAG TCTATAAAATAC AGCTGGCTGAAA TAAC (2) | 0 | 72 | 6.19 | 1.51E-10 | 3'ss | Mel. |
| 518 | chr19: 57908542-57909780 | chr19: 57908542-57909797 | GGCCCTTTTGTC CTCACTAGCATT TCTGTTCTGACA GGTT (7) | GGCCCTTTTGTC CTCACTAGGTTC TTGGCATGGAGC TGAG (8) | 0 | 72 | 6.19 | 7.67E-09 | 3'ss | Mel. |
| 519 | chr2: 232196609-232209660 | chr2: 232196609-232209686 | TGACCACGGAGT ACCTGGGGCCCT TTTTCTCTTTC CTTC (37) | TGACCACGGAGT ACCTGGGGATCA TGACCAACACGG GGAA (38) | 0 | 59 | 5.91 | 1.12E-08 | 3'ss | Mel. |
| 520 | chr1: 245246990-245288006 | chr1: 245246990-245250546 | CAAGTATATGAC TGAAGAAGATCC TGAATTCCAGCA AAAC (21) | CAAGTATATGAC TGAAGAAGGTGA GCCTTTTTCTCA AGAG (22) | 0 | 56 | 5.83 | 3.98E-05 | 3'ss | Mel. |
| 521 | chr11: 65635911-65635980 | chr11: 65635892-65635980 | GGCCACACGCCT CTGCCAAGCCCC TCTCCCCTGGCA CAGA (854) | GGCCACACGCCT CTGCCAAGACAT TGATGAGTGTGA GTCT (855) | 0 | 54 | 5.78 | 1.58E-06 | 3'ss | Mel. |
| 522 | chr3: 9960293-9962150 | chr3: 9960293-9962174 | TGCAGTTTGGTC AGTCTGTGCCTT CCTCACCCCTCT CCTC (23) | TGCAGTTTGGTC AGTCTGTGGGCT CTGTGGTATATG ACTG (24) | 0 | 49 | 5.64 | 5.19E-07 | 3'ss | Mel. |
| 523 | chr3: 48457878-48459319 | chr3: 48457860-48459319 | GAGTACGAGGTC TCCAGCAGCCTG CCCTGTGCCTAC AGCC (856) | GAGTACGAGGTC TCCAGCAGCCTC GTGTGCATCACC GGGG (857) | 0 | 48 | 5.61 | 2.52E-15 | 3'ss | Mel. |
| 524 | chr10: 99214556-99215395 | chr10: 99214556-99215416 | TACCTCTGGTTC CTGTGCAGTCTT CGCCCCTCTTTT CTTA (13) | TACCTCTGGTTC CTGTGCAGTTCT GTGGCACTTGCC CTGG (14) | 0 | 47 | 5.58 | 5.54E-06 | 3'ss | Mel. |
| 525 | chr1: 101458310-101460665 | chr1: 101458296-101460665 | TCTTTGGAAAAT CTAATCAATTTT CTGCCTATAGGG GAAG (25) | TCTTTGGAAAAT CTAATCAAGGGA AGGAAGATCTAT GAAC (26) | 0 | 45 | 5.52 | 3.06E-06 | 3'ss | Mel. |
| 526 | chr9: 90582559-90584108 | chr9: 90582574-90584108 | AGCGCATCGCAG CTTCCAAGTACT TCTTCACAGCTC CCCT (858) | AGCGCATCGCAG CTTCCAAGGCTC TCCTCCATCAGT ACTT (859) | 0 | 45 | 5.52 | 1.42E-03 | 3'ss | Mel. |

TABLE 1-continued

| | Aberrant junction | WT junction | Aberrant sequence (SEQ ID NO) | WT sequence (SEQ ID NO) | Avg WT % | Avg Ab. % | Log₂ Fold Diff. | FDR Q-Value | Event | Type |
|---|---|---|---|---|---|---|---|---|---|---|
| 527 | chr1: 179835004-179846373 | chr1: 179834989-179846373 | TCACTCAAACAGTAAACGAGTTTTATCATTTACAGGTATG (53) | TCACTCAAACAGTAAACGAGGTATGTGACGCATTCCCAGA (54) | 0 | 44 | 5.49 | 1.90E-07 | 3'ss | Mel. |
| 528 | chr14: 74358911-74360478 | chr14: 74358911-74360499 | AGTTAGAATCCAAACCAGAGTGTTGTCTTTTCTCCCCCCA (61) | AGTTAGAATCCAAACCAGAGCTCCTGGTACAGTTTGTTCA (62) | 0 | 41 | 5.39 | 4.30E-08 | 3'ss | Mel. |
| 529 | chr11: 117167925-117186250 | chr11: 117167677-117186250 | TGGGCAGCCCCCCGCAGACGTTGGTTTTTCAGCAGACCTG (860) | TGGGCAGCCCCCCGCAGACGCTCAACATCCTGGTGGATAC (861) | 0 | 39 | 5.32 | 2.61E-02 | 3'ss | Mel. |
| 530 | chr20: 62701988-62703210 | chr20: 62701988-62703222 | AGAACTGCACCTACACACAGCCCTGTTCACAGGTGCAGAC (29) | AGAACTGCACCTACACACAGGTGCAGACCCGCAGCTCTGA (30) | 0 | 36 | 5.21 | 6.58E-07 | 3'ss | Mel. |
| 531 | chr18: 33605641-33606862 | chr18: 33573263-33606862 | AGAAAGAGCATAAATTGGAAATATTGGACATGGGCGTATC (91) | AGAAAGAGCATAAATTGGAAGAGTACAAGCGCAAGCTAGC (92) | 0 | 33 | 5.09 | 6.82E-09 | 3'ss | Mel. |
| 532 | chr3: 52283338-52283671 | chr3: 52283338-52283685 | AACCAAGAGGACCCACACAGGATGGTCTTCACAGGTTCTC (862) | AACCAAGAGGACCCACACAGGTTCTCAAAGCTGGCCCAGA (863) | 0 | 32 | 5.04 | 1.83E-02 | 3'ss | Mel. |
| 533 | chr9: 125759640-125760854 | chr9: 125759640-125760875 | AAATGAAGAAACTCCTAAAGCCTCTCTCTTTCTTTGTTTA (67) | AAATGAAGAAACTCCTAAAGATAAAGTCCTGTTTATGACC (68) | 0 | 32 | 5.04 | 6.82E-09 | 3'ss | Mel. |
| 534 | chr12: 116413154-116413319 | chr12: 116413118-116413319 | AATATTGCTTTACCAAACAGGGACCCCTTCCCCTTCCCCA (77) | AATATTGCTTTACCAAACAGGTCACGGAGGAGTAAAGTAT (78) | 0 | 31 | 5.00 | 9.14E-06 | 3'ss | Mel. |
| 535 | chr18: 683395-685920 | chr18: 683380-685920 | TTGGACCGGAAAAGACTTTGAGTCTCTTTTTGCAGATGAT (15) | TTGGACCGGAAAAGACTTTGATGATGGATGCCAACCAGCG (16) | 1 | 62 | 4.98 | 1.13E-06 | 3'ss | Mel. |
| 536 | chr1: 212515622-212519131 | chr1: 212515622-212519144 | ATCAGAAATTCGTACAACAGGTTTCTTTTAAAGCTCCTGG (65) | ATCAGAAATTCGTACAACAGCTCCTGGAGCTTTTTGATAG (66) | 0 | 29 | 4.91 | 8.06E-03 | 3'ss | Mel. |
| 537 | chr1: 35871069-35873587 | chr1: 35871069-35873608 | CTCAGAGCCAGGCTGTAGAGATGTTTTTCTACCTTTCCACA (105) | CTCAGAGCCAGGCTGTAGAGTCCGCTCTATCAAGCTGAAG (106) | 0 | 29 | 4.91 | 3.06E-05 | 3'ss | Mel. |
| 538 | chrX: 47059943-47060292 | chrX: 47059013-47060292 | GTCTTGAGAATTGGAAGCAGGTGGTGGTGCTCACCAACAC (113) | ACTTCCTTAGTGGTTTCCAGGTGGTGGTGCTCACCAACAC (112) | 0 | 29 | 4.91 | 1.16E-06 | 5'ss | Mel. |
| 539 | chr2: 24207701-24222524 | chr2: 24207701-24222541 | AAATTTAACATTACTCATAGTTTTTGCTGTTTTACAGAGT (546) | AAATTTAACATTACTCATAGAGTAAGCCATATCAAAGACT (547) | 0 | 28 | 4.86 | 3.75E-06 | 3'ss | Mel. |
| 540 | chr5: 869519-870587 | chr5: 865696-870587 | CTCCATGCTCAGCTCTCTGGTTTCTTTCAGGGCCTGCCAT (128) | CTCCATGCTCAGCTCTCTGGGGAAGGTGAAGAAGGAGCTG (129) | 0 | 28 | 4.86 | 8.03E-04 | 3'ss | Mel. |
| 541 | chr20: 34144042-34144725 | chr20: 34144042-34144743 | ACATGAAGGTGAACGGAGAGGCTCCCCTCCCACCCCAGGT (49) | ACATGAAGGTGAACGGAGAGGTACTGAGGACAAATCAGTT (50) | 0 | 27 | 4.81 | 4.86E-06 | 3'ss | Mel. |

TABLE 1-continued

| | Aberrant junction | WT junction | Aberrant sequence (SEQ ID NO) | WT sequence (SEQ ID NO) | Avg WT % | Avg Ab. % | Log₂ Fold Diff. | FDR Q-Value | Event | Type |
|---|---|---|---|---|---|---|---|---|---|---|
| 542 | chr2: 97285513-97297048 | chr2: 97285499-97297048 | TGGGAGGAGCATGTCAACAGAGTTTCCCTTATAGGACTGG (9) | TGGGAGGAGCATGTCAACAGGACTGGCTGGACAATGGCCC (10) | 0 | 27 | 4.81 | 1.72E-04 | 3'ss | Mel. |
| 543 | chr19: 9728842-9730107 | chr19: 9728855-9730107 | AGCCATTTATTTGTCCCGTGGAACCAATCTGCCCTTTTG (160) | AGCCATTTATTTGTCCCGTGGGTTTTTTTCCAGGGAACCA (161) | 1 | 54 | 4.78 | 1.18E-09 | 3'ss | Mel. |
| 544 | chr15: 49420970-49421673 | chr15: 49420957-49421673 | ATATTCCTTTTATTTCTAAGTCTTTTGTCTTAGGAGTTAA (864) | ATATTCCTTTTATTTCTAAGGAGTTAAACATAGATGTAGC (865) | 0 | 25 | 4.70 | 3.65E-06 | 3'ss | Mel. |
| 545 | chr12: 105601825-105601935 | chr12: 105601807-105601935 | ATTTGGACTCGCTAGCAATGATGTCTGTTTATTTTTAGAG (41) | ATTTGGACTCGCTAGCAATGAGCATGACCTCTCAATGGCA (42) | 1 | 49 | 4.64 | 6.42E-06 | 3'ss | Mel. |
| 546 | chr14: 75356052-75356580 | chr14: 75356052-75356599 | AGATGTCAGGTGGGAGAAAGCCTTTGATTGTCTTTTCAGC (89) | AGATGTCAGGTGGGAGAAAGCTGTTGGAGACACAGTTGCA (90) | 0 | 24 | 4.64 | 2.35E-03 | 3'ss | Mel. |
| 547 | chr11: 4104212-4104471 | chr11: 4104212-4104492 | CATAAAATTCTAACAGCTAATTCTCTTTCCTCTGTCTTCA (69) | CATAAAATTCTAACAGCTAAGCAAGCACTGAGCGAGGTGA (70) | 0 | 23 | 4.58 | 4.56E-05 | 3'ss | Mel. |
| 548 | chr15: 59209219-59224554 | chr15: 59209198-59224554 | GAAACCAACTAAAGGCAAAGCCCATTTTCCTTCTTTCGCA (101) | GAAACCAACTAAAGGCAAAGGTAAAAAACATGAAGCAGAT (102) | 0 | 23 | 4.58 | 2.75E-04 | 3'ss | Mel. |
| 549 | chr22: 19044699-19050714 | chr22: 19044675-19050714 | CTGGGAGGTGGCATTCAAAGCCCCACCTTTTGTCTCCCCA (45) | CTGGGAGGTGGCATTCAAAGGCTCTTCAGAGGTGTTCCTG (46) | 0 | 23 | 4.58 | 1.03E-06 | 3'ss | Mel. |
| 550 | chr3: 129284872-129285369 | chr3: 129284860-129285369 | CACTGCTGGGAGAGTGGAAGTTGCTTCCACAGATTCCTGA (524) | CACTGCTGGGAGAGTGGAAGATTCCTGAGAGCTGCCGGCC (525) | 0 | 23 | 4.58 | 5.29E-10 | 3'ss | Mel. |
| 551 | chr9: 138903859-138905044 | chr9: 138903870-138905044 | GGTCCTGAACGCTGTGAAATAACTTCGCCCCCAGCTTCAA (866) | GGTCCTGAACGCTGTGAAATTGTACTGTCAGAACTTCGCC (867) | 0 | 23 | 4.58 | 1.89E-04 | 3'ss | Mel. |
| 552 | chr6: 35255622-35258029 | chr6: 35255622-35258042 | TGGAGCAGTATGCCAGCAAGACTTTTCCCCCAGGTTCTTC (868) | TGGAGCAGTATGCCAGCAAGGTTCTTCATGACAGCCAGAT (869) | 0 | 22 | 4.52 | 8.93E-03 | 3'ss | Mel. |
| 553 | chr8: 28625893-28627405 | chr8: 28625839-28627405 | TCGTGCAGACCCTGGAGAAGATCTCACAGATGTGCAGTCT (870) | TCGTGCAGACCCTGGAGAAGCATGGCTTCAGTGATATTAA (871) | 0 | 22 | 4.52 | 3.21E-11 | 3'ss | Mel. |
| 554 | chr6: 10723474-10724788 | chr6: 10723474-10724802 | CCGGGGCCTTCGTGAGACCGCTTGTTTTCTGCAGGTGCAG (95) | CCGGGGCCTTCGTGAGACCGGTGCAGGCCTGGGGTAGTCT (96) | 2 | 67 | 4.5 | 2.74E-12 | 3'ss | Mel. |
| 555 | chr4: 184577127-184580081 | chr4: 184577114-184580081 | GTGCCAACGAGGACCAGGAGTTCTTTATTTCAGATGGAAC (734) | GTGCCAACGAGGACCAGGAGATGGAACTAGAAGCATTACG (735) | 2 | 65 | 4.46 | 9.90E-07 | 3'ss | Mel. |
| 556 | chr22: 39064137-39066874 | chr22: 39064137-39066888 | CTCTCTCCAACCTGCATTCTCATCTCGCCCCACAGTTGGAT (140) | CTCTCTCCAACCTGCATTCTTTGGATCGATCAACCCGGGA (141) | 0 | 21 | 4.46 | 4.84E-04 | 3'ss | Mel. |

TABLE 1-continued

| | Aberrant junction | WT junction | Aberrant sequence (SEQ ID NO) | WT sequence (SEQ ID NO) | Avg WT % | Avg Ab. % | Log₂ Fold Diff. | FDR Q-Value | Event | Type |
|---|---|---|---|---|---|---|---|---|---|---|
| 557 | chr9: 37501841- 37503015 | chr9: 37501841- 37503039 | TTGAAGCTCAGT GAGAAAAGTTCT TCTGTTTATGTC TTCC (872) | TTGAAGCTCAGT GAGAAAAGGATG ATGGAGATAGCC AAAG (873) | 0 | 21 | 4.46 | 3.30E-03 | 3'ss | Mel. |
| 558 | chr14: 71059726- 71060012 | chr14: 71059705- 71060012 | CAGTTATAAACT CTAGAGTGAGTT TATTTTCCTTTT ACAA (79) | CAGTTATAAACT CTAGAGTGCTTA CTGCAGTGCATG GTAT (80) | 0 | 20 | 4.39 | 2.55E-03 | 3'ss | Mel. |
| 559 | chr17: 71198039- 71199162 | chr17: 71198039- 71199138 | GGAGCAGTGCAG TTGTGAAATCAT TACTTCTAGATG ATGC (31) | GGAGCAGTGCAG TTGTGAAAGTTT TGATTCATGGAT TCAC (32) | 0 | 20 | 4.39 | 2.74E-12 | 3'ss | Mel. |
| 560 | chr9: 35608506- 35608842 | chr9: 35608506- 35608858 | CGCCCTGACACA CAATCAGGACTT CTCTATCTACAG GCTC (874) | CGCCCTGACACA CAATCAGGGCTC TGTTGCAAGAGG GGGT (875) | 0 | 20 | 4.39 | 1.26E-04 | 3'ss | Mel. |
| 561 | chrX: 47059013- 47059808 | chrX: 47059013- 47060292 | ACTTCCTTAGTG GTTTCCAGGTTG CCAGGGCACTGC AGCT (111) | ACTTCCTTAGTG GTTTCCAGGTGG TGGTGCTCACCA ACAC (112) | 0 | 20 | 4.39 | 2.32E-03 | 3'ss | Mel. |
| 562 | chr12: 107378993- 107380746 | chr12: 107379003- 107380746 | CTTGGAGCTGAC GCCGACGGGGAA CTGACAAGATCA CATT (130) | CTTGGAGCTGAC GCCGACGGTTTA TTGCAGGGAACT GACA (131) | 4 | 96 | 4.28 | 5.10E-13 | 3'ss | Mel. |
| 563 | chr10: 133782836- 133784141 | chr10: 133782073- 133784141 | TTGCTGGCCATC GGATTGGGCCCT TCGTTTCAGGAT GGAT (876) | TTGCTGGCCATC GGATTGGGGATC TATATTGGAAGG CGTC (877) | 0 | 18 | 4.25 | 1.13E-14 | 3'ss | Mel. |
| 564 | chr11: 64877395- 64877934 | chr11: 64877395- 64877953 | CCACCGCCATCG ACGTGCAGTACC TCTTTTTACCAC CAGG (167) | CCACCGCCATCG ACGTGCAGGTGG GGCTCCTGTACG AAGA (168) | 0 | 18 | 4.25 | 6.04E-04 | 3'ss | Mel. |
| 565 | chr21: 37416267- 37417879 | chr21: 37416254- 37417879 | ATCATAGCCCAC ATGTCCAGTTTT TCTTTCTAGGTA AAAG (695) | ATCATAGCCCAC ATGTCCAGGTAA AAGCAGCGTTTA ATGA (696) | 1 | 35 | 4.17 | 1.72E-04 | 3'ss | Mel. |
| 566 | chr15: 25213229- 25219533 | chr15: 25213229- 25219457 | TGATTCCAAGCA AAAACCAGCCTT CCCCTAGGTCTT CAGA (230) | TGATTCCAAGCA AAAACCAGGCTC CATCTACTCTTT GAAG (231) | 1 | 34 | 4.13 | 1.03E-06 | 3'ss | Mel. |
| 567 | chr17: 34942628- 34943454 | chr17: 34942628- 34943426 | TACTGAAATGTG ATGAACATATCC AGGTAATCGAGA GACC (124) | TACTGAAATGTG ATGAACATATCC AGAAGCTTGGAA GCTG (125) | 0 | 16 | 4.09 | 5.46E-04 | 3'ss | Mel. |
| 568 | chr2: 219610954- 219611752 | chr2: 219610954- 219611725 | CCATTCGAGAGC ATCAGAAGATTG GGAGGAAGGACC GGCT (878) | CCATTCGAGAGC ATCAGAAGCTAA ACCATTTCCCAG GCTC (879) | 0 | 16 | 4.09 | 2.25E-03 | 3'ss | Mel. |
| 569 | chr10: 99219232- 99219415 | chr10: 99219283- 99219415 | TCTTGCCAGAGC TGCCCACGCTCT CCACCCTCAGCT GCCT (587) | TCTTGCCAGAGC TGCCCACGCTTC TTTTCCTTGCTGC TGGA (588) | 0 | 15 | 4.00 | 9.94E-07 | 3'ss | Mel. |
| 570 | chr11: 3697619- 3697738 | chr11: 3697606- 3697738 | AGATCGCCTGGC TCAGTCAGTTTT TCTCTCTAGACA TGGC (187) | AGATCGCCTGGC TCAGTCAGACAT GGCCAAACGTGT AGCC (188) | 0 | 15 | 4.00 | 9.65E-05 | 3'ss | Mel. |
| 571 | chr11: 62648919- 62649352 | chr11: 62648919- 62649364 | CGGCGCGGGCAA CCTGGCGGCCCC CATTTCAGGTCT GAAG (165) | CGGCGCGGGCAA CCTGGCGGGTCT GAAGGGGCGTCT CGAT (166) | 0 | 15 | 4.00 | 4.00E-05 | 3'ss | Mel. |

TABLE 1-continued

| | Aberrant junction | WT junction | Aberrant sequence (SEQ ID NO) | WT sequence (SEQ ID NO) | Avg WT % | Avg Ab. % | Log₂ Fold Diff. | FDR Q-Value | Event | Type |
|---|---|---|---|---|---|---|---|---|---|---|
| 572 | chr1: 113195986-113196219 | chr1: 113192091-113196219 | TCAGGAGCAGAGAGGAAAAGTGCATTTGCCCAGTATAACA (880) | CTCAGGGAAGGGGCAGCACATGCATTTGCCCAGTATAACA (881) | 0 | 15 | 4.00 | 2.96E-02 | 5'ss | Mel. |
| 573 | chr1: 52880319-52880412 | chr1: 52880319-52880433 | CGATCTCCCAAAAGGAGAAGTCTGACCAGTCTTTTCTACA (55) | CGATCTCCCAAAAGGAGAAGCCCCTCCCCTCGCCGAGAAA (56) | 0 | 15 | 4.00 | 5.55E-03 | 3'ss | Mel. |
| 574 | chr15: 25212299-25213078 | chr15: 25207356-25213078 | TCACACAGGATAATTTGAAAGTGTCAGTTGTACCCGAGGC (164) | GCCTCACTGAGCAACCAAGAGTGTCAGTTGTACCCGAGGC (145) | 1 | 30 | 3.95 | 6.03E-06 | exon incl. | Mel. |
| 575 | chr11: 64002365-64002911 | chr11: 64002365-64002929 | TGCAGCTGGCCCCCGCCCAGGTCTTTTCTCTCCCACAGGC (638) | TGCAGCTGGCCCCCGCCCAGGCCCCTGTCTCCCAGCCTGA (639) | 0 | 14 | 3.91 | 1.39E-07 | 3'ss | Mel. |
| 576 | chr12: 113346629-113348840 | chr12: 113346629-113348855 | GCCTGCCTTTGATGCCCTGGATTTTGCCCGAACAGGTCAG (71) | GCCTGCCTTTGATGCCCTGGGTCAGTTGACTGGCGGCTAT (72) | 0 | 14 | 3.91 | 1.83E-03 | 3'ss | Mel. |
| 577 | chr17: 78188582-78188831 | chr17: 78188564-78188831 | CCAAGCTGGTGTGCGCACAGGCCTCTCTTCCCGCCCAGGC (73) | CCAAGCTGGTGTGCGCACAGGCATCATCGGGAAGAAGCAC (74) | 0 | 14 | 3.91 | 1.08E-03 | 3'ss | Mel. |
| 578 | chr2: 85848702-85850728 | chr2: 85848702-85850768 | GTGTGGCAAGTACTTTCAAGTATCTGCCCTTCTATTACAG (882) | GTGTGGCAAGTACTTTCAAGGCCGGGGTTTGAAGTCTCAC (883) | 0 | 14 | 3.91 | 1.45E-02 | 3'ss | Mel. |
| 579 | chr12: 29450133-29460566 | chr12: 29450133-29460590 | AAAATCATTGATTCCCTTGAAATTCTCTTTACTCTACCTT (884) | AAAATCATTGATTCCCTTGAGTGGTTAGACGATGCTATTA (885) | 0 | 13 | 3.81 | 1.44E-03 | 3'ss | Mel. |
| 580 | chr14: 23237380-23238985 | chr14: 23237380-23238999 | GTGGGGGGCCATTGCTGCATTTTGTATTTTCCAGGTACAG (122) | GTGGGGGGCCATTGCTGCATGTACAGTCTTTGCCCGCTGC (123) | 0 | 13 | 3.81 | 2.75E-04 | 3'ss | Mel. |
| 581 | chr22: 36627480-36629198 | chr22: 36627512-36629198 | CGCTGGCACCATGAACCCAGTATTTCCAGGACCAAGTGAG (199) | CGCTGGCACCATGAACCCAGAGAGCAGTATCTTTATTGAG (200) | 0 | 13 | 3.81 | 5.09E-08 | 3'ss | Mel. |
| 582 | chr19: 14031735-14034130 | chr19: 14031735-14034145 | TGCCTGTGGACATCACCAAGCCTCGTCCTCCCCAGGTGCC (59) | TGCCTGTGGACATCACCAAGGTGCCGCCTGCCCCTGTCAA (60) | 0 | 12 | 3.70 | 4.53E-04 | 3'ss | Mel. |
| 583 | chr20: 35282126-35284762 | chr20: 35282104-35284762 | TTTGCAGGGAATGGGCTACATCCCCTTGGTTCTCTGTTAC (35) | TTTGCAGGGAATGGGCTACATACCATCTGCCAGCATGACT (36) | 0 | 12 | 3.70 | 9.65E-05 | 3'ss | Mel. |
| 584 | chr22: 19948812-19950181 | chr22: 19948812-19950049 | TGCTCAGAGGTGCTTTGAAGCCCATCCACAACCTGCTCAT (886) | TGCTCAGAGGTGCTTTGAAGATGCCGGAGGCCCCGCTCT (887) | 0 | 12 | 3.70 | 8.43E-07 | 3'ss | Mel. |
| 585 | chr2: 170669034-170671986 | chr2: 170669016-170671986 | CAAGATAGATATTATAGCAGGTGGCTTTTGTTTTACAGAA (99) | CAAGATAGATATTATAGCAGAACTTCGATATGACCTGCCA (100) | 0 | 12 | 3.70 | 3.94E-03 | 3'ss | Mel. |
| 586 | chr15: 25207356-25212175 | chr15: 25207356-25213078 | GCCTCACTGAGCAACCAAGAGTAGTGACTTGTCAGGAGGA (144) | GCCTCACTGAGCAACCAAGAGTGTCAGTTGTACCCGAGGC (145) | 2 | 37 | 3.66 | 8.44E-08 | exon incl. | Mel. |

TABLE 1-continued

| | Aberrant junction | WT junction | Aberrant sequence (SEQ ID NO) | WT sequence (SEQ ID NO) | Avg WT % | Avg Ab. % | Log₂ Fold Diff. | FDR Q-Value | Event | Type |
|---|---|---|---|---|---|---|---|---|---|---|
| 587 | chr11: 8704812-8705536 | chr11: 8704812-8705552 | CCACGGCCACGGCCGCATAGCTTTGTATTCCTGCAGGCAA (888) | CCACGGCCACGGCCGCATAGGCAAGCACCGGAAGCACCCC (889) | 4 | 60 | 3.61 | 3.80E-03 | 3'ss | Mel. |
| 588 | chr11: 11988666-11989941 | chr11: 11988645-11989941 | CATGCCGGGCCAGAGGATGGCTCTTTCCACCTGTCTGCA (890) | CATGCCGGGCCAGAGGATGCTCTGCACCCGGGACAGTGA (891) | 0 | 11 | 3.58 | 1.83E-02 | 3'ss | Mel. |
| 589 | chr16: 19838459-19843229 | chr16: 19838459-19867808 | GGCGAAGCAAGAACAAAAAGTATTTTCTTCTAGGATGGAA (892) | GGCGAAGCAAGAACAAAAAGTGAAATGCAAAATGGAGGAC (893) | 0 | 11 | 3.58 | 1.88E-02 | 3'ss | Mel. |
| 590 | chr1: 155630724-155631097 | chr1: 155630704-155631097 | GGCTCCCATTCTGGTTAAAGAGTGTTCTCATTTCCAATAG (195) | GGCTCCCATTCTGGTTAAAGGCCAGTCTGCCATCCATCCA (196) | 0 | 11 | 3.58 | 2.42E-03 | 3'ss | Mel. |
| 591 | chr1: 219366593-219383856 | chr1: 219366593-219383873 | GAAGAACAGGATATTAATAGTATGTTTTTGTTTTAGGAG (894) | GAAGAACAGGATATTAATAGGAGGATTCTCTATGGGAGGA (895) | 0 | 11 | 3.58 | 1.74E-02 | 3'ss | Mel. |
| 592 | chr19: 5595521-5598803 | chr19: 5595508-5598803 | CAAGCAGGTCCAAAGAGAGATTTTGGTAAACAGAGCTCCA (138) | CAAGCAGGTCCAAAGAGAGAAGCTCCAAGAGTCAGGATCG (139) | 0 | 10 | 3.46 | 2.28E-04 | 3'ss | Mel. |
| 593 | chr5: 462644-464404 | chr5: 462422-464404 | CAATTCAGTAGATTCACCCTCAACATCTGAATGAATTGAT (896) | AGGTCTTCCTGGACCTGGAGCAACATCTGAATGAATTGAT (897) | 0 | 10 | 3.46 | 2.42E-02 | 5'ss | Mel. |
| 594 | chr9: 35813153-35813262 | chr9: 35813142-35813262 | GGGAGATGGATACCGACTTGCTCAATTTCAGTGATCAACG (146) | GGGAGATGGATACCGACTTGTGATCAACGATGGGAAGCTG (147) | 3 | 41 | 3.39 | 1.97E-10 | 3'ss | Mel. |
| 595 | chr1: 205240383-205240923 | chr1: 205240383-205240940 | AGAGGGCACGGGACATCCAGCCCCTCTGCCCCTGCAGGAG (898) | AGAGGGCACGGGACATCCAGGAGGCCGTGGAGTCCTGCCT (899) | 2 | 29 | 3.32 | 1.42E-03 | 3'ss | Mel. |
| 596 | chr11: 125442465-125445146 | chr11: 125442465-125445158 | TTCTCCAGGACCTTGCCAGACCTTTTCTATAGGGAATCAA (150) | TTCTCCAGGACCTTGCCAGAGGAATCAAAGACTCCATCTG (151) | 0 | 9 | 3.32 | 6.24E-03 | 3'ss | Mel. |
| 597 | chr11: 71939542-71939690 | chr11: 71939542-71939770 | GGATGACCGGGATGCCTCAGTCACTTTACAGCTGCATCGT (47) | GGATGACCGGGATGCCTCAGATGGGGAGGATGAGAAGCCC (48) | 0 | 9 | 3.32 | 3.79E-04 | 3'ss | Mel. |
| 598 | chr16: 70292147-70292882 | chr16: 70292120-70292882 | AGATGATTGAGGCAGCCAAGCTCTTTTCTGTCTTCTTGGT (900) | AGATGATTGAGGCAGCCAAGGCCGTCTATACCCAGGATTG (901) | 0 | 9 | 3.32 | 1.06E-02 | 3'ss | Mel. |
| 599 | chr2: 220044485-220044888 | chr2: 220044485-220044831 | GAGGAGCCACACTCTGACAGATACCTGGCTGAGAGCTGGC (107) | GAGGAGCCACACTCTGACAGTGAGGGTGCGGGTCAGGCG (108) | 0 | 9 | 3.32 | 2.20E-02 | 3'ss | Mel. |
| 600 | chr3: 45043100-45046767 | chr3: 45043100-45046782 | GCTGCTCTCTTCAATACAAGTGCTTCTGCTTCCAGGATAC (902) | GCTGCTCTCTTCAATACAAGGATACCAAGGGTTCGAGTTT (903) | 0 | 9 | 3.32 | 2.87E-06 | 3'ss | Mel. |
| 601 | chr9: 101891382-101894778 | chr9: 101891382-101894790 | AATAGAACTTCCAACTACTGGCCCTTTTTCAGTAAAGTCA (904) | AATAGAACTTCCAACTACTGTAAAGTCATCACCTGGCCTT (905) | 7 | 76 | 3.27 | 4.47E-08 | 3'ss | Mel. |

TABLE 1-continued

| Aberrant junction | WT junction | Aberrant sequence (SEQ ID NO) | WT sequence (SEQ ID NO) | Avg WT % | Avg Ab. % | Log$_2$ Fold Diff. | FDR Q-Value | Event | Type |
|---|---|---|---|---|---|---|---|---|---|
| 588 chr11: 11988666-11989941 | chr11: 11988645-11989941 | CATGCCGGGCC AGAGGATGGCTC TTTCCACCTGTC TGCA (890) | CATGCCGGGCC AGAGGATGCTCT GCACCCGGGACA GTGA (891) | 0 | 11 | 3.58 | 1.83E-02 | 3'ss | Mel. |
| 589 chr16: 19838459-19843229 | chr16: 19838459-19867808 | GGCGAAGCAAGA ACAAAAAGTATT TTCTTCTAGGAT GGAA (892) | GGCGAAGCAAGA ACAAAAAGTGAA ATGCAAAATGGA GGAC (893) | 0 | 11 | 3.58 | 1.88E-02 | 3'ss | Mel. |
| 590 chr1: 155630724-155631097 | chr1: 155630704-155631097 | GGCTCCCATTCT GGTTAAAGAGTG TTCTCATTTCCA ATAG (195) | GGCTCCCATTCT GGTTAAAGGCCA GTCTGCCATCCA TCCA (196) | 0 | 11 | 3.58 | 2.42E-03 | 3'ss | Mel. |
| 591 chr1: 219366593-219383856 | chr1: 219366593-219383873 | GAAGAACAGGAT ATTAATAGTATG TTTTTGTTTTTA GGAG (894) | GAAGAACAGGAT ATTAATAGGAGG ATTCTCTATGGG AGGA (895) | 0 | 11 | 3.58 | 1.74E-02 | 3'ss | Mel. |
| 592 chr19: 5595521-5598803 | chr19: 5595508-5598803 | CAAGCAGGTCCA AAGAGAGATTTT GGTAAACAGAGC TCCA (138) | CAAGCAGGTCCA AAGAGAGAAGCT CCAAGAGTCAGG ATCG (139) | 0 | 10 | 3.46 | 2.28E-04 | 3'ss | Mel. |
| 593 chr5: 462644-464404 | chr5: 462422-464404 | CAATTCAGTAGA TTCACCCTCAAC ATCTGAATGAAT TGAT (896) | AGGTCTTCCTGG ACCTGGAGCAAC ATCTGAATGAAT TGAT (897) | 0 | 10 | 3.46 | 2.42E-02 | 5'ss | Mel. |
| 594 chr9: 35813153-35813262 | chr9: 35813142-35813262 | GGGAGATGGATA CCGACTTGCTCA ATTTCAGTGATC AACG (146) | GGGAGATGGATA CCGACTTGTGAT CAACGATGGGAA GCTG (147) | 3 | 41 | 3.39 | 1.97E-10 | 3'ss | Mel. |
| 595 chr1: 205240383-205240923 | chr1: 205240383-205240940 | AGAGGGCACGGG ACATCCAGCCCC TCTGCCCCTGCA GGAG (898) | AGAGGGCACGGG ACATCCAGGAGG CCGTGGAGTCCT GCCT (899) | 2 | 29 | 3.32 | 1.42E-03 | 3'ss | Mel. |
| 596 chr11: 125442465-125445146 | chr11: 125442465-125445158 | TTCTCCAGGACC TTGCCAGACCTT TTCTATAGGGAA TCAA (150) | TTCTCCAGGACC TTGCCAGAGGAA TCAAAGACTCCA TCTG (151) | 0 | 9 | 3.32 | 6.24E-03 | 3'ss | Mel. |
| 597 chr11: 71939542-71939690 | chr11: 71939542-71939770 | GGATGACCGGGA TGCCTCAGTCAC TTTACAGCTGCA TCGT (47) | GGATGACCGGGA TGCCTCAGATGG GGAGGATGAGAA GCCC (48) | 0 | 9 | 3.32 | 3.79E-04 | 3'ss | Mel. |
| 598 chr16: 70292147-70292882 | chr16: 70292120-70292882 | AGATGATTGAGG CAGCCAAGCTCT TTTCTGTCTTCT TGGT (900) | AGATGATTGAGG CAGCCAAGGCCG TCTATACCCAGG ATTG (901) | 0 | 9 | 3.32 | 1.06E-02 | 3'ss | Mel. |
| 599 chr2: 220044485-220044888 | chr2: 220044485-220044831 | GAGGAGCCACAC TCTGACAGATAC CTGGCTGAGAGC TGGC (107) | GAGGAGCCACAC TCTGACAGTGAG GGTGCGGGTCA GGCG (108) | 0 | 9 | 3.32 | 2.20E-02 | 3'ss | Mel. |
| 600 chr3: 45043100-45046767 | chr3: 45043100-45046782 | GCTGCTCTCTTC AATACAAGTGCT TCTGCTTCCAGG ATAC (902) | GCTGCTCTCTTC AATACAAGGATA CCAAGGGTTCGA GTTT (903) | 0 | 9 | 3.32 | 2.87E-06 | 3'ss | Mel. |
| 601 chr9: 101891382-101894778 | chr9: 101891382-101894790 | AATAGAACTTCC AACTACTGGCCC TTTTTCAGTAAA GTCA (904) | AATAGAACTTCC AACTACTGTAAA GTCATCACCTGG CCTT (905) | 7 | 76 | 3.27 | 4.47E-08 | 3'ss | Mel. |
| 602 chr17: 7131030-7131295 | chr17: 7131102-7131295 | CTATTTCACTCT CCCCCGAACCTA TCCAGGTTCCTC CTCC (33) | CTATTTCACTCT CCCCCGAAATGA GCCCATCCAGCC AATT (34) | 2 | 27 | 3.22 | 1.02E-05 | 3'ss | Mel. |

TABLE 1-continued

| | Aberrant junction | WT junction | Aberrant sequence (SEQ ID NO) | WT sequence (SEQ ID NO) | Avg WT % | Avg Ab. % | Log₂ Fold Diff. | FDR Q-Value | Event | Type |
|---|---|---|---|---|---|---|---|---|---|---|
| 603 | chr17: 79556145- 79563141 | chr17: 79556145- 79563141 | TGTTACTGCAGT GGCTACAGGTCT CTCTCTTGCAGG TGGT (906) | TGTTACTGCAGT GGCTACAGGTGG TCCTGACAACCA AGTC (907) | 1 | 17 | 3.17 | 2.33E-03 | 3'ss | Mel. |
| 604 | chr13: 45841511- 45857556 | chr13: 45841511- 45857576 | ACATCACAAAGC AACCTGTGGGGT TTTGTTTTTGTT TTAG (908) | ACATCACAAAGC AACCTGTGGTGT ACCTGAAGGAAA TCTT (909) | 0 | 8 | 3.17 | 1.95E-03 | 3'ss | Mel. |
| 605 | chr14: 105176525- 105177255 | chr14: 105176525- 105177273 | GGTGCTGGCTGC CTGCGAAACCCT GGCTGCCCCTGC AGGC (910) | GGTGCTGGCTGC CTGCGAAAGCCT GCTCACCCAGCCG CCAG (911) | 0 | 8 | 3.17 | 3.94E-03 | 3'ss | Mel. |
| 606 | chr16: 15129410- 15129852 | chr16: 15129410- 15129872 | CACCAAGCAGAG GCTTCCAGTTCT TCTGCCCTTTCT GTAG (216) | CACCAAGCAGAG GCTTCCAGGCCA GAAGCCTTTTAA AAGG (217) | 0 | 8 | 3.17 | 7.87E-04 | 3'ss | Mel. |
| 607 | chr17: 17062316- 17064532 | chr17: 17062316- 17064553 | CCTCTCTGCTCG AGAAGGAGTGTG TGTCTTTTTGCC AACA (912) | CCTCTCTGCTCG AGAAGGAGCTGG AGCAGAGCCAGA AGGA (913) | 0 | 8 | 3.17 | 7.21E-08 | 3'ss | Mel. |
| 608 | chr19: 15491444- 15507960 | chr19: 15491423- 15507960 | ATCACAACCGGA ACCGCAGGCTCC TTCTGCCCTGCC CGCA (661) | ATCACAACCGGA ACCGCAGGCTCA TGATGGAGCAGT CCAA (662) | 0 | 8 | 3.17 | 1.45E-02 | 3'ss | Mel. |
| 609 | chr3: 112724877- 112727017 | chr3: 112724851- 112727017 | CTGGAAGCTCAA GGTACTAGATTT TTCCTCTCTCTG TCTT (914) | CTGGAAGCTCAA GGTACTAGTTTG CCAAAGAAACTA GAGT (915) | 0 | 8 | 3.17 | 4.68E-04 | 3'ss | Mel. |
| 610 | chr1: 3548881- 3549961 | chr1: 3548902- 3549961 | CCCGAGCTCAGA GAGTAAATTCTC CTTACAGACACT GAAA (177) | CCCGAGCTCAGA GAGTAAATATGA GATCGCCTCTGT CCCA (178) | 4 | 41 | 3.07 | 3.31E-04 | 3'ss | Mel. |
| 611 | chr2: 178096758- 178097119 | chr2: 178096736- 178097119 | TATCCATTCCTG AGTTACAGTATA AACTTCCTTCTC ATGC (156) | TATCCATTCCTG AGTTACAGTGTC TTAATATTGAAA ATGA (157) | 1 | 15 | 3.00 | 3.44E-05 | 3'ss | Mel. |
| 612 | chr11: 62554999- 62556481 | chr11: 62554999- 62556494 | CGGCGATGACTC GGACCCAGCTTC TCTCCACAGGGC TCCT (916) | CGGCGATGACTC GGACCCAGGGCT CCTTCAGTGGTA GATG (917) | 0 | 7 | 3.00 | 2.48E-02 | 3'ss | Mel. |
| 613 | chr15: 41102168- 41102274 | chr15: 41102168- 41102268 | CCGCCAGGAGAA CAAGCCCATCCC CTCACAGGCAGA GATA (918) | CCGCCAGGAGAA CAAGCCCAAGTT AGTCCCCTCACA GGCA (919) | 0 | 7 | 3.00 | 9.38E-04 | 3'ss | Mel. |
| 614 | chr16: 48311390- 48330007 | chr16: 48311390- 48329925 | CAGCAGCAGCTC TGCTTGAGCTAC TGCCAACACCAC TGCT (920) | CAGCAGCAGCTC TGCTTGAGGTGT TGGATCCTGAAC AAAA (921) | 0 | 7 | 3.00 | 9.09E-03 | 3'ss | Mel. |
| 615 | chr2: 26437445- 26437921 | chr2: 26437430- 26437921 | AGACAAGGGATT GGTGGAAACATT TTATTTTACAGA ATTG (295) | AGACAAGGGATT GGTGGAAAAATT GACAGCGTATGC CATG (296) | 0 | 7 | 3.00 | 6.35E-04 | 3'ss | Mel. |
| 616 | chr3: 48638222- 48638407 | chr3: 48638273- 48638407 | GCACTTATGGTG GTGGCGTGAGTT TCCAGACCTTCA GCAT (922) | GCACTTATGGTG GTGGCGTGCACC TGTCCAGCCCAC TGGC (923) | 0 | 7 | 3.00 | 1.74E-07 | 3'ss | Mel. |
| 617 | chr19: 55776746- 55777253 | chr19: 55776757- 55777253 | GTGCTTGGAGCC CTGTGCAGACTT TCCGCAGGGTGT GCGC (179) | GTGCTTGGAGCC CTGTGCAGCCTG GTGACAGACTTT CCGC (180) | 4 | 35 | 2.85 | 1.91E-07 | 3'ss | Mel. |

TABLE 1-continued

| Aberrant junction | WT junction | Aberrant sequence (SEQ ID NO) | WT sequence (SEQ ID NO) | Avg WT % | Avg Ab. % | Log$_2$ Fold Diff. | FDR Q-Value | Event | Type |
|---|---|---|---|---|---|---|---|---|---|
| 618 chr9: 119414072- 119488049 | chr9: 119414072- 119449344 | GTGGCTCCAGTA TCAGAAAGAGAC CACAGAGCTGGG CAGC (924) | GACCTGCTCAAG TTCACTCAAGAC CACAGAGCTGGG CAGC (925) | 8 | 63 | 2.83 | 2.74E-02 | 5'ss | Mel. |
| 619 chr10: 82264534- 82266954 | chr10: 82264534- 82266983 | TGTGGGCATGGA GCGAAAAGTGCT GCCCTGCTTTCT CTGT (926) | TGTGGGCATGGA GCGAAAAGGGTG TGCTGTCCGACC TCAC (927) | 0 | 6 | 2.81 | 8.27E-08 | 3'ss | Mel. |
| 620 chr12: 56361953- 56362539 | chr12: 56361953- 56362561 | TTCCTCTTCCCC TCATCAAGTCCT CTCTTTCTCCTT TGTC (928) | TTCCTCTTCCCC TCATCAAGAGCT ATCTGTTCCAGC TGCT (929) | 0 | 6 | 2.81 | 4.32E-06 | 3'ss | Mel. |
| 621 chr19: 50149459- 50149761 | chr19: 50149459- 50149782 | GGGGCACTGACA CGGCTACTAGCC TCTCTGGCCTCT TCCA (930) | GGGGCACTGACA CGGCTACTGTGT TGGACATGGCCA CGGA (931) | 0 | 6 | 2.81 | 2.67E-02 | 3'ss | Mel. |
| 622 chr20: 34144042- 34144761 | chr20: 34144042- 34144743 | ACATGAAGGTGG ACGGAGAGTTCT CTGTGACCAGAC ATGA (250) | ACATGAAGGTGG ACGGAGAGGTAC TGAGGACAAATC AGTT (50) | 0 | 6 | 2.81 | 1.25E-04 | 3'ss | Mel. |
| 623 chrX: 118923962- 118925536 | chrX: 118923974- 118925536 | TGACTCCGCTGC TCGCCATGACTT TCAGGATTAAGC GATT (697) | TGACTCCGCTGC TCGCCATGTCTT CTCACAAGACTT TCAG (698) | 0 | 6 | 2.81 | 1.80E-02 | 3'ss | Mel. |
| 624 chr2: 27260570- 27260682 | chr2: 27260570- 27261013 | CCCCTGAGATGA AGAAAGAGCTCC CTGTTGACAGCT GCCT (183) | CCCCTGAGATGA AGAAAGAGCTCC TGAGCAGCCTGA CTGA (184) | 3 | 25 | 2.70 | 6.46E-06 | exon incl. | Mel. |
| 625 chr2: 99225189- 99226105 | chr2: 99225189- 99226218 | AGGCTGTAGCAG GACTCCAGGGTT GGGAAGAACATG GAAA (932) | AGGCTGTAGCAG GACTCCAGGAAG ATGTTACCGAGT ACTT (933) | 1 | 12 | 2.70 | 2.24E-02 | 3'ss | Mel. |
| 626 chr8: 133811106- 133811328 | chr8: 133811106- 133816063 | CCGAGGATGCTA AGGGGCAGTTTC TGTTCCAGGTGA AATC (934) | CCGAGGATGCTA AGGGGCAGGATT GGATAGCTTTAG TCAA (935) | 4 | 30 | 2.63 | 6.42E-03 | 3'ss | Mel. |
| 627 chr21: 46935066- 46945730 | chr21: 46936054- 46945730 | GCCTCCCGGTCC GCAAGCAGAATG AAGAACTGCATG TGGC (936) | GCCTCCCGGTCC GCAAGCAGTTCC AGTTATACTCCG TGTA (937) | 4 | 29 | 2.58 | 9.60E-04 | 3'ss | Mel. |
| 628 chr17: 27210249- 27212874 | chr17: 27210249- 27211242 | TCGTAACAGGGG TTGCACAGGTGA AGATCATGACGG AGAA (938) | CTGTGACGGGTG TCGCCCAGGTGA AGATCATGACGG AGAA (939) | 3 | 23 | 2.58 | 1.22E-02 | exon skip | Mel. |
| 629 chr6: 112020873- 112021306 | chr6: 112017659- 112021306 | GTTTGGGGAAGT ATGGATGGAGAA AGCTGATGGTTT GTGT (940) | GTTTGGGGAAGT ATGGATGGGTAC CTGGAATGGAAA CACA (941) | 1 | 11 | 2.58 | 2.07E-05 | exon incl. | Mel. |
| 630 chr6: 39854223- 39855261 | chr6: 39851845- 39855261 | TAACTAATCCTT CTCAGCAGAAAG AGCTGGGCTCCA CTGA (942) | CAGCCTACCAGA GGCACCAGAAAG AGCTGGGCTCCA CTGA (943) | 1 | 11 | 2.58 | 4.06E-02 | 5'ss | Mel. |
| 631 chr11: 64900740- 64900940 | chr11: 64900723- 64900940 | AGTCCAGCCCCA GCATGGCACCTC TCCCCACTCCTA GGTC (136) | AGTCCAGCCCCA GCATGGCAGTCC TGTACATCCAGG CCTT (137) | 0 | 5 | 2.58 | 9.35E-03 | 3'ss | Mel. |
| 632 chr16: 1402307- 1411686 | chr16: 1402307- 1411743 | GGATCCTTCACC CGTGTCTGTCTT TGCAGACAGGTT CTGT (85) | GGATCCTTCACC CGTGTCTGGACC CGTGCATCTCTT CCGA (86) | 0 | 5 | 2.58 | 1.87E-03 | 3'ss | Mel. |

TABLE 1-continued

| | Aberrant junction | WT junction | Aberrant sequence (SEQ ID NO) | WT sequence (SEQ ID NO) | Avg WT % | Avg Ab. % | Log$_2$ Fold Diff. | FDR Q-Value | Event | Type |
|---|---|---|---|---|---|---|---|---|---|---|
| 633 | chr17: 16344444-16344670 | chr17: 16344444-16344681 | GCATCTCAGCCC AAGAGAAGTTTC TTTGCAGGTTAT ATTC (287) | GCATCTCAGCCC AAGAGAAGGTTA TATTCCCAGAGG ATGT (288) | 0 | 5 | 2.58 | 1.16E-05 | 3'ss | Mel. |
| 634 | chr1: 32096333-32098095 | chr1: 32096443-32098095 | CTACACAGAGCT GCAGCAAGGTGT GCACCCAGCTGC AGGT (291) | CTACACAGAGCT GCAGCAAGCTCT GTCCCAAATGGG CTAC (292) | 0 | 5 | 2.58 | 2.48E-06 | 3'ss | Mel. |
| 635 | chr22: 19164146-19164358 | chr22: 19164206-19164358 | CCTGCGCAACTG GTACCGAGGCGC AGCCAGTGTCTT TGGA (944) | CCTGCGCAACTG GTACCGAGGGGA CAACCCCAACAA GCCC (945) | 0 | 5 | 2.58 | 1.56E-04 | 3'ss | Mel. |
| 636 | chr3: 131181737-131186934 | chr3: 131181719-131186934 | ATAAAAATTGCT TAGTAAAGATTT TTGCCTTCTCTC AGGT (946) | ATAAAAATTGCT TAGTAAAGGTCA AAGATTCTAAAC TGCC (947) | 0 | 5 | 2.58 | 2.28E-03 | 3'ss | Mel. |
| 637 | chrX 98817692-98827531 | chr8: 98817692-98827555 | TGAGTTCATGGA TGATGCCAAAAT TCTTTTTAATCT TTCG (948) | TGAGTTCATGGA TGATGCCAACAT GTGCATTGCCAT TGCG (949) | 0 | 5 | 2.58 | 3.48E-02 | 3'ss | Mel. |
| 638 | chrX: 24091380-24092454 | chrX: 24091380-24094838 | AGAGTTGAAAAA CACTGGCGTCTC CTTTTCAGGAAT CACA (950) | AGAGTTGAAAAA CACTGGCGTTTA ATTGGTTGGGGT CAGA (951) | 0 | 5 | 2.58 | 4.97E-03 | 3'ss | Mel. |
| 639 | chr12: 120934019-120934204 | chr12: 120934019-120934218 | GGCCAGCCCCCT TCTCCACGGCCT TGCCCACTAGGT AACC (206) | GGCCAGCCCCCT TCTCCACGGTAA CCATGTGCGACC GAAA (207) | 8 | 51 | 2.53 | 3.07E-09 | 3'ss | Mel. |
| 640 | chr9: 125023777-125026993 | chr9: 125023787-125026993 | CACCACGCCGAG GCCACGAGACAT TGATGGAAGCAG AAAC (142) | CACCACGCCGAG GCCACGAGTATT TCATAGACATTG ATGG (143) | 3 | 21 | 2.46 | 2.87E-02 | 3'ss | Mel. |
| 641 | chr10: 74994698-74999069 | chr10: 74994698-74994950 | TGGGGCCACAAA GACAGATGCTGG ATACACAGTATC GTCG (952) | TGGGGCCACAAA GACAGATGAAAC CCCATGGCGACT CTAG (953) | 4 | 24 | 2.32 | 1.77E-02 | exon skip | Mel. |
| 642 | chr1: 154246074-154246225 | chr1: 154246074-154246249 | CTTGCCTTCCCA TCCTCCTGCAAA CACCTGCCACCT TTCT (289) | CTTGCCTTCCCA TCCTCCTGAACT TCCAGGTCCTGA GTCA (290) | 1 | 9 | 2.32 | 1.49E-04 | 3'ss | Mel. |
| 643 | chr11: 57100545-57100908 | chr11: 57100623-57100908 | GGGGACAGTGAA ATTTGGTGGCAA GAATGAGGTGAC ACTG (103) | GGGGACAGTGAA ATTTGGTGGGCA GCTGCTTTCCTT TGAC (104) | 0 | 4 | 2.32 | 1.19E-05 | 3'ss | Mel. |
| 644 | chr16: 313774-313996 | chr16: 313774-314014 | GAACTGGCACCG ACAGACAGTGTC CCCTCCCTCCCC AGAT (244) | GAACTGGCACCG ACAGACAGATCC TGTTTCTGGACC TTGG (245) | 0 | 4 | 2.32 | 1.03E-03 | 3'ss | Mel. |
| 645 | chr17: 34147441-34149625 | chr17: 34147441-34149643 | AACATGGAATCA TCAGGAAGTTCT CCATTTCTATTT AGCC (954) | AACATGGAATCA TCAGGAAGCCAA GGTGGAAGAGCA CCTT (955) | 0 | 4 | 2.32 | 1.03E-03 | 3'ss | Mel. |
| 646 | chr1: 1480382-1497319 | chr1: 1480382-1500152 | CGTGCGTGTGTG TGCTCTTGCTAT ACACAGAATGGG ATTT (956) | CTTAGGAAAGAC AAAGAACTCTAT ACACAGAATGGG ATTT (957) | 0 | 4 | 2.32 | 2.87E-02 | 5'ss | Mel. |
| 647 | chr22: 24108483-24109560 | chr22: 24108462-24109560 | CCCAGCCTGCTG TCCAGCAGCCTC TTGCACTGTACC CCCA (958) | CCCAGCCTGCTG TCCAGCAGGCCC CCACCCCGCTG CCCC (959) | 0 | 4 | 2.32 | 3.33E-02 | 3'ss | Mel. |

TABLE 1-continued

| | Aberrant junction | WT junction | Aberrant sequence (SEQ ID NO) | WT sequence (SEQ ID NO) | Avg WT % | Avg Ab. % | Log₂ Fold Diff. | FDR Q-Value | Event | Type |
|---|---|---|---|---|---|---|---|---|---|---|
| 648 | chr22: 44559810-44564460 | chr22: 44559810-44564481 | ACCCAAGGCTCGTCCTGAAGTTTCTCTGTTTCCTTCTGCA (960) | ACCCAAGGCTCGTCCTGAAGACGTGGTTAACTTGGACCTC (961) | 0 | 4 | 2.32 | 5.75E-03 | 3'ss | Mel. |
| 649 | chr5: 132439718-132439902 | chr5: 132439718-132439924 | AGATTGAAGCTAAAATTAAGTTTTCTGTCTTACCCATTCC (348) | AGATTGAAGCTAAAATTAAGGAGCTGACAAGTACTTGTAG (349) | 0 | 4 | 2.32 | 1.38E-03 | 3'ss | Mel. |
| 650 | chr5: 175815974-175816311 | chr5: 175815974-175816331 | GAACCCGGTGGTACCCATAGTTGCTTTGTCCCCTCCTCAG (962) | GAACCCGGTGGTACCCATAGGTTGCCTGGCCACGGGGCC (963) | 0 | 4 | 2.32 | 5.33E-04 | 3'ss | Mel. |
| 651 | ch17: 74131270-74133179 | chr7: 74131270-74133197 | AATGGAAGTACCAGCAGAAGAATTTTATTTTTTCAAGAT (964) | AATGGAAGTACCAGCAGAAGATTCTACTCAACATGTCCCT (965) | 0 | 4 | 2.32 | 7.50E-03 | 3'ss | Mel. |
| 652 | chr20: 57227143-57234678 | chr20: 57227143-57242545 | GGCAGCTGTTAGCCGAGCAAGAGCTGGACGAGGTATTGTG (966) | GGCAGCTGTTAGCCGAGCAACTTGCTGATGACCGTATGGC (967) | 7 | 37 | 2.25 | 4.91E-02 | exon incl. | Mel. |
| 653 | chr16: 54954250-54957496 | chr16: 54954322-54957496 | GAGATTCTGAAGATAAGGAGTTCTCTTGTAGGATGCCACT (313) | GAGATTCTGAAGATAAGGAGTAAAACCTGTTTAGAAATT (314) | 3 | 18 | 2.25 | 1.03E-03 | 3'ss | Mel. |
| 654 | chrX: 129771378-129790554 | chrX: 129771384-129790554 | AAAAGAAACTGAGGAATCAGTATCACAGGCAGAAGCTCTG (303) | AAAAGAAACTGAGGAATCAGCCTTAGTATCACAGGCAGAA (304) | 14 | 70 | 2.24 | 5.98E-06 | 3'ss | Mel. |
| 655 | chr13: 45911538-45912794 | chr13: 45911523-45912794 | GTTTAGAAATGGAAAAATGTTTTTTGCTTTTACAGTAACA (968) | GTTTAGAAATGGAAAAATGTTAACAAATGTGGCAATTATT (969) | 18 | 88 | 2.23 | 1.12E-04 | 3'ss | Mel. |
| 656 | chr2: 27260760-27261013 | chr2: 27260570-27261013 | CCAAGAGACAGCACATTCAGCTCCTGAGCAGCCTGACTGA (315) | CCCCTGAGATGAAGAAAGAGCTCCTGAGCAGCCTGACTGA (184) | 5 | 27 | 2.22 | 4.64E-05 | exon incl. | Mel. |
| 657 | chr1: 23398690-23399766 | chr1: 23398690-23399784 | TTGGAAGCGAATCCCCCAAGTCCTTTGTTCTTTTGCAGTG (210) | TTGGAAGCGAATCCCCCAAGTGATGTATATCTCTCATCAA (211) | 1 | 8 | 2.17 | 6.85E-03 | 3'ss | Mel. |
| 658 | chr6: 31602334-31602574 | chr6: 31602334-31602529 | AGGATGTGGCTGGCACAGAAGTGTCATCAGGTCCCTGCAG (148) | AGGATGTGGCTGGCACAGAAATGAGTCAGTCTGACAGTGG (149) | 1 | 8 | 2.17 | 2.70E-05 | 3'ss | Mel. |
| 659 | chr3: 16310782-16312435 | chr3: 16310782-16312451 | AAATCTCGTGGACTTCTAAGTTTTCTGTTTGCCCAGAAAG (970) | AAATCTCGTGGACTTCTAAGAAAGCGCCATGGCCTGCT (971) | 7 | 33 | 2.09 | 4.05E-02 | 3'ss | Mel. |
| 660 | chr11: 68838888-68839375 | chr11: 68838888-68839390 | AGTTCCGGGGCTACCTGATGCCTTCCTCTTTGCAGAAATC (972) | AGTTCCGGGGCTACCTGATGAATCTCTCCAGACCTCGCT (973) | 0 | 3 | 2.00 | 2.75E-02 | 3'ss | Mel. |
| 661 | chr12: 58109976-58110164 | chr12: 58109976-58110194 | GGCACCCCAAAAGATGGCAGATCAGTCTCTCCCTGTTCTC (285) | GGCACCCCAAAAGATGGCAGGTGCGAGCCCGACCAAGGAT (286) | 0 | 3 | 2.00 | 1.12E-02 | 3'ss | Mel. |
| 662 | chr1: 32377442-32381495 | chr1: 32377427-32381495 | AAGAAGGAATCCACGTTCTAGTCATTTCTTTTCAGGATTG (974) | AAGAAGGAATCCACGTTCTAGATTGGCCATTTGATGATGG (975) | 0 | 3 | 2.00 | 7.34E-03 | 3'ss | Mel. |

TABLE 1-continued

| | Aberrant junction | WT junction | Aberrant sequence (SEQ ID NO) | WT sequence (SEQ ID NO) | Avg WT % | Avg Ab. % | Log₂ Fold Diff. | FDR Q-Value | Event | Type |
|---|---|---|---|---|---|---|---|---|---|---|
| 663 | chr22: 36627471-36629198 | chr22: 36627512-36629198 | CGCTGGCACCAT GAACCCAGGACC AAGTGAGCAGAG AGAA (976) | CGCTGGCACCAT GAACCCAGAGAG CAGTATCTTTAT TGAG (200) | 0 | 3 | 2.00 | 2.55E-02 | 3'ss | Mel. |
| 664 | chr3: 49395199-49395459 | chr3: 49395180-49395459 | GCAACCAGTTTG GGCATCAGCTGC CCTTCTCTCCTG TAGG (342) | GCAACCAGTTTG GGCATCAGGAGA ACGCCAAGAACG AAGA (343) | 0 | 3 | 2.00 | 3.20E-03 | 3'ss | Mel. |
| 665 | chr6: 170844509-170846321 | chr6: 170844493-170846321 | AGCCCCTGCTTG ACAACCAGTTTC ATGTCCCACCAG GTTG (977) | AGCCCCTGCTTG ACAACCAGGTTG GTTTTAAGAACA TGCA (978) | 0 | 3 | 2.00 | 4.68E-04 | 3'ss | Mel. |
| 666 | chr9: 139837449-139837800 | chr9: 139837395-139837800 | CCAAGGACTGCA CTGTGAAGGCCC CCGCCCCGCGAC CTGG (175) | CCAAGGACTGCA CTGTGAAGATCT GGAGCAACGACC TGAC (176) | 0 | 3 | 2.00 | 4.46E-02 | 3'ss | Mel. |
| 667 | chr10: 103904064-103908128 | chr10: 103904064-103904776 | TTGGCTGTAGGA AACTCAGGGTCC AGCTGTAGTTCC TCTG (979) | TTGGCTGTAGGA AACTCAGGCGGC GTTGACATTCCC CAGG (980) | 8 | 34 | 1.96 | 2.70E-05 | exon skip | Mel. |
| 668 | chr17: 27212965-27215962 | chr17: 27211333-27215962 | TGTATCTCCGAC ACTCAGAGACTG TCTCTGGAGGTT ATGA (981) | TGTATCTCCGAC ACTCAGAGGATT TCCCTAGAGATT ATGA (982) | 6 | 26 | 1.95 | 3.79E-02 | exon incl. | Mel. |
| 669 | chrX: 15849691-15863501 | chrX: 15845495-15863501 | AGGCTGATCTAC TGCAGGAGCCAC GTCATGAATATT TTAA (983) | AGGCTGATCTAC TGCAGGAGGAAG CTGAAACCCCAC GTAG (984) | 2 | 10 | 1.87 | 5.30E-03 | 3'ss | Mel. |
| 670 | chr2: 230657846-230659894 | chr2: 230657861-230659894 | GGAAATGGGACA GGAGGCAGAGGA TCACAGGCTTTA AAAT (387) | GGAAATGGGACA GGAGGCAGCTTT TCTCTCAACAGA GGAT (388) | 14 | 52 | 1.82 | 4.43E-06 | 3'ss | Mel. |
| 671 | chr5: 141694720-141699308 | chr5: 141694720-141704408 | GCTCAGCCCCCT CCCCACAGGGCC CCTAGAAGCCTG TTTC (985) | TGACCCTGCAGC TCCTCAAAGGCC CCTAGAAGCCTG TTTC (986) | 5 | 20 | 1.81 | 2.74E-03 | exon incl. | Mel. |
| 672 | chr19: 3542975-3544806 | chr19: 3544730-3544806 | GCCGACCCGCCT GCGACGCTCTTT TCTTGCCTGGAG AAGA (987) | GCCGACCCGCCT GCGACGCTGGGA CCGTGATGCCCG GCCC (988) | 3 | 13 | 1.81 | 4.16E-03 | 3'ss | Mel. |
| 673 | chr3: 58417711-58419494 | chr3: 58419411-58419494 | TGCGGAGACCCC TTCGGGAGGTGA CAGTTCGTGATG CTAT (989) | TGCGGAGACCCC TTCGGGAGGTCT CCGGGCTGCTGA AGAG (990) | 1 | 6 | 1.81 | 2.67E-02 | exon skip | Mel. |
| 674 | chr6: 108370622-108370735 | chr6: 108370622-108372234 | CTATCAGTAGGT TTTTAGAGATGA ACATCACTCGAA AACT (991) | GCATTGATGTGG AAGATGCAATGA ACATCACTCGAA AACT (992) | 1 | 6 | 1.81 | 2.71E-03 | exon incl. | Mel. |
| 675 | chr6: 108370787-108372234 | chr6: 108370622-108372234 | GCATTGATGTGG AAGATGCAGTTT TTTTCCTGGCAG AAGA (993) | GCATTGATGTGG AAGATGCAATGA ACATCACTCGAA AACT (992) | 1 | 6 | 1.81 | 1.84E-03 | exon incl. | Mel. |
| 676 | chr6: 166779550-166780282 | chr6: 166779594-166780282 | CAGTGGGCGGAT GACATTTGGTAC AGCCTCGGAACT GGCT (994) | CAGTGGGCGGAT GACATTTGCCCT CTGTTGCTATTC TTTG (995) | 1 | 6 | 1.81 | 1.04E-02 | 3'ss | Mel. |
| 677 | chr7: 128033792-128034331 | chr7: 128033082-128034331 | GGTGTCCATGGC CTGCACTCCTAT ACCTTTTCTGCCG TGTA (996) | GGTGTCCATGGC CTGCACTCTTAC GAAAGCGGCTG TACT (997) | 1 | 6 | 1.81 | 4.73E-02 | exon incl. | Mel. |

TABLE 1-continued

| | Aberrant junction | WT junction | Aberrant sequence (SEQ ID NO) | WT sequence (SEQ ID NO) | Avg WT % | Avg Ab. % | Log$_2$ Fold Diff. | FDR Q-Value | Event | Type |
|---|---|---|---|---|---|---|---|---|---|---|
| 678 | chr6: 136597127-136599002 | chr6: 136597646-136599002 | ACTGGGAAGTTCTTAAAAAGTCCCCCTCTACACAAGAATC (998) | ACTGGGAAGTTCTTAAAAGGTTCACAGATGAAGAGTCTA (999) | 10 | 37 | 1.79 | 1.30E-02 | exon skip | Mel. |
| 679 | chr16: 54954239-54957496 | chr16: 54954322-54957496 | GAGATTCTGAAGATAAGGAGGATGCCACTGGAAATGTTGA (322) | GAGATTCTGAAGATAAGGAGGTAAAACCTGTTTAGAAATT (314) | 20 | 69 | 1.74 | 1.28E-05 | 3'ss | Mel. |
| 680 | chr4: 17806394-17812069 | chr4: 17806394-17806729 | GCTGAGCGGGGCGACCCGAGTCTTCTCATTCACAGGTTAA (1000) | TCCAACAAGCACCTCTGAAGTCTTCTCATTCACAGGTTAA (832) | 20 | 69 | 1.74 | 4.13E-05 | exon skip | Mel. |
| 681 | chr19: 6731065-6731209 | chr19: 6731122-6731209 | AGTGGCAGTGGCTGTACCAGCCCACAGGAAACAACCCGTA (311) | AGTGGCAGTGGCTGTACCAGCTCTTGGTGGAGGGCTCCAC (312) | 8 | 29 | 1.74 | 8.03E-04 | 3'ss | Mel. |
| 682 | chr16: 28842393-28843507 | chr16: 28842393-28843525 | TGTTCCACCTCCTCCTGCAGCTCCCCCTTTTCTTCCAGTG (1001) | TGTTCCACCTCCTCCTGCAGTGGGCCCGGATGTATCCCCCG (1002) | 6 | 22 | 1.72 | 2.96E-02 | 3'ss | Mel. |
| 683 | chr3: 50615004-50617274 | chr3: 50616357-50617274 | ACCCATGAGAATGCTCAGAGCTATGAAGACCCCGCGGCCC (1003) | CTGGCCCCTGAGATCCGCAGCTATGAAGACCCCGCGGCCC (1004) | 8 | 28 | 1.69 | 8.95E-03 | exon skip | Mel. |
| 684 | chr11: 772521-774007 | chr11: 773629-774 (X)7 | CAAGCTCGAGTCCATCGATGAACCCATCTGCGCCGTCGGC (1005) | CAAGCTCGAGTCCATCGATGGTGCCCGGTACCATGCCCTC (1006) | 4 | 15 | 1.68 | 8.31E-03 | exon skip | Mel. |
| 685 | chr2: 220424219-220427123 | chr2: 220426730-220427123 | CTTCACTGTCACCGTCACAGAACCCCCAGTGCGGATCATA (1007) | CTTCACTGTCACCGTCACAGAGTCTTACCAAAGTCAGGAC (1008) | 9 | 30 | 1.63 | 2.25E-02 | 3'ss | Mel. |
| 686 | chr3: 148759467-148759952 | chr3: 148759455-148759952 | GTCTTCCAATGGCCCCTCAGCCTTTTCTCTAGGAAATGAT (234) | GTCTTCCAATGGCCCCTCAGGAAATGATACACCTGAAGAA (235) | 10 | 33 | 1.63 | 1.04E-02 | 3'ss | Mel. |
| 687 | chr5: 34945908-34949647 | chr5: 34945908-34950274 | AGAAACAGAAACCAGCACAGGATGTACCTGGCAAAGATTC (1009) | AGAAACAGAAACCAGCACAGAATTATGATGACAATTTCAA (1010) | 5 | 17 | 1.58 | 1.55E-02 | exon incl. | Mel. |
| 688 | ch16: 158589427-158613008 | chr6: 158591570-158613008 | TTCTGCATCTGTGGGCCGAGTGATCCTGCCATGAAGCAGT (1011) | AAAGGAGTGCTTATAGAATGTGATCCTGCCATGAAGCAGT (1012) | 2 | 8 | 1.58 | 1.45E-02 | exon skip | Mel. |
| 689 | chr14: 23495584-23496953 | chr14: 23495584-23502576 | AGGATCGGCAACATGGCAAGGCCTCTACTACGTGGACAGT (1013) | CTGGGATAAGAGAGGCCCTGGCCTCTACTACGTGGACAGT (1014) | 1 | 5 | 1.58 | 1.98E-02 | exon incl. | Mel. |
| 690 | chr6: 33669197-33678471 | chr6: 33669197-33679325 | GTTCAGGACACAATAAGCAGGTTGCAGAGCCTGAGGCCTG (1015) | GGGAGGGAGAGAATACCCAGGTTGCAGAGCCTGAGGCCTG (1016) | 1 | 5 | 1.58 | 1.23E-02 | exon incl. | Mel. |
| 691 | chr10: 102286851-102289136 | chr10: 102286831-102289136 | TACCCGGATGATGGCATGGGAAGTTCTTGCTGTCTTTCAG (1017) | TACCCGGATGATGGCATGGGGTATGGCGACTACCCGAAGC (1018) | 0 | 2 | 1.58 | 2.58E-04 | 3'ss | Mel. |
| 692 | chr11: 66333872-66334716 | chr11: 66333875-66334716 | GACATATGAGTCAAAGGAAGCCCGGTGGCGCCTGTCGTC (1019) | GACATATGAGTCAAAGGAAGAAGCCCGGTGGCGCCTGTCC (1020) | 0 | 2 | 1.58 | 2.45E-02 | 3'ss | Mel. |

TABLE 1-continued

| | Aberrant junction | WT junction | Aberrant sequence (SEQ ID NO) | WT sequence (SEQ ID NO) | Avg WT % | Avg Ab. % | Log₂ Fold Diff. | FDR Q-Value | Event | Type |
|---|---|---|---|---|---|---|---|---|---|---|
| 693 | chr11: 8705628-8706243 | chr11: 8705628-8706264 | CGGATCAACTTC GACAAATAGTGG TTGTTACCTCTT CCTA (1021) | CGGATCAACTTC GACAAATACCAC CCAGGCTACTTT GGGA (1022) | 0 | 2 | 1.58 | 2.65E-03 | 3'ss | Mel. |
| 694 | chr12: 53421972-53427574 | chr12: 53421972-53427589 | TTATAGGCGTGA TGATAGAGTTTC ATTTAACTTAGG TCCC (1023) | TTATAGGCGTGA TGATAGAGGTCC CCCCAAAGACC CAAA (1024) | 0 | 2 | 1.58 | 1.03E-03 | 3'ss | Mel. |
| 695 | chr15: 25212387-25213078 | chr15: 25207356-25213078 | TGGAAATATTTC TAGACTTGGTGT CAGTTGTACCCG AGGC (1025) | GCCTCACTGAGC AACCAAGAGTGT CAGTTGTACCCG AGGC (145) | 0 | 2 | 1.58 | 7.87E-03 | exon incl. | Mel. |
| 696 | chr1: 1480382-1497338 | chr1: 1480382-1500152 | TCGGCCCAGAAG AACCCCGCCTAT ACACAGAATGGG ATTT (1026) | CTTAGGAAAGAC AAAGAACTCTAT ACACAGAATGGG ATTT (957) | 0 | 2 | 1.58 | 4.66E-02 | 5'ss | Mel. |
| 697 | chr5: 177576859-177577888 | chr5: 177576839-177577888 | TCTATATCCCCT CTAAGACGCACT TCTTTCCCCTCT GTAG (299) | TCTATATCCCCT CTAAGACGGACC TGGGTGCAGCCG CAGG (300) | 0 | 2 | 1.58 | 1.26E-04 | 3'ss | Mel. |
| 698 | chr6: 42905945-42911535 | chr6: 42905945-42906305 | GCTGAAGGGAAA AGACACCAAAAC ACAAACAGCAGA ATGG (1027) | GCTGAAGGGAAA AGACACCAGTTG CCTGGCAGAGCA GTGG (1028) | 0 | 2 | 1.58 | 4.68E-02 | 3'ss | Mel. |
| 699 | chr17: 2282497-2282499 | chr17: 2282497-2282725 | CATCATCAAGTT TTTCAATGACGA GCTGGTCCAGCC ATCC (1029) | CATCATCAAGTT TTTCAATGAACG TGCTGAGCATCA CGAT (1030) | 5 | 16 | 1.5 | 1.74E-04 | intron retention | Mel. |
| 700 | chr8: 74601048-74621266 | chr8: 74601048-74650518 | GAGGGCCTGCTC ATTCAAAGATGT TCTCAGTGCAGC TGAG (1031) | ACATGCTTCAAA TAAATCAGATGT TCTCAGTGCAGC TGAG (1032) | 23 | 66 | 1.48 | 1.49E-03 | exon incl. | Mel. |
| 701 | chr10: 35495979-35500583 | chr10: 35495979-35500181 | CTGAGGCTAATG AAAAACAGGGAA GCTGCCAAAGAA TGTC (1033) | CTGAGGCTAATG AAAAACAGGGAA GCTGCCCGGGAG TGTC (1034) | 14 | 40 | 1.45 | 2.13E-02 | 3'ss | Mel. |
| 702 | chr3: 119180951-119182182 | chr3: 119180995-119182182 | CGGCTGGGACTC TTCCATGCGTGG CACTGGAAGCAG ACTG (1035) | CGGCTGGGACTC TTCCATGCAGTT GAAACTGGTTGA CAAC (1036) | 12 | 34 | 1.43 | 1.81E-02 | 3'ss | Mel. |
| 703 | chr4: 169919436-169923221 | chr4: 169911479-169923221 | AGTGAATGTAGT TGCACCAGTGAC AATACTTGTATG GAGT (1037) | AGTGAATGTAGT TGCACCAGGATT TGTACACACAGA TATG (1038) | 17 | 47 | 1.42 | 2.45E-02 | exon incl. | Mel. |
| 704 | chr17: 55074416-55078215 | chr17: 55075859-55078215 | ATTCACACAGAG CCACCTAGGCCA GGCTACCAACGT CTTT (1039) | TGAGGATCAATC CTGGGGAGGCCA GGCTACCAACGT CTTT (1040) | 2 | 7 | 1.42 | 1.30E-02 | exon skip | Mel. |
| 705 | chrX: 2310515-2326785 | chrX: 2209644-2326785 | AGAAACCTTGAA CGACAAAGAGAC GTGAGTCTTGCT GTGT (496) | AGAAACCTTGAA CGACAAAGTGGA ATTTTATACTG TGAC (495) | 7 | 20 | 1.39 | 3.40E-02 | exon incl. | Mel. |
| 706 | chrY: 2260515-2276785 | chrY: 2159644-2276785 | AGAAACCTTGAA CGACAAAGAGAC GTGAGTCTTGCT GTGT (496) | AGAAACCTTGAA CGACAAAGTGGA ATTTTATACTG TGAC (495) | 7 | 20 | 1.39 | 3.40E-02 | exon incl. | Mel. |
| 707 | chr5: 54456224-54459882 | chr5: 54456224-54456821 | TGGAAAAGTATA AAGGCAAAATTC TTCAAAGAAGGA ACCA (1041) | TGGAAAAGTATA AAGGCAAAGTTT CACTAGTTGTAA ACGT (1042) | 4 | 12 | 1.38 | 2.71E-02 | exon skip | Mel. |

TABLE 1-continued

| Aberrant junction | WT junction | Aberrant sequence (SEQ ID NO) | WT sequence (SEQ ID NO) | Avg WT % | Avg Ab. % | Log$_2$ Fold Diff. | FDR Q-Value | Event | Type |
|---|---|---|---|---|---|---|---|---|---|
| 708 chr15: 76146828-76161291 | chr15: 76146828-76152218 | ATACTAAGAACAACAATTTGAATGGGACAACAGAAGAAGT (1043) | ATACTAAGAACAACAATTTGCTTCGTCAGCAATTGAAGTG (1044) | 19 | 50 | 1.35 | 2.54E-02 | exon skip | Mel. |
| 709 chr8: 38270113-38271435 | chr8: 38271322-38271435 | TGGCCTTGACCTCCAACCAGGTCCTGCACCCAGACCTCAC (1045) | TGGCCTTGACCTCCAACCAGGAGTACCTGGACCTGTCCAT (1046) | 7 | 19 | 1.32 | 3.77E-02 | 3'ss | Mel. |
| 710 chr1: 11131045-11132143 | chr1: 11131030-11132143 | GAAGGCAGCTGAGCAAACAGTTCTCTCCCTTGCAGCTGCC (393) | GAAGGCAGCTGAGCAAACAGCTGCCCGGGAACAGGCAAAG (394) | 3 | 9 | 1.32 | 1.42E-02 | 3'ss | Mel. |
| 711 chr11: 62556898-62557357 | chr11: 62556898-62557072 | TCCTTGAACACTACAATTAGACCTcttcttgggtgaATTT (1047) | TCCTTGAACACTACAATTAGCTGTTCTGAAGCCCAGAAAA (1048) | 1 | 4 | 1.32 | 2.52E-02 | exon skip exon | Mel. |
| 712 chr14: 69349309-69350884 | chr14: 69349772-69350884 | ACACCATTGAGGAGATCCAGGTGCGGCAGCTGGTGCCTCG (1049) | ACACCATTGAGGAGATCCAGGGACTGACCACAGCCCATGA (1050) | 1 | 4 | 1.32 | 1.92E-02 | skip | Mel. |
| 713 chr1: 155227125-155227288 | chr1: 155227177-155227288 | CCCATGTATAAGGCTTTCCGGATGTGCTCTTTGTCCTCCA (1051) | CCCATGTATAAGGCTTTCCGGAGTGACAGTTCATTCAATT (1052) | 1 | 4 | 1.32 | 2.77E-02 | 3'ss | Mel. |
| 714 chr20: 25281520-25281967 | chr20: 25281520-25282854 | CTCCCAGTGCTGTATATCCCGGAATTCCTGGGGAAGTCGG (1053) | GAGCTGCCACGGATACTGAGGGAATTCCTGGGGAAGTCGG (1054) | 1 | 4 | 1.32 | 2.02E-02 | exon incl. | Mel. |
| 715 Chr7: 142962185-142964709 | chr7: 142962389-142964709 | GGATGCGCGTCTGGTCAAGGGCTGCAGAGAAGGCTGGTAT (1055) | AGCCGCAGAGCATCCTGGCGGCTGCAGAGAAGGCTGGTAT (1056) | 1 | 4 | 1.32 | 4.91E-02 | exon skip | Mel. |
| 716 chr8: 74621397-74650518 | chr8: 74601048-74650518 | ACATGCTTCAAATAAATCAGCTTCTCTCCAAGATAAAATG (1057) | ACATGCTTCAAATAAATCAGATGTTCTCAGTGCAGCTGAG (1032) | 24 | 61 | 1.31 | 1.74E-02 | exon incl. | Mel. |
| 717 chr15: 49309825-49319561 | chr15: 49309825-49311614 | AACAAAGAAATAATTCACAGGATGAAGATGGGTTTCAAGA (1058) | CTGAGTCTTTATATTTTGAGGATGAAGATGGGTTTCAAGA (1059) | 16 | 41 | 1.3 | 1.66E-03 | exon skip | Mel. |
| 718 chrX: 148582568-148583604 | chrX: 148582568-148584841 | TAGCCACCACTGTGTGCCAGGATATCCTTCTAACCATACC (1060) | GGGAAAAGTCTTTCACCCTGGATATCCTTCTAACCATACC (1061) | 11 | 28 | 1.27 | 1.07E-02 | exon incl. | Mel. |
| 719 chr12: 49918679-49919860 | chr12: 49918679-49919726 | CCTACCAGCCACTTCGGGAGGTATCAGAGTGCTCCATCTC (1062) | CCTACCAGCCACTTCGGGAGGTATTGCCAGGGAACAGACG (1063) | 4 | 11 | 1.26 | 2.42E-02 | 3'ss | Mel. |
| 720 chr1: 46654652-46655129 | chr1: 46655029-46655129 | GTCCCGGCTTCCCCCTACTCGCCTGGCTCAGAATCTAACC (1064) | GTCCCGGCTTCCCCCTACTCAGTGAAGAAGCCACCTCAG (1065) | 4 | 11 | 1.26 | 2.67E-02 | exon skip | Mel. |
| 721 chr3: 105397415-105400567 | chr3: 105400454-105400567 | CTTAAGCATATATTTAAGGGTGAAGATGCTTTTGATGCC (1066) | CTTAAGCATATATTTAAGGGAGATGTTTTTGATTCAGCC (1067) | 28 | 68 | 1.25 | 2.24E-02 | exon skip | Mel. |
| 722 chr3: 10023431-10028190 | chr3: 10019130-10028190 | CAGGAACAAGTATCTGACAGAAAATATCTTTCAGGCTGG (1068) | CAGGAACAAGTATCTGACAGTCAAGTCCTAATTCGAAGCA (1069) | 2 | 6 | 1.22 | 4.97E-02 | exon incl. | Mel. |

TABLE 1-continued

| | Aberrant junction | WT junction | Aberrant sequence (SEQ ID NO) | WT sequence (SEQ ID NO) | Avg WT % | Avg Ab. % | Log$_2$ Fold Diff. | FDR Q-Value | Event | Type |
|---|---|---|---|---|---|---|---|---|---|---|
| 723 | chr4: 88898249- 88901544 | chr4: 88898249- 88901197 | GAAGTTCTGAGG AAAAGCAGAATG CTGTGTCCTCTG AAGA (1070) | GAAGTTCTGAGG AAAAGCAGCTTT ACAACAAATACC CAGA (1071) | 2 | 6 | 1.22 | 1.07E-02 | 3'ss | Mel. |
| 724 | chr7: 23313233- 23313672 | chr7: 23313233- 23313683 | ATCTCCCTCTTG GTGTACAAATTG TTTTCAGAAAAC ACAA (1072) | ATCTCCCTCTTG GTGTACAAAAAA CACAAGGAATAC AACC (1073) | 2 | 6 | 1.22 | 1.94E-03 | 3'ss | Mel. |
| 725 | chr1: 214454770- 214488104 | chr1: 214454770- 214478529 | TGCGAGTACTGC TTCACCAGAAAG AAGATTGGCCCA TGCA (1074) | TGCGAGTACTGC TTCACCAGGAAA GAAGGATTGTCC AAAT (1075) | 6 | 15 | 1.19 | 3.00E-03 | exon skip | Mel. |
| 726 | chr15: 101826006- 101827112 | chr15: 101826498- 101827112 | TCCAGAAAGTGA AACTAAAATTTT AATCCAGGTGCT GGTT (1076) | TCCAGAAAGTGA AACTAAAAGAGC GTCAGGAAGCAG AGAA (1077) | 15 | 35 | 1.17 | 2.02E-04 | exon skip | Mel. |
| 727 | chr15: 74326871- 74327483 | chr15: 74326871- 74327512 | ACTCAGATGCCG AAAACTCGCCCT CAGTCTGAGGTT CTGT (748) | ACTCAGATGCCG AAAACTCGTGCA TGGAGCCCATGG AGAC (749) | 39 | 88 | 1.15 | 2.54E-04 | 3'ss | Mel. |
| 728 | chrX: 15706981- 15720904 | chrX: 15706981- 15711085 | AGATTCTACAGA TAAATCAGATTT CGGAAACTTCTG GCAG (1078) | AGATTCTACAGA TAAATCAGCTGC ACTTAGTGCATT GGAA (1079) | 17 | 39 | 1.15 | 2.23E-02 | exon skip | Mel. |
| 729 | chr3: 183703166- 183705557 | chr3: 183700795- 183705557 | TGGCTGGCTTCA GTGGACCAAATT TTCAGGATGGCT GTAT (1080) | TGGCTGGCTTCA GTGGACCAGCCT TCATGGTGAAAC ACCT (1081) | 40 | 90 | 1.15 | 1.67E-02 | exon incl. | Mel. |
| 730 | chr16: 684797- 685280 | chr16: 684956- 685280 | CCCTGCTCATCA CCTACGGGGAAC CCAGAATGGGGG CTTC (1082) | CCCTGCTCATCA CCTACGGGCCCT ATGCCATCAATG GGAA (194) | 19 | 40 | 1.04 | 9.38E-04 | exon skip | Mel. |
| 731 | chrX: 123224614- 123224703 | chrX: 123224614- 123227867 | CAAACACCTCTT GATTATAACACG CAGGTAACATGG ATGT (468) | CAAACACCTCTT GATTATAATCGG CGTGGCACAAGC CTAA (457) | 11 | 23 | 1.00 | 2.44E-04 | exon incl. | Mel. |
| 732 | chr20: 48700791- 48729643 | chr20: 48700791- 48713208 | GGCAGCCACCAC GGGCTCGGACAA TTTATGAAAACC GAAT (1083) | TGATAATTGGGC CTCCAAGAACAA TTTATGAAAACC GAAT (1084) | 10 | 21 | 1.00 | 2.87E-02 | exon skip | Mel. |
| 733 | chr19: 617870- 618487 | chr19: 617849- 618487 | ACCGCCCTGCAC TGCTACAGGAGT CCTCCGCTCTGC CACA (1085) | ACCGCCCTGCAC TGCTACAGGAAG GGCCTGACCTTC GTCT (1086) | 7 | 15 | 1.00 | 2.95E-02 | 3'ss | Mel. |
| 734 | chr1: 220242774- 220247308 | chr1: 220242774- 220246191 | TCACAATTATAG GGGAAGAGCTCG TGGTCTGGGTTG ATCC (1087) | GTGCTATTAAAG AAGAAGATCTCG TGGTCTGGGTTG ATCC (1088) | 7 | 15 | 1.00 | 1.48E-02 | exon skip | Mel. |
| 735 | chr1: 229431657- 229433266 | chr1: 229431657- 229433228 | CTCGTCTATGAT ATCACCAGATGC CCGAATGCTAGC GAGC (1089) | CTCGTCTATGAT ATCACCAGCCGA GAAACCTACAAT GCGC (1090) | 6 | 13 | 1.00 | 3.26E-02 | 3'ss | Mel. |
| 736 | chr11: 57193182- 57193461 | chr11: 57193143- 57193461 | CAATGCCACAGG GCAGGCTGGAAG GCTGGGATGCAT GGGA (1091) | CAATGCCACAGG GCAGGCTGACTG CAAAGCCCAGGA TGAG (1092) | 4 | 9 | 1.00 | 1.30E-02 | 3'ss | Mel. |
| 737 | chr11: 66105278- 66105713 | chr11: 66105360- 66105713 | TCAGAAGAGAAA ATCGGATGACAG GCGGACCCCAG GCCC (1093) | TCAGAAGAGAAA ATCGGATGGACC TTGACCCTGCTG TTCA (1094) | 3 | 7 | 1.00 | 3.02E-02 | 3'ss | Mel. |

TABLE 1-continued

| Aberrant junction | WT junction | Aberrant sequence (SEQ ID NO) | WT sequence (SEQ ID NO) | Avg WT % | Avg Ab. % | Log$_2$ Fold Diff. | FDR Q-Value | Event | Type |
|---|---|---|---|---|---|---|---|---|---|
| 738 chr7: 44251203-44251845 | chr7: 44250723-44251845 | TGACTGCCGCTTTCTCTCAGGCCCGGAAACAAAACTCATG (1095) | CTAAAGCCTTCTATAAAACTGCCCGGAAACAAAACTCATG (1096) | 3 | 7 | 1.00 | 2.44E-02 | exon incl. | Mel. |
| 739 chr12: 57925889-57926354 | chr12: 57926098-57926354 | ATGCAGATACACAAAGCAAGCCATGCAGTTTGGTCAGCTC (1097) | ATGCAGATACACAAAGCAAGGTGCACCAGCTATATGAAAC (1098) | 2 | 5 | 1.00 | 1.43E-02 | exon skip | Mel. |
| 740 chr4: 48853992-48862741 | chr4: 48859382-48862741 | TACTGATCATATTGTCCAAGTCAAAGTAAACAAGTATGGA (1099) | AAGAGTGCCAAAAAAAGAAGTCAAAGTAAACAAGTATGGA (1100) | 2 | 5 | 1.00 | 2.55E-03 | exon skip | Mel. |
| 741 chr2: 27604588-27604992 | chr2: 27604672-27604992 | TGTCATCCATTGTGGAAGAGCCCCGAAACACAGCAGAGCT (1101) | TGTCATCCATTGTGGAAGCTGCTGGATCAGTGCCTGGC (1102) | 1 | 3 | 1.00 | 2.77E-02 | 3'ss | Mel. |
| 742 chr6: 133136363-133137599 | chr6: 133136227-133137599 | TACCGGAAACCTAGGAAAAGGCGCCAAGCCCATCTTTGTG (1103) | GCTGCCAAAGCCTTAGACAAGCGCCAAGCCCATCTTTGTG (1104) | 1 | 3 | 1.00 | 4.97E-02 | 5'ss | Mel. |
| 743 chr12: 57032980-57033763 | chr12: 57033091-57033763 | GGGTGCAAAGATCCTGCAGCCATTCCAGGTTGCTGAGGT (283) | GGGTGCAAAGATCCTGCAGGACTACAAATCCCTCCAGGA (284) | 0 | 1 | 1.00 | 8.93E-03 | 3'ss | Mel. |
| 744 chr14: 50044571-50052667 | chr14: 50050393-50052667 | AGGATATCGGTTTCATTAAGAAAGACCTGAGCTGTCTTCC (1105) | AGGATATCGGTTTCATTAAGTTGGACTAAATGCTCTTCCT (1106) | 0 | 1 | 1.00 | 1.46E-02 | 3'ss | Mel. |
| 745 chr16: 85833358-85834789 | chr16: 85833358-85834810 | GCGGCGGGCAGTGGCGGCAGGTGTACATTTTTATCTTTCA (1107) | GCGGCGGGCAGTGGCGGCAGAATGTTGGCTACCAGGGTAT (1108) | 0 | 1 | 1.00 | 1.39E-02 | 3'ss | Mel. |
| 746 chr19: 35647877-35648323 | chr19: 35646514-35648323 | TATCCAGCACTGACCACATGGACAGACGTTGAAAGATACC (1109) | CCTGATTCTCCCCACCAGAGGACAGACGTTGAAAGATACC (1110) | 0 | 1 | 1.00 | 3.56E-02 | exon incl. | Mel. |
| 747 chr21: 27254101-27264033 | chr21: 27254082-27264033 | TTCATCATGGTGTGGTGGAGCTCTCCTCTTGTTTTTCAGG (1111) | TTCATCATGGTGTGGTGGAGGTTGACGCCGCTGTCACCCC (1112) | 0 | 1 | 1.00 | 1.84E-02 | 3'ss | Mel. |
| 748 chr21: 46271557-46275124 | chr21: 46271542-46275124 | TGAAATCAGAAAAAAATATGTTTATTTTGTTTCAGGCCTG (1113) | TGAAATCAGAAAAAAATATGGCCTGTTTAAGAAGAAAAC (1114) | 0 | 1 | 1.00 | 3.04E-02 | 3'ss | Mel. |
| 749 chr3: 101401353-101401614 | chr3: 101401336-101401614 | CAACGAGAACAAGCTATCAGTTACTTTTACCCCACAGGGC (297) | CAACGAGAACAAGCTATCAGGGCTGCTAAGGAAGCAAAA (298) | 0 | 1 | 1.00 | 4.76E-04 | 3'ss | Mel. |
| 750 chr4: 152022314-152024139 | chr4: 152022314-152024022 | CCATGGTCAAAAATGGCAGCACCAACAGGTTCCGCCAAAT (344) | CCATGGTCAAAAATGGCAGCAACAATGATTGAAGCTCACGT (345) | 0 | 1 | 1.00 | 4.92E-05 | 3'ss | Mel. |
| 751 chr9: 86593213-86593287 | chr9: 86593194-86593287 | GCAAGGATATATAATAACTGCTGCTTTATTTTTCCACAGA (1115) | GCAAGGATATATAATAACTGATTGGTGTGCCCGTTTAATA (1116) | 0 | 1 | 1.00 | 4.68E-04 | 3'ss | Mel. |
| 752 chr4: 169911479-169919352 | chr4: 169911479-169923221 | GAACTGCAAAGGCTTCAGAGGATTTGTACACACAGATATG (1117) | AGTGAATGTAGTTGCACCAGGATTTGTACACACAGATATG (1038) | 27 | 54 | 0.97 | 4.49E-02 | exon incl. | Mel. |

TABLE 1-continued

| | Aberrant junction | WT junction | Aberrant sequence (SEQ ID NO) | WT sequence (SEQ ID NO) | Avg WT % | Avg Ab. % | Log₂ Fold Diff. | FDR Q-Value | Event | Type |
|---|---|---|---|---|---|---|---|---|---|---|
| 753 | chrX: 102940188-102942916 | chrX: 102940188-102941558 | TTGGAGATCAGGACGCAAAGGTCACCATCAGAAAAGCTAA (1118) | GATCTGGATTCTCGTTTCAGGTCACCATCAGAAAAGCTAA (1119) | 21 | 42 | 0.97 | 2.52E-02 | 5'ss | Mel. |
| 754 | chr5: 137503767-137504910 | chr5: 137504377-137504910 | TGGAAGAGGCTACCTCTGGGGTCAATGAGAGTGAAATGGC (1120) | TGGAAGAGGCTACCTCTGGGGTAACCCCCGGGACTTTGCC (1121) | 13 | 26 | 0.95 | 2.18E-02 | exon skip | Mel. |
| 755 | chr13: 114291015-114294434 | chr13: 114291015-114292132 | TCTGGAGCCATACGTGACAGTGACCTGACCAACGGTGCAG (1122) | TCTGGAGCCATACGTGACAGAAATGGCTCAGGGAACTGTT (1123) | 11 | 22 | 0.94 | 4.45E-02 | exon skip | Mel. |
| 756 | chr16: 57473207-57474683 | chr16: 57473246-57474683 | CATCAAGCAGCTGTTGCAATGTTTAGTCCCAGGAAGCACC (822) | CATCAAGCAGCTGTTGCAATCTGCCCACAAAGAATCCAGC (823) | 11 | 22 | 0.94 | 4.68E-04 | 3'ss | Mel. |
| 757 | chr22: 31724845-31731677 | chr22: 31724910-31731677 | CTGCAGTATCTGTAACCGAGGTCTCCAGGCACCAGAGCC (1124) | CTGCAGTATCTGTAACCGAGGTTTCTCCTCTGCCTCCTAC (1125) | 28 | 52 | 0.87 | 1.79E-02 | 3'ss | Mel. |
| 758 | chrX: 123224814-123227867 | chrX: 123224614-123227867 | ACTAATCTTCAGCATGCCATTCGGCGTGGCACAAGCCTAA (456) | CAAACACCTCTTGATTATAATCGGCGTGGCACAAGCCTAA (457) | 14 | 26 | 0.85 | 1.55E-02 | exon incl. | Mel. |
| 759 | chr7: 5028808-5036240 | chr7: 5035213-5036240 | TGATTTCAAGTTTGAACAAGGGGTTGGCATCTGCACATCC (1126) | TGATGAGACTCCAGACAGAGGGGTTGGCATCTGCACATCC (1127) | 56 | 100 | 0.83 | 5.42E-03 | exon skip | Mel. |
| 760 | chr8: 146076780-146078756 | chr8: 146076780-146078377 | AGCGAGCTCCTCAGCCTCAGGCATCTGCATCTGGGACCGA (1128) | CCGGGGATTGCCGGCGCCAGGCATCTGCATCTGGGACCGA (1129) | 29 | 52 | 0.82 | 4.95E-02 | 5'ss | Mel. |
| 761 | chr5: 139909381-139916922 | chr5: 139909381-139914946 | AGTTTCTACTAGTCCAGTTGGTGACTCTCCTATTCCATCT (1130) | AGTTTCTACTAGTCCAGTTGGGTTACCATCCATTGACCCA (1131) | 7 | 13 | 0.81 | 3.69E-03 | exon skip | Mel. |
| 762 | chr1: 67890660-67890765 | chr1: 67890642-67890765 | CATAGTGGAAGTGATAGATCTTCTTTTTCACATTACAGTG (444) | CATAGTGGAAGTGATAGATCTGGCCTGAAGCACGAGGACA (445) | 42 | 69 | 0.70 | 1.02E-05 | 3'ss | Mel. |
| 763 | chr22: 42557364-42564614 | chr22: 42557364-42565852 | GGAAAGGACAGCAAGCACAGGTGAGACTGTGGAGATGAGA (1132) | TGAGGTGCCCTAAGCACAAGGTGAGACTGTGGAGATGAGA (1133) | 40 | 65 | 0.69 | 3.49E-02 | exon incl. | Mel. |
| 764 | chr6: 30587766-30592659 | chr6: 30587766-30590608 | AGTTGCATGTTGACTTTAGGGAGTCTGTGTGAAGCAGCAC (1134) | AGTTGCATGTTGACTTTAGGAACGTGAAGCTCTTGGAGCA (1135) | 4 | 7 | 0.68 | 3.75E-03 | exon skip | Mel. |
| 765 | chr19: 2112966-2113334 | chr19: 2112930-2113334 | CCGCCCCCGTTCCATCCACGGGGGAGCTCAGTGTGAACAC (1136) | CCGCCCCCGTTCCATCCACGGACGAGTGTGAGGACGCCAA (1137) | 41 | 65 | 0.65 | 1.89E-02 | 3'ss | Mel. |
| 766 | chr16: 89960266-89961490 | chr16: 89960266-89961445 | TGGAGCCGAACAACATCGTGCTCAGCGATGCCTGCCGCTT (1138) | TGGAGCCGAACAACATCGTGGTTCTGCTCCAGACGAGCCC (1139) | 8 | 13 | 0.64 | 4.20E-03 | 3'ss | Mel. |
| 767 | chr10: 75554088-75554298 | chr10: 75554088-75554313 | TGACGTTCTCTGTGCTCCAGTGGTTTCTCCCACAGGTTCC (466) | TGACGTTCTCTGTGCTCCAGGTTCCCGGCCCCCAAGTCGC (467) | 47 | 73 | 0.62 | 1.42E-03 | 3'ss | Mel. |

TABLE 1-continued

| | Aberrant junction | WT junction | Aberrant sequence (SEQ ID NO) | WT sequence (SEQ ID NO) | Avg WT % | Avg Ab. % | Log$_2$ Fold Diff. | FDR Q-Value | Event | Type |
|---|---|---|---|---|---|---|---|---|---|---|
| 768 | chr12: 6675490-6675694 | chr12: 6675502-6675694 | GCCTGGAAAGCTACCAAAAGGAGCTGTCCAGACAGCTGGT (1140) | GCCTGGAAAGCTACCAAAAGGGATCTCTGCAGGAGCTGTC (1141) | 28 | 42 | 0.57 | 1.37E-03 | 3'ss | Mel. |
| 769 | chr11: 85693031-85694908 | chr11: 85693046-85694908 | TGTTATTGTAGATTCTGGGGGTGGACTTCTCAAACCAACA (1142) | TGTTATTGTAGATTCTGGGGGCTTTGATGAACTAGGTGGA (1143) | 37 | 55 | 0.56 | 4.34E-05 | 3'ss | Mel. |
| 770 | chr2: 55530288-55535944 | chr2: 55529208-55535944 | GGGGACCAAGAAAAGCAGCATGGTTGCACTGAAAAGACTG (1144) | GGGGACCAAGAAAAGCAGCACCATGAATGACCTGGTGCAG (1145) | 59 | 86 | 0.54 | 2.26E-02 | exon incl. | Mel. |
| 771 | chr12: 7043741-7044712 | chr12: 7043741-7044709 | CAAAAAAGACCAAAACTGAGGAACTCCCTCGGCCAAGTC (1146) | CAAAAAAGACCAAAACTGAGCAGGAACTCCCTCGGCCACA (1147) | 13 | 19 | 0.51 | 2.94E-02 | 3'ss | Mel. |
| 772 | chr1: 40209596-40211085 | chr1: 40209596-40211046 | CCAAAGCAGAGACCCAGGAGGTGTACATGGACATCAAGAT (1148) | CCAAAGCAGAGACCCAGGAGGGAGAGCCCATTGCTAAAAA (1149) | 9 | 13 | 0.49 | 3.58E-02 | 3'ss | Mel |
| 773 | chr4: 54266006-54280781 | chr4: 54266006-54292038 | ACTGGGCTTCCACCGAGCAGAAACAGCACTTCTTCTCAGT (848) | ACTGGGCTTCCACCGAGCAGGAGATTACCTGGGCAATTG (849) | 63 | 86 | 0.44 | 9.76E-04 | exon incl. | Mel. |
| 774 | chr20: 30310151-30310420 | chr20: 30310133-30310420 | TGCCTAAGGCGGATTTGAATCTCTTTCTCTCCCTTCAGAA (479) | TGCCTAAGGCGGATTTGAATAATCTTATCTTGGCTTTGGA (480) | 61 | 83 | 0.44 | 3.34E-02 | 3'ss | Mel. |
| 775 | chr4: 54280889-54292038 | chr4: 54266006-54292038 | GCCGAATCACCTGATCTAAGGAGATTACCTGGGCAATTG (1150) | ACTGGGCTTCCACCGAGCAGGAGATTACCTGGGCAATTG (849) | 63 | 84 | 0.41 | 3.70E-03 | exon incl. | Mel. |
| 776 | chr1: 47024472-47025905 | chr1: 47024472-47027149 | ACGCCGCAAGTCCTCCAGAGGAACAGCAGCACAATGGACC (1151) | AGCACCCATGGGTGCAGGGGAACAGCAGCACAATGGACC (1152) | 66 | 87 | 0.39 | 2.24E-02 | exon incl. | Mel. |
| 777 | chr1: 150249040-150252050 | chr1: 150249040-150252053 | AACCAGTAACAACGGAACCTCAGAGTCCAGATCTGAACGA (1153) | AACCAGTAACAACGGAACCTAGTCCAGATCTGAACGATGC (1154) | 59 | 76 | 0.36 | 1.42E-02 | 3'ss | Mel. |
| 778 | chr20: 62577996-62587612 | chr20: 62577993-62587612 | GAGACCGCGTGCGAGGACCGCAGCAATGCAGAGTCCCTGG (1155) | GAGACCGCGTGCGAGGACCGCAATGCAGAGTCCCTGGACA (1156) | 70 | 90 | 0.36 | 3.80E-03 | 3'ss | Mel. |
| 779 | chr1: 211836994-211840447 | chr1: 211836970-211840447 | GTCTCTGGCAAGTAATCCAGAACTTCTTAATCTTCCATCC (1157) | GTCTCTGGCAAGTAATCCAGTAATTAAGAAGAAAGTTCAT (1158) | 78 | 100 | 0.35 | 3.86E-02 | 3'ss | Mel. |
| 780 | chr3: 133305566-133306002 | chr3: 133305566-133306739 | AAGCATGTAGAAAGCCGGAACAGGTACTTAAAATGAATGC (1159) | AAGCATGTAGAAAGCCGGAAGGATAAAGAAATGGAGAAGA (1160) | 44 | 56 | 0.34 | 4.73E-02 | 3'ss | Mel. |
| 781 | chr1: 47025949-47027149 | chr1: 47024472-47027149 | AGCACCCATGGGTGCAGGGGAAGCTCCAGAAAAGGGACT (1161) | AGCACCCATGGGTGCAGGGGAACAGCAGCACAATGGACC (1152) | 69 | 87 | 0.33 | 4.36E-02 | exon incl. | Mel. |
| 782 | chr1: 17330906-17331201 | chr1: 17330906-17331186 | TCCACAAGAGCGAGGAGGCGAAGCGGGTGCTGCGGTATTA (1162) | AGGCGGTGAGTGTCGGACAGAAGCGGGTGCTGCGGTATTA (1163) | 46 | 58 | 0.33 | 4.32E-02 | 5'ss | Mel. |

TABLE 1-continued

| | Aberrant junction | WT junction | Aberrant sequence (SEQ ID NO) | WT sequence (SEQ ID NO) | Avg WT % | Avg Ab. % | Log₂ Fold Diff. | FDR Q-Value | Event | Type |
|---|---|---|---|---|---|---|---|---|---|---|
| 783 | chr1: 155917806-155920089 | chr1: 155917806-155920059 | TCCGCCCCACAG TCCACGAGACTT TACCAGAATGCA GGAC (1164) | GGCGGAGACATG GACCAGAGACTT TACCAGAATGCA GGAC (1165) | 74 | 91 | 0.29 | 8.93E-03 | 5'ss | Mel. |
| 784 | chr17: 38080478-38083736 | chr17: 38080473-38083736 | TTGATCTTCGGC CCCACACGAACA GCAGAGAGGGGC AGCA (1166) | TTGATCTTCGGC CCCACACGCAGA GAGGGGCAGCAG GATG (1167) | 72 | 84 | 0.22 | 4.78E-02 | 3'ss | Mel. |
| 785 | chr2: 242590750-242592926 | chr2: 242590750-242592721 | GAAAAACTTTCC AGCCATTGGGGG GACAGGCCCCAC CTCG (1168) | GAAAAACTTTCC AGCCATTGGAGG TTGTCGGGACAT TTCA (1169) | 81 | 94 | 0.21 | 4.90E-02 | 3'ss | Mel. |
| 786 | chr9: 37422830-37424841 | chr9: 37422802-37424841 | GCGCTCGCCCGG GCGGCAGACTGT GAGGTGGAGCAG TGGG (1170) | CCGCAGGATACC CGCCGAGGCTGT GAGGTGGAGCAG TGGG (1171) | 76 | 86 | 0.18 | 2.12E-02 | 5'ss | Mel. |
| 787 | chr20: 32661672-32663679 | chr20: 32661441-32663679 | CGGGACGACTTC TACGACAGGCTC TTCGACTACCGG GGCC (1172) | GCAGCATCTGCC ATATACAGGCTC TTCGACTACCGG GGCC (1173) | 78 | 86 | 0.14 | 3.03E-02 | exon incl. | Mel. |
| 788 | chr3: 184084588-184085964 | chr3: 184084588-184085900 | ACTGAAGCAGCA ACACGCCTCTCT GCGTACGTGTCC TATG (1174) | ACTGAAGCAGCA ACACGCCTGCTG AGATTGAGAGCT GCTG (1175) | 92 | 98 | 0.09 | 3.80E-03 | 3'ss | Mel. |
| 789 | chr19: 58817582-58823531 | chr19: 58817582-58823562 | CTGCCGGCGGAG AATATAAGGAGA TGGACAAACCGT GTGG (1176) | CTGCCGGCGGAG AATATAAGGTGT GTGTGACCATGG AACG (1177) | 93 | 99 | 0.09 | 7.19E-03 | 3'ss | Mel. |
| 790 | chr5: 179225591-179225927 | chr5: 179225576-179225927 | CAACCTCTAAGA CTGGAGCGGTTC TTCTTCCGCAGT GGGA (1178) | CAACCTCTAAGA CTGGAGCGTGGG AACATCGAGCAC CCGG (1179) | 97 | 99 | 0.03 | 2.75E-02 | 3'ss | Mel. |

Certain splice variants are associated with more than one disease, and thus appear in Table 1 more than one time. In certain instances, splice variants associated with more than one cancer type may have different expression levels in each disease, so there may be more than one set of expression data for a given splice variant. Variants differentially expressed across all tested cancer types can be used to evaluate cells having SF3B1 neomorphic mutations in additional cancer types. Such variants are shown in the following rows of Table 1 (triplicates represent the same splice junction, measured in different cancer types): [13, 272, 525], [27, 286, 527], [33, 536, 330], [107, 445, 657], [28, 350, 573], [229, 762, 467], [240, 508, 767], [7, 356, 524], [76, 374, 596], [35, 547, 280], [84, 364, 571], [85, 564, 297], [24, 597, 296], [21, 372, 545], [36, 576, 407], [105, 423, 639], [62, 580, 447], [31, 279, 528], [235, 758, 439], [306, 89, 666], [34, 295, 533], [390, 72, 640], [48, 343, 554], [360, 65, 540], [178, 329, 750], [71, 265, 556], [15, 283, 530], [18, 267, 583], [129, 418, 622], [333, 25, 541], [247, 500, 774], [259, 5, 542], [152, 438, 615], [292, 1, 517], [81, 543, 443], [347, 70, 592], [91, 431, 617], [30, 298, 582], [17, 334, 602], [16, 276, 559], [51, 426, 548], [118, 401, 566], [83, 435, 574], and [269, 45, 546]. In certain embodiments, variants that are nonspecific to a particular cancer type can be chosen from the following rows of Table 1: [13, 272, 525], [27, 286, 527], [33, 536, 330], [107, 445, 657], [28, 350, 573], [240, 508, 767], [7, 356, 524], [84, 364, 571], [24, 597, 296], [21, 372, 545], [105, 423, 639], [62, 580, 447], [31, 279, 528], [235, 758, 439], [306, 89, 666], [34, 295, 533], [390, 72, 640], [360, 65, 540], [178, 329, 750], [71, 265, 556], [15, 283, 530], [18, 267, 583], [247, 500, 774], [152, 438, 615], [292, 1, 517], [81, 543, 443], [91, 431, 617], [30, 298, 582], [16, 276, 559], or [51, 426, 548].

Certain embodiments of the invention provide splice variants as markers for cancer. In certain circumstances, cancer cells with a neomorphic SF3B1 protein demonstrate differential expression of certain splice variants compared to cells without a neomorphic SF3B1 protein. The differential expression of one or more splice variants therefore may be used to determine whether a patient has cancer with a neomorphic SF3B1 mutation. In certain embodiments, the patient is also determined to have a cancer cell having a mutant SF3B1 protein. In these methods, one or more of the splice variants listed in Table 1 can be measured to determine whether a patient has cancer with a neomorphic SF3B1 mutation. In certain embodiments, one or more aberrant splice variants from Table 1 are measured. In other embodiments, one or more canonical splice variants are measured. Sometimes, both aberrant and canonical variants are measured.

In some embodiments, one or more aberrant splice variants selected from rows 260, 262, 263, 265, 266, 267, 272, 273, 275, 276, 277, 279, 281, 282, 286, 287, 288, 290, 294, 295, 296, 298, 299, 301, 302, 304, 305, 306, 308, 310, 312, 313, 315, 316, 318, 320, 321, 322, 323, 324, 325, 326, 327, 328, 329, 330, 331, 335, 337, 339, 342, 346, 348, 349, 350, 352, 353, 354, 355, 356, 357, 358, 362, 363, 365, 366, 368, 369, 370, 372, 375, 377, 378, 379, 380, 381, 382, 383, 384, 387, 388, 389, 390, 391, 392, 393, 394, 397, 398, 400, 402, 403, 404, 405, 406, 413, 415, 416, 417, 419, 420, 421, 424, 425, 428, 429, 430, 431, 432, 433, 436, 437, 438, 439, 440, 441, 442, 443, 444, 445, 446, 447, 448, 449, 450, 451, 452, 454, 455, 456, 458, 459, 460, 461, 462, 464, 465, 468, 469, 471, 472, 473, 474, 475, 476, 477, 478, 480, 481, 483, 484, 485, 486, 487, 488, 490, 491, 494, 496, 497, 498, 500, 501, 502, 503, 504, 505, 506, 507, 508, 509, 510, 511, 513, 514, 515, or 516 of Table 1 can be measured in a patient suspected of having CLL. In additional embodiments, a patient suspected of having CLL can be identified by measuring the amounts of one or more of the following aberrant splice variants listed in Table 1: row 259, 269, 270, 271, 274, 278, 280, 282, 292, 296, 297, 302, 306, 330, 331, 333, 343, 347, 355, 360, 361, 371, 373, 376, 378, 390, 391, 407, 408, 423, 424, 425, 433, 434, 439, 443, 447, 448, 451, 452, 453, 458, 459, 460, 462, 463, 466, 467, 468, 469, 470, 472, 479, 482, or 489. In additional embodiments, a patient suspected of having CLL can be identified by measuring the amounts of one or more of the following aberrant splice variants listed in Table 1: row 282, 292, 296, 302, 306, 330, 331, 343, 355, 360, 373, 378, 390, 391, 423, 424, 425, 433, 434, 439, 443, 447, 448, 451, 452, 458, 459, 460, 462, 463, 466, 468, 469, 470, 472, 479, 482, or 489. In still further embodiments, a patient suspected of having CLL can be identified by measuring the amount of one or more of the following aberrant splice variants listed in Table 1: row 282, 296, 302, 306, 330, 331, 355, 378, 390, 391, 424, 425, 433, 439, 443, 447, 448, 451, 452, 458, 459, 460, 462, 468, 469, or 472.

In other embodiments, one or more aberrant splice variants selected from rows 2, 3, 4, 7, 9, 10, 11, 13, 16, 18, 19, 20, 21, 22, 23, 24, 27, 28, 30, 31, 32, 33, 34, 37, 38, 39, 40, 41, 42, 43, 46, 47, 49, 50, 52, 53, 54, 56, 57, 58, 61, 62, 63, 64, 66, 67, 68, 71, 72, 75, 77, 78, 79, 80, 81, 82, 84, 87, 88, 89, 90, 91, 92, 94, 95, 97, 98, 99, 100, 101, 103, 104, 106, 107, 108, 109, 110, 111, 112, 113, 114, 116, 117, 119, 120, 121, 122, 123, 124, 125, 126, 127, 131, 132, 133, 134, 135, 136, 138, 139, 140, 141, 142, 143, 144, 146, 147, 150, 152, 154, 155, 156, 157, 159, 163, 164, 165, 167, 168, 169, 170, 171, 172, 173, 174, 175, 176, 177, 178, 179, 180, 181, 182, 183, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 230, 231, 232, 233, 235, 236, 237, 238, 239, 240, 241, 242, 243, 244, 247, 249, 250, 251, 252, 253, 254, 255, 256, or 257 of Table 1 can be measured in a patient suspected of having breast cancer. In additional embodiments, a patient suspected of having breast cancer can be identified by measuring the amounts of one or more of the following aberrant splice variants listed in Table 1: row 7, 8, 9, 10, 26, 48, 66, 105, 121, 135, 136, or 166. In additional embodiments, a patient suspected of having breast cancer can be identified by measuring the amounts of one or more of the following aberrant splice variants listed in Table 1: row 7, 8, 9, 10, 26, 48, 66, 105, 121, 135, or 136. In still further embodiments, a patient suspected of having breast cancer can be identified by measuring the amount of one or more of the following aberrant splice variants listed in Table 1: row 7, 9, 10, 66, 121, 135, or 136.

In further embodiments, one or more aberrant splice variants selected from rows 518, 519, 520, 521, 523, 524, 525, 526, 527, 528, 529, 531, 533, 534, 536, 537, 538, 539, 543, 544, 545, 549, 551, 552, 553, 555, 556, 557, 558, 559, 560, 561, 562, 563, 565, 567, 568, 569, 570, 572, 573, 575, 577, 578, 579, 580, 581, 582, 583, 584, 585, 588, 589, 590, 591, 593, 595, 597, 598, 599, 600, 601, 603, 604, 605, 606, 607, 608, 609, 610, 611, 612, 613, 614, 615, 616, 617, 618, 619, 620, 621, 623, 625, 627, 628, 629, 630, 632, 634, 635, 636, 637, 638, 640, 641, 643, 644, 645, 646, 647, 648, 649, 650, 651, 652, 654, 657, 658, 659, 661, 662, 663, 664, 665, 666, 667, 668, 669, 670, 671, 672, 673, 674, 675, 676, 677, 678, 680, 682, 683, 684, 685, 686, 687, 688, 689, 690, 692, 694, 696, 697, 698, 699, 700, 701, 702, 703, 705, 706, 707, 708, 709, 710, 711, 712, 713, 714, 715, 716, 717, 718, 719, 720, 721, 722, 723, 724, 725, 726, 727, 728, 730, 731, 732, 733, 734, 735, 736, 737, 738, 739, 740, 741, 742, 743, 744, 745, 746, 747, 748, 750, 751, 752, 753, 754, 755, 756, 757, 758, 759, 760, 763, 764, 765, 766, 767, 768, 770, 771, 772, 773, 774, 775, 776, 777, 778, 779, 780, 781, 782, 783, 784, 785, 786, 787, 788, 789, or 790 of Table 1 can be measured in a patient suspected of having melanoma. In additional embodiments, a patient suspected of having melanoma can be identified by measuring the amounts of one or more of the following aberrant splice variants listed in Table 1: row 519, 521, 522, 535, 554, 587, 594, 601, 618, 639, 654, 655, 670, 679, 680, 727, 729, or 730. In additional embodiments, a patient suspected of having melanoma can be identified by measuring the amounts of one or more of the following aberrant splice variants listed in Table 1: row 519, 521, 522, 535, 554, 587, 601, 618, 639, 654, 670, 680, 727, or 730. In still further embodiments, a patient suspected of having melanoma can be identified by measuring the amount of one or more of the following aberrant splice variants listed in Table 1: row 519, 521, 601, 618, 654, 670, 680, 727, or 730.

In some embodiments, one or more of the aberrant variants are selected from rows 21, 31, 51, 81, 118, 279, 372, 401, 426, 443, 528, 543, 545, 548 or 566 of Table 1. In certain embodiments, a patient suspected of having cancer can be identified by measuring the amount of one or more of the aberrant variants selected from 21, 31, 51, 81, 118, 279, 372, 401, 426, 443, 528, 543, 545, 548 or 566. In various embodiments the cancer may be CLL, breast cancer, or melanoma, for example.

Additional methods include predicting or monitoring the efficacy of a treatment for cancer by measuring the level of one or more aberrant splice variants in samples obtained from patients before or during the treatment. For example, a decrease in the levels of one or more aberrant splice variants over the course of treatment may indicate that the treatment is effective. In other cases, the absence of a decrease or an increase in the levels of one or more aberrant splice variants over the course of treatment may indicate that the treatment is not effective and should be adjusted, supplemented, or terminated. In some embodiments, the splice variants are used to track and adjust individual patient treatment effectiveness.

Embodiments of the invention also encompass methods of stratifying cancer patients into different categories based on the presence or absence of one or more particular splice variants in patient samples or the detection of one or more particular splice variants at levels that are elevated or reduced relative to those in normal cell samples. Categories may be different prognostic categories, categories of patients with varying rates of recurrence, categories of patients that respond to treatment and those that do not, and categories of patients that may have particular negative side effects, and the like. According to the categories in which individual patients fall, optimal treatments may then be selected for those patients, or particular patients may be selected for clinical trials.

Embodiments also encompass methods of distinguishing cancerous cells with SF3B1 neomorphic mutations from normal cells by using the splice variants disclosed herein as markers. Such methods may be employed, for example, to assess the growth or loss of cancerous cells and to identify cancerous cells to be treated or removed. In some embodiments, the splice variants are measured in cancerous tissue having cells with a neomorphic SF3B1 mutation before and after anti-cancer treatment, for the purpose of monitoring the effect of the treatment on cancer progression.

In additional embodiments, administering an SF3B1 modulator to a cell, such as a cancer cell, can alter the differential expression of splice variants. Accordingly, the change in expression of one or more splice variants can be used to evaluate the effect of the SF3B1 modulator on the SF3B1 protein. In one embodiment, the effect of an SF3B1 modulator on a CLL cell is evaluated by applying an SF3B1 modulator to such a cell, then detecting or quantifying one or more of the splice variants in Table 1. In additional embodiments the one or more splice variants are chosen from rows 258-516 of Table 1. In further embodiments, the one or more splice variants are chosen from rows 260, 262, 263, 265, 266, 267, 272, 273, 275, 276, 277, 279, 281, 282, 286, 287, 288, 290, 294, 295, 296, 298, 299, 301, 302, 304, 305, 306, 308, 310, 312, 313, 315, 316, 318, 320, 321, 322, 323, 324, 325, 326, 327, 328, 329, 330, 331, 335, 337, 339, 342, 346, 348, 349, 350, 352, 353, 354, 355, 356, 357, 358, 362, 363, 365, 366, 368, 369, 370, 372, 375, 377, 378, 379, 380, 381, 382, 383, 384, 387, 388, 389, 390, 391, 392, 393, 394, 397, 398, 400, 402, 403, 404, 405, 406, 413, 415, 416, 417, 419, 420, 421, 424, 425, 428, 429, 430, 431, 432, 433, 436, 437, 438, 439, 440, 441, 442, 443, 444, 445, 446, 447, 448, 449, 450, 451, 452, 454, 455, 456, 458, 459, 460, 461, 462, 464, 465, 468, 469, 471, 472, 473, 474, 475, 476, 477, 478, 480, 481, 483, 484, 485, 486, 487, 488, 490, 491, 494, 496, 497, 498, 500, 501, 502, 503, 504, 505, 506, 507, 508, 509, 510, 511, 513, 514, 515, or 516 of Table 1. In further embodiments, the one or more splice variants are chosen from rows 259, 269, 270, 271, 274, 278, 280, 282, 292, 296, 297, 302, 306, 330, 331, 333, 343, 347, 355, 360, 361, 371, 373, 376, 378, 390, 391, 407, 408, 423, 424, 425, 433, 434, 439, 443, 447, 448, 451, 452, 453, 458, 459, 460, 462, 463, 466, 467, 468, 469, 470, 472, 479, 482, or 489. In additional embodiments, the one or more splice variants are chosen from rows 282, 292, 296, 302, 306, 330, 331, 343, 355, 360, 373, 378, 390, 391, 423, 424, 425, 433, 434, 439, 443, 447, 448, 451, 452, 458, 459, 460, 462, 463, 466, 468, 469, 470, 472, 479, 482, or 489 of Table 1. In still further embodiments, the one or more splice variants are chosen from rows 282, 296, 302, 306, 330, 331, 355, 378, 390, 391, 424, 425, 433, 439, 443, 447, 448, 451, 452, 458, 459, 460, 462, 468, 469, or 472 of Table 1.

In certain embodiments, the effect of an SF3B1 modulator on a breast cancer cell is evaluated by applying an SF3B1 modulator to such a cell, then detecting or quantifying one or more of the splice variants in Table 1. In additional embodiments the one or more splice variants are chosen from rows 1-257 of Table 1. In further embodiments, the one or more splice variants are chosen from rows 2, 3, 4, 7, 9, 10, 11, 13, 16, 18, 19, 20, 21, 22, 23, 24, 27, 28, 30, 31, 32, 33, 34, 37, 38, 39, 40, 41, 42, 43, 46, 47, 49, 50, 52, 53, 54, 56, 57, 58, 61, 62, 63, 64, 66, 67, 68, 71, 72, 75, 77, 78, 79, 80, 81, 82, 84, 87, 88, 89, 90, 91, 92, 94, 95, 97, 98, 99, 100, 101, 103, 104, 106, 107, 108, 109, 110, 111, 112, 113, 114, 116, 117, 119, 120, 121, 122, 123, 124, 125, 126, 127, 131, 132, 133, 134, 135, 136, 138, 139, 140, 141, 142, 143, 144, 146, 147, 150, 152, 154, 155, 156, 157, 159, 163, 164, 165, 167, 168, 169, 170, 171, 172, 173, 174, 175, 176, 177, 178, 179, 180, 181, 182, 183, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 230, 231, 232, 233, 235, 236, 237, 238, 239, 240, 241, 242, 243, 244, 247, 249, 250, 251, 252, 253, 254, 255, 256, or 257 of Table 1. In additional embodiments, the one or more splice variants are chosen from rows 7, 8, 9, 10, 26, 48, 66, 105, 121, 135, 136, or 166 of Table 1. In further embodiments, the one or more splice variants are chosen from rows 7, 8, 9, 10, 26, 48, 66, 105, 121, 135, or 136 of Table 1. In still further embodiments, the one or more splice variants are chosen from rows 7, 9, 10, 66, 121, 135, or 136 of Table 1.

In a further embodiment, the effect of an SF3B1 modulator on a melanoma cell is evaluated by applying an SF3B1 modulator to such a cell, then detecting or quantifying one or more of the splice variants in Table 1. In additional embodiments the one or more splice variants are chosen from rows 517-790 of Table 1. In further embodiments, the one or more splice variants are chosen from rows 518, 519, 520, 521, 523, 524, 525, 526, 527, 528, 529, 531, 533, 534, 536, 537, 538, 539, 543, 544, 545, 549, 551, 552, 553, 555, 556, 557, 558, 559, 560, 561, 562, 563, 565, 567, 568, 569, 570, 572, 573, 575, 577, 578, 579, 580, 581, 582, 583, 584, 585, 588, 589, 590, 591, 593, 595, 597, 598, 599, 600, 601, 603, 604, 605, 606, 607, 608, 609, 610, 611, 612, 613, 614, 615, 616, 617, 618, 619, 620, 621, 623, 625, 627, 628, 629, 630, 632, 634, 635, 636, 637, 638, 640, 641, 643, 644, 645, 646, 647, 648, 649, 650, 651, 652, 654, 657, 658, 659, 661, 662, 663, 664, 665, 666, 667, 668, 669, 670, 671, 672, 673, 674, 675, 676, 677, 678, 680, 682, 683, 684, 685, 686, 687, 688, 689, 690, 692, 694, 696, 697, 698, 699, 700, 701, 702, 703, 705, 706, 707, 708, 709, 710, 711, 712, 713, 714, 715, 716, 717, 718, 719, 720, 721, 722, 723, 724, 725, 726, 727, 728, 730, 731, 732, 733, 734, 735, 736, 737, 738, 739, 740, 741, 742, 743, 744, 745, 746, 747, 748, 750, 751, 752, 753, 754, 755, 756, 757, 758, 759, 760, 763, 764, 765, 766, 767, 768, 770, 771, 772, 773, 774, 775, 776, 777, 778, 779, 780, 781, 782, 783, 784, 785, 786, 787, 788, 789, or 790 of Table 1. In still further embodiments, the one or more splice variants are chosen from rows 519, 521, 522, 535, 554, 587, 594, 601, 618, 639, 654, 655, 670, 679, 680, 727, 729, or 730 of Table 1. In additional embodiments, the one or more splice variants are chosen from rows 519, 521, 522, 535, 554, 587, 601, 618, 639, 654, 670, 680, 727, or 730 of Table 1. In still further embodiments, the one or more splice variants are chosen from rows 519, 521, 601, 618, 654, 670, 680, 727, or 730 of Table 1.

In some embodiments, the effect of an SF3B1 modulator on a cancer cell is evaluated by applying an SF3B1 modulator to such a cell, then detecting or quantifying one or more of the aberrant variants selected from rows 21, 31, 51, 81, 118, 279, 372, 401, 426, 443, 528, 543, 545, 548 or 566 of Table 1. In various embodiments, the cancer cell may be a CLL cell, a breast cancer cell, or a melanoma cell, for example.

The specific splice variants that are useful for demonstrating the effect of an SF3B1 modulator on one type of cancer cell may not be useful for demonstrating an effect of the modulator on another type of cancer cell. Aberrant splice variants that are appropriate for revealing such effects in particular cancer cells will be apparent from the description and examples provided herein.

In some embodiments, aberrant splice variants that are present at elevated levels in a cell having a neomorphic SF3B1 protein are used as markers. In other embodiments, splice variants that have reduced levels in a cell having a neomorphic SF3B1 protein are used as markers. In some embodiments, more than one splice variant will be measured. When more than one splice variant is used, they may all have elevated levels, all have reduced levels, or a mixture of splice variants with elevated and reduced levels may be used. In certain embodiments of the methods described herein, more than one aberrant splice variant is measured. In other embodiments, at least one aberrant and at least one canonical splice variant is measured. In some cases, both an aberrant and canonical splice variant associated with a particular genomic location will be measured. In other circumstances, a measured canonical splice variant will be at a different genomic location from the measured aberrant splice variant(s).

Before performing an assay for splice variants in a cell, one may determine whether the cell has a mutant SF3B1 protein. In certain embodiments, the assay for splice variants is performed if the cell has been determined to have a neomorphic SF3B1 mutant protein.

Samples

Cell samples can be obtained from a variety of biological sources. Exemplary cell samples include but are not limited to a cell culture, a cell line, a tissue, oral tissue, gastrointestinal tissue, an organ, an organelle, a biological fluid, a blood sample, a urine sample, a skin sample, and the like. Blood samples may be whole blood, partially purified blood, or a fraction of whole or partially purified blood, such as peripheral blood mononucleated cells (PBMCs). The source of a cell sample may be a solid tissue sample such as a tissue biopsy. Tissue biopsy samples may be biopsies from breast tissue, skin, lung, or lymph nodes. Samples may be samples of bone marrow, including bone marrow aspirates and bone marrow biopsies.

In certain embodiments, the cells are human cells. Cells may be cancer cells, for example hematological cancer cells or solid tumor cells. Hematological cancers include chronic lymphocytic leukemia, acute lymphoblastic leukemia, acute myeloid leukemia, chronic myeloid leukemia, chronic myelomonocytic leukemia, acute monocytic leukemia, Hodgkin's lymphoma, Non-Hodgkin's lymphoma, and multiple myeloma. Solid tumors include carcinomas, such as adenocarcinomas, and may be selected from breast, lung, liver, prostate, pancreatic, colon, colorectal, skin, ovarian, uterine, cervical, or renal cancers. Cell samples may be obtained directly from a patient or derived from cells obtained from a patient, such as cultured cells derived from a biological fluid or tissue sample. Samples may be archived samples, such as kryopreserved samples, of cells obtained directly from a subject or of cells derived from cells obtained from a patient.

In certain embodiments, cells are obtained from patients suspected of having cancer. The patients may show signs and symptoms of cancer, such as one or more common symptoms of CLL, which include enlarged lymph nodes, liver, or spleen, higher-than-normal white blood cell counts, recurring infections, loss of appetite or early satiety, abnormal bruising, fatigue, and night sweats. In additional embodiments, the cells have a mutant SF3B1 protein.

Cell samples described herein may be used in any of the methods presently disclosed.

Detection of Splice Variants

Certain embodiments of the methods described herein involve detection or quantification of splice variants. A variety of methods exists for detecting and quantifying nucleic acids, and each may be adapted for detection of splice variants in the described embodiments. Exemplary methods include an assay to quantify nucleic acid such as nucleic acid barcoding, nanoparticle probes, in situ hybridization, microarray, nucleic acid sequencing, and PCR-based methods, including real-time PCR (RT-PCR).

Nucleic acid assays utilizing barcoding technology such as NanoString® assays (NanoString Technologies) may be performed, for example, as described in U.S. Pat. Nos. 8,519,115; 7,919,237; and in Kulkarni, M. M., 2011, "Digital Multiplexed Gene Expression Analysis Using the NanoString nCounter System." *Current Protocols in Molecular Biology*, 94:25B.10.1-25B.10.17. In an exemplary assay, a pair of probes is used to detect a particular nucleotide sequence of interest, such as a particular splice variant of interest. The probe pair consists of a capture probe and a reporter probe and that each include a sequence of from about 35 to 50 bases in length that is specific for a target sequence. The capture probe includes an affinity label such as biotin at its 3' end that provides a molecular handle for surface-attachment of target mRNAs for digital detection, and the reporter probe includes a unique color code at its 5' end that provides molecular barcoding of the hybridized mRNA target sequence. Capture and reporter probe pairs are hybridized to target mRNA in solution, and after excess probes are removed, the target mRNA-probe complexes are immobilized in an nCounter® cartridge. A digital analyzer acquires direct images of the surface of the cartridge to detect color codes corresponding to specific mRNA splice variant sequences. The number of times a color-coded barcode for a particular splice variant is detected reflects the levels of a particular splice variant in the mRNA library. For the detection of splice variants, either the capture or the reporter probe may span a given splice variant's exon-exon or intron-exon junction. In other embodiments, one or both of the capture and reporter probes' target sequences correspond to the terminal sequences of two exons at an exon-exon junction or to the terminal sequences of an intron and an exon at an intron-exon junction, whereby one probe extends to the exon-exon or intron-exon junction, but does not span the junction, and the other probe binds a sequence that begins on opposite side of the junction and extends into the respective exon or intron.

In exemplary PCR-based methods, a particular splice variant may be detected by specifically amplifying a sequence that contains the splice variant. For example, the method may employ a first primer specifically designed to hybridize to a first portion of the splice variant, where the splice variant is a sequence that spans an exon-exon or intron-exon junction at which alternative splicing occurs. The method may further employ a second opposing primer that hybridizes to a segment of the PCR extension product of the first primer that corresponds to another sequence in the gene, such as a sequence at an upstream or downstream location. The PCR detection method may be quantitative (or real-time) PCR. In some embodiments of quantitative PCR, an amplified PCR product is detected using a nucleic acid probe, wherein the probe may contain one or more detectable labels. In certain quantitative PCR methods, the amount of a splice variant of interest is determined by detecting and comparing levels of the splice variant to an appropriate internal control.

Exemplary methods for detecting splice variants using an in situ hybridization assay such as RNAscope® (Advanced Cell Diagnostics) include those described by Wang, F., et al., "RNAscope: a novel in situ RNA analysis platform for formalin-fixed, paraffin-embedded tissues," *J. Mol. Diagn.* 2012 January; 14(1):22-9. RNAscope® assays may be used to detect splice variants by designing a pair of probes that targets a given splice variant, and are hybridized to target RNA in fixed and permeabilized cells. Target probes are designed to hybridize as pairs which, when hybridized to the target sequence, create a binding site for a preamplifier nucleic acid. The preamplifier nucleic acid, in turn, harbors multiple binding sites for amplifier nucleic acids, which in turn contain multiple binding sites for a labeled probe carrying a chromogenic or fluorescent molecule. In some embodiments, one of the RNAscope® target probes spans a given splice variant's exon-exon or intron-exon junction. In other embodiments, the target probes' target sequences correspond to the terminal sequences of two exons at an exon-exon junction or to the terminal sequences of an intron and an exon at an intron-exon junction, whereby one probe in the target probe pair extends to the exon-exon or intron-exon junction, but does not span the junction, and the other probe binds a sequence beginning on opposite side of the junction and extending into the respective exon or intron.

Exemplary methods for detecting splice variants using nanoparticle probes such as SmartFlare™ (Millipore) include those described in Seferos et al., "Nano-flares: Probes for Transfection and mRNA Detection in Living Cells," *J. Am. Chem. Soc.* 129(50):15477-15479 (2007) and Prigodich, A. E., et al., "Multiplexed Nanoflares: mRNA Detection in Live Cells," *Anal. Chem.* 84(4):2062-2066 (2012). SmartFlare™ detection probes may be used to detect splice variants by generating gold nanoparticles that are modified with one or more nucleic acids that include nucleotide recognition sequences that (1) are each complementary to a particular splice variant to be detected and (2) are each hybridized to a complementary fluorophore-labeled reporter nucleic acid. Upon uptake of the probe by a cell, a target splice variant sequence may hybridize to the one or more nucleotide recognition sequences and displace the fluorophore-labeled reporter nucleic acid. The fluorophore-labeled reporter nucleic acid, whose fluorophore had been quenched due to proximity to the gold nanoparticle surface, is then liberated from the gold nanoparticle, and the fluorophore may then be detected when free of the quenching effect of the nanoparticle. In some embodiments, nucleotide recognition sequences in the probes recognize a sequence that spans a given splice variant's exon-exon or intron-exon junction. In some embodiments, nucleotide recognition sequences in the probes recognize a sequence that is only on one side of the splice variant's exon-exon or intron-exon junction, including a sequence that terminates at the junction and a sequence that terminates one or more nucleotides away from the junction.

Exemplary methods for detecting splice variants using nucleic acid sequencing include RNA sequencing (RNA-Seq) described in Ren, S. et al. "RNA-Seq analysis of prostate cancer in the Chinese population identifies recurrent gene fusions, cancer-associated long noncoding RNAs and aberrant alternative splicings." *Cell Res* 22, 806-821, doi: 10.1038/cr.2012.30 (2012); and van Dijk et al., "Ten years of next-generation sequencing technology." *Trends Genet* 30(9):418-26 (2014). In some embodiments, high-throughput sequencing, such as next-generation sequencing (NGS) technologies, may be used to detected splice variants. For example, the method may employ commercial sequencing platforms available for RNA-Seq, such as, e.g., Illumina, SOLID, Ion Torrent, and Roche 454. In some embodiments, the sequencing method may include pyrosequencing. For example, a sample may be mixed with sequencing enzymes and primer and exposed to a flow of one unlabeled nucleotide at a time, allowing synthesis of the complementary DNA strand. When a nucleotide is incorporated, pyrophosphate is released leading to light emission, which is monitored in real time. In some embodiments, the sequencing method may include semiconductor sequencing. For example, proton instead of pyrophosphate may be released during nucleotide incorporation and detected in real time by ion sensors. In some embodiments, the method may include sequencing with reversible terminators. For example, the synthesis reagents may include primers, DNA polymerase, and four differently labelled, reversible terminator nucleotides. After incorporation of a nucleotide, which is identified by its color, the 3' terminator on the base and the fluorophore are removed, and the cycle is repeated. In some embodiments, the method may include sequencing by ligation. For example, a sequencing primer may be hybridized to an adapter, with the 5' end of the primer available for ligation to an oligonucleotide hybridizing to the adjacent sequence. A mixture of octamers, in which bases 4 and 5 are encoded by one of four color labels, may compete for ligation to the primer. After color detection, the ligated octamer may be cleaved between position 5 and 6 to remove the label, and the cycle may be repeated. Thereby, in the first round, the process may determine possible identities of bases in positions 4, 5, 9, 10, 14, 15, etc. The process may be repeated, offset by one base using a shorter sequencing primer, to determine positions 3, 4, 8, 9, 13, 14, etc., until the first base in the sequencing primer is reached.

Other nucleic acid detection and analytical methods that also distinguish between splice variants of a given exon-exon or intron-exon junction in a gene by identifying the nucleotide sequence on both sides of the junction may be utilized to detect or quantify the splice variants disclosed herein. For example, splice variants of an exon-exon junction may be detected by primer extension methods in which a primer that binds to one exon is extended into the exon on the other side of the junction according to the sequence of that adjacent exon. See, for example, McCullough, R. M., et al., "High-throughput alternative splicing quantification by primer extension and matrix-assisted laser desorption/ionization time-of-flight mass spectrometry," *Nucleic Acids Research*, 2005 Jun. 20; 33(11):e99; and Milani, L., et al., "Detection of alternatively spliced transcripts in leukemia cell lines by minisequencing on microarrays," *Clin. Chem.* 52: 202-211 (2006). Detection of variants on a large scale may be performed using expression microarrays that carry exon-exon or intron-exon junction probes, as described, for example, in Johnson, J. M. et al., "Genome-wide survey of human alternative pre-mRNA splicing with exon junction microarrays," Science 302: 2141-2144 (2003); and Modrek, B., et al., "Genome-wide detection of alternative splicing in expressed sequences of human genes," *Nucleic Acids Res* 29: 2850-2859 (2001).

Various embodiments include reagents for detecting splice variants of the invention. In one example, reagents include NanoString® probes designed to measure the amount of one or more of the aberrant splice variants listed in Table 1. Probes for nucleic acid quantification assays such as barcoding (e.g. NanoString®), nanoparticle probes (e.g. SmartFlare™), in situ hybridization (e.g. RNAscope®), microarray, nucleic acid sequencing, and PCR-based assays may be designed as set forth above.

In these exemplary methods or in other methods for nucleic acid detection, aberrant splice variants may be identified using probes, primers, or other reagents which specifically recognize the nucleic acid sequence that is present in the aberrant splice variant but absent in the canonical splice variant. In other embodiments, the aberrant splice variant is identified by detecting the sequence that is specific to the aberrant splice variant in the context of the junction in which it occurs, i.e., the unique sequence is flanked by the sequences which are present on either side of the splice junction in the canonical splice variant. In such cases, the portion of the probe, primer, or other detection reagent that specifically recognizes its target sequence may have a length that corresponds to the length of the aberrant sequence or to or a portion of the aberrant sequence. In other embodiments, the portion of the probe, primer, or other detection reagent that specifically recognizes its target sequence may have a length that corresponds to the length of the aberrant sequence plus the length of a chosen number of nucleotides from one or both of the sequences which flank the aberrant sequence at the splice junction. Generally, the probe or primer should be designed with a sufficient length to reduce non-specific binding. Probes, primers, and other reagents that detect aberrant or canonical splice variants may be designed according to the technical features and formats of a variety of methods for detection of nucleic acids.

SF3B1 Modulators

A variety of SF3B1 modulating compounds are known in the art, and can be used in accordance with the methods described herein. In some embodiments, the SF3B1 modulating compound is a pladienolide or pladienolide analog. A "pladienolid analog" refers to a compound which is structurally related to a member of the family of natural products known as the pladienolides. Plandienolides were first identified in the bacteria *Streptomyces platensis* (Sakai, Takashi; Sameshima, Tomohiro; Matsufuji, Motoko; Kawamura, Naoto; Dobashi, Kazuyuki; Mizui, Yoshiharu. "Pladienolides, New Substances from Culture of *Streptomyces platensis* Mer-11107. I. Taxonomy, Fermentation, Isolation and Screening." *The Journal of Antibiotics*. 2004, Vol. 57, No. 3). One of these compounds, pladienolide B, targets the SF3B spliceosome to inhibit splicing and alter the pattern of gene expression (Kotake et al., "Splicing factor SF3b as a target of the antitumor natural product pladienolide", *Nature Chemical Biology* 3:570-575 [2007]). Certain pladienolide B analogs are described in WO 2002/060890; WO 2004/011459; WO 2004/011661; WO 2004/050890; WO 2005/052152; WO 2006/009276; and WO 2008/126918.

U.S. Pat. Nos. 7,884,128 and 7,816,401, both entitled "Process for Total Synthesis of Pladienolide B and Pladienolide D," describe methods for synthesizing pladienolide B and D. Synthesis of pladienolide B and D may also be performed using methods described in Kanada et al., "Total Synthesis of the Potent Antitumor Macrolides Pladienolide B and D," *Angew. Chem. Int. Ed.* 46:4350-4355 (2007). Kanada et al., U.S. Pat. No. 7,550,503, and International Publication No. WO 2003/099813 (WO '813), entitled "Novel Physiologically Active Substances," describe methods for synthesizing E7107 (Compound 45 of WO '813) from pladienolide D (11107D of WO '813). In some embodiments, the SF3B1 modulator is pladienolide B. In other embodiments, the SF3B1 modulator is pladienolide D. In further embodiments, the SF3B1 modulator is E7107.

In some embodiments, the SF3B1 modulator is a compound described in U.S. application Ser. No. 14/710,687, filed May 13, 2015, which is incorporated herein by reference in its entirety. In some embodiments, the SF3B1 modulating compound is a compound having one of formulas 1-4 as set forth in Table 2. Table 2. Exemplary SF3B1 modulating compounds.

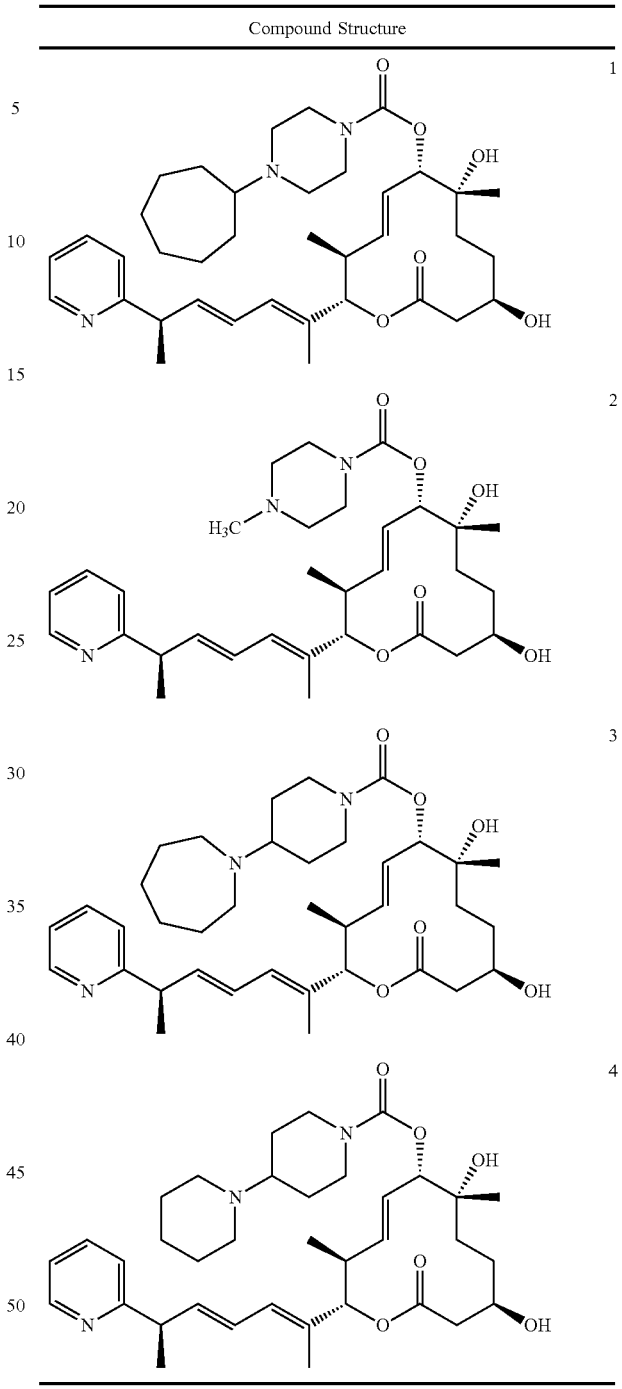

| Compound | Structure |
|---|---|
| 1 | 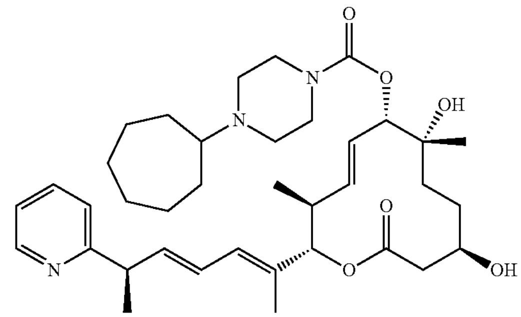 [SMILES: C/C(=C\C=C\[C@@H](C)c1ccccn1)[C@H]1OC(=O)C[C@H](O)CC[C@@](C)(O)[C@@H](OC(=O)N2CCN(C3CCCCCC3)CC2)/C=C/[C@@H]1C] |
| 2 | 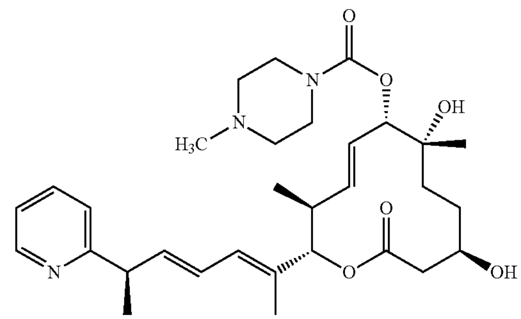 [SMILES: C/C(=C\C=C\[C@@H](C)c1ccccn1)[C@H]1OC(=O)C[C@H](O)CC[C@@](C)(O)[C@@H](OC(=O)N2CCN(C)CC2)/C=C/[C@@H]1C] |
| 3 | 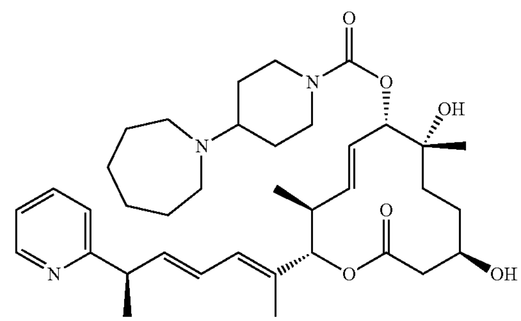 [SMILES: C/C(=C\C=C\[C@@H](C)c1ccccn1)[C@H]1OC(=O)C[C@H](O)CC[C@@](C)(O)[C@@H](OC(=O)N2CCC(N3CCCCCC3)CC2)/C=C/[C@@H]1C] |
| 4 | 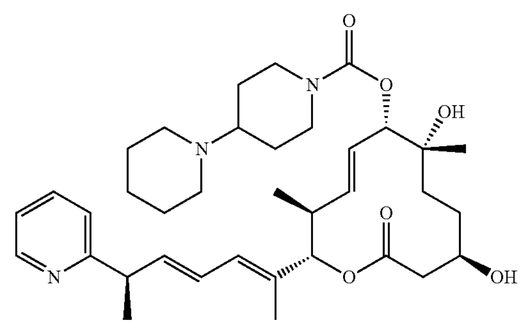 [SMILES: C/C(=C\C=C\[C@@H](C)c1ccccn1)[C@H]1OC(=O)C[C@H](O)CC[C@@](C)(O)[C@@H](OC(=O)N2CCC(N3CCCCC3)CC2)/C=C/[C@@H]1C] |

The methods described herein may be used to evaluate known and novel SF3B1 modulating compounds.

Methods of Treatment

Various embodiments of the invention include treating a patient diagnosed with cancer using an SF3B1 modulator. In certain instances, cancer cells from the patient have been determined to have a mutant SF3B1 protein. Specific SF3B1 mutants include E622D, E622K, E622Q, E622V, Y623C, Y623H, Y623S, R625C, R625G, R625H, R625L, R625P, R625S, N626D, N626H, N626I, N626S, N626Y, H662D, H662L, H662Q, H662R, H662Y, T663I, T663P, K666E, K666M, K666N, K666Q, K666R, K666S, K666T, K700E, V701A, V701F, V701I, I704F, I704N, I704S, I704V, G740E, G740K, G740R, G740V, K741N, K741Q, K741T, G742D, D781E, D781G, or D781N. In certain embodiments, SF3B1 mutants are chosen from K700E, K666N, R625C, G742D, R625H, E622D, H662Q, K666T, K666E, K666R, G740E, Y623C, T663I, K741N, N626Y, T663P, H662R, G740V, D781E, or R625L. In additional embodiments, the cancer cells have been tested to measure the amount of one or more splice variants selected from Table 1. Specific splice variants associated with neomorphic SF3B1 mutations are shown in Table 1 and described in the section on splice variants above.

In certain embodiments, a cancer patient determined to have a mutant SF3B1 protein is treated with an SF3B1 modulator as described in U.S. application Ser. No. 14/710,687, filed May 13, 2015.

EXAMPLES

Example 1: SF3B1 Mutations Induce Abnormal Splicing in a Lineage-Specific Manner To investigate splicing alterations associated with SF3B1 mutations ("SF3B1$^{MUT}$") across multiple tumor types, an RNA-Seq quantification and differential splicing pipeline was developed and used to analyze RNA-Seq profiles from the following samples:

all SF3B1$^{MUT}$ samples in The Cancer Genome Atlas (TCGA; from 81 patients in all, representing 16 cancer types), and 40 wild type SF3B1 (SF3B1$^{WT}$) samples from each of the breast cancer (20) and melanoma (20) cohorts in TCGA, seven SF3B1$^{MUT}$ and seven SF3B1$^{WT}$ CLL patient samples obtained from the Lymphoma/Myeloma Service in the Division of Hematology/Oncology at the New York Weill Cornell Medical Center.

RNA-Seq Quantification Methods

Splice junctions were quantified directly from alignments (BAM files) to facilitate discovery of unannotated splice variants. For internally generated RNA-Seq data, reads were aligned to the human reference genome hg19 (GRCh37) by MapSplice and quantified by RSEM against the TCGA GAF 2.1 isoform and gene definition, emulating the TCGA "RNASeqV2" pipeline. Splice junction counts generated by MapSplice were used for downstream processing. For TCGA RNA-Seq data, comprehensive splice junction counts generated by MapSplice were not available; instead TCGA "Level 3" splice junction data reports mapped read counts for a predefined set of splice junctions from reference transcriptomes. To reconstruct genome-wide splice junction counts comparable to internally-generated RNA-Seq samples, raw RNA-Seq alignments (BAM files) were obtained from CGHub and any reads that span across a potential splice junction were directly counted. RSEM-estimated gene expression read counts were gathered directly from the TCGA RNA-SeqV2 Level 3 data matrices.

Because MapSplice only provides exon-exon junction counts, estimates of read counts spanning each intron-exon junction were required for identification of intron-retention splice variants. For every splice junction in each BAM file, reads with at least a 3-bp overhang across each of the 3' and 5' intron-exon junctions were counted.

For all manipulation of spliced reads within BAM files, a custom Python module "splicedbam" was used, which uses the "pysam" extension of samtools (Li, H., et al., "The Sequence Alignment/Map format and SAMtools." *Bioinformatics*, 2009 Aug. 15; 25(16):2078-9).

In some instances, splice junctions had very low counts, occasionally due to sequencing and alignment errors. Therefore, only splice junctions that had at least a total of 10 counts on average from either SF3B1$^{WT}$ or SF3B1$^{MUT}$ cohorts were included in downstream analyses.

Differential Splicing Detection Methods

In order to detect differential usage of a splice variant in one cohort relative to another, independent of gene expression changes and pre-defined alternative splicing models, a computational differential splicing pipeline was developed that converts splice junction counts into percentages of junction usage at splice sites with multiple possible junctions. The percentage of junction usage is a measurement of the occurrence of one splice variant relative to all other splice variants that share the same splice site. For instance, a splice variant with an alternative 3' splice site must share its 5' splice site with another splice variant. Therefore, for each shared splice site, the raw counts of each splice variant were divided by the total counts of all splice variants that utilize the shared splice site in order to derive a ratio. This ratio was then multiplied by 100 to convert it to a percentage. For each sample, the sum of all of the percentages of splice variants that share the same splice site will equal 100. The transformation of raw counts of each splice variant into a percentage of all splice variants sharing a splice site is itself a normalization to reduce the effect of gene expression changes. The percentages for canonical and aberrant junctions are listed in Table 1 as "Avg WT %" and "Avg Ab. %," respectively. Differences between these percentages were assessed for statistical significance by using the moderated t-test defined in the Bioconductor's limma package. The statistical p-values were corrected into q values using the Benjamini-Hochberg procedure, and listed as "FDR Q-Values" in Table 1. Any splice variant that satisfied a q value of less than or equal to 0.05 was considered statistically significant.

The conversion of raw junction counts into percentage junction usage can introduce noise in some instances, i.e., when a gene in which a splice variant occurs is expressed in one cohort but has very low expression or is not expressed at all in another cohort. To address this, an additional filtering step was introduced. For each up-regulated splice variant in an SF3B1$^{MUT}$ sample that satisfies the above q value threshold, its corresponding canonical splice variant must be down-regulated in the SF3B1$^{MUT}$ sample and also must also satisfy the q value threshold for the up-regulated splice variant to be considered an aberrant splice variant.

Identification of Aberrant Splice Variants in Neomorphic SF3B1$^{MUT}$ Patient Samples Initially, this framework was applied to a subset of known SF3B1$^{MUT}$ cancers or wild-type counterparts from The Cancer Genome Atlas (TCGA; luminal A primary breast cancer: 7 SF3B1$^{K700E}$ and 20 SF3B1$^{WT}$; metastatic melanoma: 4 SF3B1$^{MUT}$; and 20 SF3B1$^{WT}$) and internally generated 7 SF3B1$^{MUT}$ and 7 SF3B1$^{WT}$ CLL patient samples. This analysis revealed 626 aberrant splice junctions to be significantly upregulated in SF3B1$^{MUT}$ compared to SF3B1$^{WT}$. The vast majority of aberrant splicing events use an alternative 3'ss (see Table 1, "Event" column).

Figure 2:
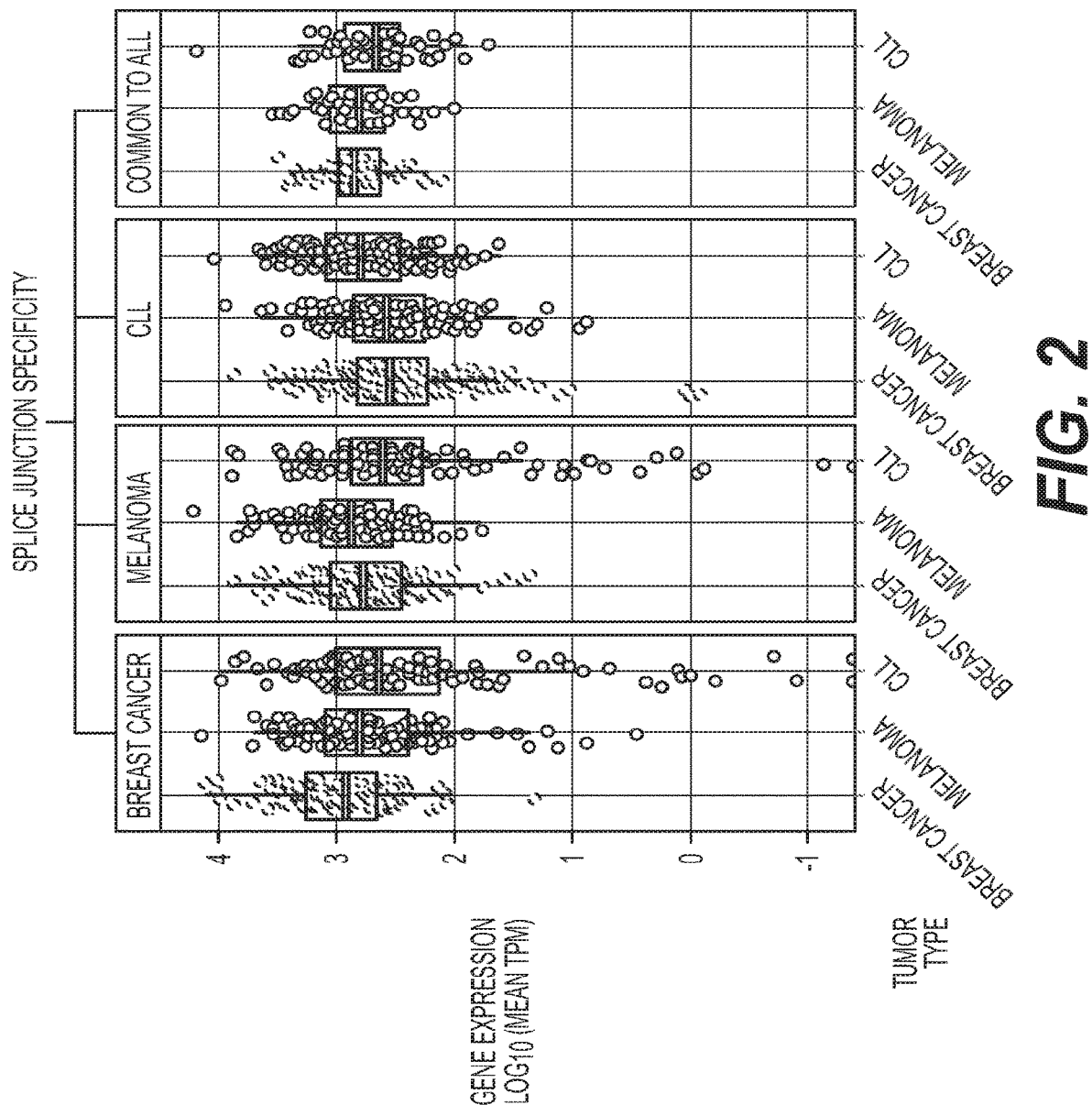
FIG. 2 is a graph depicting levels of gene expression for abnormally spliced genes across different cancers in patient samples.

The computational screening of aberrant splicing events revealed a pattern of tumor-specific splicing events in breast cancer, melanoma and CLL in neomorphic SF3B1$^{MUT}$ samples (Table 1). In addition, a set of tumor-non-specific events (i.e., splicing events found in at least two tumor types) was observed. Some splice variants of genes with tumor-specific splicing events occur in genes with higher mRNA expression, indicating that some of the observed tumor-specific splicing results from gene expression differences (FIG. 2).

Figure 3:
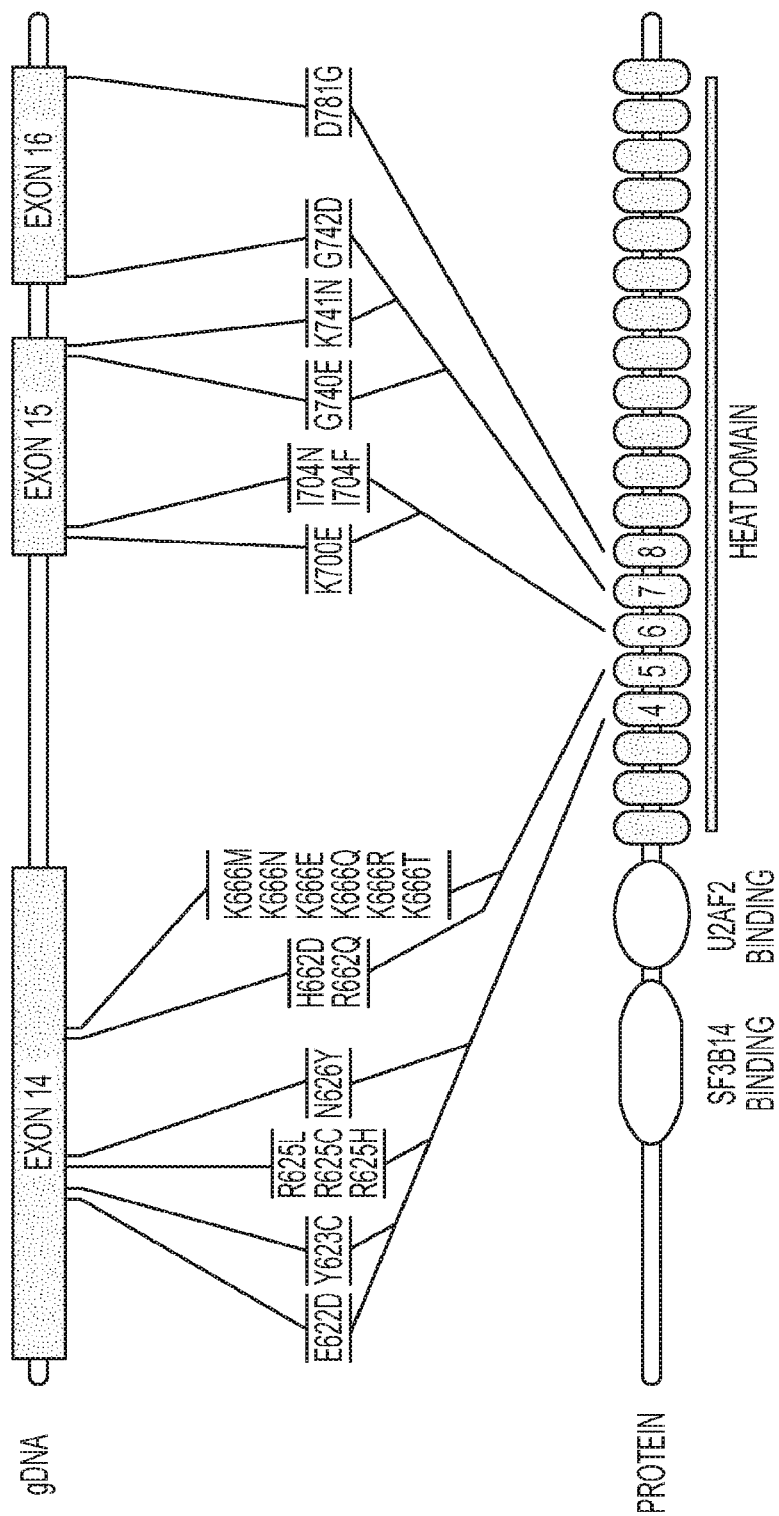
FIG. 3 is a schematic diagram showing the locations of certain neomorphic mutations in the SF3B1 protein and corresponding coding regions of the SF3B1 gene.

To characterize the effect of aberrant splicing in all SF3B1 variants across cancer types, RNA-Seq data for the remaining 70 SF3B1$^{MUT}$ patients from 14 cancer types in TCGA were quantified, and an unsupervised clustering analysis was done using all 136 samples. This clustering separated splicing events associated with neomorphic SF3B1 mutants from those associated with wild-type SF3B1 or non-neomorphic SF3B1 mutants. For example, splicing patterns associated with neomorphic SF3B1 mutants were observed in breast cancer (SF3B1$^{K666E}$, SF3B1$^{2626D}$), lung adenocarcinoma (SF3B1$^{K741N}$, SF3B1$^{G740V}$), and bladder cancer (SF3B1$^{R625C}$) patient samples, as splicing events in these samples clustered with those in SF3B1$^{K700E}$ neomorphic samples, whereas the splicing profiles for other SF3B1 mutant samples were similar to those of SF3B1' samples of the same tumor type. A listing of SF3B1 mutants whose splicing profiles clustered with those of neomorphic SF3B1 mutants is provided in Table 3, column 1. Additional SF3B1 mutations that are predicted to be neomorphic are listed in Table 3, column 2. A schematic diagram showing the locations of all mutations provided in Table 3 is shown in FIG. 3.

TABLE 3

Select SF3B1 mutations

| SF3B1 Mutations with Splicing Profiles Clustering with Neomorphic SF3B1 Mutations | Predicted Neomorphic SF3B1 Mutations |
|---|---|
| K700E | K666Q |
| K666N | K666M |
| R625C | H662D |
| G742D | D781G |
| R625H | I704F |
| E622D | I704N |
| H662Q | V701F |
| K666T | R625P |
| K666E | R625G |
| K666R | N626D |
| G740E | H662Y |
| Y623C | N626S |
| T663I | G740R |
| K741N | N626I |
| N626Y | N626H |
| T663P | V701I |
| H662R | R625S |
| G740V | K741T |
| D781E | K741Q |
| R625L | I704V |
|  | I704S |
|  | E622V |
|  | Y623S |
|  | Y623H |
|  | V701A |
|  | K666S |
|  | H662L |
|  | G740K |
|  | E622Q |
|  | E622K |
|  | D781N |

Example 2: Validation of Aberrant Splice Variants in Cell Lines

Aberrant splicing in cell line models was analyzed by collecting RNA-Seq profiles for a panel of cell lines with endogenous SF3B1 neomorphic mutations (pancreatic adenocarcinoma Panc 05.04: SF3B1$^{Q699H/K700E}$ double mutant; metastatic melanoma Colo829: SF3B1$^{P718L}$; and lung cancer NCI-H358: SF3B1$^{A745V}$; obtained from the American Type Culture Collection [ATCC] or RIKEN BioResource Center and cultured as instructed) and from several SF3B1$^{WT}$ cell lines from either the same tumor types (pancreatic adenocarcinoma Panc 10.05, HPAF-II, MIAPaCa-2, Panc04.03, PK-59, lung cancer NCI-H358, NCI-H1792, NCI-H1650, NCI-H1975, NCI H1838) or normal control cells of the same patient (Epstein-Barr virus [EBV]-transformed B lymphoblast colo829BL). RNA-Seq profiles were also collected from isogenic pre B-cell lines (Nalm-6) engineered via AAV-mediated homology to express SF3B1$^{K700E}$ (Nalm-6 SF3B1$^{K700E}$) or a synonymous mutation (Nalm-6 SF3B1$^{K700K}$). The isogenic cell lines Nalm-6 SF3B1$^{K700E}$ and Nalm-6 SF3B1$^{K700K}$, generated at Horizon Discovery, were cultured in presence of Geneticin (0.7 mg/ml, Life Technologies) for selection. All RNA-Seq analysis was performed using the same pipeline described for patient samples in Example 1. Unsupervised clustering of cell lines using the aberrant splice junctions identified in patients resulted in clear segregation of Panc 05.04 and Nalm-6 SF3B1$^{K700E}$ from wild-type and other SF3B1-mutant cells.

A NanoString® assay was developed to quantify aberrant and canonical splice variants and was validated using the same cell panel. For the NanoString® assay, 750 ng of purified total RNA was used as template for the nCounter® (NanoString Technologies®) expression assay using a custom panel of NanoString® probes. The sample preparation was set up as recommended (NanoString® Technologies protocol no. C-0003-02) for an overnight hybridization at 65° C. The following day, samples were processed through the automated nCounter® Analysis System Prep Station using the high sensitivity protocol (NanoString® Technologies protocol no. MAN-00029-05) followed by processing through the nCounter® Analysis System Digital Analyzer (protocol no. MAN-00021-01) using 1150 FOVs for detection. Data was downloaded and analyzed for quality control metrics and normalization using the nSolver™ Analysis Software (NanoString Technologies®). The data was first normalized for lane-to-lane variation using the positive assay controls provided by the manufacturer (NanoString® positive controls A-F [containing in vitro transcribed RNA transcripts at concentrations of 128 fM, 32 fM, 8 fM, 2 fM, 0.5 fM, and 0.125 fM, each pre-mixed with NanoString® Reporter CodeSet probes])). Any samples with normalization factors <0.3 and >3 were not considered for further analysis. This was followed by content normalization using the geo-mean of GAPDH, EEF1A1 and RPLP0. All samples were within the recommended 0.1-10 normalization factor range. Each normalized value was then checked to ensure that it was at least two standard deviations higher than the average of background signal recorded for that lane. Any value below that was considered below detection limit. These normalized values were taken for further bioinformatics and statistical analysis.

Figure 4:
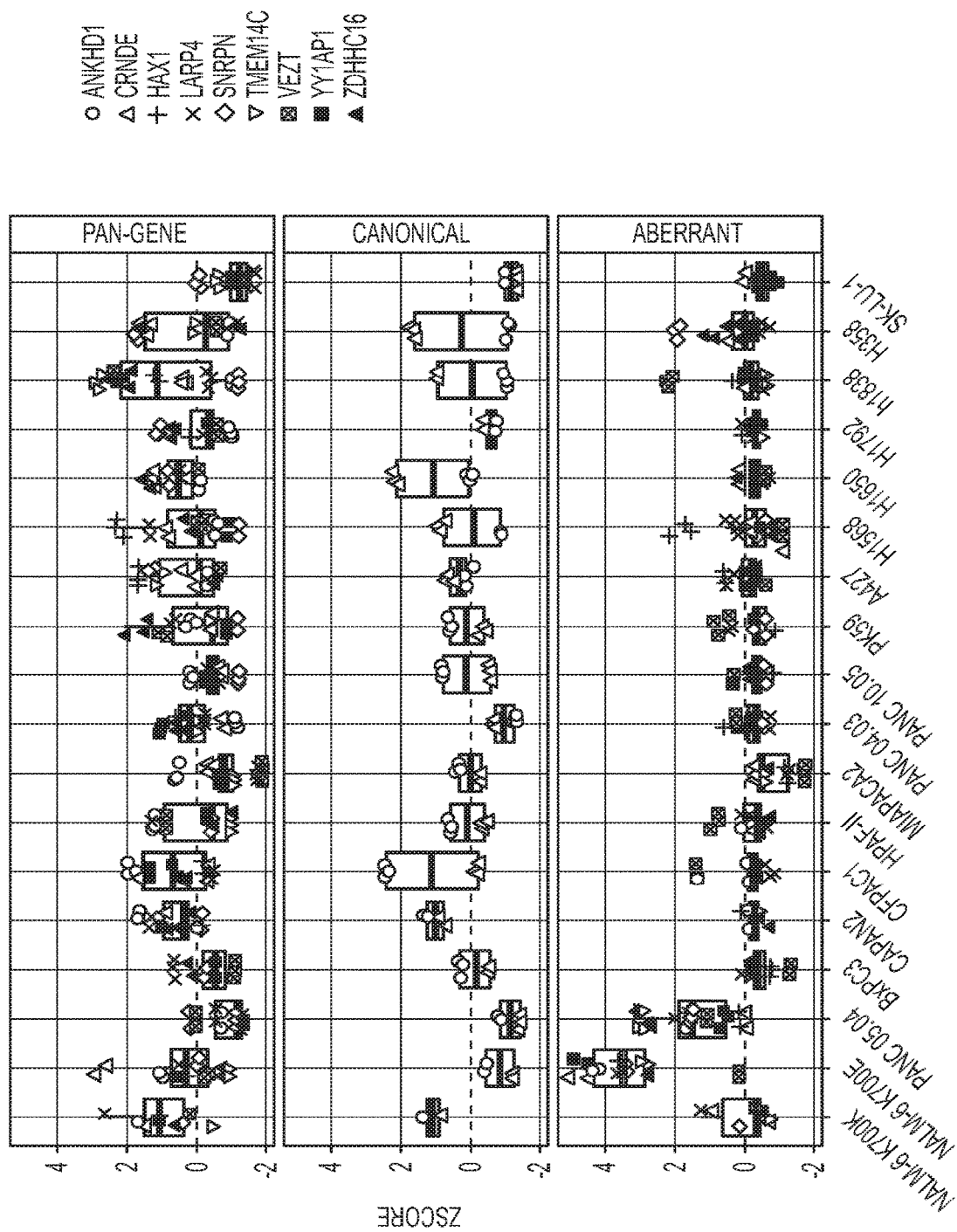
FIG. 4 is a graph depicting levels of aberrant splice variants detected in RNA isolated from pancreatic, lung cancer, and Nalm-6 isogenic cell lines using a NanoString® assay. Data are represented as the mean of three replicates.

As observed in the RNA-Seq analysis, only the Panc 05.04 and isogenic Nalm-6 SF3B1$^{K700E}$ cell lines showed clear presence of aberrant splicing (FIG. 4).

Analysis of SF3B1 Mutant SF3B1$^{Q699H}$

Figure 5:
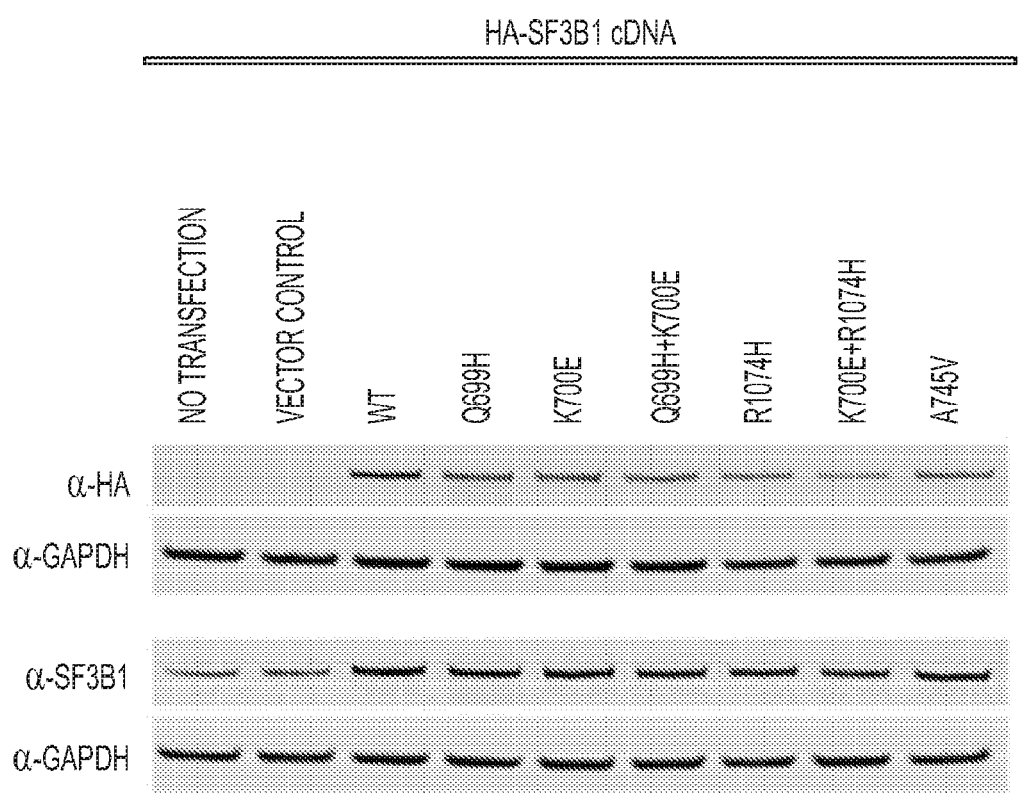
FIG. 5 is a set of western blot images that confirm overexpression of SF3B1 proteins in 293FT cells.

The Panc 05.04 cell line carries the neomorphic mutation SF3B1$^{K700E}$ and an additional mutation at position 699 (SF3B1$^{Q699H}$). To evaluate the functional relevance of this second mutation, SF3B1$^{Q699H}$ and SF3B1$^{K700E}$ mutant SF3B1 proteins were expressed alone or in combination in 293FT cells (FIG. 5) for analysis of RNA by NanoString®. To express the mutants in 293FT cells, mammalian expression plasmids were generated using the Gateway technology (Life Technologies). First, the HA-tag mxSF3B1 wild-type (Yokoi, A. et al. "Biological validation that SF3b is a target of the antitumor macrolide pladienolide." FEBS J. 278: 4870-4880 [2011]) was cloned by PCR into the pDONR221, then the mutations were introduced using the site-directed mutagenesis kit (QuikChange II XL, Agilent). LR reaction was performed to clone all the HA-tag mxSF3B1 wild-type and mutants into the pcDNA-DEST40 (Life Technologies). 293FT cells (Life Technologies), cultured according to the manufacturer's instructions, were seeded on 6 wells/plate and transfected with generated plasmid using Fugene (Roche). One μg of DNA per pcDNA-DEST40 HA-mxSF3B1 construct was used for each transient transfection, generated in triplicates. Forty-eight hours after transfection, cells were collected to isolate protein and RNA for western blot and NanoString® analysis, respectively. Protein extracts were prepared by lysing the cells with RIPA (Boston BioProducts). Twenty-three μg of protein was loaded in a SDS-PAGE gel and identified using SF3B1 antibody (a-SAP 155, MBL) and anti-GAPDH (Sigma). Li-Cor donkey-anti-mouse 800CW and Li-Cor donkey-anti-rabbit 800CW were used as secondary antibodies and detected by Odyssey imager (Li-Cor). RNA was isolated from the cells and retrotranscribed using MagMax for Microarray and Superscript VILO II (Life Technologies), respectively, according to the manufacturer manual, and then analyzed with the NanoString® assay.

Figure 6:
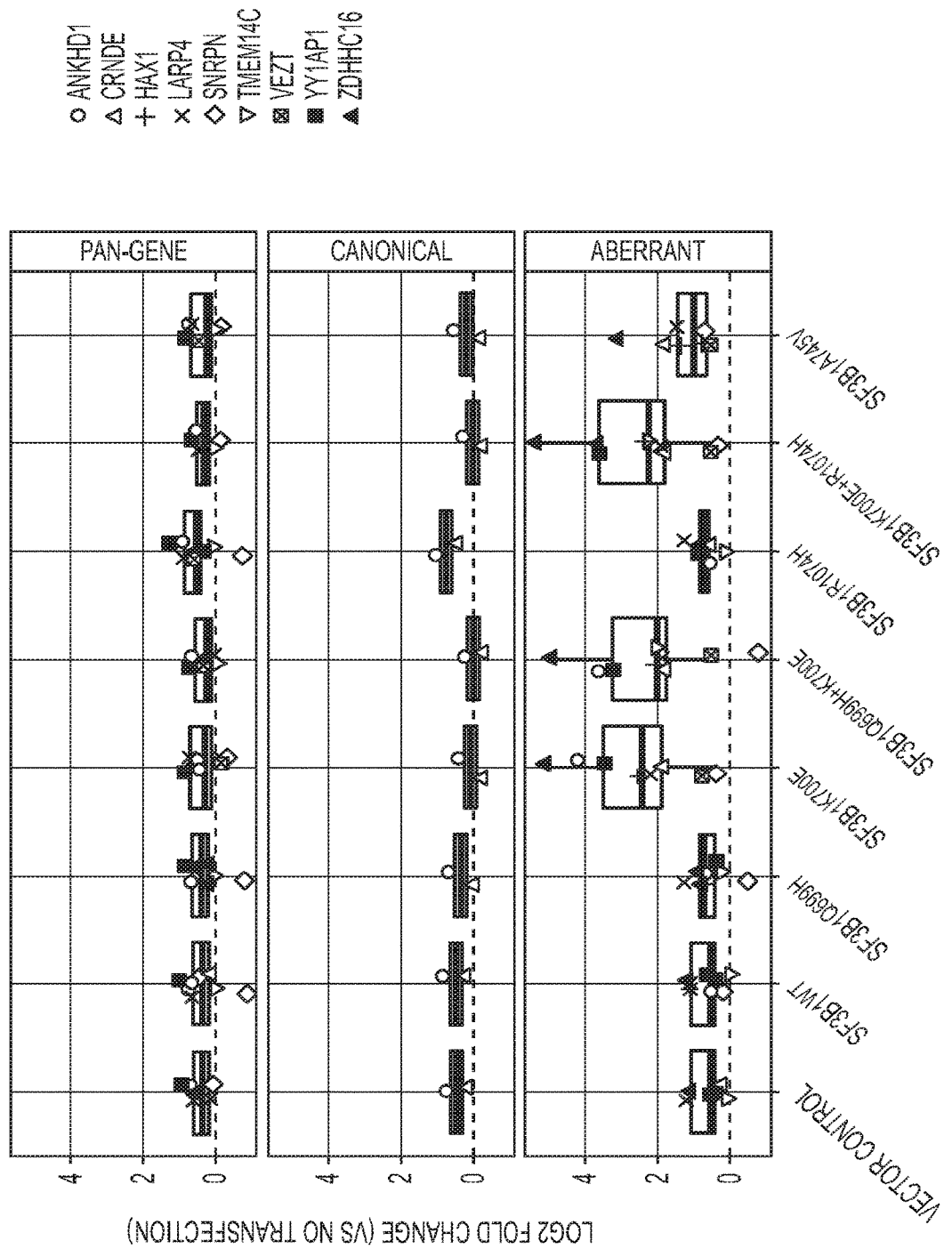
FIG. 6 is a graph depicting levels of aberrant splice variants in RNA isolated from 293FT cells expressing wild type SF3B1 (SF3B1$^{WT}$) or mutant SF3B1 proteins, as measured in a NanoString® assay. Data are represented as the mean of three replicates.

Expression of $SF3B1^{K700E}$ and $SF3B1^{Q699H/K700E}$ induced aberrant splicing, whereas $SF3B1^{Q699H}$ alone or $SF3B1^{A745V}$ or $SF3B1^{R1074H}$ (a substitution conferring resistance to the spliceosome inhibitor pladienolide B) did not induce aberrant splicing (FIG. 6), indicating that $SF3B1^{Q999H}$ is a non-functional substitution.

These data confirm that Panc 05.04 and Nalm-6 $SF3B1^{K700E}$ isogenic cells are representative models to study the functional activity of SF3B1 neomorphic mutations and the activity of splicing inhibitors in vitro and in vivo.

Example 3: Neomorphic SF3B1 Mutations Induce Abnormal mRNA Splicing

Figure 7:
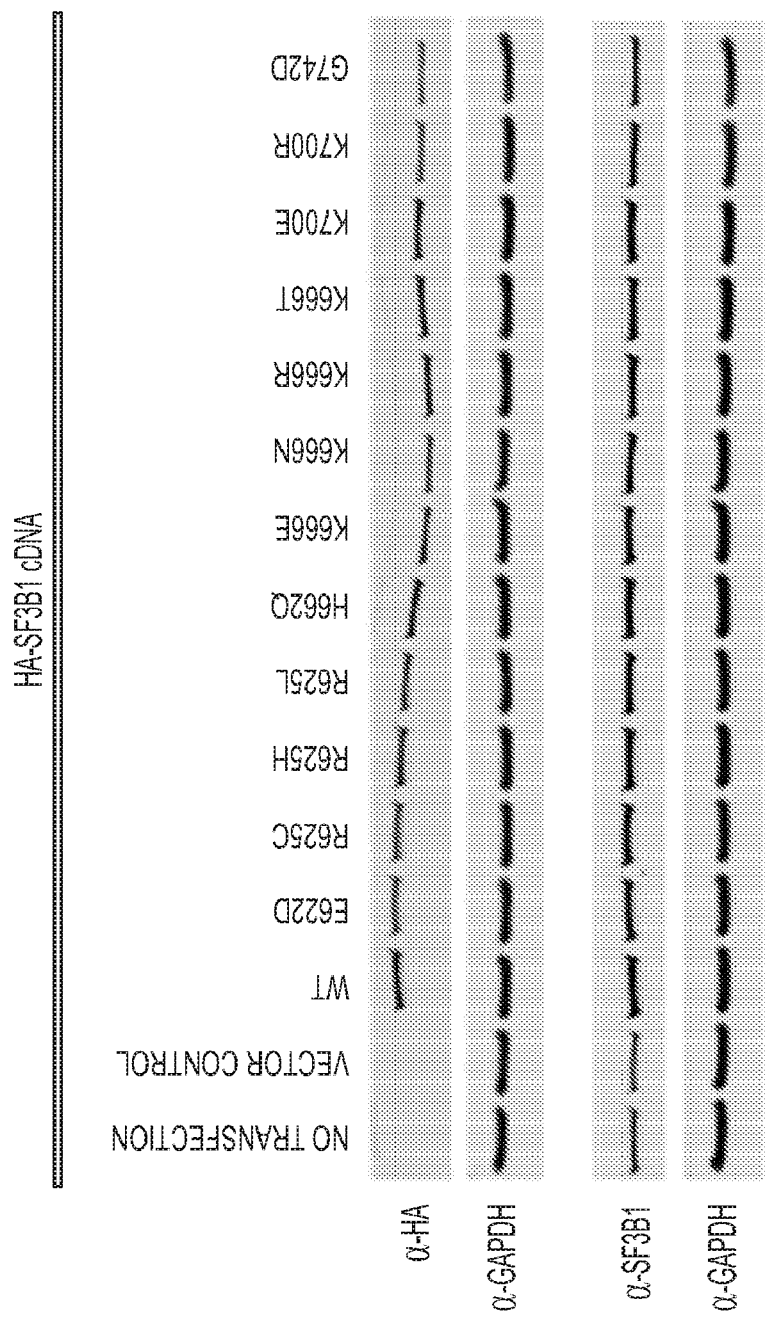
FIG. 7 is a set of western blot images that confirm overexpression of SF3B1 proteins in 293FT cells.
Figure 8:
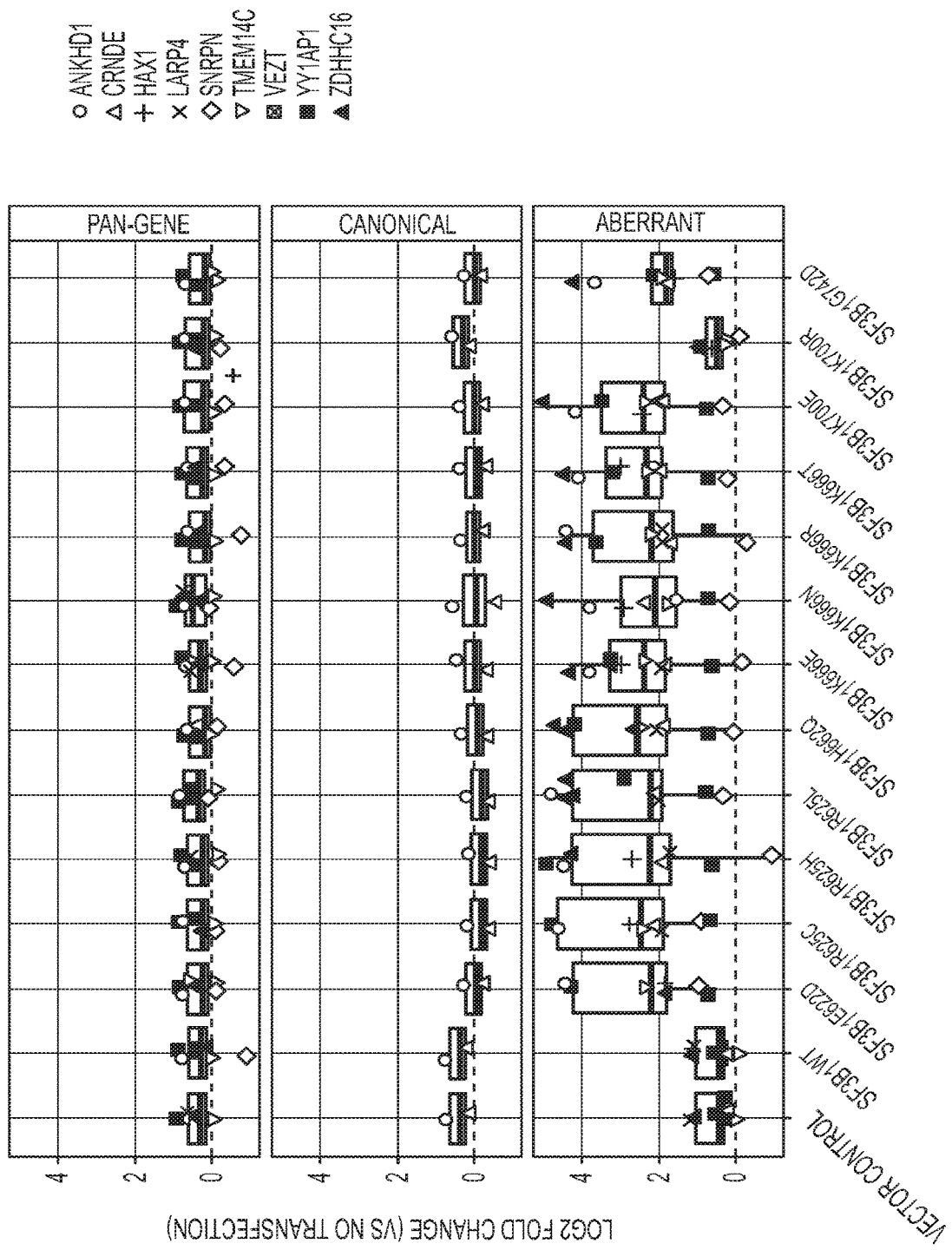
FIG. 8 is a graph depicting levels of aberrant splice variants in RNA isolated from 293FT cells expressing SF3B1$^{WT}$ or mutant SF3B1 proteins, as measured in a NanoString® assay.

The functional activity of neomorphic mutations found in $SF3B1^{MUT}$ cancers was analyzed by expressing $SF3B1^{WT}$, neomorphic SF3B1 mutants, or $SF3B1^{K700R}$ (the mutation observed in a renal clear cell carcinoma patient that clusters with $SF3B1^{WT}$ patients) in 293FT cells and determining splicing aberrations by NanoString®. The expression of all constructs was confirmed by western blot (FIG. 7). All SF3B1 neomorphic mutations tested demonstrated the same usage of alternative splice sites observed in patient samples ("MUT isoform" in FIG. 8), but $SF3B1^{K700R}$ and $SF3B1^{WT}$ did not show aberrant splicing (FIG. 8). Moreover, the expression of none of the SF3B1 constructs changed the overall gene expression ("PAN-gene" in FIG. 8) or the canonical splice isoforms ("WT isoform" in FIG. 8). This indicated both a correlation between the presence of the neomorphic SF3B1 mutations and alternative splicing as well as similar functional activity of the different neomorphic mutations, as was indicated by the RNA-Seq analysis of patient samples.

The correlation between the $SF3B1^{K700E}$ neomorphic mutation and aberrant splicing was analyzed using tetracycline-inducible shRNA to selectively knockdown the neomorphic SF3B1 mutant or $SF3B1^{WT}$ allele in Panc 05.04 and Panc 10.05 cell lines (neomorphic $SF3B1^{MUT}$ and $SF3B1^{WT}$ cell lines, respectively; obtained from the American Type Culture Collection [ATCC] or from RIKEN BioResource Center and cultured as instructed).

For the knockdown experiment, virus encoding shRNA was prepared in LentiX-293T cells (Clontech), which were cultured according to the manufacturer's instruction. The inducible shRNA were cloned into AgeI and EcoRI of the pLKO-iKD-H1 puro vector. The sequences of hairpins were:

```
shRNA #13 SF3B1^PAN
                              (SEQ ID NO: 1180)
GCGAGACACACTGGTATTAAG, shRNA #8 SF3B1^WT
                              (SEQ ID NO: 1181)
TGTGGATGAGCAGCAGAAAGT;
and shRNA #96 SF3B1^MUT
                              (SEQ ID NO: 1182)
GATGAGCAGCATGAAGTTCGG.
```

Cells were transfected with 2.4 μg of target pLKO-shRNA plasmid, plus 2.4 μg of p Δ8.91 (packaging), and 0.6 μg VSVG (envelope) using TransIT reagent (Mirus). The virus was used to infect Panc 05.04 and Panc 10.05 by spin infection using Polybrene (Millipore). The day after infection, the cells were cultured in selecting media (1.25 μg/ml Puromycin [Life Technologies]) for 7 days to select for shRNA-expressing cells. The selected cells were cultured in the presence or absence of Doxycycline hyclate (100 ng/mL; Sigma) to induce the shRNA. Cells were harvested for protein and RNA at day 4 post-induction. In addition, cells were seeded for colony forming assay and CellTiter-Glo® assay (Promega). At day 9, cells were fixed with formaldehyde and stained with crystal violet.

To confirm SF3B1 knockdown using western blots, protein extracts were prepared by lysing the cells with RIPA (Boston BioProducts). Twenty to 25 μg of protein from each sample was separated by SDS-PAGE and transferred to nitrocellulose membranes (iblot, Life Technologies). Membranes were first blocked with Odyssey Blocking Buffer (Li-Cor) and then incubated with SF3B1 antibody (a-SAP 155, MBL) and anti-GAPDH (Sigma). Li-Cor donkey-anti-mouse 800CW and Li-Cor donkey-anti-rabbit 800CW were used as secondary antibodies and detected by Odyssey imager (Li-Cor).

To confirm SF3B1 knockdown by allele specific qPCR, RNA was isolated from the cells and retrotranscribed using MagMax for Microarray and Superscript VILO II (Life Technologies), respectively according to the manufacturer manual. qPCR was performed using ViiA7 (Life Technologies). The reaction included 20-50 ng cDNA, Power SYBR green master mix (Life Technologies) and 300 nM primers. The following primers were used:

```
SF3B1^WT: FW
                              (SEQ ID NO: 1183)
5'-GACTTCCTTCTTTATTGCCCTTC
and

RW
                              (SEQ ID NO: 1184)
5'-AGCACTGATGGTCCGAACTTTC,

SF3B1^MUT: FW
                              (SEQ ID NO: 1185)
5'-GTGTGCAAAAGCAAGAAGTCC
and
```

```
RW
                                 (SEQ ID NO: 1186)
5'-GCACTGATGGTCCGAACTTCA,

SF3B1^PAN: FW
                                 (SEQ ID NO: 1187)
5'-GCTTGGCGGTGGGAAAGAGAAATTG
and RW
                                 (SEQ ID NO: 1188)
5'-AACCAGTCATACCACCCAAAGGTGTTG, β-actin (internal control): FW
                                 (SEQ ID NO: 1189)
5'-GGCACCCAGCACAATGAAGATCAAG
and RW
                                 (SEQ ID NO: 1190)
5'-ACTCGTCATACTCCTGCTTGCTGATC.
```

Biological and technical triplicates were performed.

Figure 9A:
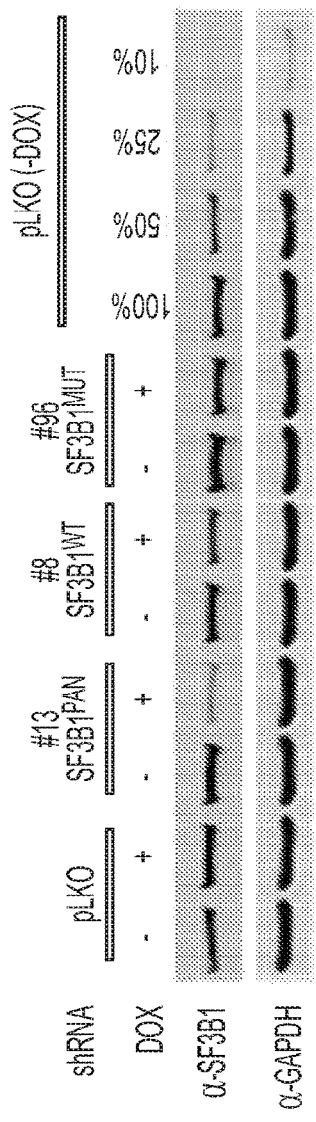
FIG. 9A depicts a set of western blot images showing expression of SF3B1 alleles before and after shRNA-knockdown in Panc 05.04 cells.
Figure 9B:
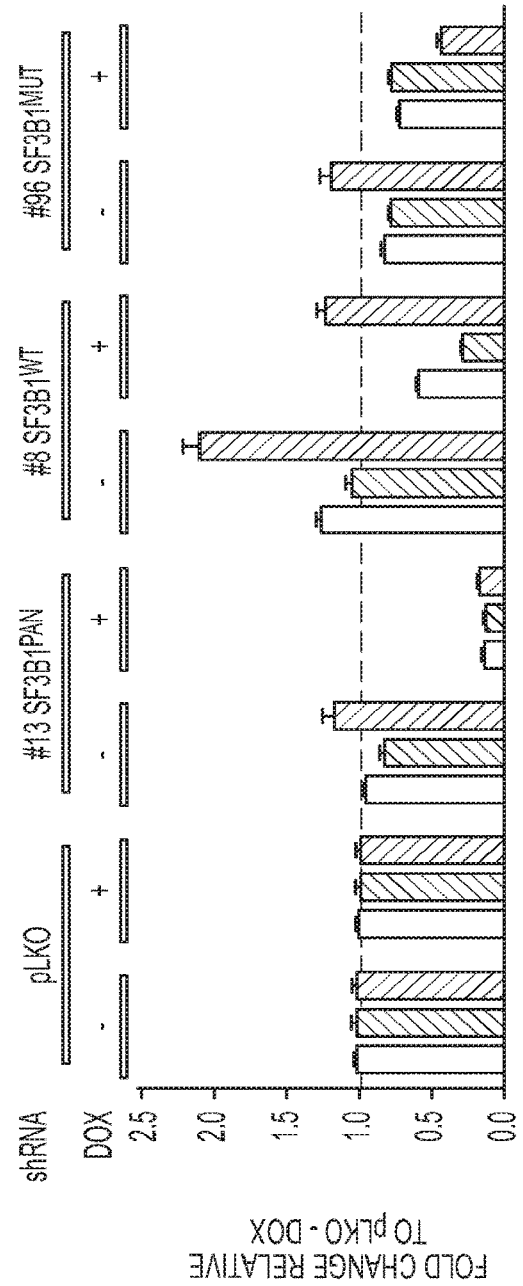
FIG. 9B depicts a graph showing levels of SF3B1 RNA detected by qPCR in Panc 05.04 cells before and after shRNA-knockdown of all SF3B1 alleles ("SF3B1$^{PAN}$") or SF3B1$^{WT}$ or mutant SF3B1 (SF3B1$^{MUT}$) alleles. qPCR data are represented as fold change relative to pLKO non-treated with doxycycline (mean±SD, n=3). Solid black, outlined, and gray bars indicate SF3B1$^{PAN}$, SF3B1$^{WT}$, and SF3B1$^{MUT}$ allele-specific qPCR data, respectively.
Figure 10A:
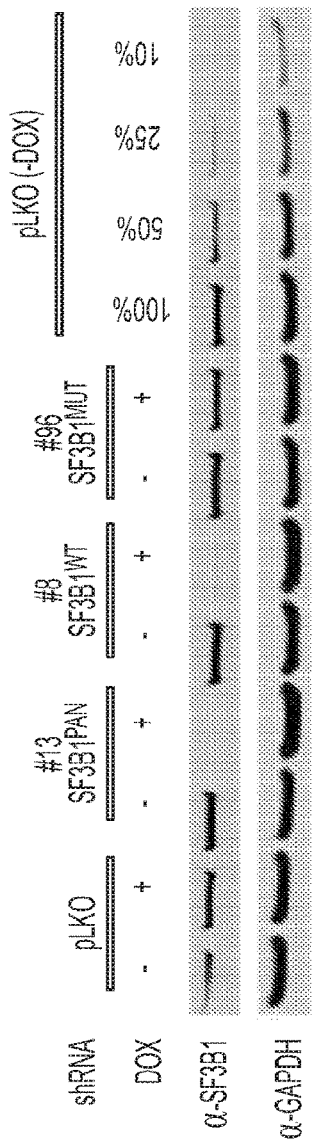
FIG. 10A depicts a set of western blot images showing expression of SF3B1 alleles before and after shRNA-knockdown in Panc 10.05 cells.
Figure 10B:
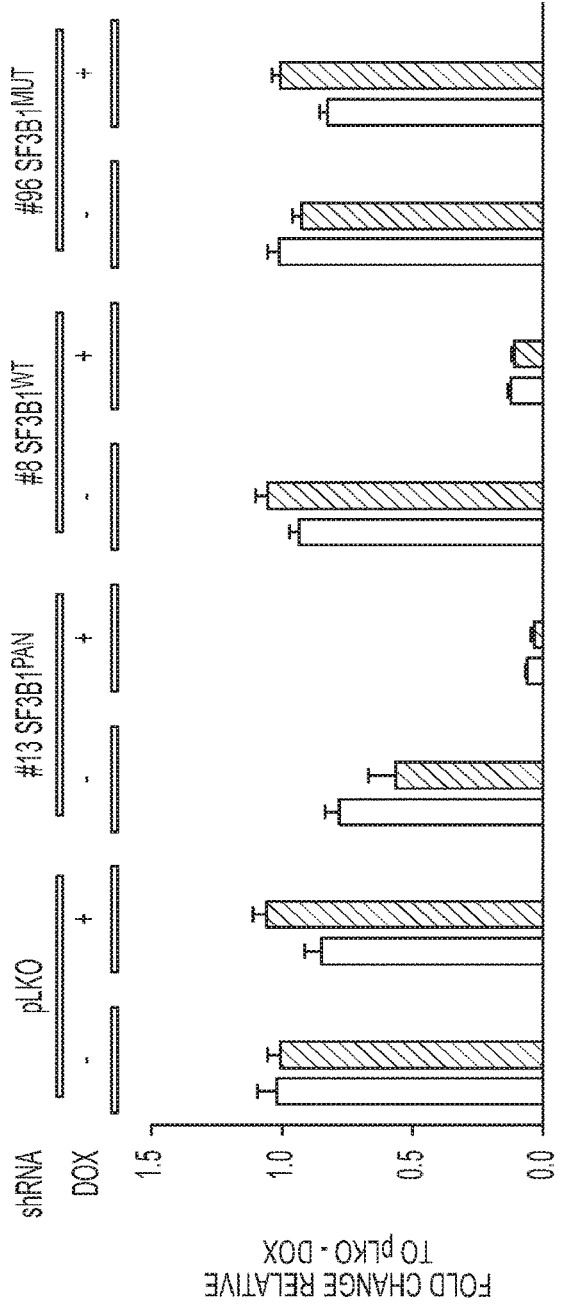
FIG. 10B depicts a graph showing levels of SF3B1 RNA detected by qPCR in Panc 10.05 cells before and after shRNA-knockdown of SF3B1 alleles. qPCR data are represented as fold change relative to pLKO non-treated with doxycycline (mean±SD, n=3). Solid black, outlined, and gray bars indicate SF3B1$^{PAN}$, SF3B1$^{WT}$, and SF3B1$^{MUT}$ allele-specific qPCR data, respectively.

The western blotting and allele specific PCR both confirmed knockdown of the SF3B1 alleles (FIGS. 9 and 10).

Figures 11A, 11B:
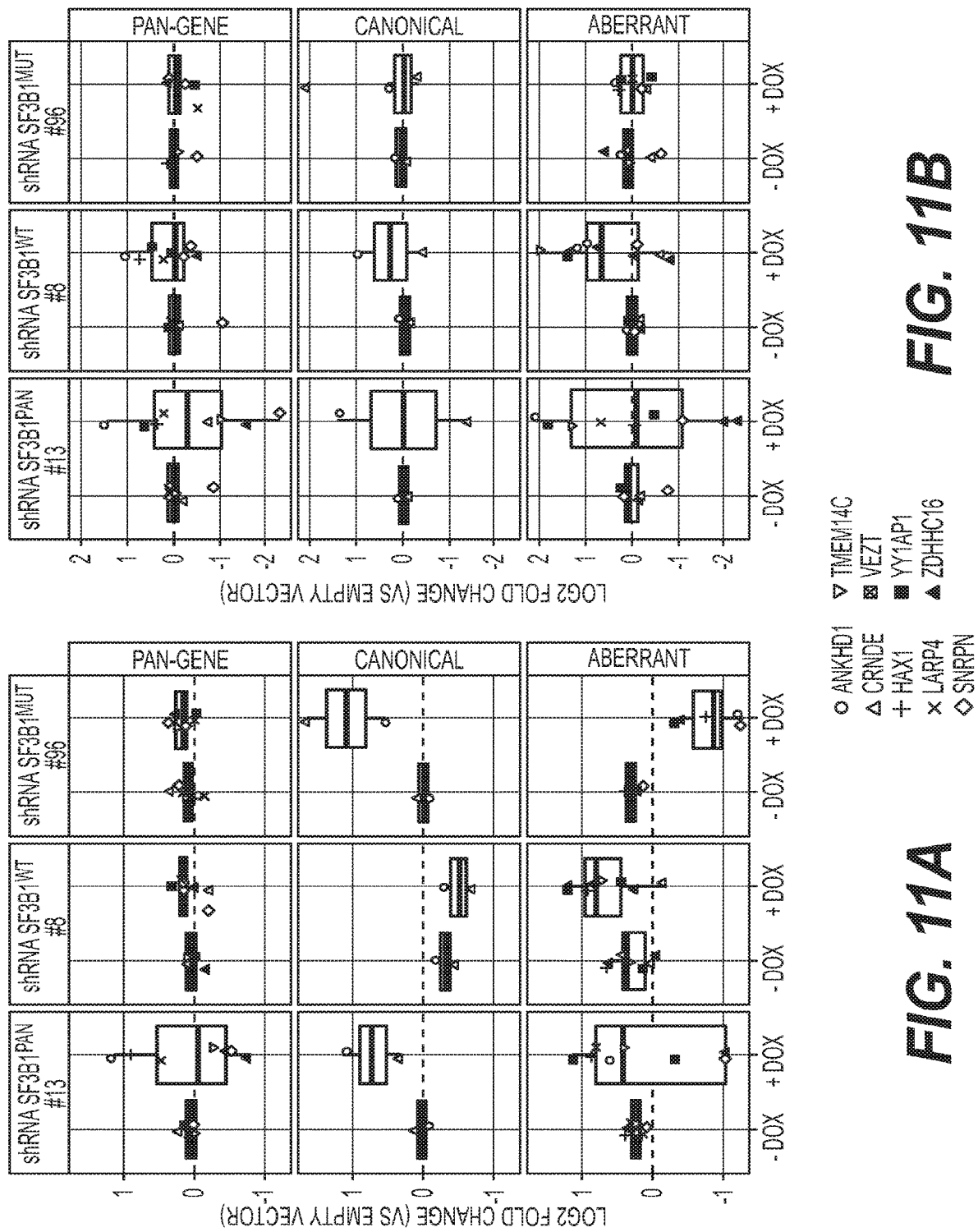
FIGS. 11A and 11B are a set of graphs depicting levels of splice variants in Panc 05.04 (FIG. 11A) and Panc 10.05 cells (FIG. 11B) before and after shRNA-knockdown of SF3B1 alleles, as measured in a NanoString® assay. Data are represented as mean of three biological replicates.
Figure 12:
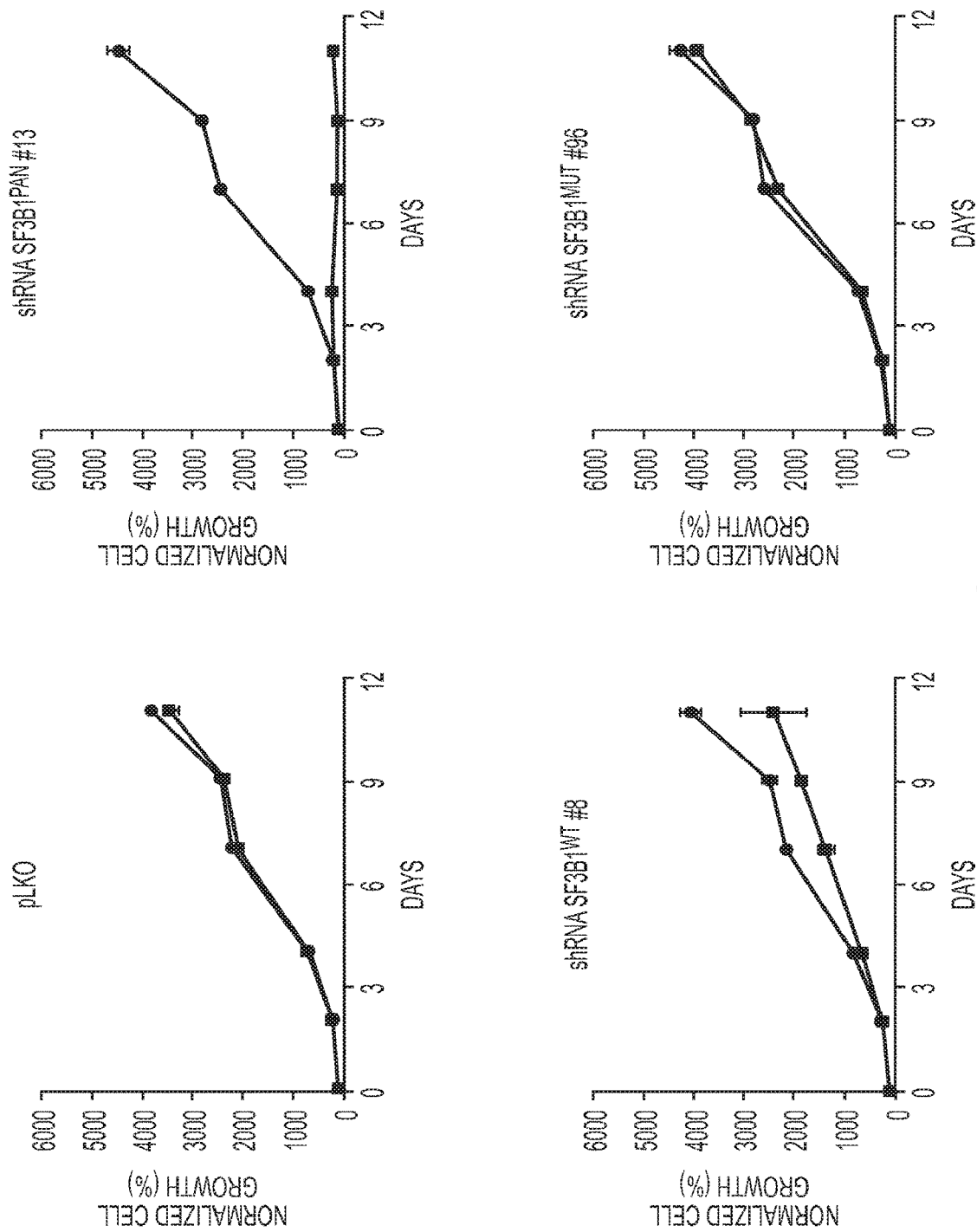
FIG. 12 is a set of graphs depicting growth curves of Panc 05.04 cells before (circles) and after (squares) shRNA-knockdown of SF3B1 alleles.
Figure 13:
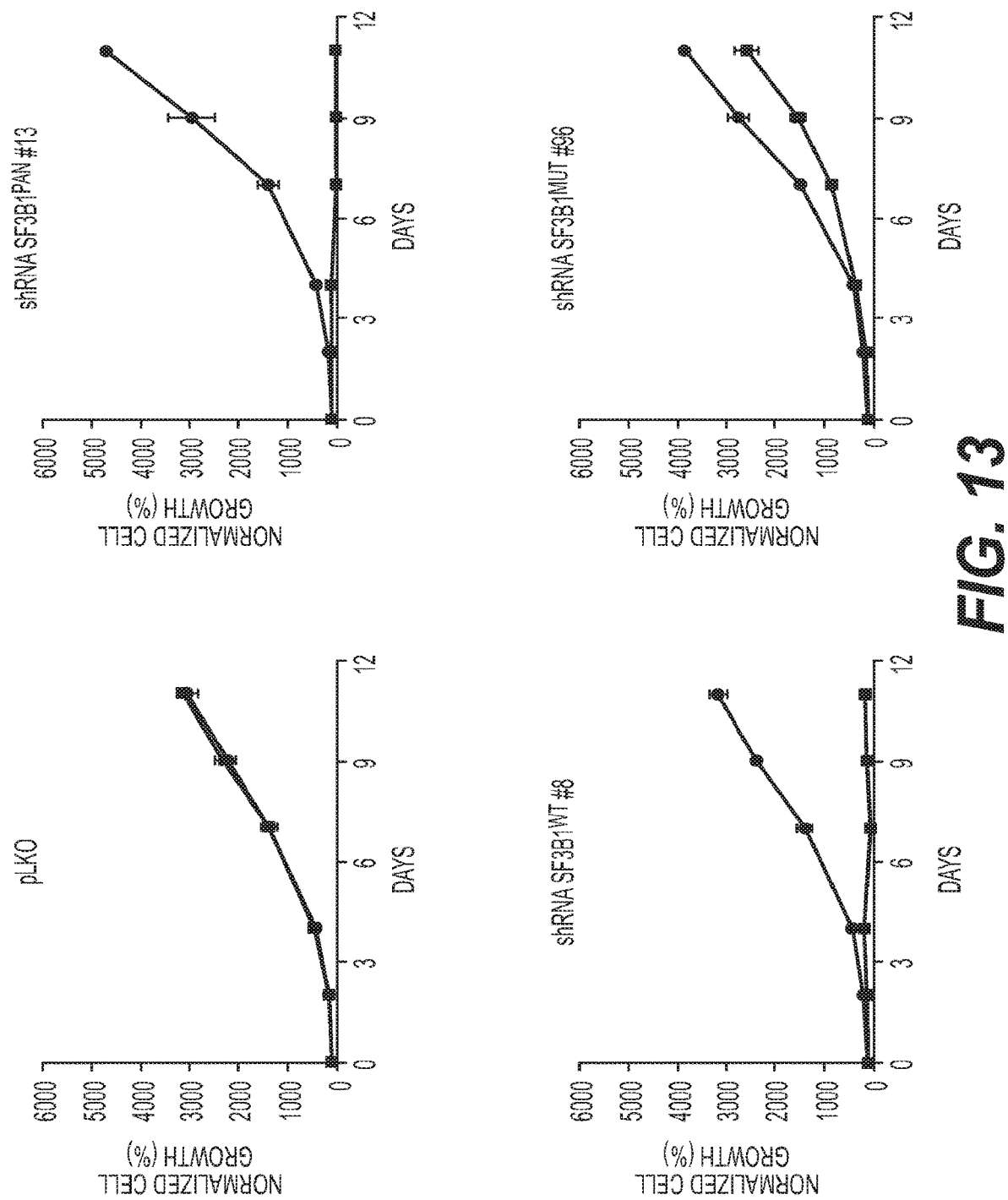
FIG. 13 is a set of graphs depicting growth curves of Panc 10.05 cells before (circles) and after (squares) shRNA-knockdown of SF3B1 alleles.
Figure 14A:
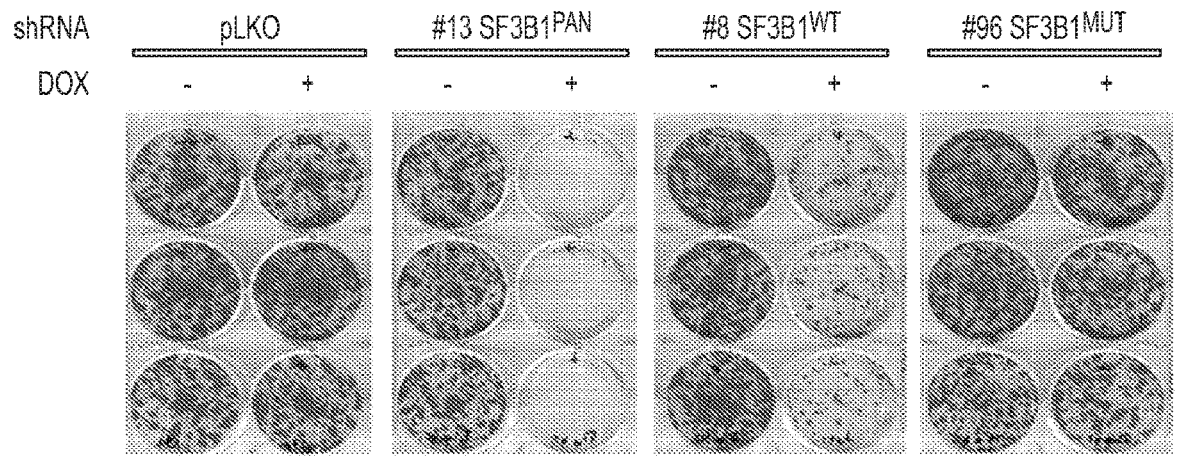
FIGS. 14A and 14B are a set of images of culture plates showing colony formation of Panc 05.04 cells (FIG. 14A) and Panc 10.05 (FIG. 14B) cells before and after shRNA-knockdown of SF3B1 alleles.
Figure 14B:
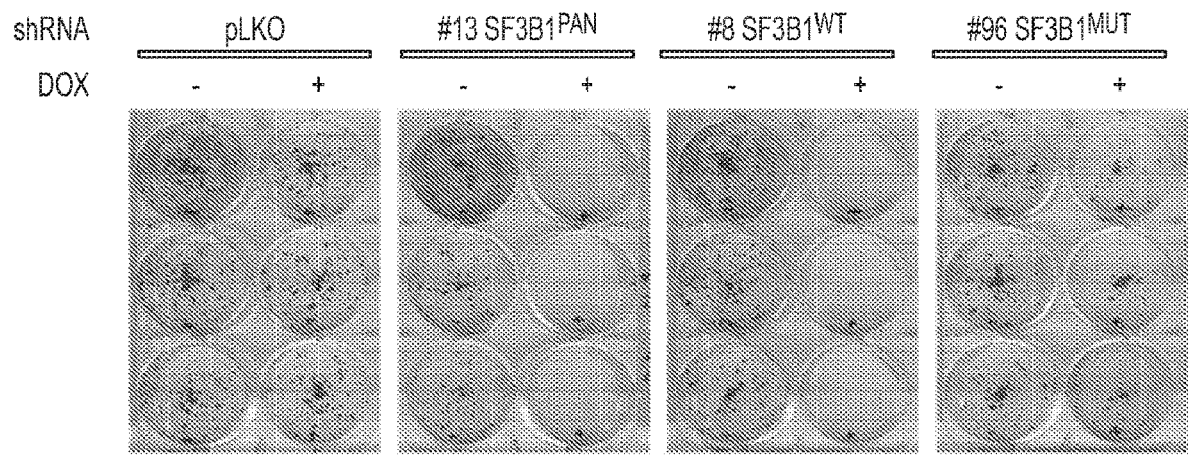

To determine the association between the expression of SF3B1 mutations and aberrant splicing, RNA isolated from the cells following doxycycline-induced knockdown was analyzed by NanoString®. In Panc 05.04, after knockdown of the neomorphic SF3B1$^{MUT}$ allele, the aberrant splice variants were downregulated and the canonical splice variants were upregulated, whereas the opposite was observed with selective depletion of the SF3B1$^{WT}$ allele (FIG. 11A), indicating that the neomorphic SF3B1$^{MUT}$ protein does not possess wild-type splicing activity. The expression of a pan shRNA induced the regulation of all splice variants as well as the depletion of SF3B1$^{WT}$ in Panc 10.05 cells (FIG. 11B). SF3B1$^{PAN}$ knockdown impaired growth and colony formation in both cell lines, while a minimal effect was observed with selective depletion of neomorphic SF3B1$^{MUT}$ in Panc05.04 cells (FIGS. 12 and 13). When the SF3B1$^{WT}$ allele was knocked down in Panc 05.04 cells, only a partial viability effect was observed, whereas SF3B1$^{PAN}$ knockdown prevented colony formation and cell proliferation (FIGS. 12 and 14), indicating that pan-inhibition of SF3B1 leads to antitumor activity in vitro and in vivo.

Example 4: Modulation of Neomorphic SF3B1$^{MUT}$ Splicing

Overall Effect of E7107 on Splicing

E7107 is a small-molecule compound that inhibits splicing by targeting the U2 snRNP-associated complex SF3B (Kotake, Y. et al. "Splicing factor SF3b as a target of the antitumor natural product pladienolide." Nat Chem Biol 3, 570-575, doi:10.1038/nchembio.2007.16 [2007]). The ability of E7107 to inhibit splicing was observed in an in vitro splicing assay (IVS) using the substrate Ad2 (Pellizzoni, L., Kataoka, N., Charroux, B. & Dreyfuss, G. "A novel function for SMN, the spinal muscular atrophy disease gene product, in pre-mRNA splicing." Cell 95, 615-624 [1998]) and nuclear extracts from the Nalm-6 isogenic cell lines or 293F cells (Life Technologies; cultured according to the manufacturer's instructions) expressing Flag-tag SF3B1$^{WT}$ or SF3B1$^{K700E}$, as follows.

Nuclear extracts were prepared from 293F cells transfected with pFLAG-CMV-2-SF3B1 plasmids, or from isogenic Nalm-6 cells (SBH Sciences). The plasmids were generated by cloning the mxSF3B1 gene into the HindIII and KpnI sites of pFLAG-CMV2 (Sigma), and the mutations mxSF3B1$^{K700E}$, mxsF3B1$^{R1074H}$ and mxSF3B1$^{K700E-R1074H}$ were introduced using the same site-directed mutagenesis kit. Cell pellets were resuspended in hypotonic buffer (10 mM HEPES pH 7.9, 1.5 mM MgCl$_2$, 10 mM KCl, 0.2 mM PMSF, and 0.5 mM DTT; for Nalm-6 cells, 40 mM KCl was used). The suspension was brought up to a total of five packed cell volumes (PCV). After centrifugation, the supernatant was discarded, and the cells were brought up to 3 PCV with hypotonic buffer, and incubated on ice for 10 minutes. Cells were lysed using a dounce homogenizer and then centrifuged. The supernatant was discarded, and the pellet was resuspended with ½ packed nuclear volume (PNV) of low salt buffer (20 mM HEPES pH 7.9, 1.5 mM MgCl$_2$, 20 mM KCl, 0.2 mM EDTA, 25% glycerol, 0.2 mM PMSF, 0.5 mM DTT), followed by ½ PNV of high salt buffer (same as low salt buffer except 1.4M KCl was used). The nuclei were gently mixed for 30 minutes before centrifuging. The supernatant (nuclear extract) was then dialyzed into storage buffer (20 mM HEPES pH 7.9, 100 mM KCl, 0.2 mM EDTA, 20% glycerol, 0.2 mM PMSF, 0.5 mM DTT). Protein concentration was determined using Nano-Drop 8000 UV-Vis spectrophotometer (Thermo Scientific).

For in vitro splicing (IVS) reactions, an Ad2-derived sequence (Pellizzoni, L., Kataoka, N., Charroux, B. & Dreyfuss, G. "A novel function for SMN, the spinal muscular atrophy disease gene product, in pre-mRNA splicing." Cell 95, 615-624 [1998]) was cloned into the pGEM-3Z vector (Promega) using EcoRI and XbaI restriction sites. The resulting pGEM-3Z-Ad2 plasmid was linearized using XbaI, purified, resuspended in TE buffer, and used as a DNA template in the in vitro transcription reaction. The Ad2 pre-mRNA was generated and purified using MEGAScript T7 and MegaClear kits, respectively (Invitrogen). Twenty μL splicing reactions were prepared using 80 μg nuclear extracts, 20 U RNAsin Ribonuclease inhibitor (Promega), 10 ng Ad2 pre-mRNA, and varying concentrations of E7107. After a 15 minute pre-incubation, activation buffer (0.5 mM ATP, 20 mM creatine phosphate, 1.6 mM MgCl$_2$) was added to initiate splicing, and the reactions were incubated for 90 minutes. RNA was extracted using a modified protocol from a RNeasy 96 Kit (Qiagen). The splicing reactions were quenched in 350 μL Buffer RLT Plus (Qiagen), and 1.5 volume ethanol was added. The mixture was transferred to an RNeasy 96 plate, and the samples were processed as described in the kit protocol. RNA was diluted 1/10 with dH$_2$O. 10 μL RT-qPCR reactions were prepared using TaqMan RNA-to-C$_T$ 1-step kit (Life Technologies), 8.5 μL RNA, and 1 μL of Ad2 mRNA primers/probe set (FW 5' ACTCTCTTCCGCATCGCTGT (SEQ ID NO: 1191), RW 5'-CCGACGGGTTTCCGATCCAA (SEQ ID NO: 1192) and probe 5' CTGTTGGGCTCGCGGTTG (SEQ ID NO: 1193)).

To evaluate pSF3B1, in vitro splicing reactions were prepared as described above. To quench the reactions, 6× Laemmli Buffer (Boston Bioproducts) was added, and the samples were subjected to SDS-PAGE gels (Life Technologies). The separated proteins were transferred onto nitrocellulose membranes then blocked with blocking buffer (50% Odyssey Blocking Buffer (Li-Cor Biosciences) and 50% TBST). The blots were incubated with anti-SF3B1 antibody overnight, after several washes in TBST, they were incubated with IRDye 680LT donkey-α-mouse-IgG antibody and visualized using an Odyssey CLx imaging system (Li-Cor Biosciences).

E7107 was able to inhibit splicing in nuclear extracts from both the Nalm-6 cells or the 293F cells expressing Flag-tag SF3B1$^{WT}$ or SF3B1$^{K700E}$ (FIGS. 15A and 15B).

E7107 Binds Both SF3B1$^{WT}$ and SF3B1$^{K700E}$ Proteins

The ability of E7107 to bind both SF3B1$^{WT}$ and SF3B1$^{K700E}$ proteins was evaluated in a competitive binding assay using Flag-tag SF3B1 proteins immunoprecipitated with anti-Flag antibody from transiently transfected 293F cells. Batch immobilization of antibody to beads was prepared by incubating 80 µg of anti-SF3B1 antibody (MBL International) and 24 mg anti-mouse PVT SPA scintillation beads (PerkinElmer) for 30 minutes. After centrifugation, the antibody-bead mixture was resuspended in PBS supplemented with PhosSTOP phosphatase inhibitor cocktail (Roche) and complete ULTRA protease inhibitor cocktail (Roche). Nuclear extracts were prepared by diluting 40 mg into a total volume of 16 mL PBS with phosphatase and protease inhibitors, and the mixture was centrifuged. The supernatant was transferred into a clean tube, and the antibody-bead mixture was added and incubated for two hours. The beads were collected by centrifuging, washed twice with PBS+0.1% Triton X-100, and resuspended with 4.8 mL of PBS. 100 µL binding reactions were prepared using slurry and varying concentrations of E7107. After 15 minutes pre-incubation at room temperature, one nM $^3$H-probe molecule (described in Kotake, Y. et al. Splicing factor SF3b as a target of the antitumor natural product pladienolide. Nat Chem Biol 3, 570-575, doi:10.1038/nchembio.2007.16 [2007]) was added. The mixture was incubated at room temperature for 15 minutes, and luminescence signals were read using a MicroBeta2 Plate Counter (PerkinElmer).

Figure 16A:
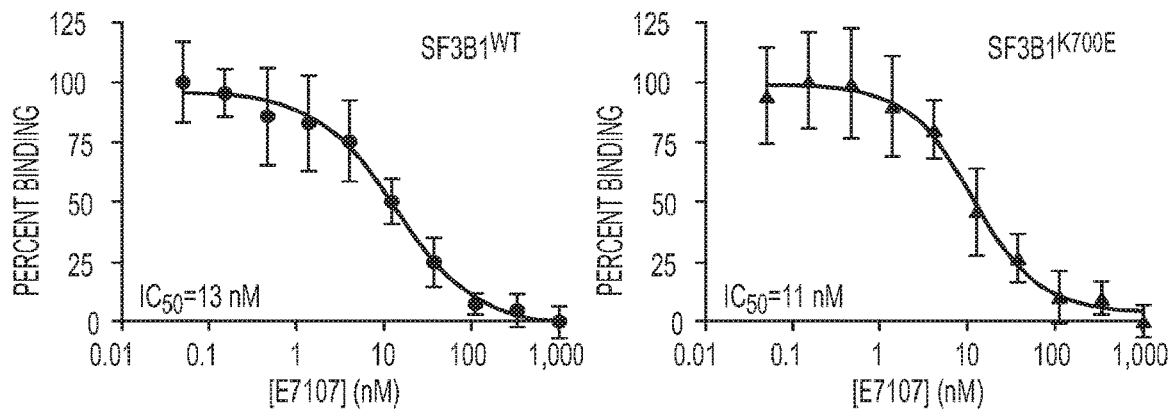
FIG. 16A depicts a pair of graphs showing the binding of a radiolabeled E7107 analog to either SF3B1$^{WT}$ (circles, left panel) or SF3B1$^{K700E}$ (triangles, right panel) after incubation of the proteins with varying concentrations of E7107.

As shown in FIG. 16A, E7107 was able to competitively inhibit binding of the $^3$H-probe molecule in a similar manner to either SF3B1$^{WT}$ (IC$_{50}$: 13 nM) or SF3B1$^{K700E}$ (IC$_{50}$: 11 nM).

Effect of E7107 and Other Compounds on Normal and Aberrant Splicing

Figure 16B:
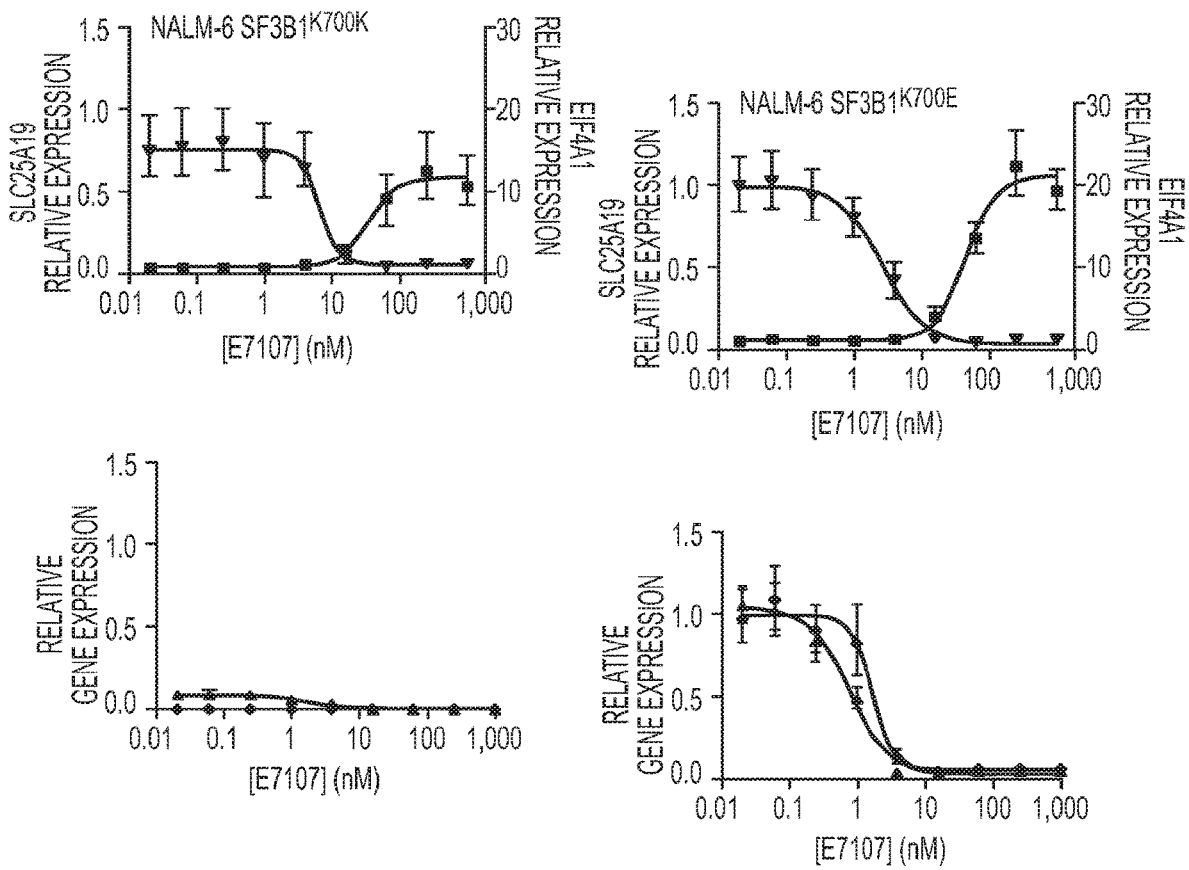
FIG. 16B depicts upper panels, a pair of graphs showing the levels of EIF4A1 pre-mRNA (squares) and SLC25A19 mature RNA (inverted triangles) in Nalm-6 SF3B1$^{K700K}$ cells (left panel) and Nalm-6 SF3B1$^{K700E}$ cells (right panel) treated with varying concentrations of E7107, as measured by qPCR.

E7107 was also tested in vitro in Nalm-6 isogenic cell lines for the ability to modulate normal and aberrant splicing induced by SF3B1$^{WT}$ and SF3B1$^{K700E}$ protein. Nalm-6 isogenic cells were treated with increasing concentrations of E7107 for six hours and RNA was analyzed by qPCR. As shown in FIG. 16B, canonical splicing was observed, with accumulation of pre-mRNA for EIF4A1 and downregulation of the mature mRNA SLC25A19 observed in both cell lines. Additionally, downregulation of mature mRNA of the two abnormally spliced isoforms of COASY and ZDHHC16 was observed in Nalm-6 SF3B1$^{K700E}$ (FIG. 16B).

Figure 17:
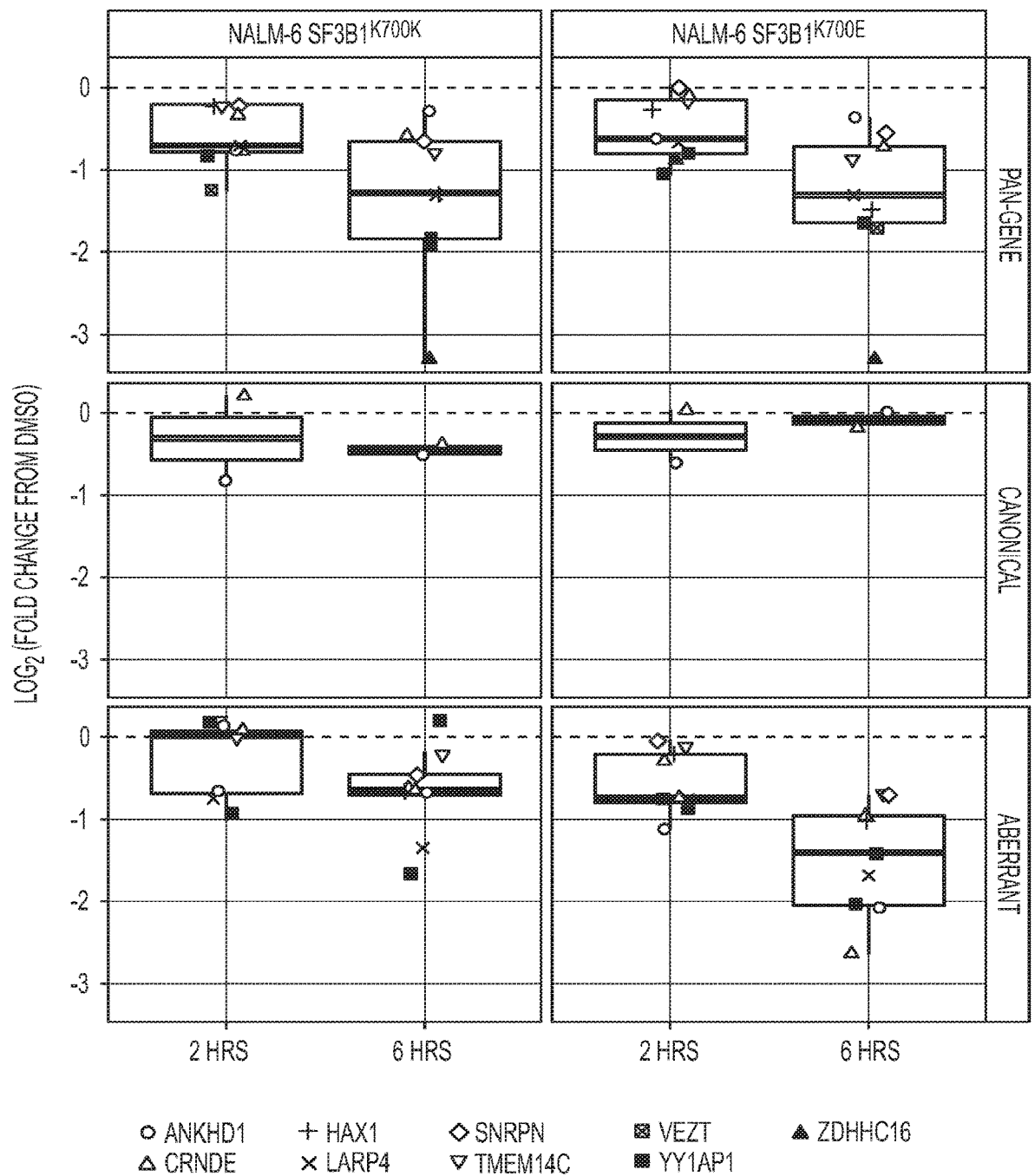
FIG. 17 is a set of graphs depicting levels of splice variants in Nalm-6 SF3B1$^{K700K}$ and Nalm-6 SF3B1$^{K700E}$ cells after treatment of cells with E7107 for two or six hours, as measured in a NanoString® assay. Data are expressed as fold change from DMSO-only treatment
Figure 18:
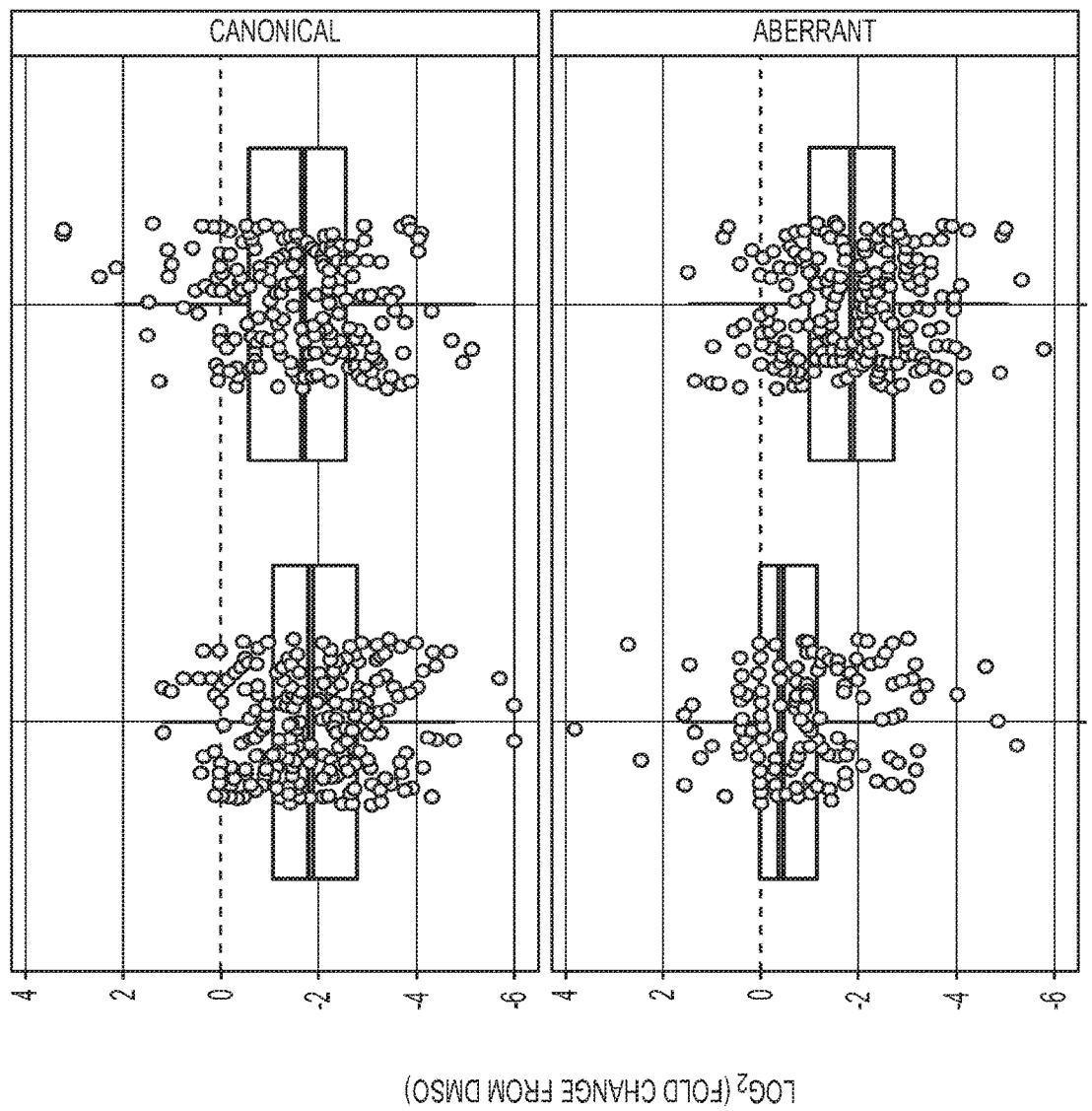
FIG. 18 is a set of graphs depicting levels of splice variants in Nalm-6 SF3B1$^{K700K}$ and Nalm-6 SF3B1$^{K700E}$ cells after treatment of cells with E7107 for six hours, as measured by RNA-Seq analysis.
Figure 19:
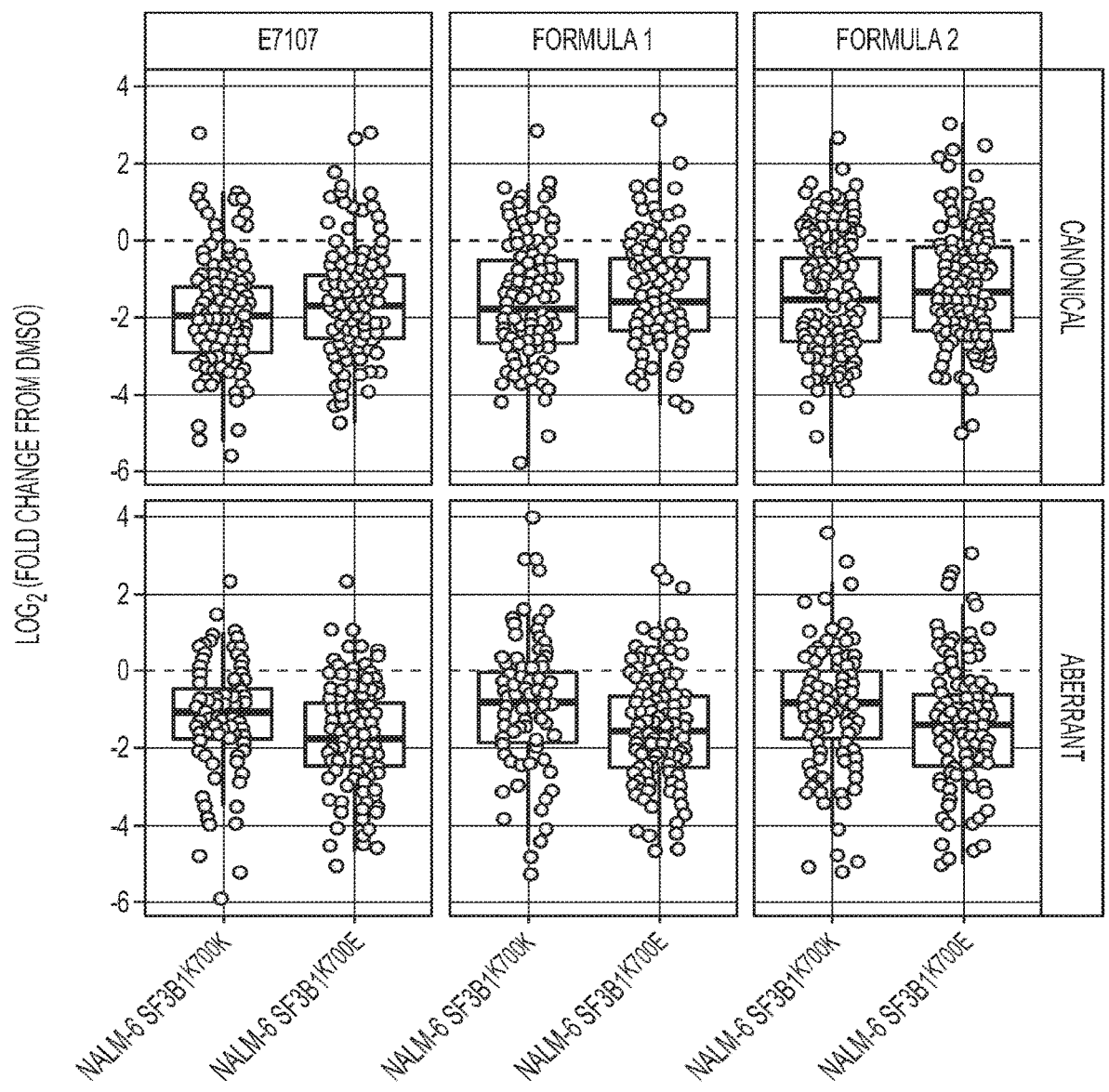
FIG. 19 is a set of graphs depicting levels of splice variants in Nalm-6 SF3B1$^{K700K}$ and Nalm-6 SF3B1$^{K700E}$ cells after treatment of cells with the numbered compounds indicated above the graphs, as measured by RNA-Seq analysis.

To investigate the broader activity of E7107 on normal and aberrant splicing, RNA from Nalm-6 isogenic cells treated for two and six hours at 15 nM was analyzed by NanoString®. Only partial inhibition of splicing was observed at two hours in both isogenic cell lines, and at the level of gene, WT-associated isoforms, and MUT-associated isoform expression. After six hours of treatment, clear inhibition was detected for all isoforms quantified (FIG. 17). Similar results were obtained by RNA-Seq analysis of isogenic cell lines treated for six hours with E7107 at 15 nM (FIG. 18). Normal and aberrant splicing in the isogenic cell lines was also analyzed by RNA-Seq following treatment with one of additional compounds having formulas 1 or 2. Like E7107, each of these additional compounds inhibited expression of both WT-associated and MUT-associated RNA isoforms (FIG. 19; compound is indicated by formula number above each vertical pair of graphs). For the RNA-Seq analysis, cells were washed with PBS after treatment with E7107 or other test compound, and RNA was isolated using PureLink (Life Technology) as reported in the manufacturer's manual. cDNA library preparation, sequencing and raw read filtering was performed as described in Ren, S. et al. "RNA-Seq analysis of prostate cancer in the Chinese population identifies recurrent gene fusions, cancer-associated long noncoding RNAs and aberrant alternative splicings." Cell Res 22, 806-821, doi:10.1038/cr.2012.30 (2012).

Figure 20:
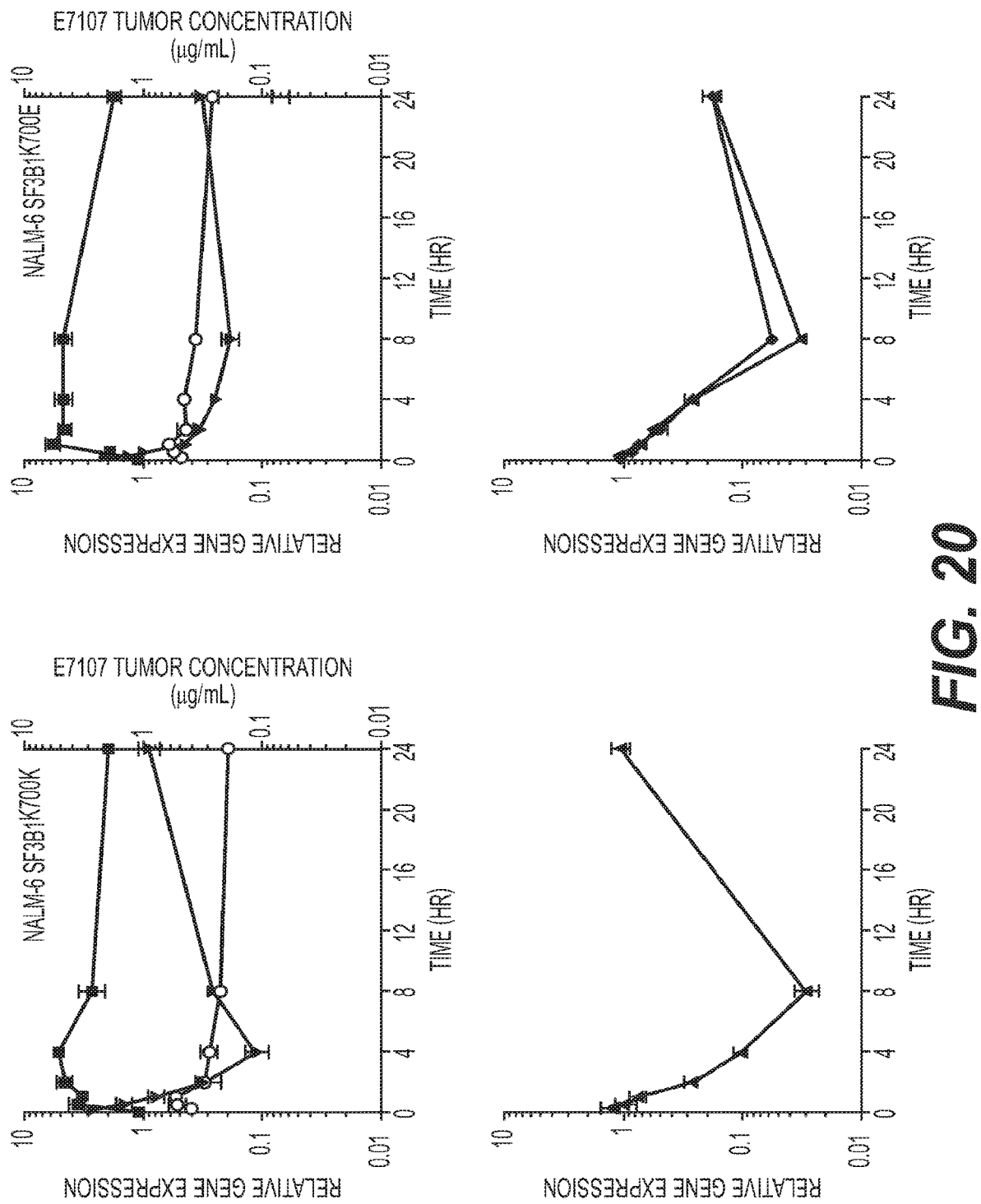
FIG. 20 is set of graphs depicting levels of splice variants in Nalm-6 SF3B1$^{K700K}$ and Nalm-6 SF3B1$^{K700E}$ cells at varying times following treatment of cells with E7107, as measured by qPCR of RNA. Data are represented as mean±SD (n=3). The upper panels of FIG. 20 depict the levels of EIF4A1 pre-mRNA (squares) and SLC25A19 mature RNA (inverted triangles) in Nalm-6 SF3B1$^{K700K}$ cells (left panel) and Nalm-6 SF3B1$^{K700E}$ cells (right panel) detected at certain times after treatment with E7107. The lower panels of FIG. 20 depict the levels of abnormally spliced isoforms of abnormally spliced genes COASY (triangles) and ZDHHC16 (diamonds) in Nalm-6 SF3B1$^{K700K}$ cells (left panel) and Nalm-6 SF3B1$^{K700E}$ cells (right panel) detected at certain times after treatment with E7107. Open circles show the concentration of E7107 (in μg/ml [right vertical axis]) as determined by mass spectrometry of tumor samples.
Figure 21:
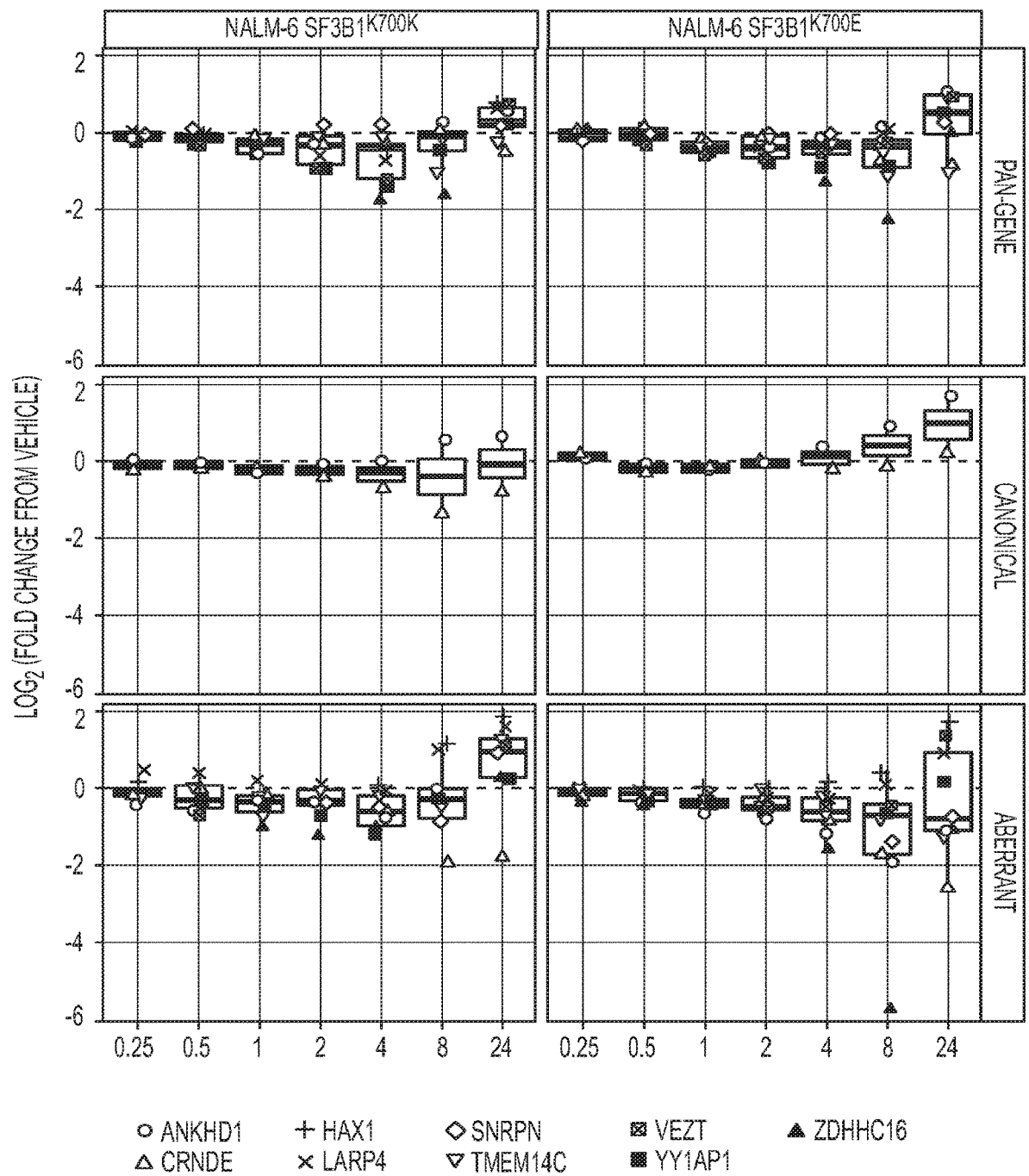
FIG. 21 is a set of graphs depicting levels of canonical and aberrant splice variants in Nalm-6 SF3B1$^{K700K}$- and Nalm-6 SF3B1$^{K700E}$-xenograft tumors (left and right sets of panels, respectively) at certain timepoints after treatment of xenograft mice with E7107, as measured in a NanoString® assay. Data are represented as mean of three replicates.
Figure 22:
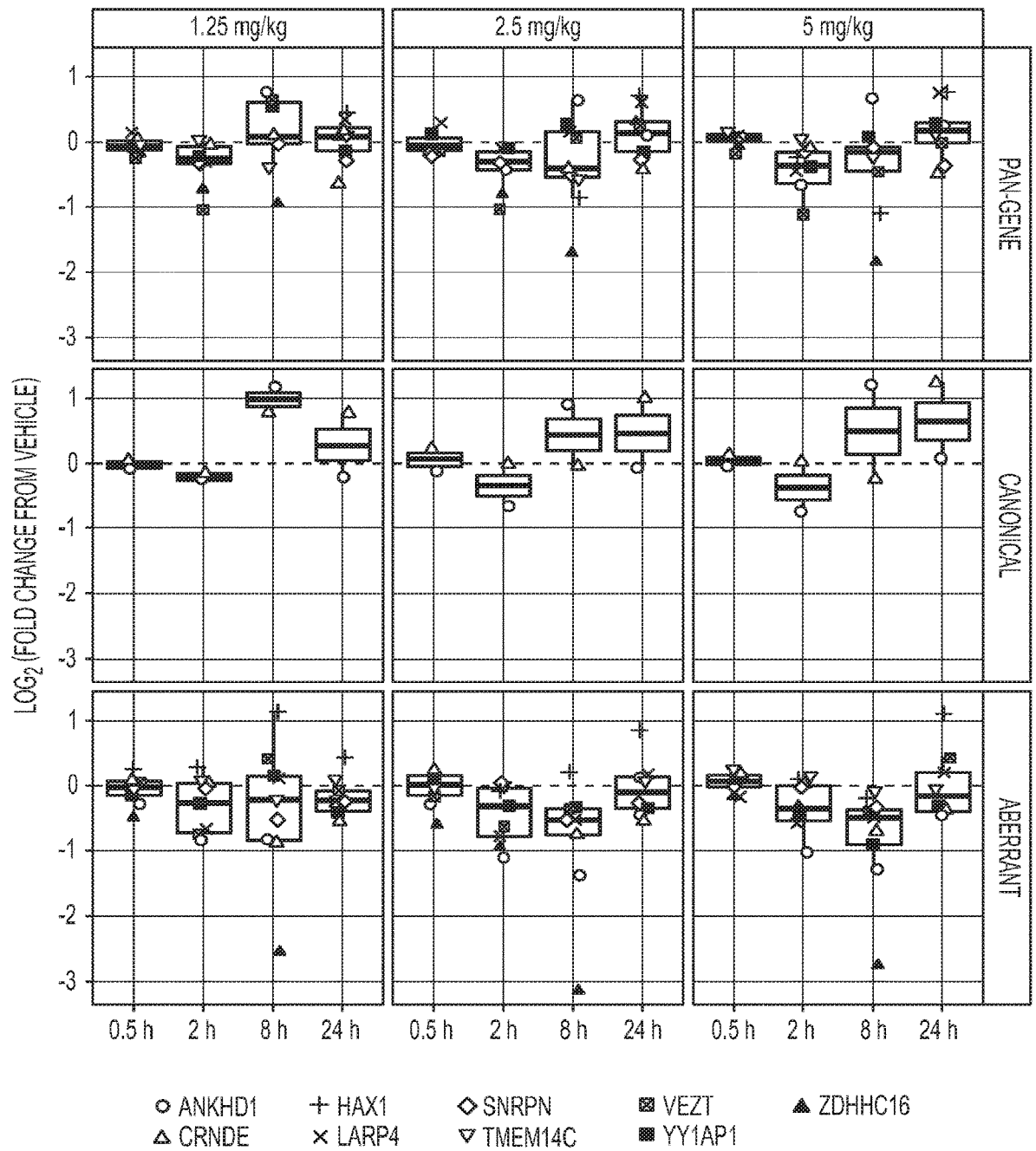
FIG. 22 is a set of graphs depicting levels of canonical and aberrant splice variants in Panc 05.04-xenograft tumors at certain timepoints after treatment of xenograft mice with E7107 at various concentrations, as measured in a NanoString® assay (n=4 mice for each group).

In addition, the ability of E7107 to modulate splicing was tested in mice bearing human tumor xenografts. Nalm-6 isogenic xenograft mice were generated by subcutaneously implanting 10×10$^6$ Nalm-6 isogenic cells into the flank of CB17-SCID mice, and tumors from these mice were collected at different timepoints after a single intravenous (IV) dose of E7107 (5 mg/kg) and analyzed to determine compound concentrations and splicing regulation. RNA was isolated from the tumors using RiboPure™ RNA purification kit (Ambion®) and used for NanoString® assay or qPCR. The RNA was retrotranscribed according to the instructions of the SuperScript® VILO™ cDNA synthesis kit (Invitrogen™) and 0.04 µl of cDNA was used for qPCR. qPCR for pre-mRNA EIF4A1 and mature mRNA SLC24A19 and pharmacokinetic evaluation were performed as described in Eskens, F. A. et al. "Phase I pharmacokinetic and pharmacodynamic study of the first-in-class spliceosome inhibitor E7107 in patients with advanced solid tumors." Clin Cancer Res 19, 6296-6304, doi:10.1158/1078-0432.CCR-13-0485 (2013). The primers and probes used for ZDHHC16 were the following: FW 5'-TCTTGTC-TACCTCTGGTTCCT (SEQ ID NO: 1194), RW 5' CCTTCTTGTTGATGTGCCTTTC (SEQ ID NO: 1195) and probe 5' FAM CAGTCTTCGCCCCTCTTTTCTTAG (SEQ ID NO: 1196). The primers and probes used for COASY were the following: FW 5'-CGGTGGTGCAAGTGGAA (SEQ ID NO: 1197), RW 5'-GCCTTGGTGTCCTCAT-TTCT (SEQ ID NO: 1198) and probe 5'-FAM-CTT-GAGGTTTCATTTCCCCCTCCC (SEQ ID NO: 1199). E7107 reached similar drug concentrations and modulated canonical splicing (accumulation of pre-mRNA for EIF4A1 and downregulation of the mature mRNA SLC25A19) in both Nalm-6 SF3B1$^{K700K}$ and Nalm-6 SF3B1$^{K700E}$ models and downregulated abnormal splicing of COASY and ZDHHC16 in the Nalm-6 SF3B1$^{K700E}$ cells (FIG. 20), as observed in vitro. The canonical and aberrant splice mRNA isoforms were downregulated by E7107 as early as one hour following administration of the compound, and expression normalized shortly after treatment (FIG. 21), consistent with E7107 pharmacokinetic profile. Similar results were observed in a Panc 05.04 neomorphic SF3B1 xenograft model (FIG. 22). All these data indicate that E7107 is a pan-splicing modulator that can bind and inhibit SF3B1$^{WT}$ and SF3B1$^{K700E}$ proteins in vitro and in vivo.

Example 5: E7107 has Anti-Tumor Activity Via SF3B1 Modulation

SF3B1 modulator E7107 was tested for antitumor activity in vivo by determining the effect of E7107 in a subcutaneous model of Nalm-6 SF3B1$^{K700E}$. 10×10$^6$ Nalm-6 SF3B1$^{K700E}$ were subcutaneously implanted into the flank of CB17-SCID mice, and mice were administered E7107 intravenously once a day for 5 consecutive days (QD×5) at three well tolerated dose levels (1.25, 2.5 and 5 mg/kg). After this dosing, the animals were monitored until they reached either of the following endpoints: 1) excessive tumor volume measured three times a week (tumor volume calculated by using the ellipsoid formula: (length×width)/2), or 2) development of any health problem such as paralysis or excessive body weight loss. Partial regression (PR) and complete regression (CR) are defined as 3 consecutive tumor measurements <50% and <30% of starting volume respectively.

Figure 23:
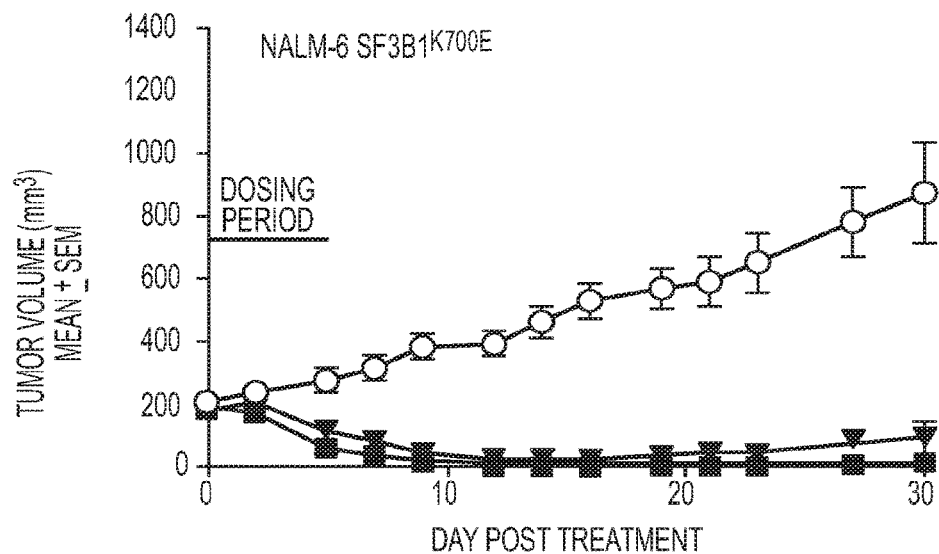
FIG. 23 is a graph depicting tumor volume (shown as mean±SEM) in Nalm-6 SF3B1$^{K700E}$-xenograft mice following treatment with E7107, with control mice treated with vehicle shown by open circles (n=10 animals for each group). For E7107-treated animals, inverted triangles=1.25 mg/kg, triangles=2.5 mg/kg, and squares=5 mg/kg.
Figure 24:
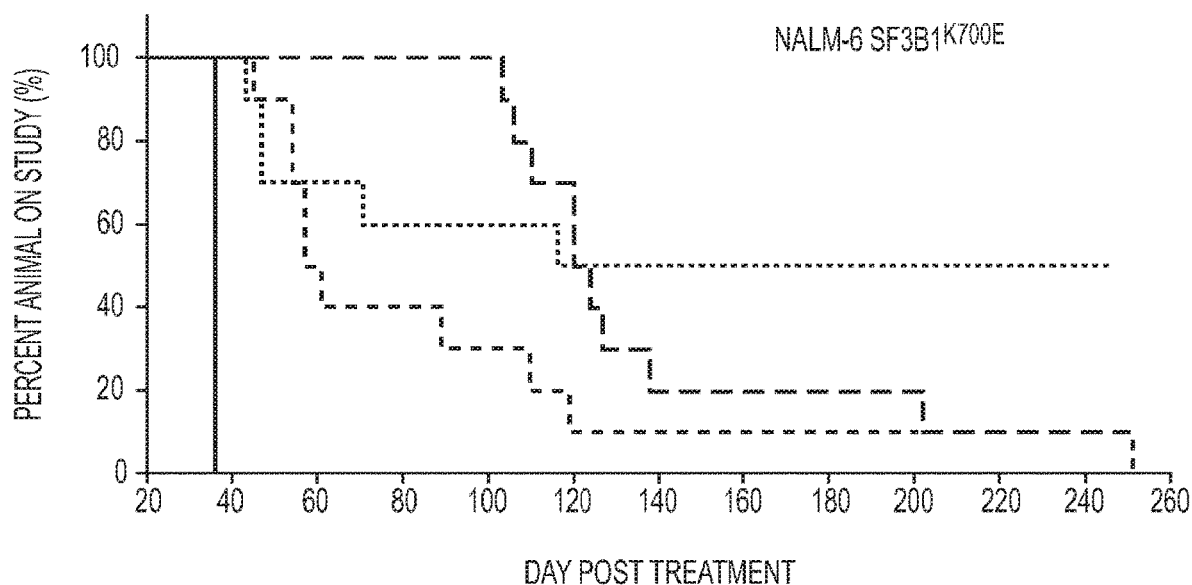
FIG. 24 is a graph depicting survival rates in 10-animal cohorts of Nalm-6 SF3B1$^{K700E}$-xenograft mice following treatment with E7107, with an untreated cohort shown by the solid black line. For E7107-treated animals, dashed line=1.25 mg/kg, gray line=2.5 mg/kg, and dotted line=5 mg/kg.

In the 1.25 mg/kg group, all animals (n=10) reached complete regression (CR) in the Nalm-6 SF3B1$^{K700E}$ xenograft group. In the 2.5 mg/kg group, 10/10 CRs were observed in the Nalm-6 SF3B1$^{K700E}$ group by day 9. In the 5 mg/kg group all Nalm-6 SF3B1$^{K700E}$ xenograft animals reached CR as early as 9 days post treatment and had mean survival times of over 250 days (FIGS. 23 and 24). These data demonstrate antitumor activity of SF3B1 modulator in SF3B1$^{K700E}$ xenografts in vivo.

Figure 25:
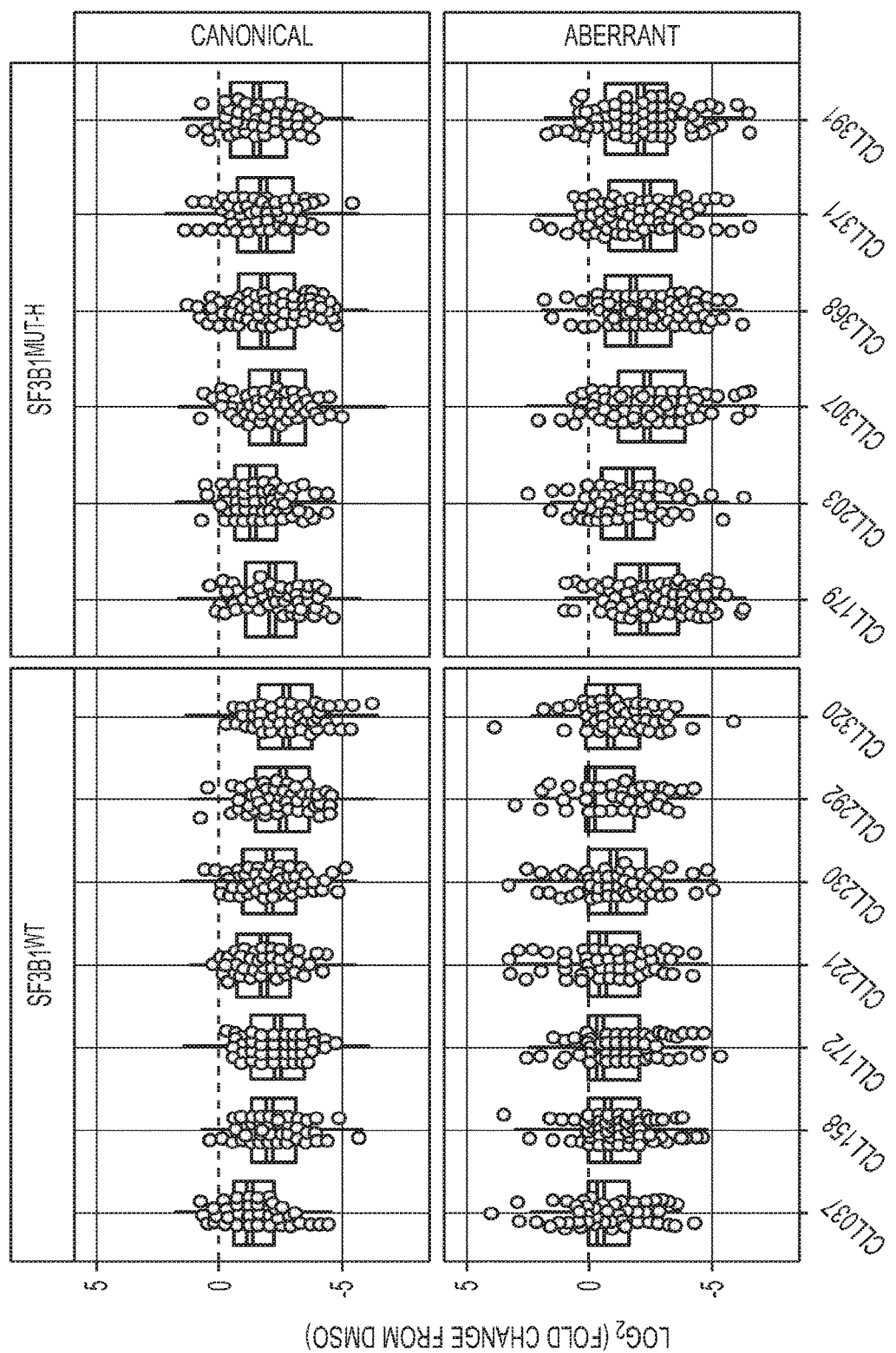
FIG. 25 is set of graphs depicting levels of splice variants in SF3B1$^{WT}$ and neomorphic SF3B1 mutant CLL cell samples following treatment with 10 nM E7107 for 6 hours, as measured by analysis. Data are represented as mean values (n=3).

The ability of E7107 to inhibit splicing in CLL patient samples in vitro was determined by isolating RNA from samples of E7107-treated patient cells treated for 6 hours with E7107 at 10 nM and performing RNA-Seq analysis. To do so, cells were washed with PBS after treatment with E7107, and RNA was isolated using PureLink (Life Technology) as reported in the manufacturer's manual. cDNA library preparation, sequencing and raw read filtering was performed as described in Ren, S. et al. "RNA-Seq analysis of prostate cancer in the Chinese population identifies recurrent gene fusions, cancer-associated long noncoding RNAs and aberrant alternative splicings." *Cell Res* 22, 806-821, doi:10.1038/cr.2012.30 (2012). As shown in FIG. 25, E7107 inhibited the expression of canonical splice isoforms in SF3B1$^{WT}$ and neomorphic SF3B1$^{MUT}$ patient samples. E7107 was able to modulate aberrant splicing in all CLL patient samples carrying neomorphic SF3B1 mutations.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method of treating a patient having a neoplastic disorder, comprising administering an SF3B1-modulating compound to the patient, wherein a sample from the patient has been tested to determine expression levels of aberrant and canonical splice variants of TMEM14C, and the sample expresses an elevated ratio of aberrant to canonical splice variants of TMEM14C relative to the ratio in a control sample, wherein the aberrant splice variant comprises SEQ ID NO: 95 and wherein the canonical splice variant comprises SEQ ID NO: 96.

2. The method of claim 1, wherein the sample comprises a blood sample, a bone marrow aspirate, and/or a bone marrow biopsy.

3. The method of claim 1, wherein the sample from the patient treated with the SF3B1-modulating compound further comprises a neomorphic SF3B1 mutation.

4. The method of claim 3, wherein the neomorphic SF3B1 mutation comprises a mutation at one or more of positions selected from E622, H662, R625, K666, K700, and V701 in SF3B1.

5. The method of claim 3, wherein the neomorphic SF3B1 mutation comprises a mutation at one or more of positions selected from H662, R625, and K700 in SF3B1.

6. The method of claim 3, wherein the neomorphic SF3B1 mutation comprises R625C and/or K700E.

7. The method of claim 3, wherein the control sample expresses a wild type or non-neomorphic SF3B1 protein.

8. The method of claim 1, wherein the neoplastic disorder is a myeloid neoplasm.

9. The method of claim 8, wherein the myeloid neoplasm is myelodysplastic syndrome, acute myeloid leukemia, or chronic myelomonocytic leukemia.

10. The method of claim 1, wherein the neoplastic disorder is myelodysplastic syndrome.

11. The method of claim 1, wherein the SF3B1-modulating compound comprises a compound of formula 2:

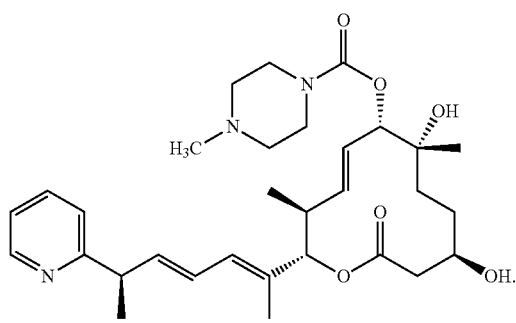

12. A method of treating a patient having a neoplastic disorder, comprising:
a) identifying an elevated ratio of aberrant to canonical splice variants of TMEM14C in a sample from the patient relative to the ratio in a control sample; and
b) administering an SF3B1-modulating compound to the patient,
wherein the aberrant splice variant comprises SEQ ID NO: 95 and wherein the canonical splice variant comprises SEQ ID NO: 96.

13. The method of claim 12, wherein identifying an elevated ratio comprises nucleic acid barcoding, real-time polymerase chain reaction (RT-PCR), microarray, nucleic acid sequencing, nanoparticle probes, and/or in situ hybridization.

14. The method of claim 12, wherein identifying an elevated ratio comprises nucleic acid barcoding.

15. The method of claim 12, wherein identifying an elevated ratio comprises RT-PCR.

16. The method of claim 12, wherein the sample comprises a blood sample, a bone marrow aspirate, and/or a bone marrow biopsy.

17. The method of claim 12, wherein the sample from the patient treated with the SF3B1-modulating compound further comprises a neomorphic SF3B1 mutation.

18. The method of claim 17, wherein the neomorphic SF3B1 mutation comprises a mutation at one or more of positions selected from E622, H662, R625, K666, K700, and V701 in SF3B1.

19. The method of claim 17, wherein the neomorphic SF3B1 mutation comprises a mutation at one or more of positions selected from H662, R625, and K700 in SF3B1.

20. The method of claim 17, wherein the neomorphic SF3B1 mutation comprises R625C and/or K700E.

21. The method of claim 17, wherein the control sample expresses a wild type or non-neomorphic SF3B1 protein.

22. The method of claim 12, wherein the neoplastic disorder is a myeloid neoplasm.

23. The method of claim 22, wherein the myeloid neoplasm is myelodysplastic syndrome, acute myeloid leukemia, or chronic myelomonocytic leukemia.

24. The method of claim 12, wherein the neoplastic disorder is myelodysplastic syndrome.

25. The method of claim 12, wherein the SF3B1-modulating compound comprises a compound of formula 2:

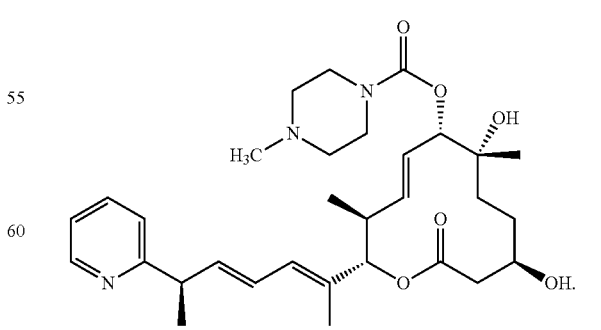

* * * * *